United States Patent
Yang et al.

(10) Patent No.: US 10,266,496 B2
(45) Date of Patent: Apr. 23, 2019

(54) CARBOXY SUBSTITUTED (HETERO) AROMATIC RING DERIVATIVES AND PREPARATION METHOD AND USES THEREOF

(71) Applicant: SUNSHINE LAKE PHARMA CO., LTD., Dongguan, Guangdong (CN)

(72) Inventors: Xinye Yang, Dongguan (CN); Changwei Huang, Dongguan (CN); Facheng Ma, Dongguan (CN); Ji Zhang, Dongguan (CN); Xiaojun Wang, Dongguan (CN); Yingjun Zhang, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

(21) Appl. No.: 15/750,205

(22) PCT Filed: Aug. 31, 2016

(86) PCT No.: PCT/CN2016/097660
§ 371 (c)(1),
(2) Date: Feb. 5, 2018

(87) PCT Pub. No.: WO2017/036404
PCT Pub. Date: Mar. 9, 2017

(65) Prior Publication Data
US 2018/0230102 A1 Aug. 16, 2018

(30) Foreign Application Priority Data

Sep. 2, 2015 (CN) .......................... 2015 1 0560190

(51) Int. Cl.
*C07D 215/48* (2006.01)
*C07D 215/02* (2006.01)
(Continued)

(52) U.S. Cl.
CPC .......... *C07D 215/48* (2013.01); *A61K 31/277* (2013.01); *A61K 31/33* (2013.01); *A61K 31/343* (2013.01); *A61K 31/36* (2013.01); *A61K 31/381* (2013.01); *A61K 31/404* (2013.01); *A61K 31/416* (2013.01); *A61K 31/4184* (2013.01); *A61K 31/4192* (2013.01); *A61K 31/42* (2013.01); *A61K 31/423* (2013.01); *A61K 31/426* (2013.01); *A61K 31/428* (2013.01); *A61K 31/437* (2013.01); *A61K 31/44* (2013.01); *A61K 31/443* (2013.01); *A61K 31/4418* (2013.01); *A61K 31/47* (2013.01); *A61K 31/502* (2013.01); *A61K 31/517* (2013.01); *A61K 31/519* (2013.01); *A61K 45/06* (2013.01); *A61P 13/02* (2018.01); *C07C 255/57* (2013.01); *C07D 209/04* (2013.01); *C07D 209/08* (2013.01); *C07D 209/10* (2013.01);
(Continued)

(58) Field of Classification Search
CPC .... A61K 31/277; A61K 31/03; A61K 31/343; A61K 31/36; A61K 31/381; A61K 31/404; A61K 31/416; A61K 31/41845; A61K 31/4192; A61K 31/42; A61K 31/423; A61K 31/426; A61K 31/428; A61K 31/437; A61K 31/44; A61K 31/4418; A61K 31/443; A61K 31/47; A61K 31/502; A61K 31/517; A61K 31/519; A61K 45/06; A61P 13/02; C07C 255/57; C07C 2602/06; C07C 2602/08; C07D 209/04; C07D 209/08; C07D 209/10; C07D 209/30; C07D 209/42; C07D 213/79; C07D 215/02; C07D 215/06; C07D 215/16; C07D 215/18; C07D 215/48; C07D 231/56; C07D 235/06; C07D 235/08; C07D 237/28; C07D 237/30; C07D 249/18; C07D 267/20; C07D 263/54; C07D 263/56; C07D 277/64; C07D 291/08; C07D 307/79; C07D 307/82; C07D 307/83; C07D 307/84; C07D 307/85; C07D 317/64; C07D 317/68; C07D 333/54; C07D 333/62; C07D 333/70; C07D 405/04; C07D 471/04; C07D 487/04
See application file for complete search history.

(56) References Cited

U.S. PATENT DOCUMENTS 5,614,520 A  3/1997 Kondo et al.
8,003,647 B2  8/2011 Shimizu et al.
(Continued)

FOREIGN PATENT DOCUMENTS

JP   2015214527 A   12/2015
WO   WO9117987 A1   11/1991
(Continued)

OTHER PUBLICATIONS

Wolff, Manfred E., Burger's Medicinal Chemistry and Drug Discovery, Fifth Ed., vol. 1: Principles and Practice, John Wiley & Sons, 1995, 975. (Year: 1995).*
(Continued)

*Primary Examiner* — Erich A Leeser
(74) *Attorney, Agent, or Firm* — Kam Wah Law

(57) ABSTRACT

Carboxy-substituted (hetero)aryl derivatives, pharmaceutical compositions comprising these compounds, and methods of preparing such compounds and compositions are provided. The compounds or compositions are useful in inhibiting xanthine oxidase and urate anion transporter 1, and also can be used in the treatment or prevention of diseases associated with high blood uric acid level in mammals, especially humans.

20 Claims, No Drawings

(51) Int. Cl.
| | |
|---|---|
| C07D 235/08 | (2006.01) |
| C07D 237/28 | (2006.01) |
| C07D 249/18 | (2006.01) |
| C07D 261/20 | (2006.01) |
| C07D 263/54 | (2006.01) |
| C07D 209/04 | (2006.01) |
| C07D 291/08 | (2006.01) |
| C07D 263/56 | (2006.01) |
| C07D 317/64 | (2006.01) |
| C07D 231/56 | (2006.01) |
| C07D 333/54 | (2006.01) |
| C07D 333/62 | (2006.01) |
| C07D 235/06 | (2006.01) |
| C07D 471/04 | (2006.01) |
| C07D 487/04 | (2006.01) |
| C07D 209/08 | (2006.01) |
| C07D 209/10 | (2006.01) |
| C07D 277/64 | (2006.01) |
| C07D 209/30 | (2006.01) |
| C07D 307/79 | (2006.01) |
| C07D 307/82 | (2006.01) |
| C07D 209/42 | (2006.01) |
| C07D 213/79 | (2006.01) |
| C07D 215/06 | (2006.01) |
| C07D 215/16 | (2006.01) |
| C07D 215/18 | (2006.01) |
| C07D 237/30 | (2006.01) |
| C07D 277/56 | (2006.01) |
| C07D 307/83 | (2006.01) |
| C07D 307/84 | (2006.01) |
| C07D 307/85 | (2006.01) |
| C07D 317/68 | (2006.01) |
| C07D 333/70 | (2006.01) |
| C07D 405/04 | (2006.01) |
| A61K 31/33 | (2006.01) |
| A61K 31/404 | (2006.01) |
| A61K 31/343 | (2006.01) |
| A61K 31/36 | (2006.01) |
| A61K 31/381 | (2006.01) |
| A61K 31/4192 | (2006.01) |
| A61K 31/42 | (2006.01) |
| A61K 31/428 | (2006.01) |
| A61K 31/437 | (2006.01) |
| A61K 31/44 | (2006.01) |
| A61K 31/517 | (2006.01) |
| A61K 31/519 | (2006.01) |
| A61K 31/277 | (2006.01) |
| A61K 31/416 | (2006.01) |
| A61K 31/4184 | (2006.01) |
| A61K 31/423 | (2006.01) |
| A61K 31/426 | (2006.01) |
| A61K 31/4418 | (2006.01) |
| A61K 31/443 | (2006.01) |
| A61K 31/502 | (2006.01) |
| A61K 45/06 | (2006.01) |
| C07C 255/57 | (2006.01) |
| A61K 31/47 | (2006.01) |
| A61P 13/02 | (2006.01) |

(52) U.S. Cl.
CPC ......... *C07D 209/30* (2013.01); *C07D 209/42* (2013.01); *C07D 213/79* (2013.01); *C07D 215/02* (2013.01); *C07D 215/06* (2013.01); *C07D 215/16* (2013.01); *C07D 215/18* (2013.01); *C07D 231/56* (2013.01); *C07D 235/06* (2013.01); *C07D 235/08* (2013.01); *C07D 237/28* (2013.01); *C07D 237/30* (2013.01); *C07D 249/18* (2013.01); *C07D 261/20* (2013.01); *C07D 263/54* (2013.01); *C07D 263/56* (2013.01); *C07D 277/56* (2013.01); *C07D 277/64* (2013.01); *C07D 291/08* (2013.01); *C07D 307/79* (2013.01); *C07D 307/82* (2013.01); *C07D 307/83* (2013.01); *C07D 307/84* (2013.01); *C07D 307/85* (2013.01); *C07D 317/64* (2013.01); *C07D 317/68* (2013.01); *C07D 333/54* (2013.01); *C07D 333/62* (2013.01); *C07D 333/70* (2013.01); *C07D 405/04* (2013.01); *C07D 471/04* (2013.01); *C07D 487/04* (2013.01); *C07C 2602/06* (2017.05); *C07C 2602/08* (2017.05)

(56) References Cited

U.S. PATENT DOCUMENTS

| | | |
|---|---|---|
| 8,263,622 B2 | 9/2012 | Shimizu et al. |
| 8,466,152 B2 | 6/2013 | Shimizu et al. |
| 8,729,273 B2 | 5/2014 | Song et al. |
| 8,748,452 B2 | 6/2014 | Shimizu et al. |
| 8,829,040 B2 | 9/2014 | Shimizu et al. |
| 8,993,616 B2 | 3/2015 | Shimizu et al. |
| 9,643,969 B2 | 5/2017 | Iizuka et al. |
| 9,670,142 B2 | 6/2017 | Tsaklakidis et al. |
| 2011/0201815 A1 | 8/2011 | Shimizu et al. |
| 2012/0184582 A1 | 7/2012 | Song |

FOREIGN PATENT DOCUMENTS

| | | | | |
|---|---|---|---|---|
| WO | WO 2010/093191 | * | 8/2010 | ........... C07D 487/04 |
| WO | WO2010093191 A2 | | 8/2010 | |

OTHER PUBLICATIONS

Banker, Gilbert S. et al., Modern Pharmaceutics, Marcel Dekker, New York, 1996 (Year: 1996).*
West, Anthony R., Solid State Chemistry and Its Applications, Wiley, New York, 1988, 358. (Year: 1988).*
Eng. translation of the abstract of JP2015214527.
International Search Report of PCT/CN2016/097660.
Written Opinion of PCT/CN2016/097660.

* cited by examiner

CARBOXY SUBSTITUTED (HETERO) AROMATIC RING DERIVATIVES AND PREPARATION METHOD AND USES THEREOF

CROSS-REFERENCE TO RELATED APPLICATIONS

This is a U.S. national stage application of the International Patent Application No. PCT/CN2016/097660, filed Aug. 31, 2016, which claims priorities to Chinese Patent Application No. 201510560190.7, filed Sep. 2, 2015, both of which are incorporated herein by reference in their entirety.

FIELD OF THE INVENTION

The present invention belongs to the field of medical technology, and in particular refers to the compounds, compositions, preparation and use thereof, wherein the compounds or compositions disclosed herein can be used to inhibit activities of xanthine oxidase and urate anion transporter 1, and also can be used for preventing or treating diseases related to high blood uric acid.

BACKGROUND OF THE INVENTION

Uric acid, terminal metabolites of purine compounds in humans, is mainly excreted by the kidney, accounting for two-thirds of total excretion. The accumulation of uric acid caused by overproduction or excretion disorders results in high levels of blood uric acid, and then leads to hyperuricemia. In the normal state of purine diet, two fasting serum blood uric acid level in different days is more than 420 μmol/L for men, and more than 360 μmol/L for women, that is known as hyperuricemia. Causes of hyperuricemia can be classified in three types: (1) increased production of uric acid, (2) poor excretion of uric acid, and (3) mixed type, such classification is useful for discovering the cause of hyperuricemia and giving the targeted treatment.

With supersaturation levels of uric acid in blood, the sodium urate begins to form crystals and deposits in synovium of joint, bursae, cartilage or other tissues. The rapid changes of uric acid levels, the release of tiny crystals caused by local trauma and changes in the coating of uric acid crystals can cause repeated and paroxysmal inflammatory response, and then induce gout. Gout refers in particular to acute arthritis and chronic tophi diseases, mainly including acute onset of arthritis, tophi formation, tophi chronic arthritis, urate nephropathy, uric acid urinary tract calculi and severe symptoms such as joint disability and renal insufficiency. In addition, gout is also associated with hypertension, metabolic syndrome, hyperlipidemia, diabetes and insulin resistance and other diseases. (Terkeltaub R A. Clinical practice. Gout [J]. N Engl J Med. 2003, 349: 1647-1655)(Schlesinger N, Schumacher H R Jr. Gort: can management be improved [J]. Curr Opin Rheumatol. 2001, 13: 240-244).

Hyperuricemia and gout that endanger human health is a severe metabolic disease. The data shows that about 5%~12% of patients with hyperuricemia eventually develop into gout. Uric acid is material basis of hyperuricemia and gout, therefore lowering the concentration of blood uric acid can be used to prevent or treat hyperuricemia and gout, and reduce the risk of complications of hyperuricemia and gout.

Currently, there are two types of drugs used for lowering uric acid level, one type of drugs is used for inhibiting uric acid production, and the other type of drugs is used for increasing uric acid excretion.

Uric acid is derived from dietary intake and endogenous synthesis of purine, which is finally generated by the oxidation of xanthine oxidase. Therefore, xanthine oxidase is regarded as an important target for drugs as inhibitors of uric acid production. Although available drug used for inhibiting production of uric acid named Lopurin has been reported to be effective in treating hyperuricemia and various diseases caused by hyperuricemia, Lopurin also has been noted having serious side effects such as toxidrome, aplastic anemia, abnormal liver function, exfoliative dermatitis and Stevens-Johnson syndrome, etc. (Kazuhide Ogino and 2 persons, Nippon Rinsho (*Japan Clinical*), 2003, Vol. 61, Extra edition 1, pp. 197-201). So it is necessary to develop the drugs with high efficiency, low toxicity and little side effects.

On the other hand, about 90% of hyperuricemia is caused by reduced excretion of uric acid, and uric acid excretion by the kidneys mainly includes four processes: glomerular filtration, renal tubule and collecting duct reabsorption, renal tubule and collecting duct secretion as well as reabsorption after the secretion, and the corresponding protein is involved in each process, at last, only 8%~12% of uric acid is excreted (Liu Ruoxia, Cang Luping, Wu Xinrong, Shangdong Medical Journal [J], 2002, 52(28)). Urate anion transporter 1 (URAT1) is a transmembrane protein disclosed by Enomoto etc., which is located in the brush border side of the renal proximal tubule epithelial cell and participates in reabsorption of uric acid in the renal proximal tubule. hURAT1, encoded by SLC22A12 gene (containing 10 exons and 9 introns) on chromosome 11q13, contains 555 amino acid residues, 12 transmembrane domains, a —NH2 terminal domain and a —COOH terminal domain located inside the cell. Studies found that SLC22A12 gene carried in renal hyperuricemia patients occurred mutation, thereby losing the ability of encoding the mature URAT1 protein, which suggested that URAT1 was the pathogenic gene for renal hyperuricemia (Enomoto, Kimura H, Chairoungdua A, et al. Molecular identification of a renal urate anion exchanger that regulates blood urate levels [J]. Nature, 2002, 417 (6887): 447-452), and URAT1 was important for uric acid reabsorption in the kidney and closely related to the regulation of blood uric acid. Thus, the compounds inhibiting activity of URAT1 can be used for promoting the excretion of the blood uric acid, and treating or preventing the diseases associated with high levels of blood uric acid, including hyperuricemia, gout, tophi, gouty arthritis, renal disorders associated with hyperuricemia, urinary calculi and so on.

It has been reported that the combination of allopurinol and uricosuric drugs is more effective than allopurinol alone in lowing serum uric acid (S Takahashi, Ann. Rheum. Dis., 2003, 62, 572-575). Thus, the combination of uricosuric drug and uric acid production inhibitor can achieve therapeutic effect which monotherapy can not achieve, and can avoid the corresponding risks, for example, momotherapy of uricosuric drugs for treating hyperuricemia of poor uric acid excretion can cause the risk of urinary calculi, whereas the combination of ricosuric drug and uric acid production inhibitor can achieve better therapeutic effect.

The drugs, inhibiting both xanthine oxidase and URAT1, will provide better therapeutic effect for patients and be more convenient than combined drugs. It has been a hot topic for treating hyperuricemia, gout and diseases associated with hyperuricemia.

SUMMARY OF THE INVENTION

The following merely summarizes some aspects of the present invention, but is not limited thereto. These aspects and other aspects and embodiments are described more fully below. There is a more complete description behind about these and other parts. All references of this specification are incorporated herein by reference in their entirety. When the disclosure of this specification is different with citations, the disclosure of this specification shall prevail.

The present invention provides compounds with both xanthine oxidase and URAT1 antagonist activity, which can be used in the manufacture of a medicament for preventing or treating diseases associated with high levels of blood uric acid, such as hyperuricemia, gout, tophi, gouty arthritis, renal disorders associated with hyperuricemia and urolithiasis etc. The compounds of the present invention have good hibitory activity against both xanthine oxidase and URAT1, and also have excellent physicochemical properties and pharmacokinetic properties.

The present invention also provides a method of preparing such compounds and pharmaceutical compositions containing these compounds, and a method of using these compounds or compositions to treat the diseases described above in mammals, especially in humans.

Specifically,

In one aspect, provided herein is a compound having Formula (I) or a stereoisomer, a geometric isomer, a tautomer, an N-oxide, a hydrate, a solvate, a metabolite, an ester, a pharmaceutically acceptable salt or a prodrug thereof,

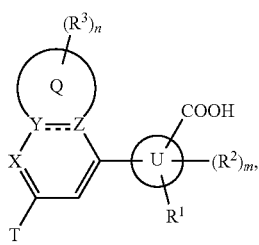

wherein:

U is phenyl or 5- to 6-membered heteroaryl;

each $R^1$ and $R^2$ is independently H, D, halogen, OH, $NH_2$, $NO_2$, CN, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylamino, $C_{1-6}$ haloalkylamino, 3- to 8-membered cycloalkyl or 3- to 8-membered heterocyclyl, wherein each of the $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylamino, $C_{1-6}$ haloalkylamino, 3- to 8-membered cycloalkyl or 3- to 8-membered heterocyclyl is independently and optionally substituted with 1, 2, 3, 4 or 5 substituents selected from OH, oxo (=O), $NH_2$, $NO_2$ or CN;

T is H, D, F, Cl, Br, $NO_2$, CN or $CF_3$;

X is $CR^4$ or N;

$R^4$ is H, D, halogen, $C_{1-6}$ alkyl, $C_{1-6}$ haloalkyl, $C_{1-6}$ alkoxy, $C_{1-6}$ alkylamino or $C_{1-6}$ haloalkoxy;

each of Y and Z is independently C, CH or N;

"-----" refers to a single bond or a double bond;

Q is phene, $C_{4-7}$ carbocycle, 4- to 7-membered heterocycle or 5- to 6-membered heteroaromatic ring;

each $R^3$ is independently H, D, halogen, oxo (=O), OH, $NH_2$, $NO_2$, CN, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylamino, $C_{1-6}$ haloalkylamino, 3- to 8-membered cycloalkyl, 3- to 8-membered heterocyclyl, 5- to 10-membered heteroaryl, phenyl, naphthyl or G, wherein each of the $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylamino, $C_{1-6}$ haloalkylamino, 3- to 8-membered cycloalkyl, 3- to 8-membered heterocyclyl, 5- to 10-membered heteroaryl is independently and optionally substituted with 1, 2, 3, 4 or 5 substituents selected from OH, oxo (=O), $NH_2$, $NO_2$, CN or G;

G is substituted $C_{1-6}$ aliphatic hydrocarbon, wherein each of the methylenes of the $C_{1-6}$ aliphatic hydrocarbon is optionally and independently substituted with J;

J is —NH—, —S—, —O—, —C(=O)—, —C(=O)NH—, —SO—, —SO$_2$—, —NHC(=O)—, —C(=O)O—, —SO$_2$NH— or —NHC(=O)NH—;

m is 0, 1, 2 or 3; and n is 0, 1, 2, 3 or 4;

with the proviso that:

1. when T is F, Cl, Br or $CF_3$, $R^1$ is OH;

2. when T is H,

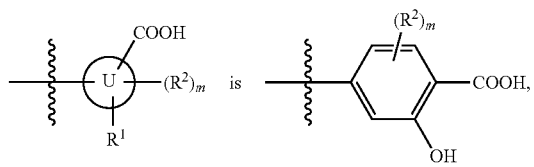

and Q is not phene 3. when T is $NO_2$, $R^1$ is not H.

In some embodiments, a compound having Formula (I) provided herein is a compound having Formula (II) or a stereoisomer, a geometric isomer, a tautomer, an N-oxide, a hydrate, a solvate, a metabolite, an ester, a pharmaceutically acceptable salt and a prodrug thereof,

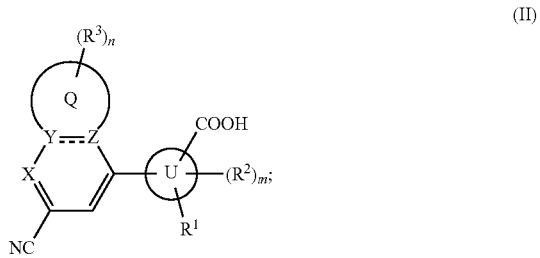

wherein Q, U, X, Y, Z, $R^1$, each $R^2$, each $R^3$, m and n are as defined herein.

In some embodiments, U is phenyl, pyridinyl, pyrimidinyl, pyrazinyl, pyridazinyl, 1,3,5-triazinyl, pyrrolyl, furanyl, thiazolyl, thienyl, oxazolyl or isoxazolyl.

In other embodiments, U is phenyl,

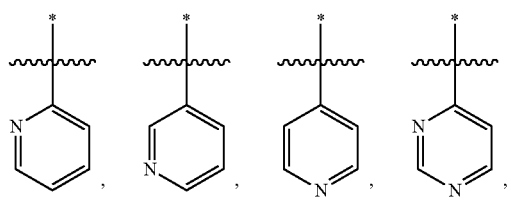

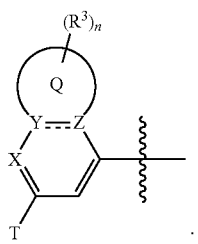

wherein "*" refers to the position of the ring attached to

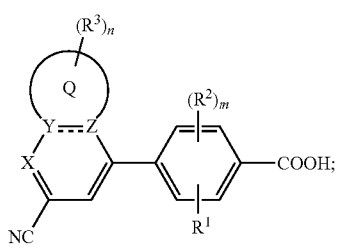

In some embodiments, a compound having Formula (I) provided herein is a compound having Formula (III) or a stereoisomer, a geometric isomer, a tautomer, an N-oxide, a hydrate, a solvate, a metabolite, an ester, a pharmaceutically acceptable salt and a prodrug thereof, (III)

wherein Q, X, Y, Z, $R^1$, each $R^2$, each $R^3$, m and n are as defined herein.

In some embodiments, each $R^1$ and $R^2$ is independently H, D, halogen, OH, $NH_2$, $NO_2$, CN, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ haloalkoxy, $C_{1-4}$ alkylamino, $C_{1-4}$ haloalkylamino, 3- to 6-membered cycloalkyl or 3- to 6-membered heterocyclyl, wherein each of the $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ haloalkoxy, $C_{1-4}$ alkylamino, $C_{1-4}$ haloalkylamino, 3- to 6-membered cycloalkyl or 3- to 6-membered heterocyclyl is independently and optionally substituted with 1, 2 or 3 substituents selected from OH, oxo (=O), $NH_2$, $NO_2$ or CN.

In other embodiments, each $R^1$ and $R^2$ is independently H, D, halogen, OH, $NH_2$, $NO_2$, CN, methyl, ethyl, i-propyl, butyl, hydroxymethyl, hydroxyethyl, aminomethyl, difluoromethyl, trifluoromethyl, methoxy, ethoxy, i-propoxy, t-butoxy, n-butoxy, methylamino, ethylamino, difluoromethoxy, trifluoromethoxy, acetyl, acetoxy, acetylamino, cyclopropyl, cyclobutyl, cyclopentyl, cyclohexyl, oxiranyl, pyrrolidinyl or tetrahydrofuranyl.

In some embodiments, each $R^3$ is independently H, D, halogen, oxo (=O), OH, $NH_2$, $NO_2$, CN, methyl, ethyl, i-propyl, difluoromethyl, trifluoromethyl, methoxy, ethoxy, i-propoxy, difluoromethoxy, trifluoromethoxy, formyl, carboxy, formamido, acetyl, carbamoyl, propylsulfonamido, cyclopropyl, cyclobutyl, imidazolyl, pyrazolyl, thiazolyl, oxazolyl, pyridyl, pyrimidinyl, quinolyl, indolyl, phenyl or naphthyl.

In some embodiments, each $R^4$ is H, D, halogen, methyl, ethyl, i-propyl, t-butyl, n-butyl, difluoromethyl, trifluoromethyl, methoxy, ethoxy, t-butoxy, methylamino, difluoromethoxy or trifluoromethoxy.

In some embodiments,

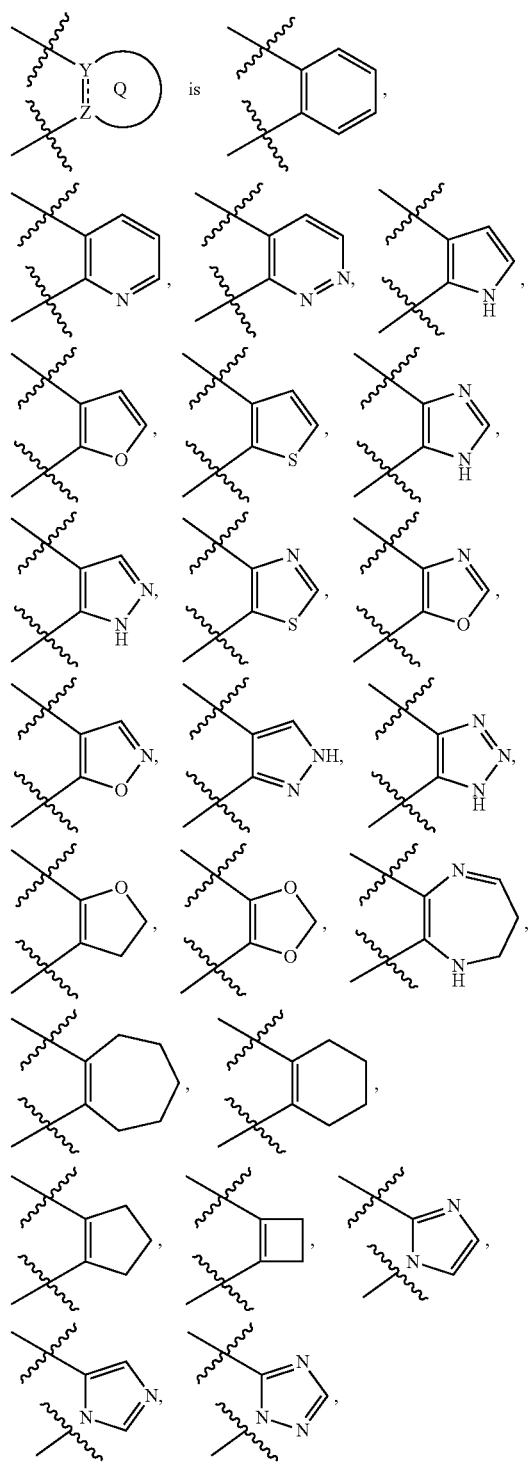

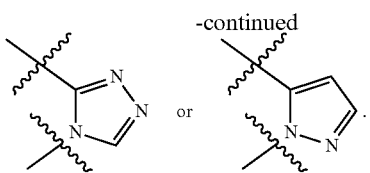

In some embodiments,

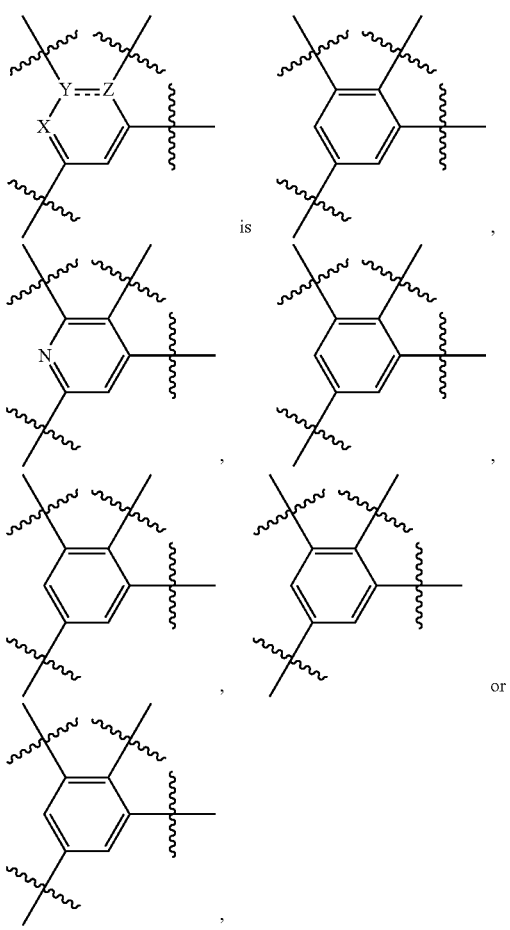

wherein *[1] refers to the position attached to the U ring.

In other aspect, provided herein is a pharmaceutical composition comprising the compound disclosed herein.

In some embodiments, provided herein is a pharmaceutical composition further comprising a pharmaceutically acceptable excipient, carrier, adjuvant, solvent or a combination thereof.

In other embodiments, provided herein is a pharmaceutical composition further comprising a drug for the preventing or treating hyperuricemia, tophi, gouty arthritis, kidney disorders associated with hyperuricemia or urolithiasis, wherein the active constituent of the drug is different from the compound of the present invention, and the drug comprises colchicine, a nonsteroidal anti-inflammatory drug, a glucocorticoid, an anti-uric acid drug, a uricosuric drug, a urinary alkalizing agent or a combination thereof.

In other aspect, provided herein is use of the compound or the pharmaceutical composition disclosed herein in the manufacture of a medicament for preventing or treating hyperuricemia, tophi, gouty arthritis, kidney disorders associated with hyperuricemia or urolithiasis in a subject.

In other aspect, provided herein is a method for the preventing or treating hyperuricemia, tophi, gouty arthritis, kidney disorders associated with hyperuricemia or urolithiasis in a subject, comprising administering to the subject a therapeutically effective amount of the compound or the pharmaceutical composition disclosed herein.

In other aspect, provided herein is the compound or the pharmaceutical composition disclosed herein for use in the preventing or treating hyperuricemia, tophi, gouty arthritis, kidney disorders associated with hyperuricemia or urolithiasis in a subject.

In other aspect, provided herein is use of the compound or the pharmaceutical composition disclosed herein in the manufacture a medicament for lowering the level of uric acid in blood.

In other aspect, provided herein is a method for lowering the level of uric acid in blood of a subject comprising administering to the subject a therapeutically effective amount of the compound or the pharmaceutical composition disclosed herein.

In other aspect, provided herein is a compound or the pharmaceutical composition disclosed herein for use in lowering the level of uric acid in blood.

In other aspect, provided herein is use of the compound or the pharmaceutical composition disclosed herein in the manufacture a medicament for inhibiting both xanthine oxidase and urate anion transporter 1.

In other aspect, provided herein is a method for inhibiting xanthine oxidase and urate anion transporter 1 in a subject comprising administering to the subject a therapeutically effective amount of the compound or the pharmaceutical composition disclosed herein.

In other aspect, provided herein is the compound or the pharmaceutical composition disclosed herein for use in inhibiting xanthine oxidase and urate anion transporter 1.

In other aspect, provided herein is a method of preparing, separating or purifying the compound of Formula (I).

Biological tests show that the compounds of the present invention can be used as good inhibitors of xanthine oxidase and urate anion transporter 1.

Any embodiment disclosed herein can be combined with other embodiments as long as they are not contradictory to one another, even though the embodiments are described in different aspects of the invention. In addition, any technical feature in one embodiment can be applied to the corresponding technical feature in other embodiments as long as they are not contradictory to one another, even though the embodiments are described in different aspects of the invention.

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry", Thomas Sorrell, University Science Books, Sausalito: 1999, and "March's Advanced Organic Chemistry" by Michael B. Smith and Jerry March, John Wiley & Sons, New York: 2007, the entire contents of which are hereby incorporated by reference.

The grammatical articles "a", "an" and "the", as used herein, are intended to include "at least one" or "one or more" unless otherwise indicated herein or clearly contradicted by the context. Thus, the articles are used herein to refer to one or more than one (i.e. at least one) of the grammatical objects of the article. By way of example, "a component" means one or more components, and thus, possibly, more than one component is contemplated and may be employed or used in an implementation of the described embodiments.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, "patient" refers to a human (including adults and children) or other animal. In some embodiments, "patient" refers to a human.

The term "comprise" is an open expression, it includes the contents disclosed herein, but don't exclude other contents.

"Stereoisomer" refers to compounds which have identical chemical constitution, but differ with regard to the arrangement of the atoms or groups in space. Stereoisomers include enantiomer, diastereomers, conformer (rotamer), geometric (cis/trans) isomer, atropisomer, etc.

"Chiral" refers to molecules which have the property of non-superimposability of the mirror image partner, while the term "achiral" refers to molecules which are superimposable on their mirror image partner.

"Enantiomers" refers to two stereoisomers of a compound which are non-superimposable mirror images of one another.

"Diastereomer" refers to a stereoisomer with two or more centers of chirality and whose molecules are not mirror images of one another. Diastereomers have different physical properties, e.g. melting points, boiling points, spectral properties or biological activities. Mixture of diastereomers may separate under high resolution analytical procedures such as electrophoresis and chromatography such as HPLC.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994.

Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such stereoisomers is called an enantiomeric mixture. A 50:50 mixture of enantiomers is referred to as a racemic mixture or a racemate, which may occur where there has been no stereoselection or stereospecificity in a chemical reaction.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any resulting mixtures of stereoisomers can be separated on the basis of the physicochemical differences of the constituents, into the pure or substantially pure geometric isomers, enantiomers, diastereomers, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., Enantiomers, Racemates and Resolutions (Wiley Interscience, New York, 1981); Principles of Asymmetric Synthesis (2nd Ed. Robert E. Gawley, Jeffrey Aubé, Elsevier, Oxford, UK, 2012); Eliel, E. L. Stereochemistry of Carbon Compounds (McGraw-Hill, N Y, 1962); Wilen, S. H. Tables of Resolving Agents and Optical Resolutions p. 268 (E. L. Eliel, Ed., Univ. of Notre Dame Press, Notre Dame, Ind. 1972); Chiral Separation Techniques: A Practical Approach (Subramanian, G Ed., Wiley-VCH Verlag GmbH & Co. KGaA, Weinheim, Germany, 2007).

As described herein, compounds disclosed herein may optionally be substituted with one or more substituents, such as are illustrated generally below, or as exemplified by particular classes, subclasses, and species of the invention.

In general, the term "substituted" refers to the replacement of one or more hydrogen radicals in a given structure with the radical of a specified substituent. Unless otherwise indicated, an substituted group may have a substituent at each substitutable position of the group. When more than one position in a given structure can be substituted with more than one substituent selected from a specified group, the substituent may be either the same or different at each position.

The term "unsubstituted" refers to the specified group bears no substituents.

The term "optionally substituted with . . . " can be used interchangeably with the term "unsubstituted or substituted with . . . ", i.e., the structure is unsubstituted or substituted with one or more substituents defined herein Substituents of the present invention include, but are not limited to D, F, Cl, Br, I, $N_3$, CN, $NO_2$, OH, SH, $NH_2$, alkyl, haloalkyl, alkenyl, alkynyl, alkoxy, alkylamino, cycloalkyl, heterocyclyl, aryl, heteroaryl, and the like.

Furthermore, what need to be explained is that the phrase "each . . . is independently" and "each of . . . and . . . is independently", unless otherwise stated, should be broadly understood. The specific options expressed by the same symbol are independent of each other in different groups; or the specific options expressed by the same symbol are independent of each other in same groups.

At various places in the present specification, substituents of compounds disclosed herein are disclosed in groups or in ranges. It is specifically indicated that the invention includes each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" or "alkyl group" refers to a saturated linear or branched-chain monovalent hydrocarbon group, wherein the alkyl group is optionally substituted with one or more substituents described herein. Unless otherwise stated, the alkyl group contains 1-20 carbon atoms. In some embodiments, the alkyl group contains 1-12 carbon atoms. In other embodiments, the alkyl group contains 3-12 carbon atoms. In still other embodiments, the alkyl group contains 1-6 carbon atoms. In yet other embodiments, the alkyl group contains 1-4 carbon atoms.

Some non-limiting examples of alkyl groups include, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH($CH_3$)$_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —CH($CH_3$)$CH_2CH_3$), 2-methyl-2-propyl (t-Bu, t-butyl, —C($CH_3$)$_3$), 1-pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2CH_2CH_3$), 3-methyl-2-butyl (—CH($CH_3$)CH($CH_3$)$_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2CH_2CH_2CH_3$), 3-methyl-2-pentyl (—CH($CH_3$)CH($CH_3$)$CH_2CH_3$), 4-methyl-2-pentyl (—CH($CH_3$)$CH_2CH(CH_3)_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2$CH($CH_3$)$_2$), 3,3-dimethyl-2-butyl (—CH($CH_3$)C($CH_3$)$_3$, 1-heptyl, 1-octyl, and the like.

The term "alkylene" refers to a saturated divalent hydrocarbon group derived from a straight or branched chain saturated hydrocarbon by the removal of two hydrogen atoms. Unless otherwise specified, the alkylene group contains 1-12 carbon atoms. In some embodiments, the alkylene group contains 1-6 carbon atoms. In other embodiments, the alkylene group contains 1-4 carbon atoms. In still other embodiments, the alkylene group contains 1-3 carbon atoms. In yet other embodiments, the alkylene group contains 1-2 carbon atoms. And alkylene group is exemplified by methylene (—$CH_2$—), ethylene (—$CH_2CH_2$—), isopropylene (—CH($CH_3$)$CH_2$—), and the like.

The term "alkenyl" refers to linear or branched-chain monovalent hydrocarbon radical with at least one unsaturated carbon-carbon double bond ($sp^2$) site, wherein the alkenyl radical may be optionally substituted independently with one or more substituents described herein, and includes radicals having "cis" and "trans" orientations, or alternatively, "E" and "Z" orientations. In some embodiments, the alkenyl contains 2 to 12 carbon atoms. In other embodiments, the alkenyl contains 3 to 12 carbon atoms. In still other embodiments, the alkenyl contains 2 to 6 carbon atoms. In yet other embodiments, the alkenyl contains 2 to 4 carbon atoms. Examples of alkenyl groups include, but are not limited to, ethylenyl or vinyl (—CH═$CH_2$), allyl (—$CH_2$CH═$CH_2$), and the like.

The term "alkynyl" refers to a linear or branched monovalent hydrocarbon radical of 2 to 12 carbon atoms with at least one site of unsaturation, i.e., a carbon-carbon, sp triple bond, wherein the alkynyl radical may be optionally substituted independently with one or more substituents described herein. In some embodiments, the alkynyl contains 3 to 12 carbon atoms. In other embodiments, the alkynyl contains 2 to 6 carbon atoms. In still other embodiments, the alkynyl contains 2 to 4 carbon atoms. Examples of such groups include, but are not limited to, ethynyl (—C≡CH), propargyl (—$CH_2$C≡CH), 1-propynyl (—C≡C—$CH_3$), and the like.

The term "alkoxy" refers to an alkyl group, as previously defined, attached to the parent molecular moiety via an oxygen atom. Unless otherwise specified, the alkoxy group contains 1-12 carbon atoms. In one embodiment, the alkoxy group contains 1-6 carbon atoms. In other embodiment, the alkoxy group contains 1-4 carbon atoms. In still other embodiment, the alkoxy group contains 1-3 carbon atoms. The alkoxy group may be optionally substituted with one or more substituents disclosed herein.

Some non-limiting examples of the alkoxy group include, but are not limited to, methoxy (MeO, —$OCH_3$), ethoxy (EtO, —$OCH_2CH_3$), 1-propoxy (n-PrO, n-propoxy, —$OCH_2CH_2CH_3$), 2-propoxy (i-PrO, i-propoxy, —OCH($CH_3$)$_2$), 1-butoxy (n-BuO, n-butoxy, —OCH$_2$CH$_2$CH$_2$CH$_3$), 2-methyl-1-propoxy (i-BuO, i-butoxy, —OCH$_2$CH(CH$_3$)$_2$), 2-butoxy (s-BuO, s-butoxy, —OCH(CH$_3$)CH$_2$CH$_3$), 2-methyl-2-propoxy (t-BuO, t-butoxy, —OC(CH$_3$)$_3$), 1-pentoxy (n-pentoxy, —OCH$_2$CH$_2$CH$_2$CH$_2$CH$_3$), 2-pentoxy (—OCH(CH$_3$) CH$_2$CH$_2$CH$_3$), 3-pentoxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH (CH$_3$)CH$_2$CH$_3$), and the like.

The term "alkylamino" embraces "N-alkylamino" and "N,N-dialkylamino" where amino groups are independently substituted with one alkyl radical or with two alkyl radicals, respectively, and wherein the alkyl group is as defined herein. In some embodiments, the alkylamino group is a lower alkylamino group having one or two alkyl groups of 1 to 6 carbon atoms attached to nitrogen atom. In other embodiments, the alkylamino group is an alkylamino group having one or two lower alkyl groups of 1 to 4 carbon atoms attached to nitrogen atom. Some non-limiting examples of suitable alkylamino radical include mono or dialkylamino. Some examples include, but are not limited to, N-methylamino, N-ethylamino, N,N-dimethylamino and N,N-diethylamino, and the like.

The term "haloalkyl", "haloalkoxy" or "halogenated alkylamino" respectively refers to an alkyl, alkoxy or alkylamino group, as the case may be, substituted with one or more halogen atoms, and wherein each of the alkyl, alkoxy or alkylamino group is defined as described herein. Examples of such groups include, but are not limited to, trifluoromethyl, 2,2,3,3-tetrafluoropropyl, difluoromethoxy, trifluoromethoxy, trifluoromethylamino, and the like.

The term "cycloalkyl" refers to a monovalent or multivalent saturated ring having 3 to 12 carbon atoms as a monocyclic, bicyclic, or tricyclic hydrocarbon system. In some embodiments, the cycloalkyl group contains 7 to 12 carbon atoms. In other embodiments, the cycloalkyl group contains 3 to 8 carbon atoms. In still other embodiments, the cycloalkyl group contains 3 to 6 carbon atoms. The cycloalkyl group may be optionally substituted with one or more substituents disclosed herein.

The term "carbocyclyl" refers to a monovalent or multivalent, nonaromatic, saturated or partially unsaturated ring having 3 to 12 carbon atoms as a monocyclic, bicyclic or tricyclic hydrocarbon system. A carbobicyclyl group includes a spiro carbobicyclyl group or a fused carbobicyclyl group. Suitable carbocyclyl groups include, but are not limited to, cycloalkyl, cycloalkenyl and cycloalkynyl. In some embodiments, the carbocyclyl group contains 3 to 8 carbon atoms. In other embodiments, the carbocyclyl group contains 3 to 6 carbon atoms. Further examples of carbocyclyl groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. The carbocyclyl group may be optionally substituted with one or more substituents disclosed herein.

The term "carbocycle" or "carbocyclic ring" refers to a nonaromatic, saturated or partially unsaturated ring having 3 to 12 carbon atoms as a monocyclic, bicyclic or tricyclic hydrocarbon system. Suitable carbocycle or carbocyclic ring include, but are not limited to, cycloparaffin, cycloolefin and cycloalkyne. In some embodiments, the carbocycle or carbocyclic ring contains 3 to 8 carbon atoms. In other embodiments, the carbocycle or carbocyclic ring contains 3 to 6 carbon atoms. Further examples of carbocycle or carbocyclic ring include cyclopropane, cyclobutane, cyclopentane, cyclopentene, cyclohexane, cyclohexene, cyclohexadiene, cycloheptane, cyclooctane, cyclononane, cyclodecane, cycloundecane, cyclododecane, and the like. The carbocycle or carbocyclic ring may be optionally substituted with one or more substituents disclosed herein.

The term "heterocyclyl" refers to a monovalent or multivalent, saturated or partially unsaturated monocyclic, bicyclic or tricyclic ring containing 3 to 12 ring atoms of which at least one ring atom is selected from nitrogen, sulfur or oxygen. Unless otherwise specified, the heterocyclyl group may be carbon or nitrogen linked, and a —CH$_2$— group can be optionally replaced by a —C(=O)— group. In which, the sulfur can be optionally oxygenized to S-oxide, and the nitrogen can be optionally oxygenized to N-oxide. Some non-limiting examples of the heterocyclyl group include oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, diazepanyl, oxepanyl, thiepanyl, oxazepinyl, diazepinyl, thiazepinyl, and 2-oxa-5-azabicyclo[2.2.1]hept-5-yl. Some non-limiting examples of heterocyclyl wherein —CH$_2$— group is replaced by —C(=O)— moiety include 2-oxopyrrolidinyl, oxo-1,3-thiazolidinyl, 2-piperidinonyl, 3,5-dioxopiperidinyl and pyrimidinedionyl. Some non-limited examples of heterocyclyl wherein the ring sulfur atom is oxidized is sulfolanyl, 1,1-dioxo-thiomorpholinyl. The heterocyclyl group may be optionally substituted with one or more substituents disclosed herein.

The term "heterocycle", or "heterocyclic ring" refers to a saturated or partially unsaturated monocyclic, bicyclic or tricyclic ring containing 3 to 12 ring atoms of which at least one ring atom is selected from nitrogen, sulfur or oxygen. Unless otherwise specified, a —CH$_2$— group of the heterocycle or heterocyclic ring can be optionally replaced by a —C(=O)— group. In which, the sulfur can be optionally oxygenized to S-oxide, and the nitrogen can be optionally oxygenized to N-oxide. Some non-limiting examples of the heterocycle or heterocyclic ring include oxirane, azetidine, oxetane, thiacyclobutane, pyrrolidine, pyrroline, pyrazoline, pyrazolidine, imidazoline, imidazolidine, tetrahydrofuran, dihydrofuran, thiophane, dihydrothiophene, 1,3-dioxolane, dithiolane, tetrahydropyrane, dihydropyrane, 2H-pyrane, 4H-pyrane, tetrahydrothiopyran, piperidine, morpholine, thiomorpholine, piperazine, dioxane, dithiane, thioxane, homopiperazine, homopiperidine, diazepane, oxepane, thiacycloheptane, oxazepine, diazepine, thiazepine, and 2-oxa-5-azabicyclo[2.2.1]heptane. Some non-limited examples of heterocycle or heterocyclic ring wherein —CH$_2$— group is replaced by —C(=O)— moiety include pyrrolidone, thiazolidone, piperidone, 3,5-dioxopiperidine and pyrimidinedione. Some non-limited examples of heterocycle or heterocyclic ring wherein the ring sulfur atom is oxidized is sulfolane, 1,1-dioxo-thiomorpholine. The heterocycle or heterocyclic ring may be optionally substituted with one or more substituents disclosed herein.

The term "r-membered", where r is an integer typically describes the number of ring-forming atoms in a moiety where the number of ring-forming atoms is r. For example, piperidinyl is an example of a 6 membered heterocycloalkyl, and decalinyl is an example of a 10 membered cycloalkyl group.

The term "unsaturated" refers to a moiety having one or more units of unsaturation.

The term "heteroatom" refers to one or more of oxygen, sulfur, nitrogen, phosphorus and silicon, including any oxidized form of nitrogen, sulfur, or phosphorus; the quaternized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "halogen" refers to fluorine (F), chlorine (Cl), bromine (Br) or iodine (I).

The term "cyano" or "CN" refers to a cyano structure. Such group can be connected with other groups.

The term "nitro" or "NO$_2$" refers to a nitro structure. Such group can be connected with other groups.

The term "aryl" refers to monovalent or multivalent monocyclic, bicyclic and tricyclic carbocyclic ring systems having a total of six to fourteen ring members, or six to twelve ring members, or six to ten ring members, wherein at least one ring in the system is aromatic, and that has a single point or multipoint of attachment to the rest of the molecule. In one embodiment, the aryl group is a monovalent or multivalent carbocyclic ring system having six to ten ring members, wherein at least one ring in the system is aromatic. Examples of aryl ring may include phenyl, naphthyl and anthryl. The aryl group may be optionally and independently substituted with one or more substituents disclosed herein.

The term "aromatic ring" refers to monocyclic, bicyclic and tricyclic carbocyclic ring systems having a total of six to fourteen ring members, or six to twelve ring members, or six to ten ring members, wherein at least one ring in the system is aromatic. In one embodiment, the aryl group is a carbocyclic ring system having six to ten ring members, wherein at least one ring in the system is aromatic. Examples of aromatic ring may include phene, naphthalene and anthracene. The aromatic ring may be optionally and independently substituted with one or more substituents disclosed herein.

The term "heteroaryl" refers to monovalent or multivalent monocyclic, bicyclic and tricyclic carbocyclic ring systems having a total of five to twelve ring members, or five to ten ring members, or five to six ring members, wherein at least one ring in the system is aromatic, and in which at least one ring atom is selected from heteroatom, and that has a single point or multipoint of attachment to the rest of the molecule. The heteroaryl group is optionally substituted with one or more substituents disclosed herein. In one embodiment, the heteroaryl group is a 5 to 12 membered heteroaryl comprising 1, 2, 3 or 4 heteroatoms independently selected from O, S and N. In other embodiment, the heteroaryl group is a 5 to 6 membered heteroaryl comprising 1, 2, 3 or 4 heteroatoms independently selected from O, S and N.

Some non-limiting examples of heteroaryl include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, oxadiazolyl (e.g. 1,2,3-oxadiazolyl, 1,2,5-oxadiazolyl, 1,2,4-oxadiazolyl), oxatriazolyl (e.g., 1,2,3,4-oxatriazolyl), 2-thiazolyl, 4-thiazolyl, 5-thiazolyl, isothiazolyl, 2-thiadiazolyl (e.g. 1,3,4-thiadiazolyl, 1,2,3-thiadiazolyl, 1,2,5-thiadiazolyl), thiatriazolyl (e.g., 1,2,3,4-thiazoltriazolyl), tetrazolyl (e.g., 2H-1,2,3,4-tetrazolyl, 1H-1,2,3,4-tetrazolyl), triazolyl (e.g., 2H-1,2,3-triazolyl, 1H-1,2,4-triazolyl, 4H-1,2,4-triazolyl), 2-thienyl, 3-thienyl, 1H-pyrazolyl (e.g., 1H-pyrazol-3-yl, 1H-pyrazol-4-yl, 1H-pyrazol-5-yl), N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl, 4-pyridazinyl), 2-pyrazinyl, triazinyl (e.g., 1,3,5-triazine), tetrazinyl (e.g., 1,2,4,5-tetrazinyl, 1,2,3,5-tetrazinyl); and the following bicycles: benzimidazolyl, benzofuryl, benzothiophenyl, indolyl (e.g., 2-indolyl), purinyl, quinolyl (e.g., 2-quinolyl, 3-quinolyl, 4-quinolyl), isoquinolyl (e.g., 1-isoquinolyl, 3-isoquinolyl or 4-isoquinolyl), imidazo[1,2-a]pyridyl, pyrazolo[1,5-a]pyridyl, pyrazolo[1,5-a]pyrimidyl, imidazo[1,2-b]pyridazinyl, [1,2,4]triazolo[4,3-b]pyridazinyl, [1,2,4]triazolo[1,5-a]pyrimidinyl, or [1,2,4]triazolo[1,5-a]pyridyl, and the like.

The term "heteroaromatic ring" or "heteroaromatic compound" refers to monocyclic, bicyclic and tricyclic carbocyclic ring systems having a total of five to twelve ring members, or five to ten ring members, or five to six ring members, wherein at least one ring in the system is aromatic, and in which at least one ring atom is selected from heteroatom. The heteroaromatic ring or heteroaromatic compound is optionally substituted with one or more substituents disclosed herein. In one embodiment, the heteroaromatic ring or heteroaromatic compound is a 5 to 12 membered heteroaryl comprising 1, 2, 3 or 4 heteroatoms independently selected from O, S and N. In other embodiment, the heteroaromatic ring or heteroaromatic compound is a 5 to 6 membered heteroaryl comprising 1, 2, 3 or 4 heteroatoms independently selected from O, S and N.

Some non-limiting examples of heteroaromatic ring or heteroaromatic compound include furan, imidazole, isoxazole, oxazole, oxadiazole, oxatriazole, thiazole, isothiazole, thiadiazole, thiatriazole, tetrazole, triazole, thiophene, 1H-pyrazole, pyrrole, pyridine, pyrimidine, pyridazine, pyrazine, triazine, tetrazine; and the following bicyclo: benzimidazole, benzofuran, benzothiophene, indole, purine, quinoline, isoquinoline, imidazo[1,2-a]pyridine, pyrazolo[1,5-a]pyridine, pyrazolo[1,5-a]pyrimidine, imidazo[1,2-b]pyridazine, [1,2,4]triazolo[4,3-b]pyridazine, [1,2,4]triazolo[1,5-a]pyrimidine, or [1,2,4]triazolo[1,5-a]pyridine, and the like.

The terms "carboxy" or "carboxyl", whether used alone or with other terms, such as "carboxy", refers to —CO$_2$H. The term "carbonyl", whether used alone or with other terms, such as "aminocarbonyl" or "acyloxy", denotes —(C=O)—.

As described herein, a bond drawn from a substituent to the center of one ring within a ring system (as shown in Formula b) represents substitution of the substituent at any substitutable or reasonable position on the ring. For example, Formula b represents mono- or poly-substitutions of the substituent R at any substitutable or reasonable position on the ring C, as shown in Formula c1~Formula c19.

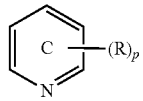

Formula b

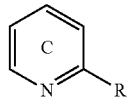

Formula c1

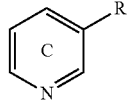

Formula c2

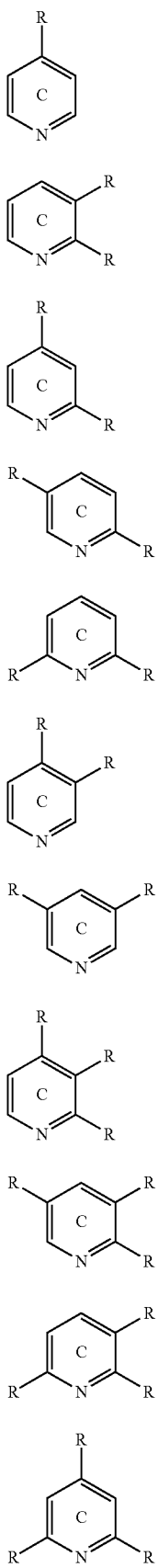
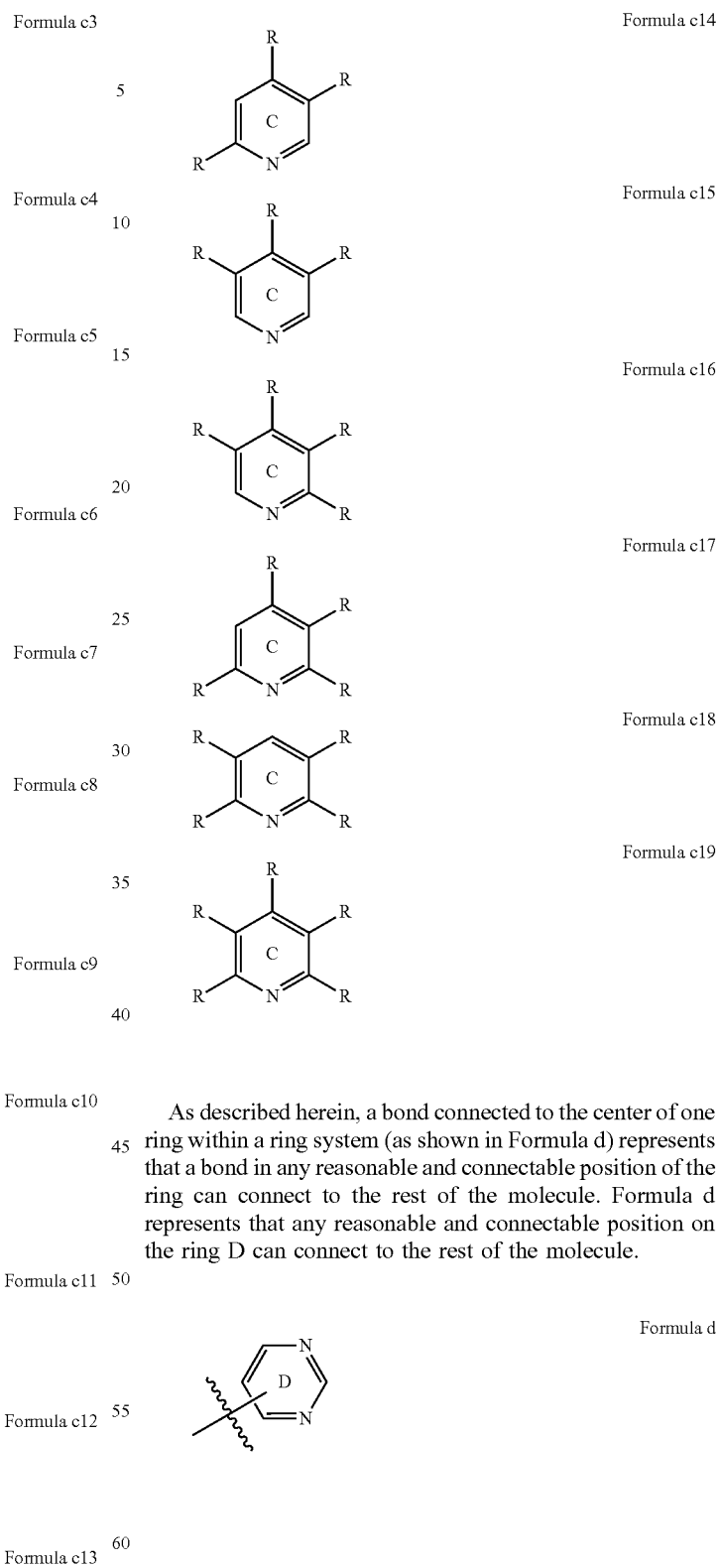

As described herein, a bond connected to the center of one ring within a ring system (as shown in Formula d) represents that a bond in any reasonable and connectable position of the ring can connect to the rest of the molecule. Formula d represents that any reasonable and connectable position on the ring D can connect to the rest of the molecule.

As described herein, a bond drawn from a substituent R to the center of one ring within a ring system represents substitution of the substituent R at any substitutable position on the ring. For example, Formula e represents the B ring may be substituted at any substitutable position by the substituent R, as shown in Formula f, g, h and i.

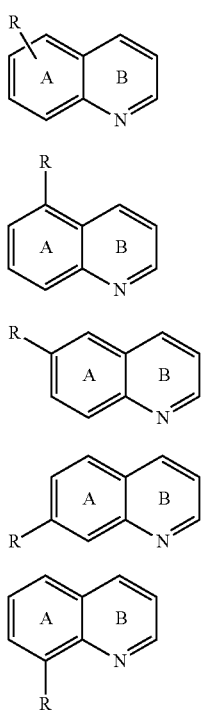

Formula e

Formula f

Formula g

Formula h

Formula i

The term "protecting group" or "PG" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl)ethyl, 2-(trimethylsilyl) ethoxy-methyl, 2-(p-toluenesulfonyl)-ethyl, 2-(p-nitrophenylsulfenyl)-ethyl, 2-(diphenylphosphino)-ethyl, nitroethyl and the like. For a general description of protecting groups and their use, see T. W. Greene, Protective Groups in Organic Synthesis, John Wiley & Sons, New York, 1991; and P. J. Kocienski, Protecting Groups, Thieme, Stuttgart, 2005.

The term "prodrug" refers to a compound that is transformed in vivo into a compound of Formula (I). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic (C$_1$-C$_{24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al., Prodrugs: Design and Clinical Applications, Nature Review Drug Discovery, 2008, 7, 255-270, and S. J. Hecker et al., Prodrugs of Phosphates and Phosphonates, Journal of Medicinal Chemistry, 2008, 51, 2328-2345.

A "metabolite" is a product produced through metabolism in the body of a specified compound or salt thereof. The metabolites of a compound may be identified using routine techniques known in the art and their activities can be determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

A "pharmaceutically acceptable salts" refers to organic or inorganic salts of a compound disclosed herein. Pharmaceutically acceptable salts are well known in the art. For example, S. M. Berge et al., describe pharmaceutically acceptable salts in detail in J. Pharmaceutical Sciences, 1977, 66: 1-19, which is incorporated herein by reference. Some non-limiting examples of pharmaceutically acceptable and nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate, and the like. Salts derived from appropriate bases include alkali metal, alkaline earth metal, ammonium and N$^+$(C$_{1-4}$ alkyl)$_4$ salts. This invention also envisions the quaternization of any basic nitrogen-containing groups of the compounds disclosed herein. Water or oil soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, C$_{1-8}$ sulfonate or aryl sulfonate.

The term "solvate" refers to an association or complex of one or more solvent molecules and a compound disclosed herein. Examples of solvents that form solvates include, but are not limited to, water, isopropanol, ethanol, methanol, DMSO, ethyl acetate, acetic acid and ethanolamine. The term "hydrate" refers to the complex where the solvent molecule is water.

The term "hydrate" can be used when said solvent is water. In one embodiment, one solvent molecule is associated with one molecule of the compounds disclosed herein, such as a hydrate. In another embodiment, more than one solvent molecule may be associated with one molecule of the compounds disclosed herein, such as a dihydrate. In still another embodiment, less than one solvent molecule may be associated with one molecule of the compounds disclosed herein, such as a hemihydrate. Furthermore, all the solvates of the invention retain the biological effectiveness of the non-hydrate form of the compounds disclosed herein.

As used herein, the term "treat", "treating" or "treatment" of any disease or disorder refers to all processes wherein there may be a slowing, interrupting, arresting, controlling, or stopping of the progression of the disease or disorder, but does not necessarily indicate a total elimination of all the disorder symptoms, as well as the prophylactic therapy of the mentioned conditions, particularly in a patient who is predisposed to such disease or disorder. In some embodiments, "treat", "treating" or "treatment" refers to ameliorating the disease or disorder (i.e., slowing or arresting or reducing the development of the disease or at least one of the clinical symptoms thereof). In other embodiments, "treat", "treating" or "treatment" refers to alleviating or ameliorating at least one physical parameter including those which may not be discernible by the patient. In other embodiments, "treat", "treating" or "treatment" refers to modulating the disease or disorder, either physically, (e.g., stabilization of a discernible symptom), physiologically, (e.g., stabilization of a physical parameter), or both. In other embodiment, "treat", "treating" or "treatment" refers to preventing or delaying the onset or development or progression of the disease or disorder.

As used herein, the term "therapeutically effective amount" or "therapeutically effective dosage" refers to the amount of the compound of the invention which is capable of eliciting biological or medical response (Such as reducing or inhibiting the activity of an enzyme or protein, or ameliorating symptoms, alleviating symptoms, slowing or delaying the development of the disease, or preventing diseases, etc.) of an individual. In one non-limiting embodiment, the term "therapeutically effective amount" refers to, when the compound of the present invention is administered to a subject, an effective amount in the following situations: (1) at least partially alleviating, inhibiting, preventing and/or ameliorating the disease or disorder (i) mediated by xanthine oxidase or urate anion transporter 1 (URAT1), or (ii) associated with anthine oxidase or urate anion transporter 1 activity, or (iii) characterized by abnormal activity of xanthine oxidase or urate anion transporter 1; or (2) reducing or inhibiting the activity of xanthine oxidase or urate anion transporter; or (3) reducing or inhibiting the expression of xanthine oxidase or urate anion transporter 1. In other embodiment, the term "therapeutically effective amount" refers to, when administering to the cell, or organ, or non-cellular biological material, or medium, an effective amount of the compounds of the present invention, which can at least partially reduce or inhibit xanthine oxidase or urate anion transporter 1 activity; or at least partially reduce or inhibit the expression of anthine oxidase and urate anion transporter 1.

As used herein, the terms "administration of" and "administering a" compound should be understood to mean providing a compound of the invention or a prodrug of a compound of the invention to an individual in need thereof. It is recognized that one skilled in the art can treat a patient presently afflicted with high uric acid, or by prophylactically treat a patient afflicted with the disorders with an effective amount of the compound of the present invention.

The term "composition" as used herein is intended to encompass a product comprising the specified ingredients in the specified amounts, as well as any product which results, directly or indirectly, from combinations of the specified ingredients in the specified amounts. Such term in relation to pharmaceutical composition, is intended to encompass a product comprising the active ingredient(s) and the inert ingredient(s) that make up the carrier, as well as any product which results, directly or indirectly, from a combination, complexation or aggregation of any two or more of the ingredients, or from the dissociation of one or more of the ingredients, or from the other types of reactions or interactions of one or more of the ingredients. Accordingly, the pharmaceutical compositions of the present invention encompass any composition made by mixing a compound of the present invention and a pharmaceutically acceptable carrier.

DESCRIPTION OF COMPOUNDS OF THE INVENTION

The present invention provides a class of carboxy-substituted (hetero) aromatic derivatives, pharmaceutically acceptable salts, pharmaceutical formulations and compositions thereof, which can be used as xanthine oxidase and urate anion transporter 1 inhibitors, and their potential use in treatment of symptoms or diseases related to high uric acid in human blood, such as hyperuricemia, tophi, gouty arthritis, kidney disorders related to hyperuricemia and urolithiasis.

In one aspect, provided herein is a compound having Formula (I) or a stereoisomer, an N-oxide, a solvate, a metabolite, a pharmaceutically acceptable salt or a prodrug thereof,

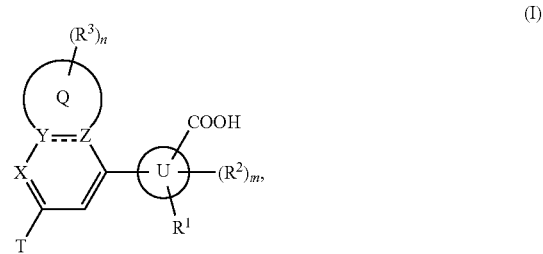

wherein Q, U, T, X, Y, Z, $R^1$, each $R^2$, each $R^3$, m and n are as defined herein.

In some embodiments, U is phenyl or 5- to 6-membered heteroaryl.

In some embodiments, each $R^1$ and $R^2$ is independently H, D, halogen, OH, $NH_2$, $NO_2$, CN, $C_{1-6}$ alkyl, $C_{2-6}$ alkenyl, $C_{2-6}$ alkynyl, $C_{1-6}$ haloalkyl, Cis alkoxy, $C_{1-6}$ haloalkoxy, $C_{1-6}$ alkylamino, $C_{1-6}$ haloalkylamino, 3- to 8-membered cycloalkyl or 3- to 8-membered heterocyclyl, wherein each of the $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylamino, $C_{1-6}$ haloalkylamino, 3- to 8-membered cycloalkyl and 3- to 8-membered heterocyclyl is independently and optionally substituted with 1, 2, 3, 4 or 5 substituents selected from OH, oxo (=O), $NH_2$, $NO_2$ or CN.

In some embodiments, T is H, D, F, Cl, Br, $NO_2$, CN or $CF_3$.

In some embodiments, X is $CR^4$ or N; and
wherein $R^4$ is as defined herein.

In some embodiments, R[4] is H, D, halogen, $C_{1-6}$ alkyl, $C_{1-6}$ haloalkyl, $C_{1-6}$ alkoxy, $C_{1-6}$ alkylamino or $C_{1-6}$ haloalkoxy.

In some embodiments, each of Y and Z is independently C, CH or N.

In some embodiments, " " is a single bond or a double bond.

In some embodiments, Q is phene, $C_{4-7}$ carbocycle, 4- to 7-membered heterocycle or 5- to 6-membered heteroaromatic ring.

In some embodiments, each R[3] is independently H, D, halogen, oxo (=O), OH, $NH_2$, $NO_2$, CN, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylamino, $C_{1-6}$ haloalkylamino, 3- to 8-membered cycloalkyl, 3- to 8-membered heterocyclyl, 5- to 10-membered heteroaryl, phenyl, naphthyl or G, wherein each of the $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylamino, $C_{1-6}$ haloalkylamino, 3- to 8-membered cycloalkyl, 3- to 8-membered heterocyclyl, 5- to 10-membered heteroaryl is independently and optionally substituted with 1, 2, 3, 4 or 5 substituents selected from OH, oxo (=O), $NH_2$, $NO_2$, CN or G; and wherein G is as defined herein.

In some embodiments, G is substituted $C_{1-6}$ aliphatic hydrocarbon, wherein each of the methylene groups of the $C_{1-6}$ aliphatic hydrocarbon is optionally and independently substituted with J; and wherein J is as defined herein.

In some embodiments, J is —NH—, —S—, —O—, —C(=O)—, —C(=O)NH—, —SO—, —SO$_2$—, —NHC(=O)—, —C(=O)O—, —SO$_2$NH— or —NHC(=O)NH—.

In some embodiments, m is 0, 1, 2 or 3.

In some embodiments, n is 0, 1, 2, 3 or 4.

In some embodiments, provided herein is a compound with the proviso that:

when T is F, Cl, Br or $CF_3$, R[1] is OH.

In some embodiments, provided herein is a compound with the proviso that:

when T is H,

In some embodiments, provided herein is a compound with the proviso that:

when T is $NO_2$, IV is not H, in other words, IV is D, halogen, OH, $NH_2$, $NO_2$, CN, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylamino, $C_{1-6}$ haloalkylamino, 3- to 8-membered cycloalkyl or 3- to 8-membered heterocyclyl, wherein each of the $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylamino, $C_{1-6}$ haloalkylamino, 3- to 8-membered cycloalkyl and 3- to 8-membered heterocyclyl is independently and optionally substituted with 1, 2, 3, 4 or 5 substituents selected from OH, oxo (=O), $NH_2$, $NO_2$ or CN.

In some embodiments, a compound having Formula (I) provided herein is a compound of Formula (II) or a stereoisomer, a geometric isomer, a tautomer, an N-oxide, a hydrate, a solvate, a metabolite, an ester, a pharmaceutically acceptable salt and a prodrug thereof,

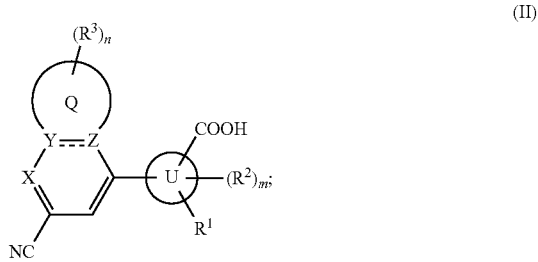

(II)

wherein Q, U, X, Y, Z, R[1], each R[2], each R[3], m and n is are as defined herein.

In some embodiments, U is phenyl, pyridinyl, pyrimidinyl, pyrazinyl, pyridazinyl, 1,3,5-triazinyl, pyrrolyl, furanyl, thiazolyl, thienyl, oxazolyl or isoxazolyl.

In other embodiments, U is phenyl,

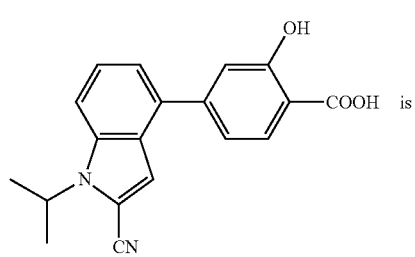

2

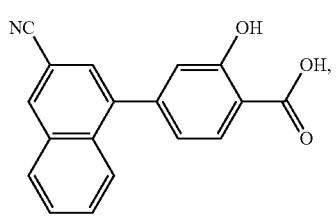

4

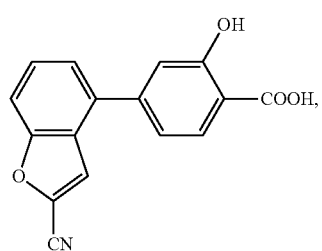

3

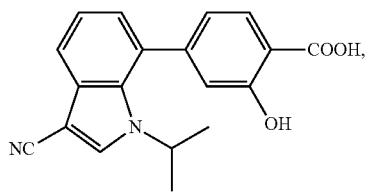

5

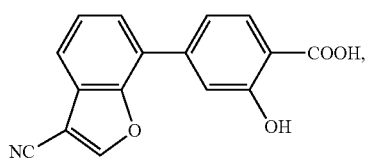

6 and Q is not phene, in other words, Q is $C_{4-7}$ carbocycle, 4- to 7-membered heterocycle or 5- to 6-membered heteroaromatic ring.

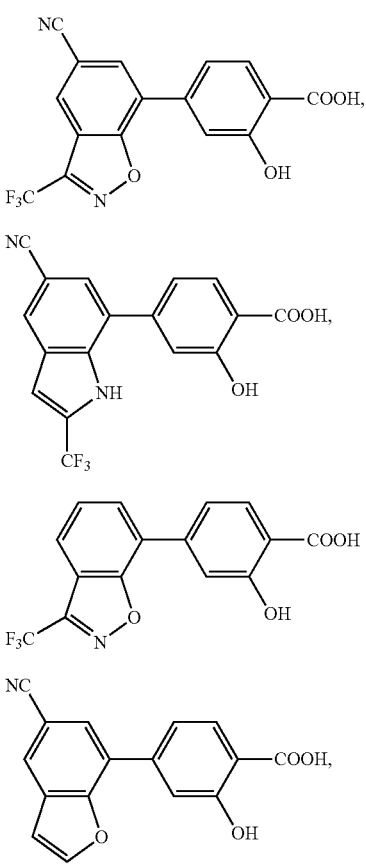

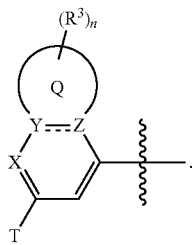

wherein "*" refers to the position of the U ring attached to

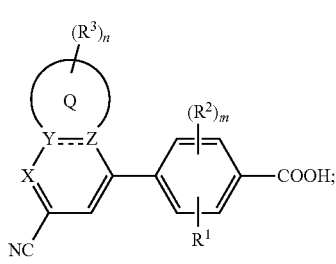

In some embodiments, a compound having Formula (I) provided herein is a compound of Formula (III) or a stereoisomer, a geometric isomer, a tautomer, an N-oxide, a hydrate, a solvate, a metabolite, an ester, a pharmaceutically acceptable salt and a prodrug thereof,

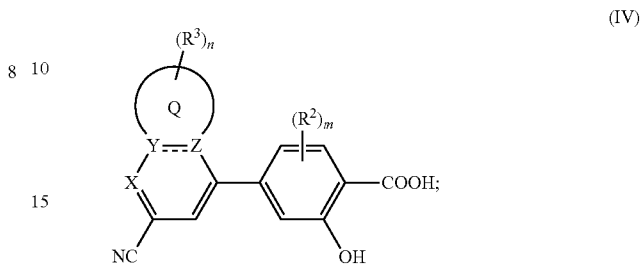

wherein Q, X, Y, Z, $R^1$, each $R^2$, each $R^3$, m and n is are as defined herein.

In some embodiments, a compound having Formula (I) provided herein is a compound of Formula (IV) or a stereoisomer, a geometric isomer, a tautomer, an N-oxide, a hydrate, a solvate, a metabolite, an ester, a pharmaceutically acceptable salt and a prodrug thereof, (IV)

wherein Q, X, Y, Z, each $R^2$, each $R^3$, m and n are as defined herein.

In some embodiments, each $R^1$ and $R^2$ is independently H, D, halogen, OH, $NH_2$, $NO_2$, CN, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ haloalkoxy, $C_{1-4}$ alkylamino, $C_{1-4}$ haloalkylamino, 3- to 6-membered cycloalkyl or 3- to 6-membered heterocyclyl, wherein each of the $C_{1-4}$ alkyl, $C_{2-4}$ alkenyl, $C_{2-4}$ alkynyl, haloalkyl, $C_{1-4}$ alkoxy, $C_{1-4}$ haloalkoxy, $C_{1-4}$ alkylamino, $C_{1-4}$ haloalkylamino, 3- to 6-membered cycloalkyl or 3- to 6-membered heterocyclyl is independently and optionally substituted with 1, 2 or 3 substituents selected from OH, oxo (=O), $NH_2$, $NO_2$ or CN.

In other embodiments, each $R^1$ and $R^2$ is independently H, D, halogen, OH, $NH_2$, $NO_2$, CN, methyl, ethyl, i-propyl, butyl, hydroxymethyl, hydroxyethyl, aminomethyl, difluoromethyl, trifluoromethyl, methoxy, ethoxy, i-propoxy, t-butoxy, n-butoxy, methylamino, ethylamino, difluoromethoxy, trifluoromethoxy, acetyl, acetoxy, acetylamino, cyclopropyl, cyclobutyl, cyclopentyl, cyclohexyl, oxiranyl, pyrrolidinyl or tetrahydrofuranyl.

In some embodiments, each $R^3$ is independently H, D, halogen, oxo (=O), OH, $NH_2$, $NO_2$, CN, methyl, ethyl, i-propyl, difluoromethyl, trifluoromethyl, methoxy, ethoxy, i-propoxy, difluoromethoxy, trifluoromethoxy, formyl, carboxy, formamido, acetyl, carbamoyl, propylsulfonamido, cyclopropyl, cyclobutyl, imidazolyl, pyrazolyl, thiazolyl, oxazolyl, pyridyl, pyrimidinyl, quinolyl, indolyl, phenyl or naphthyl.

In some embodiments, each $R^4$ is H, D, halogen, methyl, ethyl, i-propyl, t-butyl, n-butyl, difluoromethyl, trifluoromethyl, methoxy, ethoxy, t-butoxy, methylamino, difluoromethoxy or trifluoromethoxy.

In some embodiments,

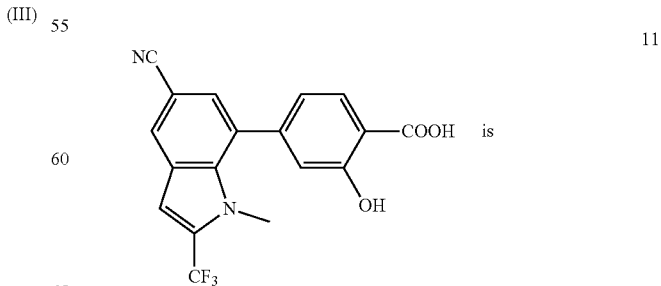

is

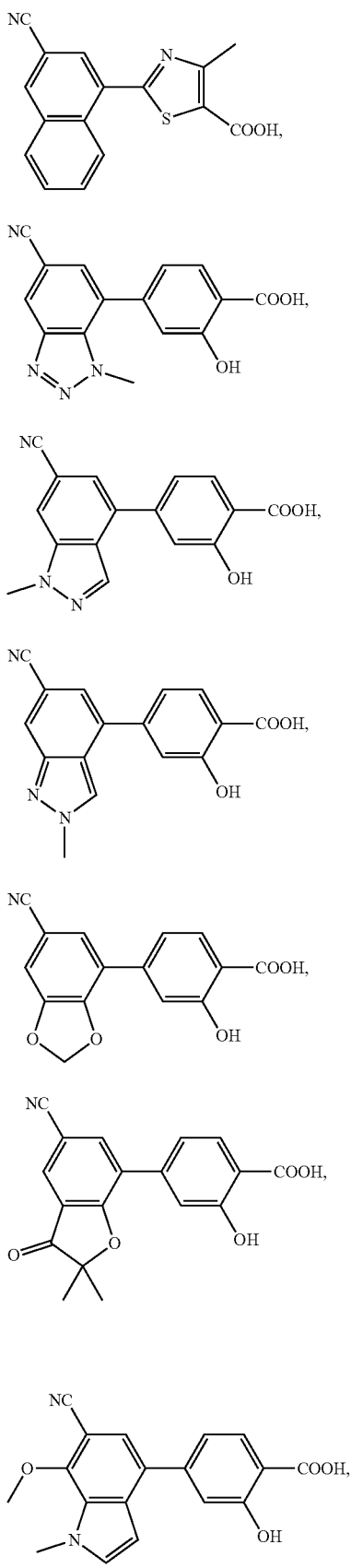
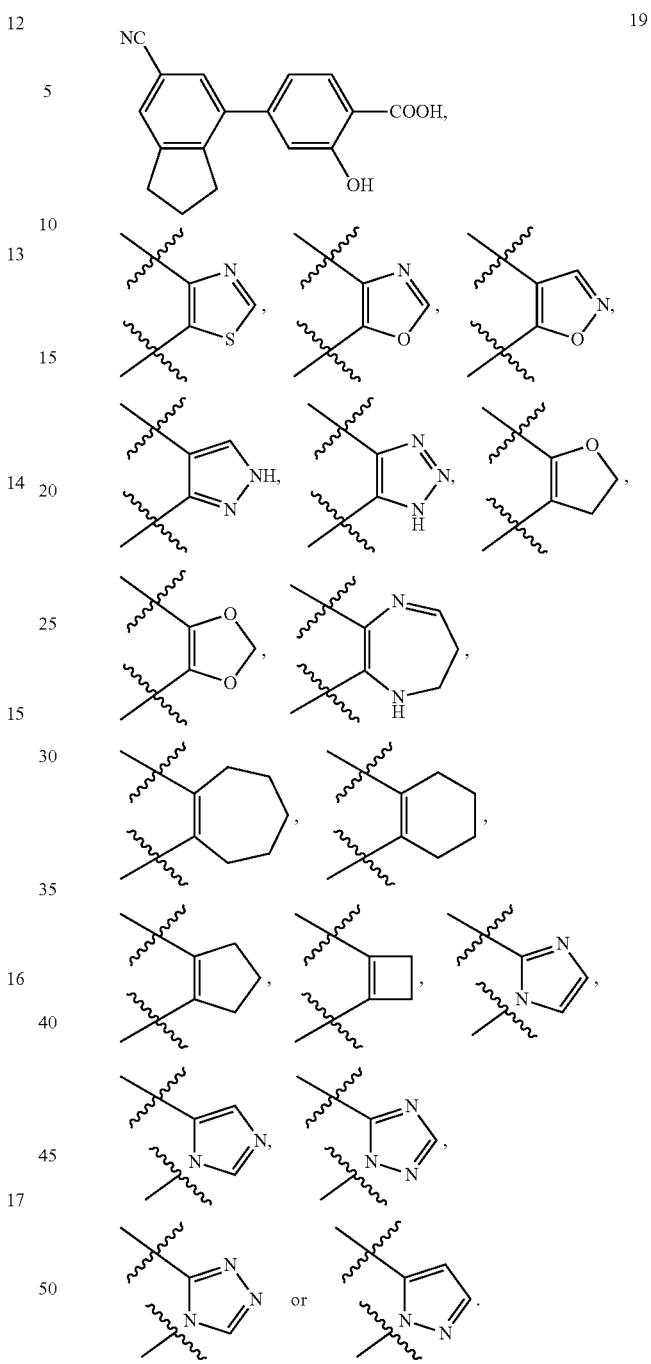
In some embodiments,
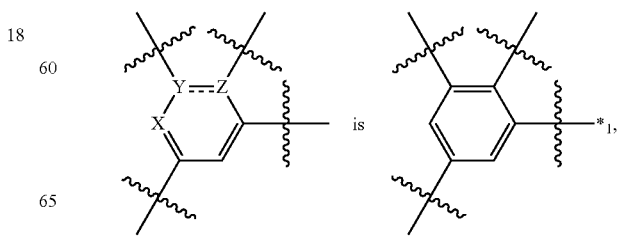

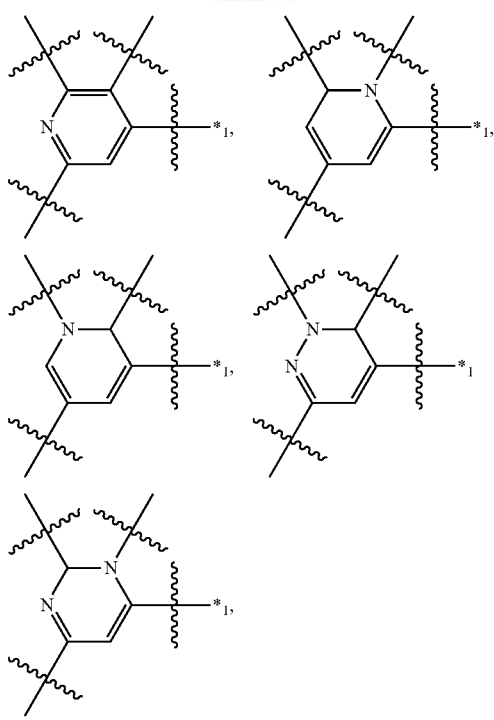
wherein *¹ refers to the position attached to the U ring.
In other embodiments, provided herein is the compound having one of the following formulas, or a stereoisomer, an N-oxide, a solvate, a metabolite, a pharmaceutically acceptable salt or a prodrug thereof, but are not limited to:
1
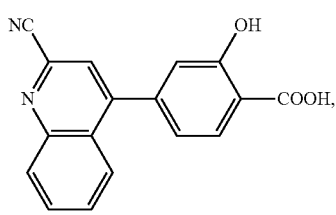
2
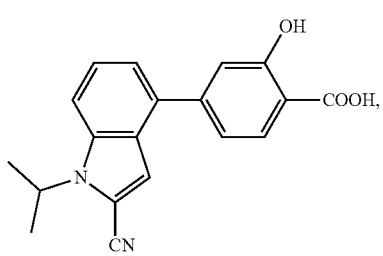
3
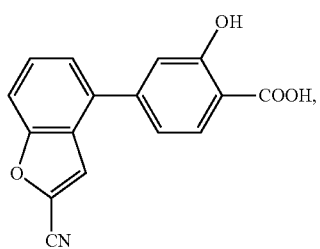
4
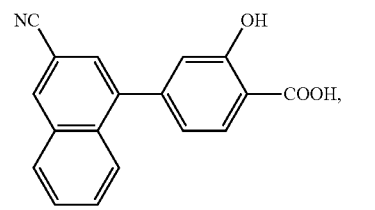
5
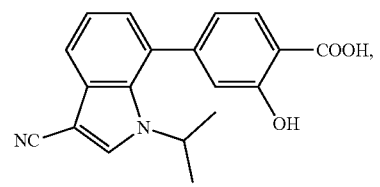
6
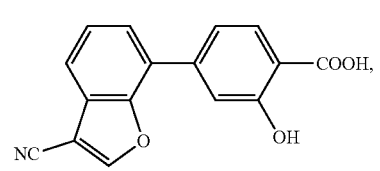
7
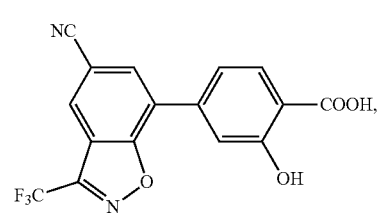
8
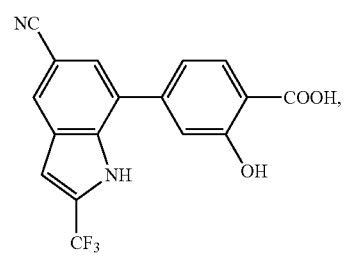
9
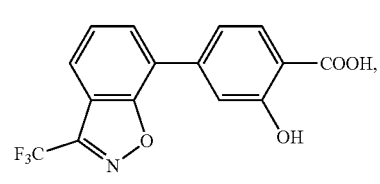
10
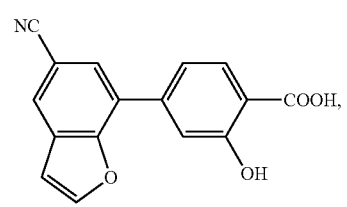

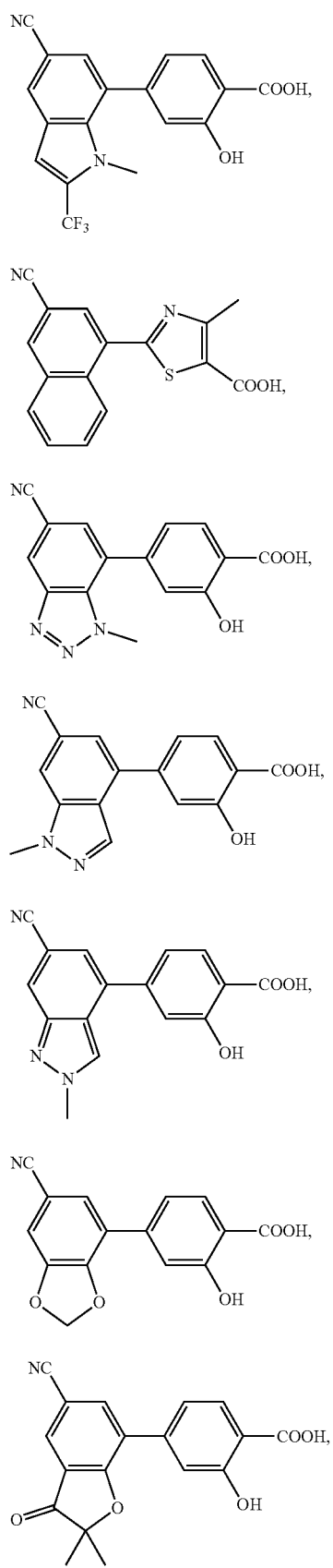
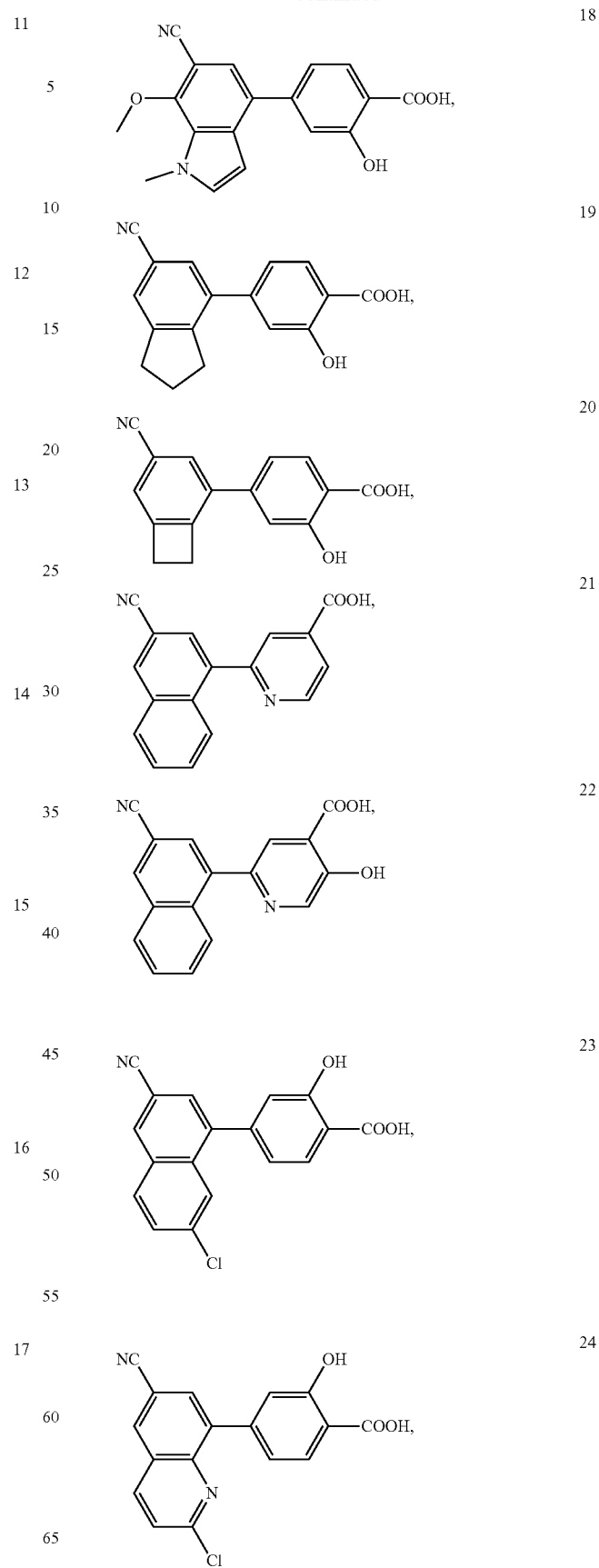

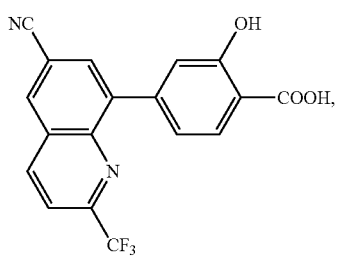
25
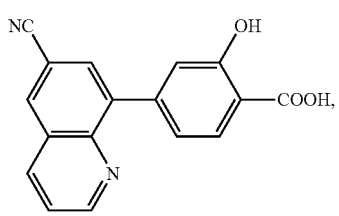
26
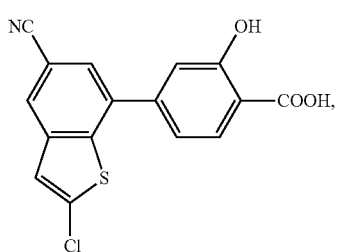
27
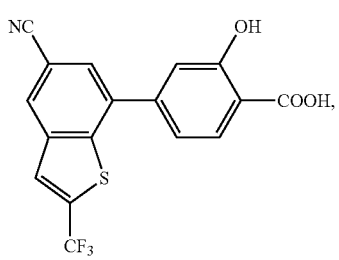
28
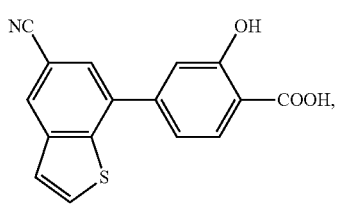
29
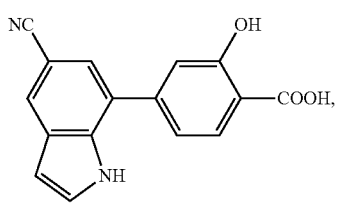
30
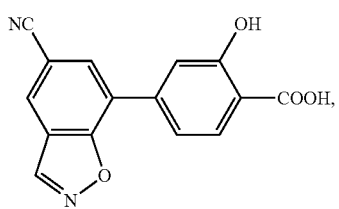
31
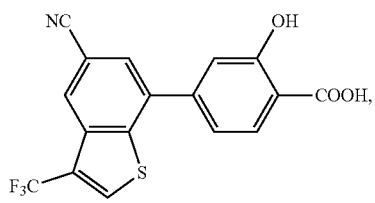
32
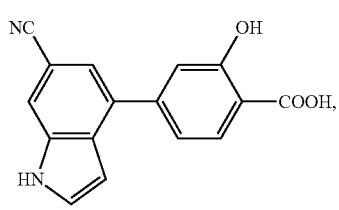
33
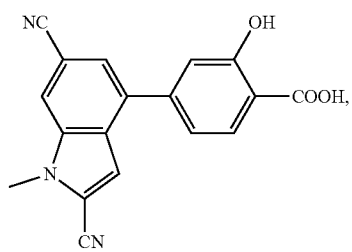
34
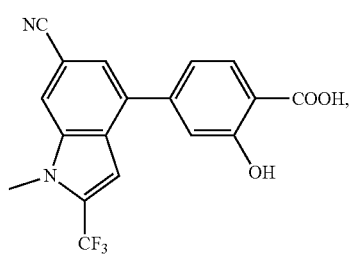
35
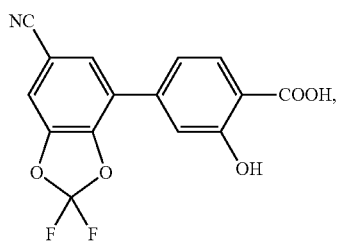
36
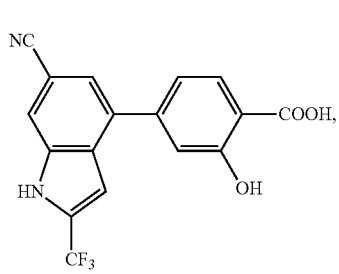
37

38 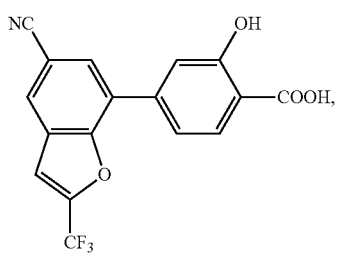
39 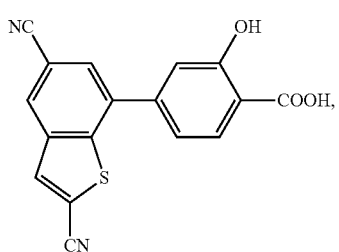
40 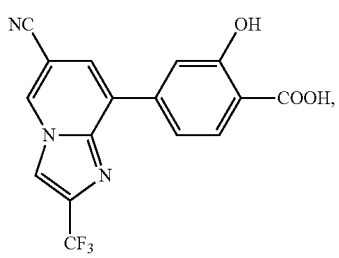
41 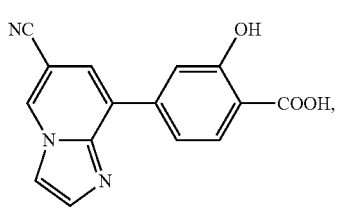
42 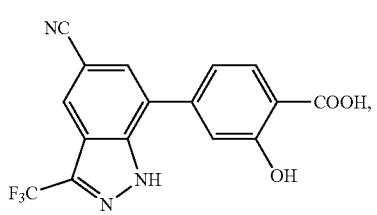
43 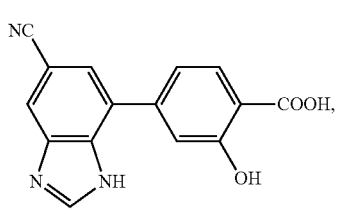
44 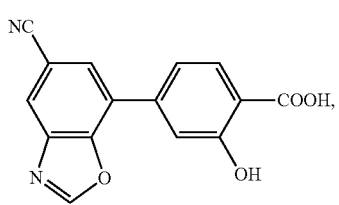
45 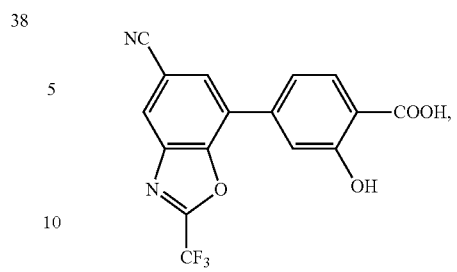
46 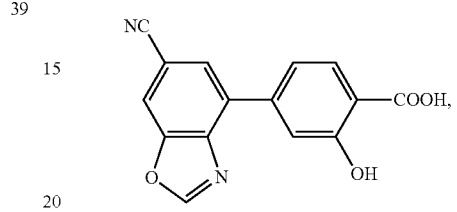
47 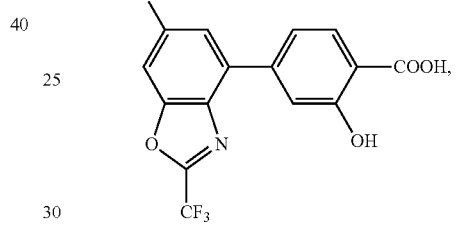
48 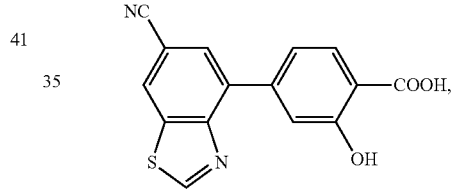
49 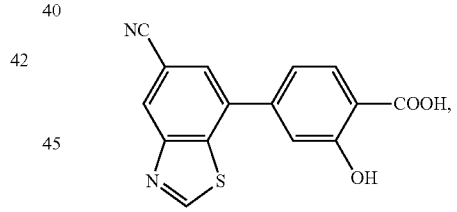
50 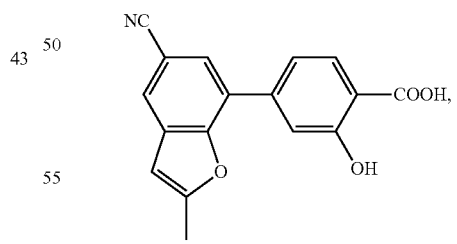
51 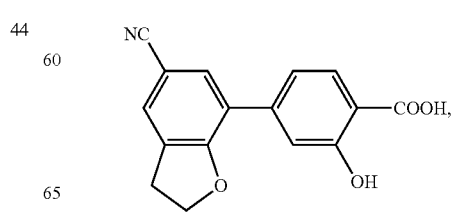

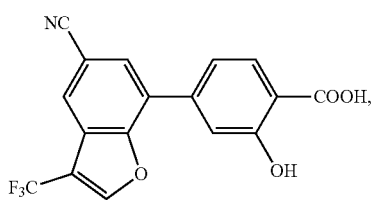
52
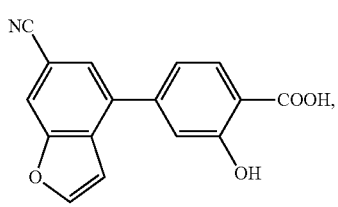
53
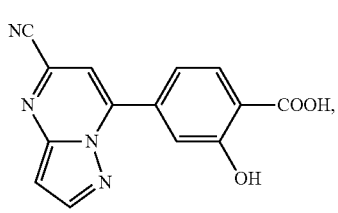
54
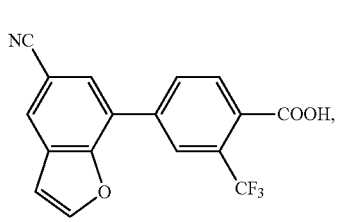
55
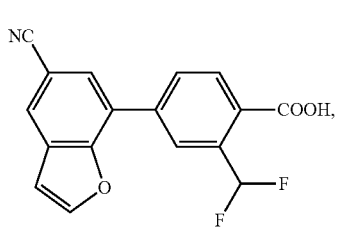
56
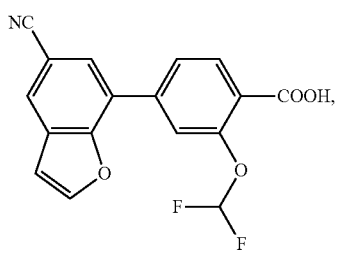
57
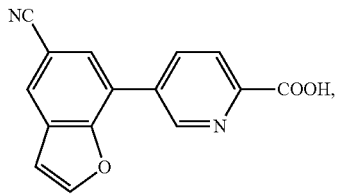
58
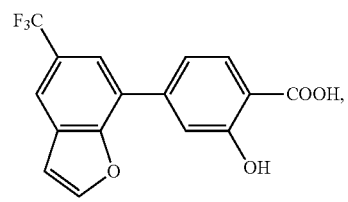
59
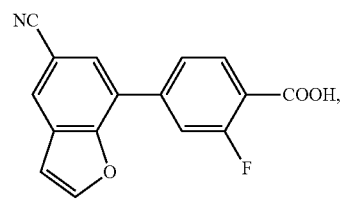
60
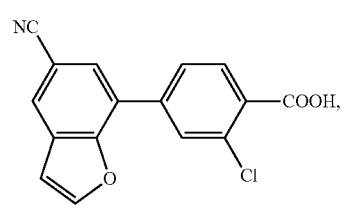
61
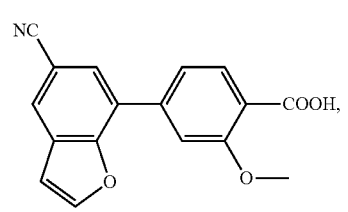
62
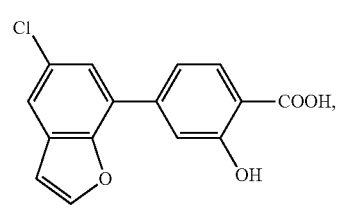
63
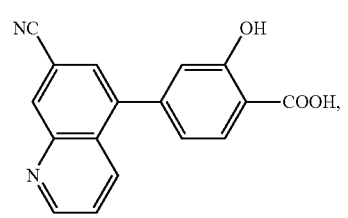
64
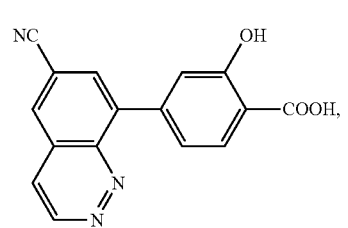
65

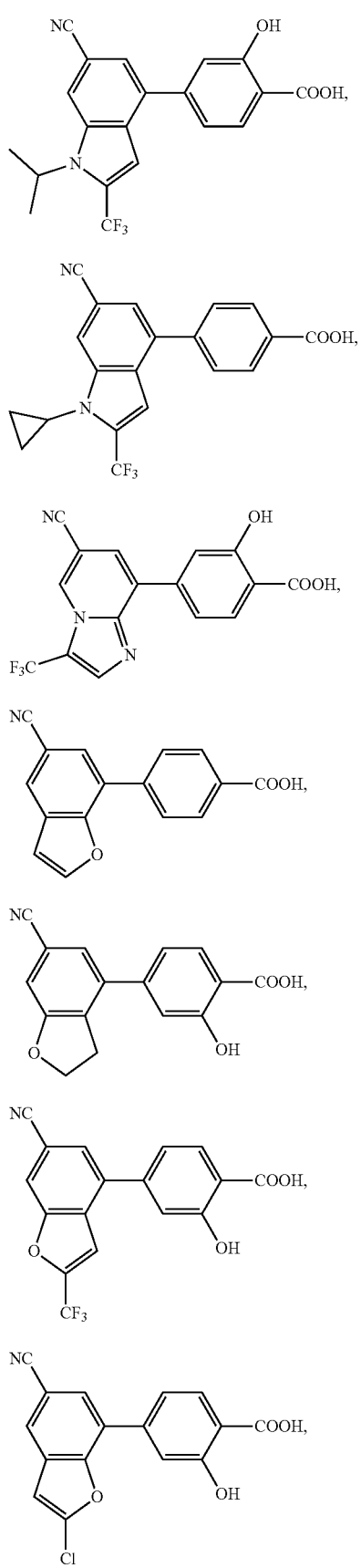
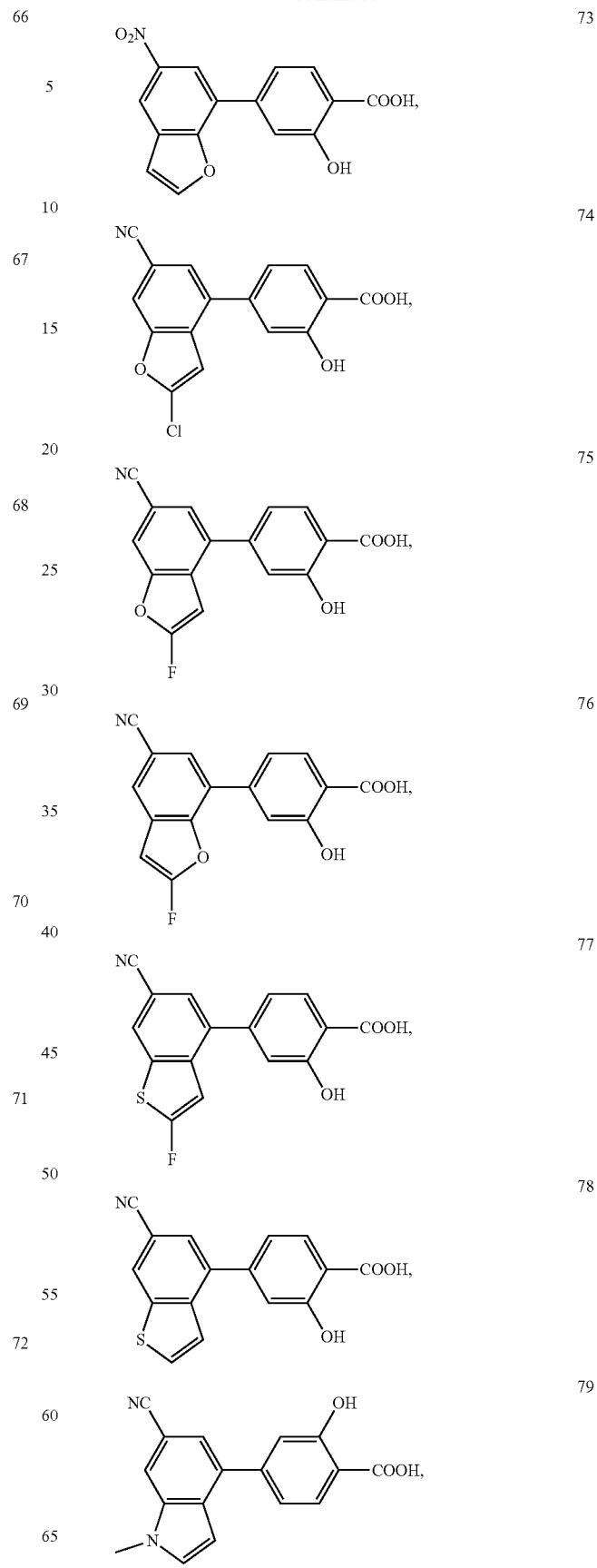

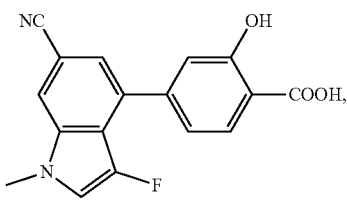
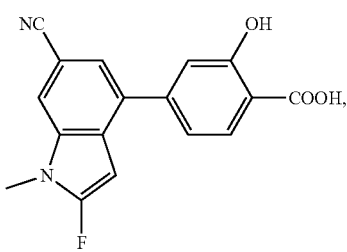
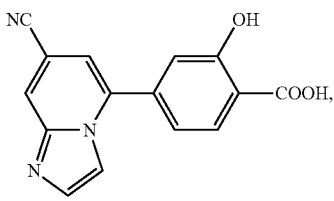
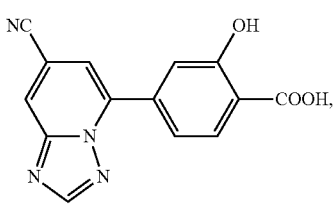
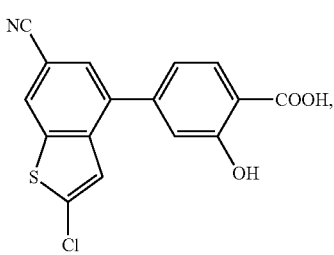
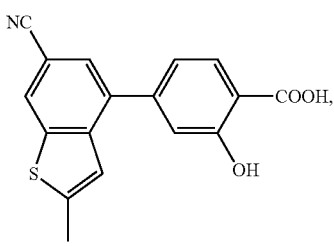
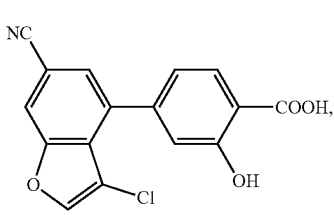
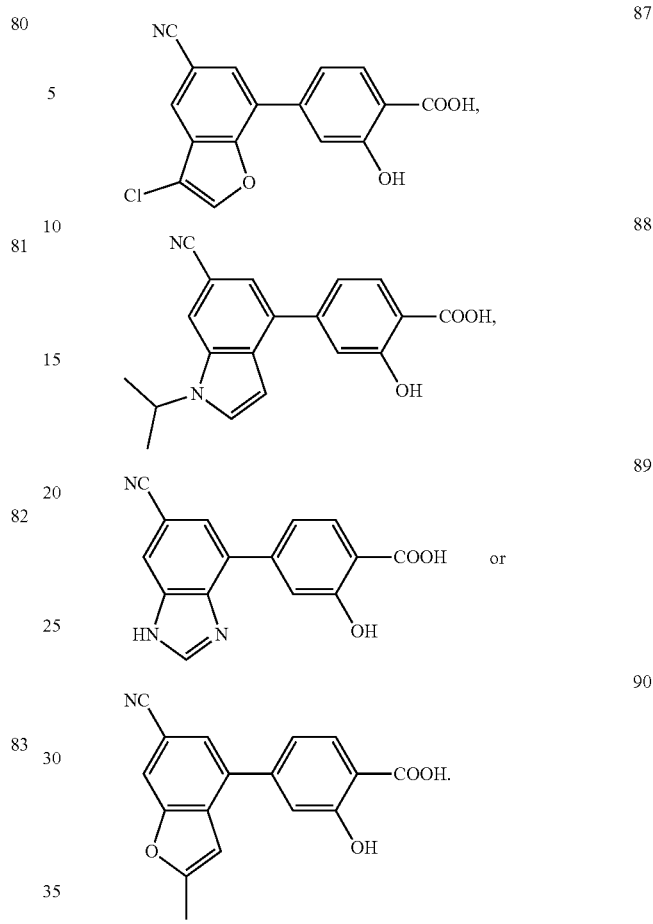

Unless otherwise specified, all stereoisomers, solvates, metabolites, pharmaceutically acceptable salts or prodrugs of a compound having Formula (I), (II), (III) or (IV) are included within the scope of the present invention.

The compounds disclosed herein can contain a asymmetric or chiral center, and therefore can exist in different stereoisomers. It is intended that all stereoisomeric forms of the compounds having Formula (I), (II), (III) or (IV) disclosed herein, include, but are not limited to, diastereomers, enantiomers, atropisomers and geometric (or conformational) isomers, as well as mixtures thereof such as racemic mixtures, form part of the present invention.

When the stereochemistry of any particular chiral atom is not specified, all stereoisomers of the structure disclosed herein are contemplated within the present invention, and as the compounds disclosed herein are included within the scope of the present invention. When stereochemistry is to denote specific configuration of a solid wedge line or a dashed line indicated, the stereoisomers of the structure is clear and defined.

The compound of Formula (I), (II), (III) or (IV) can exist in different tautomeric forms, and all of these tautomers are included within the scope of the present invention.

The compound of Formula (I), (II), (III) or (IV) can exist in the form of a salt. In one embodiment, the salt is a pharmaceutically acceptable salt thereof. The term "pharmaceutically acceptable" refers that a compound or composition must be chemically and/or toxicologically compatible with the other ingredients comprising the formulation and/or treated the mammal. In other embodiment, the salt is not necessarily a pharmaceutically acceptable salt thereof and can be a compound for the preparation and/or purification the Formula (I), (II), (III) or (IV) and/or for the separation of the enantiomers of the Formula (I), (II), (III) or (IV).

Pharmaceutically acceptable acid addition salts can be formed by the interaction of the compound disclosed herein with inorganic acids or organic acids, e.g., acetate, aspartate, benzoate, besylate, bromide/hydrobromide, bicarbonate/carbonate, bisulfate/sulfate, camphorsulfonate, chloride/hydrochloride, chlortheophyllinate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, subsalicylate, tartrate, tosylate and trifluoroacetate.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic or organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, chlorinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds disclosed herein, including their salts, can also be obtained in the form of their hydrates, or include other solvents such as ethanol, DMSO, and the like, used for their crystallization. The compounds of the present invention may inherently or by design form solvates with pharmaceutically acceptable solvents (including water); therefore, it is intended that the invention embrace both solvated and unsolvated forms of the compounds disclosed herein.

Any formula given herein is also intended to represent isotopically unenriched forms as well as isotopically enriched forms of the compounds. Any formula given herein is also intended to represent isotopically unenriched forms as well as isotopically enriched forms of the compounds. Examples of isotopes that can be incorporated into compounds of the invention include isotopes of hydrogen, carbon, nitrogen, oxygen, phosphorous, fluorine, and chlorine, such as 2H (deuterium, D), 3H, 11C, 13C, 14C, 15N, 17O, 18O, 18F, 31P, 32P, 35S, 36Cl, 125I, respectively.

In another aspect, the compounds of the invention include isotopically enriched compounds as defined herein, for example those into which radioactive isotopes, such as 3H, 14C and 18F, or those into which non-radioactive isotopes, such as 2H and 13C are present. Such isotopically enriched compounds are useful in metabolic studies (with 14C), reaction kinetic studies (with, for example 2H or 3H), detection or imaging techniques, such as positron emission tomography (PET) or single-photon emission computed tomography (SPECT) including drug or substrate tissue distribution assays, or in radioactive treatment of patients. In particular, an 18F-enriched compound may be particularly desirable for PET or SPECT studies. Isotopically-enriched compounds of Formula (I) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index, for example, increased in vivo half-life or reduced dosage requirements or an improvement in therapeutic index. It is understood that deuterium in this context is regarded as a substituent of a compound of Formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g. D2O, d6-acetone, DMSO-d6.

In other aspect, provided herein is a preparation of intermediate of the compound of Formula (I), (II), (III) or (IV).

In other aspect, provided herein is a method of preparing, separating or purifying the compound of Formula (I), (II), (III) or (IV).

In other aspect, provided herein is a pharmaceutical composition comprising the compound disclosed herein. In some embodiments, provided herein is a pharmaceutical composition, further comprising a pharmaceutically acceptable carrier, excipient, adjuvant, solvent or a combination thereof. In other embodiments, the pharmaceutical composition can be liquid, solid, semi-solid, gel or spray.

Pharmaceutical Composition of the Compound of the Invention and Preparations and Administration The present invention provides a pharmaceutical composition comprising a compound of the present invention, e.g., a compound of examples, and a pharmaceutically acceptable excipient, carrier, adjuvant, solvent or a combination thereof.

The present invention provides a method of treating, preventing or ameliorating a disease or disorder, comprising administering a safe and effective amount of a combination of drugs containing compounds of the invention and one or more therapeutic active agents. Wherein, the combination of drugs comprises one or more additional drugs for treatment of hyperuricemia, tophi, gouty arthritis, kidney disorders related to hyperuricemia or urolithiasis, and the active constituent of the additional drugs is different from the compound of the present invention.

Other drugs for treatment of hyperuricemia, tophi, gouty arthritis, kidney disorders related to hyperuricemia or urolithiasis include, but are not limited to: colchicine, nonsteroidal anti-inflammatory drugs, glucocorticoids, anti-uric acid drugs, uricosuric drugs, urinary alkalizing agents or any combination thereof.

The other drugs for prevention or treatment of hyperuricemia, tophi, gouty arthritis, kidney disorders related to hyperuricemia and urolithiasis comprise colchicine, indomethacin, etoricoxib, diclofenac, ibuprofen, rofecoxib, celecoxib, meloxicam, prednisone, succinate hydrocortisone, allopurinol, probenecid, sulfinpyrazone, benzbromarone, allopurinol, febuxostat, recombinant *aspergillus flavus* urate oxidase, pegylated recombinant urate oxidase, sodium bicarbonate tablets, potassium and sodium citrate mixture or any combination thereof.

The amount of the compound of the pharmaceutical composition disclosed herein refers to an amount which can be effectively detected to inhibiting both xanthine oxidase and urate anion transporter 1 of biology sample and patient. The dosage of active ingredient in the compositions of this invention may be varied; however, it is necessary that the amount of the active ingredient should be the amount from which a suitable dosage form can be obtained. The active ingredient may be administered to patients (animals or human) in need of such treatment in dosage that will provide optimal pharmaceutical efficacy. The selected dosage depends on the desired therapeutic effect, the route of administration and the duration of the treatment. The dosage will vary from patient to patient depending upon the nature and severity of disease, the patient's weight, special diet of the patient, concurrent medication, and other factors which those skilled in the art will recognize. The dosage range will generally be about 0.5 mg to 1.0 g per patient per day which may be administered in single or multiple doses. In one embodiment, the dosage range will be about 0.5 mg to 500 mg per patient per day; in anther embodiment about 0.5 mg to 200 mg per patient per day; and in yet another embodiment about 5 mg to 50 mg per patient per day.

It will also be appreciated that certain compounds of the present invention can exist in free form for treatment, or where appropriate, as pharmaceutically acceptable derivatives. pharmaceutically acceptable derivative include pharmaceutically acceptable prodrugs, salts, esters, salts of such esters, or any other adducts or derivatives which upon administration to a patient in need thereof is capable of providing, directly or indirectly, a compound as otherwise described herein, or a metabolite or residue thereof.

The pharmaceutical compositions of the invention may be prepared and packaged in bulk form wherein a safe and effective amount of a compound of Formula (I) disclosed herein can be extracted and then given to the patient, such as with powders or syrups. Generally, dosage levels of between 0.0001 to 10 mg/kg of body weight daily are administered to the patient to obtain effective antagonism of xanthine oxidase and urate anion transporter 1. Alternatively, the pharmaceutical compositions of the invention may be prepared and packaged in unit dosage form wherein each physically discrete unit contains a safe and effective amount of a compound of Formula (I) disclosed herein. When prepared in unit dosage form, the pharmaceutical compositions of the invention commonly contain from about 0.5 mg to 1 g, or 1 mg to 700 mg, or 5 mg to 100 mg, of the compound of the invention.

When the pharmaceutical compositions of the present invention also contain one or more other active ingredients, in addition to a compound of the present invention, the weight ratio of the compound of the present invention to the second active ingredient may be varied and depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to 1:200. Combinations of a compound of the present invention and other active ingredients will generally also be within the aforementioned range, but in each case, an effective dose of each active ingredient should be used.

"Pharmaceutically acceptable excipient" as used herein means a pharmaceutically acceptable material, composition or vehicle involved in giving form or consistency to the pharmaceutical composition. Each excipient must be compatible with the other ingredients of the pharmaceutical composition when commingled, such that interactions which would substantially reduce the efficacy of the compound of the invention when administered to a patient and would result in pharmaceutically unacceptable compositions are avoided. In addition, each excipient must of course be of sufficiently high purity to render it pharmaceutically acceptable.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound of the present invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

The pharmaceutical compositions of the invention are prepared using techniques and methods known to those skilled in the art. Some of the methods commonly used in the art are described in Remington's Pharmaceutical Sciences (Mack Publishing Company).

Therefore, another aspect of the present invention is related to a method for preparing a pharmaceutical composition. The pharmaceutical composition contains the compound disclosed herein and pharmaceutically acceptable excipient, carrier, adjuvant, vehicle or a combination thereof, the method comprises mixing various ingredients. The pharmaceutical composition containing the compound disclosed herein can be prepared at for example environment temperature and under barometric pressure.

The compound of the invention will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

In one embodiment, the compounds disclosed herein can be prepared to oral. In the other embodiment, the compounds disclosed herein can be prepared to inhalation. In the still other embodiment, the compounds disclosed herein can be prepared to nasal administration. In the yet other embodiment, the compounds disclosed herein can be prepared to transdermal administration. In the still yet other embodiments, the compounds disclosed herein can be prepared to topical administration.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxy groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfate, sodium metabisulfite, thiodipropionic acid and its esters, and dithiocarbamates.

Where appropriate, dosage unit formulations for oral administration can be microencapsulated. The formulation can also be prepared to prolong or sustain the release as for example by coating or embedding particulate material in polymers, wax, or the like.

The pharmaceutical compositions provided herein for oral administration may be also provided in the forms of liposomes, micelles, microspheres, or nanosystems. Miccellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The compounds disclosed herein can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action.

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfate and sodium metabisulfite. Suitable local anesthetics include, but are not limited to, procaine hydrochloride. Suitable suspending and dispersing agents are those as described herein, including sodium carboxymethylcellulose, hydroxypropyl methylcellulose, and polyvinylpyrrolidone. Suitable emulsifying agents include those described herein, including polyoxyethylene sorbitan monolaurate, polyoxyethylene sorbitan monooleate 80 and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

In other aspect, the pharmaceutical composition of the invention is prepared to a dosage form adapted for administration to a patient by inhalation, for example as a dry powder, an aerosol, a suspension, or a solution composition. In one embodiment, the invention is directed to a dosage form adapted for administration to a patient by inhalation as a dry powder. In one embodiment, the invention is directed to a dosage form adapted for administration to a patient by inhalation as a dry powder. Dry powder compositions for delivery to the lung by inhalation typically comprise a compound disclosed herein or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling.

Generally, the size-reduced (e.g., micronised) compound can be defined by a D50 value of about 1 to about 10 microns (for example as measured using laser diffraction).

Aerosols may be formed by suspending or dissolving a compound disclosed herein or a pharmaceutically acceptable salt thereof in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of formula (I) or a pharmaceutically acceptable salt thereof will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils. Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as *arachis* oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Topical preparations may be administered by one or more applications per day to the affected area; over skin areas occlusive dressings may advantageously be used. Continuous or prolonged delivery may be achieved by an adhesive reservoir system.

Use of the Compounds and Pharmaceutical Compositions of the Invention

Compounds or pharmaceutical compositions of the invention disclosed herein can be used in the manufacture of a medicament for treating, preventing, ameliorating, controlling or mitigating hyperuricemia, tophi, gouty arthritis, renal disorders associated with hyperuricemia or urolithiasis in mammals, including humans, as well as other medicaments for inhibiting both xanthine oxidase and urate anion transporter 1.

Specifically, the amount of the compound of compositions of the present invention can effectively and detectably inhibit both xanthine oxidase and urate anion transporter 1, and the compounds disclosed herein can be used as the medicaments for preventing or treating hyperuricemia, tophi, gouty arthritis, renal disorders associated with hyperuricemia or urolithiasis in humans.

Compounds or compositions disclosed herein would be useful for, but are not limited to, preventing or treating or lessening hyperuricemia, tophi, gouty arthritis, renal disorders associated with hyperuricemia or urolithiasis in mammals including humans by administering to the subject a compound or a composition disclosed herein in an effective amount.

Besides being useful for human treatment, these compounds and pharmaceutical compositions are also useful for veterinary treatment of animals such as companion animals, exotic animals and mammals in the farm. In other embodiments, the animals disclosed herein include horses, dogs, and cats. As used herein, the compounds disclosed herein include the pharmaceutically acceptable derivatives thereof.

Therapies

In one embodiment, the therapies disclosed herein comprise administrating a safe and effective amount of the compound of the invention or the pharmaceutical composition containing the compound of the invention to patients in need. Each example disclosed herein comprises the method of treating the diseases described above comprising administrating a safe and effective amount of the compound of the invention or the pharmaceutical composition containing the compound of the invention to patients in need.

In one embodiment, the compound of the invention or the pharmaceutical composition thereof may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. In one embodiment, the compound of the invention or the pharmaceutical composition thereof may be administered orally. In another embodiment, the compound of the invention or the pharmaceutical composition thereof may be administered by inhalation. In a further embodiment, the compound of the invention or the pharmaceutical composition thereof may be administered intranasally.

In one embodiment, the compound of the invention or the pharmaceutical composition thereof may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for the compound of the invention or the pharmaceutical composition thereof depend on the pharmacokinetic properties of that compound, such as absorption, distribution, and half-life, which can be determined by the skilled artisan. In addition, suitable dosing regimens, including the duration such regimens are administered, for the compound of the invention or the pharmaceutical composition thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

The compounds of the present invention may be administered either simultaneously, or before or after, with one or more other therapeutic agents. The compounds of the present invention and other agents may be administered separately, by the same or different route of administration, or together in the same pharmaceutical composition.

The pharmaceutical composition or combination of the present invention can be in unit dosage of about 1-1000 mg of active ingredients for a subject of about 50-70 kg, preferably about 1-500 mg or about 1-250 mg or about 1-150 mg or about 0.5-100 mg or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys, or isolated organs, tissues and specimens thereof. The compounds of the present invention can be applied in vitro in the form of solutions, e.g., preferably aqueous solutions, and in vivo either enterally or parenterally, advantageously intravenously, e.g., as a suspension or in aqueous solution.

In one embodiment, a therapeutically effective dosage of the compound disclosed herein is from about 0.1 mg to about 2,000 mg per day. The pharmaceutical composition should provide a dosage of from about 0.1 mg to about 2000 mg of the compound. In a special embodiment, pharmaceutical dosage unit forms are prepared to provide from about 1 mg to about 2,000 mg, about 10 mg to about 1,000 mg, about 20 mg to about 500 mg, or about 25 mg to about 250 mg of the active ingredient or a combination of essential ingredients per dosage unit form. In a special embodiment, pharmaceutical dosage unit forms are prepared to provide about 10 mg, 20 mg, 25 mg, 50 mg, 100 mg, 250 mg, 500 mg, 1000 mg or 2000 mg of the active ingredient.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of action of the compound in vivo; (b)

modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

General Synthetic Procedures

The following examples are provided so that the invention might be more fully understood. However, it should be understood that these embodiments merely provide a method of practicing the present invention, and the present invention is not limited to these embodiments.

Generally, the compounds disclosed herein may be prepared by methods described herein, wherein the substituents are as defined for Formula (I), (II), (III) or (IV) above, except where further noted. The following non-limiting schemes and examples are presented to further exemplify the invention.

Professionals skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, the known reaction conditions or the reaction disclosed in the present invention will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Chemical Reagent Factory, Guangzhou Reagent Chemical Factory, Tianjin YuYu Fine Chemical Ltd., Tianjin Fuchen Chemical Reagent Factory, Wuhan XinHuaYuanm Technology Development Co. Ltd., Qingdao Tenglong Reagent Chemical Ltd., and Qingdao Ocean Chemical Factory Anhydrous THF, dioxane, toluene, and ether were obtained by refluxing the solvent with sodium. Anhydrous CH2Cl2 and CHCl3 were obtained by refluxing the solvent with CaH2. EtOAc, PE, hexane, DMAc and DMF were treated with anhydrous Na2SO4 prior to use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and 1 or heat dried.

Column chromatography was conducted using a silica gel column. Silica gel (300-400 mesh) was purchased from Qingdao Ocean Chemical Factory.

1H NMR spectra were recorded with a Bruker 400 MHz or 600 MHz spectrometer using CDCl3, DMSO-d6, CD3OD or d6-acetone as solvents (reported in ppm), and using TMS (0 ppm) or chloroform (7.26 ppm) as the reference standard. When peak multiplicities were reported, the following abbreviations were used: s (singlet), d (doublet), t (triplet), m (multiplet), br (broadened), dd (doublet of doublets), and dt (doublet of triplets). Coupling constants, when given, were reported in Hertz (Hz).

Low resolution mass spectrum (MS) measurement condition data is: Agilent 6120 Quadrupole HPLC-M (column type: Zorbax SB-C18, 2.1×30 mm, 3.5 micron, 6 min, flow rate 0.6 mL/min. The mobile phases consisted of a combination of A (0.1% formic acid in CH3CN) and B (0.1% formic acid in H2O) in gradient mode (5% to 95%), and an ESI source was used. HPLC chromatogram was recorded using a UV-Vis wavelength detector at 210/254 nm Compound purity was measured by High Performance Liquid Chromatography (HPLC) using Agilent 1260 HPLC (column Model: Agilent zorbax Eclipse Plus C18) and DAD detector. Compound purity was calculated with area normalization method.

The following abbreviations are used throughout the specification:

AcOH Acetic acid
$CDCl_3$ deuterochloroform
$CD_3OD$ methanol-D4
DBU 1,8-diazabicyclo[5.4.0]undec-7-ene
DCM dichloromethane
DMAP 4-dimethylaminopyridine
DMF N,N-dimethylformamide
DMSO dimethylsulfoxide
DMSO-$d_6$ dimethylsulfoxide-D6
g gram
h hour
min minute
mmol millimole
M mole per liter
° C. celsius
$H_2SO_4$ sulfuric acid
HATU 2-(7-Aza-1H-benzotriazol-1-yl)-1,1,3,3-tetramethyluronium hexafluorophosphate
NBS N-bromosuccinimide
MeCN, $CH_3CN$ acetonitrile
MeOH methanol
mL, ml milliliter
NMP N-methyl-2-pyrrolidinone
RT, rt, r.t. Room temperature
rpm revolutions per minute
Rt retention time
TFA trifluoroacetic acid
THF tetrahydrofuran Typical synthetic procedures for preparing the compounds of the present invention disclosed are shown in the following synthetic scheme. Wherein L refers to a leaving group, including but not limited to, a halogen atom and a trifluoromethanesulfonyloxy group; $R^a$ is H or $C_{1-4}$ alkyl, or, two $R^a$, together with atoms to which they are attached, form a ring d; $R^b$ is $C_{1-4}$ alkyl; $R^c$ is $C_{1-4}$ alkyl; $R^e$, $R^d$, together with atoms to which they are attached, can form Q ring through appropriate chemical reaction, some examples of $R^e$ and $R^d$ include, but are not limited to, when $R^e$ is $C_{2-3}$ alkenyl, $R^d$ is OH, or when $R^e$ is

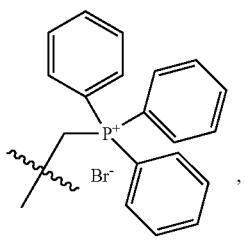 [SMILES: *C[P+](c1ccccc1)(c1ccccc1)c1ccccc1 ; [Br-]]

$R^d$ is 2,2,2-trifluoroacetamido; $R^g$, $R^h$, together with atoms to which they are attached, can form Q ring through reacting with triethyl orthoformate, some examples of $R^g$ and $R^h$ include, but are not limited to, $R^g$ is OH or $NH_2$, $R^e$ is $NH_2$. Unless otherwise specified, Q, U, T, X, Y, Z, $R^1$, each $R^2$, each $R^3$, m and n is as defined herein.

Scheme 1:

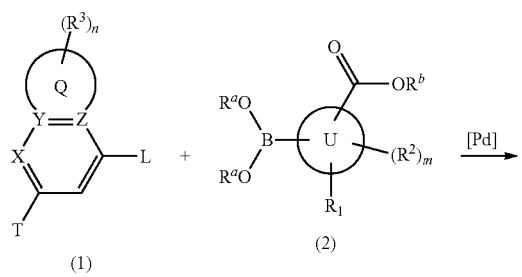

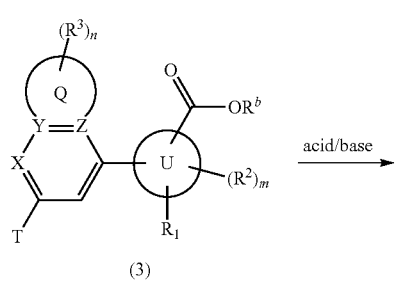

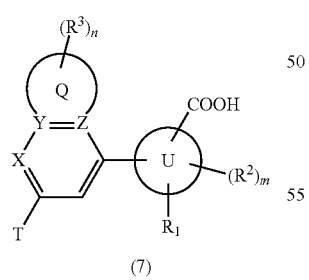

Compound (7) can be prepared by the following procedures:

Substituted heterocyclic or carbocyclic compound (1) can react with compound containing boronic ester (2) in the presence of catalyst [Pd] to give compound (3) by suzuki coupling reaction; compound (3) can be converted to compound (7) in the presence of an acid or a base.

Scheme 1 of Intermediate

Compound (1a) can be prepared by the following procedures:

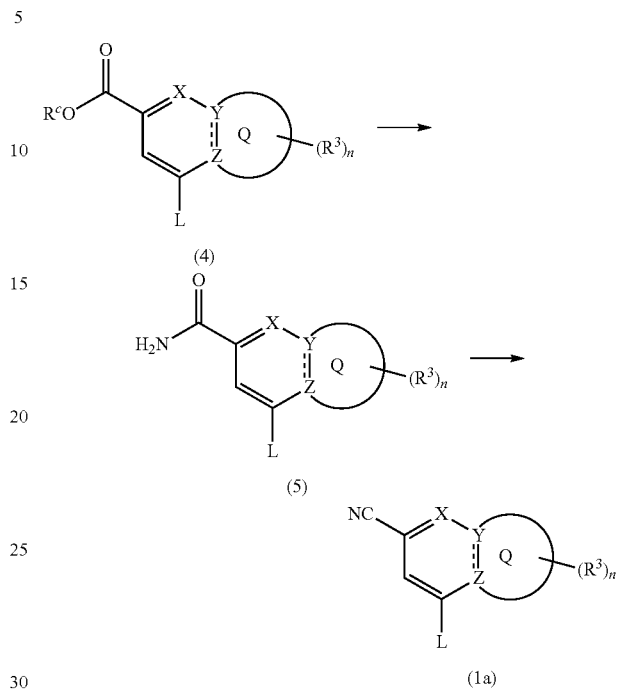

Substituted compound (4) can react with a solution of ammonia in methanol to give compound (5); compound (5) can be converted to compound (1a) in the presence of phosphorus oxychloride.

Scheme 2 of Intermediate

Compound (1a) also can be prepared by the following procedure:

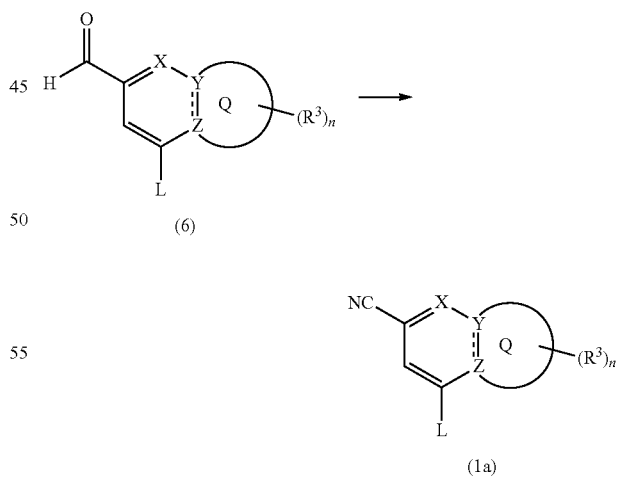

Substituted compound (4) can react with ammonium hydroxide and iodine to give compound (1a).

Scheme 3 of Intermediate

Compound (1a) also can be prepared by the following procedure:

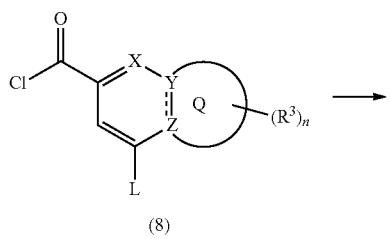

(8)

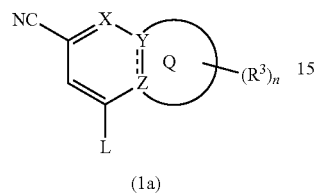

(1a)

Substituted compound (8) can react with ammonium hydroxide to give the amide product, and the amide product can be converted to compound (1a) in the presence of phosphorus oxychloride by dehydration reaction.

Scheme 4 of Intermediate

Compound (1a) also can be prepared by the following procedure:

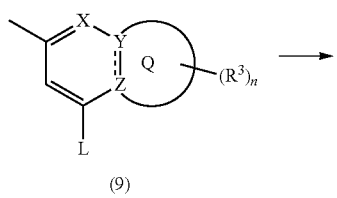

(9)

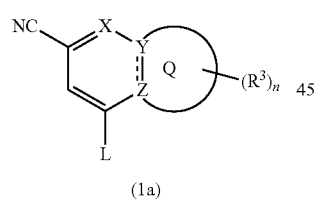

(1a)

Substituted compound (9) can react with sodium azide or tert-butyl nitrite to give compound (1a).

Scheme 5 of Intermediate

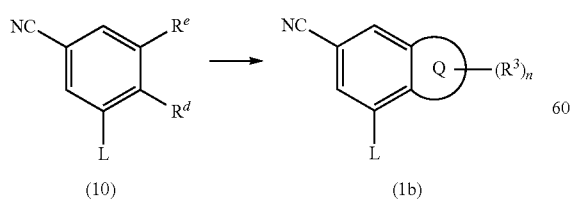

Substituted compound (10) can react under suitable conditions to give compound (1b).

Scheme 2:

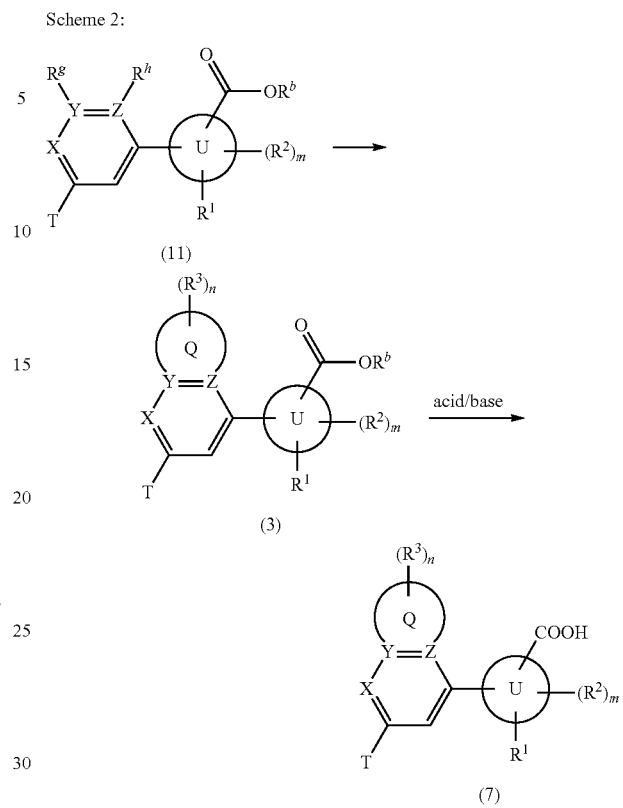

Substituted compound (11) can react with triethyl orthoformate to give compound (3). And then compound (3) can be converted to compound (7) in the presence of an acid or a base.

Compounds and pharmaceutical compositions provided herein and the application thereof are further illustrated in combination with the following examples.

EXAMPLES

Example 1:
4-(5-cyanobenzofuran-7-yl)-2-hydroxybenzoic Acid

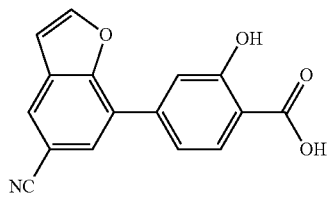

Step 1) Synthesis of methyl 3-bromo-4-hydroxybenzoate

3-Bromo-4-hydroxybenzoic acid (10.0 g, 46.1 mmol) and methanol (120 mL) were added to a 500 mL single neck flask, then thionyl chloride (7.35 mL, 101 mmol) was added dropwise at 0° C. The mixture was heated to 90° C. and stirred for 12 h under nitrogen. The resulting mixture was concentrated in vacuo to remove solvent. To the residue was added saturated aqueous sodium bicarbonate (200 mL), and the resulting mixture was extracted with ethyl acetate (100 mL×2). The combined organic phases were washed with saturated brine (100 mL), dried over anhydrous sodium sulfate, filtered, and concentrated in vacuo. The residue was purified by silica gel chromatography (ethyl acetate/petroleum ether (v/v)=1/20) to give the title compound as a pale yellow solid (10.0 g, 94%).

MS (ES-API, neg. ion) m/z: 228.0 [M−2]⁻.

Step 2) Synthesis of methyl 3-bromo-4-(2,2-diethoxyethoxy)benzoate

Methyl 3-bromo-4-hydroxybenzoate (10.0 g, 43.3 mmol), 2-bromo-1,1-diethoxyethane (8.06 mL, 52.0 mmol), cesium carbonate (28.2 g, 86.6 mmol) and anhydrous N,N-dimethylformamide (60 mL) were sequentially added to a 250 mL single neck flask, then the reaction mixture was heated to 160° C. and stirred for 6 h under nitrogen. The resulting mixture was cooled to room temperature, diluted with saturated aqueous ammonium chloride solution (200 mL), and extracted with ethyl acetate (100 mL×2). The combined organic phases were washed with saturated brine (100 mL), dried over anhydrous sodium sulfate, filtered, and concentrated in vacuo, and the residue was purified by silica gel chromatography (ethyl acetate/petroleum ether (v/v)=1/50) to give the title compound as a pale yellow solid (5.5 g, 37%).

MS (ES-API, pos. ion) m/z: 348.1 [M+2]⁺.

Step 3) Synthesis of methyl 7-bromobenzofuran-5-carboxylate

Polyphosphoric acid (5.00 g) and chlorobenzene (40 mL) were added to a 100 mL single neck flask, and the reaction mixture was heated to reflux under nitrogen, then a solution of methyl 3-bromo-4-(2,2-diethoxyethoxy)benzoate (3.68 g, 10.6 mmol) in chlorobenzene (40 mL) was added dropwise. The reaction mixture was stirred for 2 h at 145° C. The resulting mixture was cooled to room temperature. The upper organic phase was poured out, and then concentrated in vacuo. The residue was purified by silica gel chromatography (ethyl acetate/petroleum ether (v/v)=1/100) to give the title compound as a pale yellow solid (0.40 g, 15%).

$^1$H NMR (400 MHz, CDCl$_3$) δ: 8.31 (d, J=1.4 Hz, 1H), 8.22 (d, J=1.3 Hz, 1H), 7.78 (d, J=2.1 Hz, 1H), 6.95 (d, J=2.2 Hz, 1H), 3.97 (s, 3H).

Step 4) Synthesis of 7-bromobenzofuran-5-carboxamide

Methyl 7-Bromobenzofuran-5-carboxylate (400 mg, 1.56 mmol) and a solution of ammonia (20 mL, 7 M) in methanol were added sequentially to a 50 mL sealed tube. The mixture was heated to 150° C. and stirred for 24 h. The resulting mixture was cooled to room temperature, and concentrated in vacuo to remove solvent. The residue was purified by silica gel chromatography (methanol/dichloromethane (v/v) =1/50) to give the title compound as a yellow solid (0.26 g, 70%).

MS (ES-API, pos. ion) m/z: 241.0 [M+2]⁺.

Step 5) Synthesis of 7-bromobenzofuran-5-carbonitrile

7-Bromobenzofuran-5-carboxamide (0.39 g, 1.62 mmol) and toluene (20 mL) were added to a 50 mL single neck flask, then phosphorus oxychloride (0.74 mL, 8.1 mmol) was added dropwise. The reaction mixture was stirred for 24 h at 120° C. The resulting mixture was cooled to room temperature, quenched with saturated brine (80 mL), and extracted with ethyl acetate (40 mL×2). The combined organic phases were washed with saturated brine (60 mL), dried over anhydrous sodium sulfate, filtered, and concentrated in vacuo, and the residue was purified by silica gel chromatography (ethyl acetate/petroleum ether (v/v)=1/50) to give the title compound as a yellow solid (0.32 g, 90%).

MS (ES-API, pos. ion) m/z: 222.9 [M+2]⁺.

Step 6) Synthesis of methyl 4-(5-cyanobenzofuran-7-yl)-2-hydroxybenzoate

7-Bromobenzofuran-5-carbonitrile (0.32 g, 1.44 mmol), methyl 2-hydroxy-4-(4,4,5,5-tetramethyl-1,3,2-dioxaborolan-2-yl) benzoate (0.36 g, 1.31 mmol), 1,1'-Bis (diphenylphosphino) ferrocene-palladium (II) dichloride dichloromethane complex (53 mg, 0.065 mmol) and N,N-dimethylformamide (8 mL) were added sequentially to a 50 mL two-neck flask, then a solution of potassium carbonate (1.3 mL, 2 M) in water was added under nitrogen. The reaction mixture was heated to 90° C. and stirred for 0.5 h. The resulting mixture was cooled to room temperature, diluted with saturated brine (80 mL), and extracted with ethyl acetate (40 mL×2). The combined organic phases were washed with saturated brine (60 mL), dried over anhydrous sodium sulfate, filtered, and concentrated in vacuo, the residue was purified by silica gel chromatography (ethyl acetate/petroleum ether (v/v)=1/15) to give the title compound as a pale yellow solid (0.29 g, 76%).

MS (ES-API, pos. ion) m/z: 294.1 [M+1]⁺.

Step 7) Synthesis of 4-(5-cyanobenzofuran-7-yl)-2-hydroxybenzoic Acid

Methyl 4-(5-cyanobenzofuran-7-yl)-2-hydroxybenzoate (0.29 g, 0.99 mmol), methanol (8 mL), tetrahydrofuran (8 mL) and water (8 mL) were added sequentially to a 100 mL single neck flask, then sodium hydroxide (0.40 g, 9.9 mmol) was added, and the reaction mixture was stirred for 12 h at rt. The resulting mixture was concentrated in vacuo to remove solvent. To the residue was added water (60 mL). The aqueous phase was washed with diethyl ether (50 mL), then acidified to pH 1 with 2 N dilute hydrochloric acid. The resulting mixture was extracted with ethyl acetate (40 mL×2). The combined organic phases were washed with saturated brine (40 mL×2), dried over anhydrous sodium sulfate, filtered, and concentrated in vacuo, and the residue was purified by silica gel chromatography (methanol/dichloromethane (v/v)=1/50) to give the title compound as a white solid (0.18 g, 65%).

MS (ES-API, pos. ion) m/z: 280.1 [M+1]⁺;

HPLC: purity=97%; and $^1$H NMR (400 MHz, DMSO-d$_6$) δ: 8.28 (s, 2H), 8.05 (s, 1H), 7.94 (d, J=8.1 Hz, 1H), 7.52 (s, 1H), 7.47 (d, J=7.9 Hz, 1H), 7.19 (s, 1H).

Example 2: 4-(3-cyanonaphthalene-1-yl)-2-hydroxybenzoic Acid

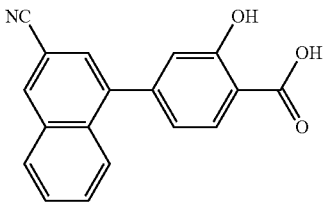 [SMILES: N#Cc1cc(-c2ccc(C(=O)O)c(O)c2)c2ccccc2c1]

Step 1) Synthesis of 3-amino-4-bromo-2-naphthoic Acid

3-Amino-2-naphthoic acid (7.48 g, 40 mmol) and anhydrous N,N-dimethylformamide (100 mL) were added sequentially to a 250 mL two-neck flask. The mixture was cooled to 0° C., and then N-bromosuccinimide (7.46 g, 42 mmol) was added in portions. The reaction mixture was stirred for 16 h at rt. To the mixture was added water (200 mL) and ethyl acetate (160 mL), then the mixture was partitioned. The organic phase was washed with saturated brine (60 mL×2), dried over anhydrous sodium sulfate, filtered, and concentrated in vacuo, and the residue was purified by silica gel chromatography (ethyl acetate/petroleum ether (v/v)=1/4) to give the title compound as a yellow solid (10.4 g, 98%).

MS (ES-API, pos. ion) m/z: 267.0 [M+2]$^+$.

Step 2) Synthesis of 4-bromo-2-naphthoic Acid

3-Amino-4-bromo-2-naphthoic acid (5.32 g, 20 mmol), toluene (100 mL) and ethanol (35 mL) were added sequentially to a 100 mL single neck flask. The mixture was cooled to 0° C., and sulfuric acid (3.5 mL, 98%) was slowly added dropwise, then sodium nitrite (3.0 g, 43 mmol) was added in portions. The reaction mixture was stirred for 0.5 h at 0° C., then heated to reflux and reacted for 1.5 h. The mixture was cooled to room temperature, and water (200 mL) and ethyl acetate (200 mL) were added. The resulting mixture was partitioned, and the organic phase was washed with saturated brine (60 mL×2), dried over anhydrous sodium sulfate, filtered, and concentrated in vacuo. The residue was purified by silica gel chromatography (ethyl acetate/petroleum ether (v/v)=1/1) to give the title compound as a yellow solid (3.57 g, 71%).

MS (ES-API, neg. ion) m/z: 247.9 [M−2]$^-$.

Step 3) Synthesis of methyl 4-bromo-2-naphthoate

4-Bromo-2-naphthoic acid (3.57 g, 14.2 mmol) and anhydrous methanol (50 mL) were added to a 100 mL single neck flask. The mixture was cooled to 0° C., then thionyl chloride (2.53 g, 1.53 mL, 21.3 mmol) was slowly added dropwise. The reaction mixture was gradually warmed to 80° C. and stirred for 12 h. The resulting mixture was cooled to room temperature and concentrated in vacuo to remove solvent. To the residue was added saturated brine (80 mL) and ethyl acetate (150 mL), and the resulting mixture was partitioned. The organic phase was washed with saturated brine (60 mL×2), dried over anhydrous sodium sulfate, filtered, and concentrated in vacuo, and the residue was purified by silica gel chromatography (ethyl acetate/petroleum ether (v/v)=1/50) to give the title compound as a pale yellow solid, 1.1 g, 34%).

$^1$H NMR (400 MHz, CDCl$_3$) δ: 8.57 (s, 1H), 8.38 (d, J=1.3 Hz, 1H), 8.28 (d, J=8.5 Hz, 1H), 7.96 (d, J=8.2 Hz, 1H), 7.72 (t, J=7.7 Hz, 1H), 7.61 (t, J=7.5 Hz, 1H), 3.99 (s, 3H).

Step 4) Synthesis of 4-bromo-2-naphthamide

Methyl 4-bromo-2-naphthoate (3.5 g, 13.2 mmol) and ammonia (50 mL, 7 M in methanol) were added to a 100 mL sealed tube. The reaction mixture was stirred for 12 h at 130° C. The resulting mixture was cooled to room temperature and concentrated in vacuo to remove solvent. The residue was purified by silica gel chromatography (ethyl acetate/petroleum ether (v/v)=1/10) to give the title compound as a white solid (2.8 g, 85%).

MS (ES-API, pos. ion) m/z: 250.9 [M+2]$^+$.

Step 5) Synthesis of 4-bromo-2-naphthonitrile

Phosphorus oxychloride (8.0 g, 52 mmol) was added to a solution of 4-bromo-2-naphthalene carboxamide (2.6 g, 10.4 mmol) in toluene (25 mL) in a 100 mL single neck flask. The reaction mixture was stirred for 12 h at 120° C. The resulting mixture was cooled to room temperature and concentrated in vacuo to remove solvent. To the residue was added saturated brine (80 mL) and ethyl acetate (100 mL), and the resulting mixture was partitioned. The organic phase was washed with saturated brine (60 mL×2), dried over anhydrous sodium sulfate, filtered, and concentrated in vacuo. The residue was purified by silica gel chromatography (ethyl acetate/petroleum ether (v/v)=1/10) to give the title compound as a white solid (2.2 g, 91%).

$^1$H NMR (400 MHz, CDCl$_3$) δ: 8.29 (d, J=8.5 Hz, 1H), 8.20 (s, 1H), 7.92-7.90 (m, 2H), 7.77 (t, J=7.7 Hz, 1H), 7.67 (t, J=7.5 Hz, 1H).

Step 6) Synthesis of methyl 4-(3-cyanonaphthalen-1-yl)-2-hydroxybenzoate

4-Bromo-2-naphthalene carbonitrile (0.417 g, 1.8 mmol), methyl 2-hydroxy-4-(4,4,5,5-tetramethyl-1,3,2-dioxaborolan-2-yl)-benzoate (0.42 g, 1.5 mmol), 1,1'-bis(diphenylphosphino)-ferrocene-palladium(II)dichloride dichloromethane complex (122 mg, 0.15 mmol) and N,N-dimethylformamide (8 mL) were gradually added to a 50 mL two-neck flask. A solution of potassium carbonate (1.5 mL, 2 M) in water was added under nitrogen, then the reaction mixture was stirred for 0.5 h at 90° C. The resulting mixture was cooled to room temperature and saturated brine (80 mL) was added. The resulting mixture was extracted with ethyl acetate (40 mL×2). The combined organic phases were washed with saturated brine (60 mL), dried over anhydrous sodium sulfate, filtered, and concentrated in vacuo, and the residue was purified by silica gel chromatography (dichloromethane/petroleum ether (v/v)=1/3) to give the title compound as a white solid (0.18 g, 40%).

MS (ES-API, pos. ion) m/z: 304.2 [M+1]$^+$.

Step 7) Synthesis of 4-(3-cyanonaphthalen-1-yl)-2-hydroxybenzoic Acid

Methyl 4-(3-cyanonaphthalen-1-yl)-2-hydroxybenzoate (0.18 g, 0.59 mmol), methanol (8 mL), tetrahydrofuran (8 mL) and water (8 mL) were gradually added to a 100 mL single neck flask, then sodium hydroxide (0.12 g, 3.0 mmol) was added. The reaction mixture was stirred for 12 h at rt. The resulting mixture was concentrated in vacuo to remove solvent. To the residue was added water (60 mL). The resulting mixture was washed with ether (50 mL), acidified to pH 1 with 2 N dilute hydrochloric acid and extracted with ethyl acetate (40 mL×2). The combined organic phases were washed with saturated brine (40 mL×2), dried over anhydrous sodium sulfate, filtered, and concentrated in vacuo. The residue was purified by silica gel chromatography (methanol/dichloromethane (v/v)=1/30) to give the title compound as a white solid (0.06 g, 35%).

MS (ES-API, neg. ion) m/z: 288.1 [M−1]⁻;
HPLC: purity=97%; and
¹H NMR (400 MHz, DMSO-d₆) δ: 8.65 (s, 1H), 8.18-8.15 (m, 1H), 7.98-7.80 (m, 2H), 7.74-7.72 (m, 3H), 7.08-6.86 (m, 2H).

Example 3: 4-(6-cyanobenzo[d][1,3]dioxole-4-yl)-2-hydroxybenzoic Acid

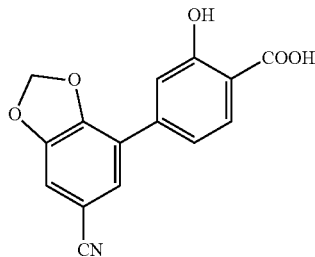 [SMILES: N#Cc1cc2c(c(-c3ccc(C(=O)O)c(O)c3)c1)OCO2]

Step 1) Synthesis of 3-bromo-4-hydroxy-5-methoxybenzonitrile

3-Bromo-4-hydroxy-5-methoxybenzaldehyde (6.93 g, 30.0 mmol), ammonium hydroxide (100 mL, 28%) and tetrahydrofuran (100 mL) were added to a 100 mL single neck flask, then iodine (7.46 g, 42 mmol) was added in portions. The reaction mixture was stirred for 12 h at rt. The mixture was quenched with saturated sodium thiosulfate (100 mL). The resulting mixture was extracted with ethyl acetate (100 mL×2). The combined organic phase was washed with saturated brine (100 mL), dried over anhydrous sodium sulfate, filtered, and concentrated in vacuo. The residue was purified by silica gel chromatography (dichloromethane/petroleum ether (v/v)=1/1) to give the title compound as a white solid (2.9 g, 43%).

MS (ES-API, neg. ion) m/z: 225.0 [M−2]⁻.

Step 2) Synthesis of 3-bromo-4,5-dihydroxybenzonitrile

3-Bromo-4-hydroxy-5-methoxybenzonitrile (2.28 g, 10.0 mmol) and dichloromethane (30 mL) were added to a 100 mL single neck flask, then boron tribromide (3.1 mL, 33 mmol) was added dropwise at −70° C. under nitrogen. The reaction mixture was stirred for 3 h at −70° C. and then stirred for 6 h at −50° C. The resulting mixture was quenched with water (100 mL). The aqueous phase was extracted with ethyl acetate (100 mL×2). The combined organic phase was washed with saturated brine (100 mL), dried over anhydrous sodium sulfate, filtered, and concentrated in vacuo. The residue was purified by silica gel chromatography (ethyl acetate/petroleum ether (v/v)=1/2) to give the title compound as a white solid (1.6 g, 75%).

MS (ES-API, neg. ion) m/z: 210.9 [M−2]⁻.

Step 3) Synthesis of 7-bromobenzene[d][1,3]dioxol-5-carbonitrile

3-Bromo-4,5-dihydroxybenzonitrile (0.26 g, 1.2 mmol), diiodomethane (0.39 g, 1.46 mmol), cesium carbonate (1.37 g, 4.2 mmol) and anhydrous N,N-dimethylformamide (8 mL) were gradually added to a 100 mL single neck flask. The reaction mixture was stirred for 12 h at 80° C. under nitrogen. The mixture was cooled to room temperature, and saturated brine (80 mL) was added. The resulting mixture was extracted with ethyl acetate (60 mL×2). The combined organic phase was washed with saturated brine (60 mL), dried over anhydrous sodium sulfate, filtered, and concentrated in vacuo. The residue was purified by silica gel chromatography (ethyl acetate/petroleum ether (v/v)=1/10) to give the title compound as a white solid (0.23 g, 85%).

MS (ES-API, pos. ion) m/z: 227.0 [M+2]⁺.

Step 4) Synthesis of methyl 4-(6-cyanobenzo[d][1,3]dioxole-4-yl)-2-hydroxybenzoate 7-Bromobenzene[d][1,3]dioxol-5-carbonitrile (0.30 g, 1.32 mmol), methyl 2-hydroxy-4-(4,4,5,5-tetramethyl-1,3,2-dioxaborolan-2-yl) benzoate (0.31 g, 1.1 mmol), 1,1'-bis (diphenylphosphino)ferrocene-palladium(II)dichloride dichloromethane complex (90 mg, 0.11 mmol) and N,N-dimethylformamide (8 mL) were added gradually to a 50 mL two-neck flask. A solution of potassium carbonate (1.1 mL, 2 M) in water was added under nitrogen, then the reaction mixture was stirred for 0.5 h at 90° C. The resulting mixture was cooled to room temperature, and saturated brine (80 mL) was added. The aqueous phase was extracted with ethyl acetate (40 mL×2). The combined organic phases were washed with saturated brine (60 mL), dried over anhydrous sodium sulfate, filtered, and concentrated in vacuo. The residue was purified by silica gel chromatography (dichloromethane/petroleum ether (v/v)=1/2) to give the title compound as a white solid (0.16 g, 49%).

MS (ES-API, neg. ion) m/z: 296.0 [M−1]⁻.

Step 5) Synthesis of 4-(6-cyanobenzo[d][1,3]dioxo-4-yl)-2-hydroxybenzoic Acid

Methyl 4-(6-cyanobenzo[d][1,3]dioxole-4-yl)-2-hydroxybenzoate (0.16 g, 0.54 mmol), methanol (8 mL), tetrahydrofuran (8 mL) and water (8 mL) were gradually added to a 100 mL single neck flask, then sodium hydroxide (0.11 g, 2.7 mmol) was added. The reaction mixture was stirred for 12 h at rt. The mixture was concentrated in vacuo to remove solvent. To the residue was added water (60 mL). The resulting mixture was washed with ether (50 mL), and the aqueous phase was acidified to pH 1 with 2 N dilute hydrochloric acid, then extracted with ethyl acetate (40 mL×2). The combined organic phases were washed with saturated brine (40 mL×2), dried over anhydrous sodium sulfate, filtered, and concentrated in vacuo, the residue was purified by silica gel chromatography (methanol/dichloromethane (v/v)=1/20) to give the title compound as a white solid (0.09 g, 59%).

MS (ES-API, neg. ion) m/z: 282.1 [M−1]⁻;
HPLC: purity=98%; and $^1$H NMR (400 MHz, DMSO-d$_6$) δ: 7.86 (d, J=8.2 Hz, 1H), 7.75 (s, 1H), 7.45 (s, 1H), 7.40-7.26 (m, 2H), 6.27 (s, 2H).

Example 4: 4-(5-cyano-2,3-dihydrobenzofuran-7-yl)-2-hydroxybenzoic Acid

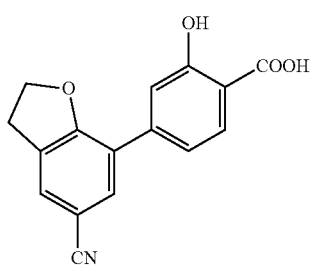 [SMILES: N#Cc1cc2c(c(-c3ccc(C(=O)O)c(O)c3)c1)OCC2]

Step 1) Synthesis of 7-bromo-2,3-dihydrobenzofuran-5-carbaldehyde 2,3-Dihydrobenzofuran-5-carbaldehyde (2.96 g, 2.0 mmol), sodium acetate (1.97 g, 24 mmol) and acetic acid (40 mL) were added to a 100 mL single neck flask, then bromine (6.39 g, 40 mmol) was added at 10° C. The reaction mixture was stirred for 1 h at rt. To the mixture was added ice water (100 mL) and saturated aqueous sodium thiosulfate (10 mL). The resulting mixture was extracted with ethyl acetate (80 mL×2). The combined organic phases were washed with saturated brine (80 mL×2), dried over anhydrous sodium sulfate, filtered, and concentrated in vacuo. The residue was purified by silica gel chromatography (ethyl acetate/petroleum ether (v/v)=1/20) to give the title compound as a pale yellow solid (4.36 g, 96%).

$^1$H NMR (400 MHz, CDCl$_3$) δ: 9.78 (s, 1H), 7.82 (s, 1H), 7.66 (d, J=0.8 Hz, 1H), 4.79 (t, J=8.8 Hz, 2H), 3.38 (t, J=8.8 Hz, 2H).

Step 2) Synthesis of 7-bromo-2,3-dihydrobenzofuran-5-carbonitrile

7-Bromo-2,3-dihydrobenzofuran-5-carbaldehyde (1.82 g, 8.0 mmol), ammonium hydroxide (20 mL, 28%) and tetrahydrofuran (20 mL) were added to a 100 mL single neck flask, then iodine (2.23 g, 8.8 mmol) was added in portions. The reaction mixture was stirred for 4 h at rt. The mixture was quenched with saturated aqueous sodium thiosulfate (100 mL). The resulting mixture was extracted with ethyl acetate (80 mL×2). The combined organic phases were washed with saturated brine (80 mL), dried over anhydrous sodium sulfate, filtered, and concentrated in vacuo. The residue was purified by silica gel chromatography (ethyl acetate/petroleum ether (v/v)=1/15) to give the title compound as a white solid (1.52 g, 85%).

MS (ES-API, pos. ion) m/z: 225.0 [M+2]$^+$.

Step 3) Synthesis of tert-butyl 4-(5-cyano-2,3-dihydrobenzofuran-7-yl)-2-hydroxybenzoate 7-Bromo-2,3-dihydrobenzofuran-5-carbonitrile (0.29 g, 1.0 mmol), tert-butyl 2-hydroxy-4-(4,4,5,5-tetramethyl-1,3,2-dioxaborolan-2-yl) benzoate (0.32 g, 1.0 mmol), 1,1'-bis(diphenylphosphino)ferrocene-palladium(II)dichloride dichloromethane complex (82 mg, 0.10 mmol) and N,N-dimethylformamide (8 mL) were added gradually to a 50 mL two-neck flask. A solution of potassium carbonate (1.0 mL, 2 M) in water was added under nitrogen, then the reaction mixture was stirred for 0.5 h at 90° C. The resulting mixture was cooled to room temperature, and to the mixture was added saturated brine (80 mL). The resulting mixture was extracted with ethyl acetate (40 mL×2). The combined organic phases were washed with saturated brine (60 mL), dried over anhydrous sodium sulfate, filtered, and concentrated in vacuo. The residue was purified by silica gel chromatography (dichloromethane/petroleum ether (v/v)=1/2) to give the title compound as a white solid (0.18 g, 53%).

MS (ES-API, pos. ion) m/z: 338.0 [M+1]$^+$.

Step 4) Synthesis of 4-(5-cyano-2,3-dihydrobenzofuran-7-yl)-2-hydroxybenzoic Acid tert-Butyl 4-(5-cyano-2,3-dihydrobenzofuran-7-yl)-2-hydroxybenzoate (0.18 g, 0.53 mmol) and dichloromethane (12 mL) were added to a 100 mL single neck flask, then trifluoroacetate (2 mL) was added. The reaction mixture was stirred for 12 h at rt. The resulting mixture was concentrated in vacuo to remove solvent. The residue was purified by silica gel chromatography (methanol/dichloromethane (v/v)=1/20) to give the title compound as a white solid (0.11 g, 73%).

MS (ES-API, neg. ion) m/z: 280.1 [M-1]$^-$;
HPLC: purity=95%; and
$^1$H NMR (400 MHz, DMSO-d$_6$) δ: 7.89 (s, 1H), 7.84 (d, J=8.3 Hz, 1H), 7.73 (s, 1H), 7.34 (d, J=1.4 Hz, 1H), 7.30 (m, 1H), 4.82-4.65 (m, 2H), 3.32-3.28 (m, 2H).

Example 5: 4-(6-cyanoimidazo[1,2-a]pyridin-8-yl)-2-hydroxybenzoic Acid

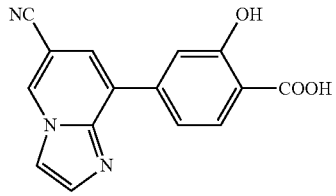 [SMILES: N#Cc1cc(-c2ccc(C(=O)O)c(O)c2)c2nccn2c1]

Step 1) Synthesis of methyl 8-bromoimidazo[1,2-a]pyridin-6-carboxylate

Methyl 6-amino-5-bromonicotinate (2.50 g, 10.8 mmol), sodium bicarbonate (1.55 g, 18.5 mmol) and ethanol (25 mL) were added to a 100 mL single neck flask, then 40% chlorine formaldehyde (8.6 mL, 54 mmol) was added. The reaction mixture was heated to reflux and reacted for 12 h. The resulting mixture was cooled to room temperature, and diluted with saturated aqueous sodium bicarbonate (100 mL). The mixture was extracted with ethyl acetate (80 mL×2). The combined organic phases were washed with saturated brine (80 mL), dried over anhydrous sodium sulfate, filtered, and concentrated in vacuo. The residue was purified by silica gel chromatography (100% dichloromethane) to give the title compound as a white solid (2.19 g, 79%).

MS (ES-API, pos. ion) m/z: 256.0 [M+2]$^+$.

Step 2) Synthesis of 8-bromoimidazo[1,2-a]pyridin-6-carboxamide

Methyl 8-bromoimidazo[1,2-a]pyridin-6-carboxylate (2.5 g, 9.8 mmol) and ammonia (20 mL, 7 M in methanol) were added sequentially to a 100 mL sealed tube. The mixture was heated to 130° C. and stirred for 48 h. The resulting mixture was cooled to room temperature and concentrated in vacuo to remove solvent. The residue was purified by silica gel chromatography (methanol/dichloromethane=1/50) to give the title compound as a white solid (1.64 g, 70%).

MS (ES-API, pos. ion) m/z: 241.0 [M+2]$^+$.

Step 3) Synthesis of 8-bromoimidazo[1,2-a]pyridin-6-carbonitrile

8-Bromoimidazo[1,2-a]pyridin-6-carboxamide (0.55 g, 2.3 mmol) and toluene (25 mL) were added to a 100 mL of single neck flask, and phosphorus oxychloride (1.5 mL, 16 mmol) was added dropwise. The reaction mixture was stirred for 12 h at 120° C. The resulting mixture was cooled to room temperature and concentrated in vacuo to remove solvent. To the residue was added saturated brine (80 mL) and ethyl acetate (100 mL), and the resulting mixture was partitioned. The organic phase was washed with saturated brine (60 mL×2), dried over anhydrous sodium sulfate, filtered, and concentrated in vacuo. The residue was purified by silica gel chromatography (ethyl acetate/petroleum ether (v/v)=1/2) to give the title compound as a white solid (0.42 g, 83%).

MS (ES-API, pos. ion) m/z: 222.9 [M+2]$^+$.

Step 4) Synthesis of methyl 4-(6-cyanoimidazo[1,2-a]pyridin-8-yl)-2-hydroxybenzoate 8-Bromoimidazo[1,2-a]pyridin-6-carbonitrile (0.40 g, 1.9 mmol), methyl 2-hydroxy-4-(4,4,5,5-tetramethyl-1,3,2-dioxaborolan-2-yl) benzoate (0.46 g, 1.7 mmol), 1,1'-bis(diphenylphosphino)ferrocene-palladium(II)dichloride dichloromethane complex (120 mg, 0.16 mmol) and N,N-dimethylformamide (8 mL) were added gradually to a 50 mL two-neck flask. A solution of potassium carbonate (1.7 mL, 2 M) in water was added under nitrogen, then the reaction mixture was stirred for 0.5 h at 90° C. The resulting mixture was cooled to room temperature, diluted with saturated brine (80 mL). The mixture was extracted with ethyl acetate (40 mL×2). The combined organic phase was washed with saturated brine (60 mL), dried over anhydrous sodium sulfate, filtered, and concentrated in vacuo. The residue was purified by silica gel chromatography (100% dichloromethane) to give the title compound as a white solid (0.21 g, 43%).

MS (ES-API, pos. ion) m/z: 294.0 [M+1]$^+$.

Step 5) Synthesis of 4-(6-cyanoimidazo[1,2-a]pyridin-8-yl)-2-hydroxybenzoic Acid Methyl 4-(6-cyanoimidazo[1,2-a]pyridin-8-yl)-2-hydroxybenzoate (0.21 g, 0.72 mmol), methanol (8 mL), tetrahydrofuran (8 mL) and water (8 mL) were gradually added to a 100 mL single neck flask, then sodium hydroxide (0.14 g, 3.6 mmol) was added. The reaction mixture was stirred for 12 h at rt. The mixture was concentrated in vacuo to remove solvent. To the residue was added water (60 mL). The resulting mixture was washed with ether (50 mL), and the aqueous phase was acidified to pH 1 with 2 N dilute hydrochloric acid, then the resulting mixture was extracted with ethyl acetate (40 mL×2). The combined organic phases were washed with saturated brine (40 mL×2), dried over anhydrous sodium sulfate, filtered, and concentrated in vacuo, the residue was purified by silica gel chromatography (methanol/dichloromethane (v/v)=1/10) to give the title compound as a white solid (0.053 g, 27%).

MS (ES-API, pos. ion) m/z: 280.1 [M+1]$^+$;
HPLC: purity=98%; and
$^1$H NMR (400 MHz, DMSO-d$_6$) δ: 9.40 (s, 1H), 8.15 (s, 1H), 7.89-7.83 (m, 4H), 7.65 (d, J=8.1 Hz, 1H).

Example 6: 4-(6-cyano-1-methyl-2-(trifluoromethyl)-1H-indol-4-yl)-2-hydroxybenzoic Acid

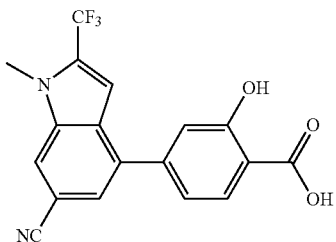 [SMILES: Cn1c(C(F)(F)F)cc2c(-c3ccc(C(=O)O)c(O)c3)cc(C#N)cc21]

Step 1) Synthesis of 3-bromo-4-methyl-5-nitrobenzoic Acid

4-Methyl-3-nitrobenzoic acid (17.7 g, 94.8 mmol) and concentrated sulfuric acid (80 mL, 98%) were added to a 250 mL two-neck flask, then 1,3-dibromo-5,5-dimethylhydantoin (13.8 g, 47.3 mmol) was added in portions. The reaction mixture was stirred for 2 h at rt. The resulting mixture was poured into ice water. The precipitated yellow solid was filtered and the filter cake was dried to give the title compound as a yellow solid (22.3 g, 86%).

MS (ES-API, neg. ion) m/z: 257.0 [M−2]$^-$.

Step 2) Synthesis of methyl 3-bromo-4-methyl-5-nitrobenzoate

3-Bromo-4-methyl-5-nitrobenzoic acid (22.3 g, 85.8 mmol) and anhydrous methanol (200 mL) were added to a 500 mL single neck flask, then thionyl chloride (13.7 mL, 189 mmol) was added at 0° C. The reaction mixture was warmed to 80° C. and reacted for 6 h. The mixture was cooled to room temperature and concentrated in vacuo to remove solvent. To the residue was added saturated brine (200 mL) and ethyl acetate (300 mL), and the resulting mixture was partioned. The organic phase was washed with saturated brine (80 mL×2), dried over anhydrous sodium sulfate, filtered, and concentrated in vacuo. The residue was purified by silica gel chromatography (ethyl acetate/petroleum ether (v/v)=1/50) to give the title compound as a pale yellow solid (21.3 g, 77%).

$^1$H NMR (400 MHz, CDCl$_3$) δ: 8.45 (d, J=1.4 Hz, 1H), 8.36 (d, J=1.3 Hz, 1H), 3.98 (s, 3H), 2.64 (s, 3H).

Step 3) Synthesis of methyl 3-amino-5-bromo-4-methylbenzoate

Methyl 3-bromo-4-methyl-5-nitrobenzoate (7.65 g, 27.9 mmol), acetic acid (20 mL), methanol (80 mL) and tetrahydrofuran (20 mL) were added to a 250 mL single neck flask, then zinc (11.0 g, 168 mmol) was added in portions. The reaction mixture was stirred for 1 h at rt. The mixture was concentrated in vacuo to remove solvent. To the residue was added saturated brine (200 mL) and ethyl acetate (200 mL), and the resulting mixture was partitioned. The organic phase was washed with saturated brine (80 mL×2), dried over anhydrous sodium sulfate, filtered, and concentrated in vacuo. The residue was purified by silica gel chromatography (ethyl acetate/petroleum ether (v/v)=1/15) to give the title compound as a yellow solid (4.3 g, 63%).

MS (ES-API, pos. ion) m/z: 245.0 [M+2]$^+$.

Step 4) Synthesis of methyl 3-bromo-4-methyl-5-(2,2,2-trifluoro acetamido) benzoate Methyl 3-amino-5-bromo-4-methylbenzoate (1.15 g, 4.62 mmol), triethylamine (1.28 mL, 9.21 mmol) and dichloromethane (20 mL) were added to a 100 mL two-neck flask, then trifluoroacetic anhydride (0.79 mL, 5.6 mmol) was added dropwise at 0° C. The reaction mixture was stirred for 1 h at rt. The mixture was concentrated in vacuo to remove solvent. To the residue was added saturated brine (80 mL) and ethyl acetate (80 mL), and the resulting mixture was partitioned. The organic phase was washed with saturated brine (40 mL×2), dried over anhydrous sodium sulfate, filtered and concentrated in vacuo to give the title compound as a yellow solid (1.5 g, 95%).

MS (ES-API, pos. ion) m/z: 341.0 [M+2]$^+$.

Step 5) Synthesis of methyl 3-bromo-4-(chloromethyl)-5-(2,2,2-trifluoroacetamido)benzoate Methyl 3-bromo-4-methyl-5-(2,2,2-trifluoroacetamido) benzoate (1.5 g, 4.4 mmol), sulfuryl chloride (1.46 mL, 17.6 mmol), benzoyl peroxide (0.21 g, 0.88 mmol) and carbon tetrachloride (20 mL) were added to a 100 mL two-neck flask. The reaction mixture was stirred for 3 h at 80° C. under nitrogen. The resulting mixture was cooled to room temperature and concentrated in vacuo to remove solvent. To the residue was added saturated brine (80 mL) and ethyl acetate (80 mL), and the resulting mixture was partitioned. The organic phase was washed with saturated brine (40 mL×2), dried over anhydrous sodium sulfate, filtered and concentrated in vacuo to give the title compound as a yellow solid (1.45 g, 88%).

MS (ES-API, neg. ion) m/z: 370.9 [M–2]$^-$.

Step 6) Synthesis of (2-bromo-4-(methoxycarbonyl)-6(2,2,2-trifluoroacetamido) benzyl) triphenylphosphonium chloride Methyl 3-bromo-4-(chloromethyl)-5-(2,2,2-trifluoroacetamido) benzoate (12.1 g, 32.4 mmol), triphenylphosphine (9.36 g, 35.7 mmol) and toluene (200 mL) were added to a 500 mL single-neck flask. The reaction mixture was stirred for 6 h at 100° C. under nitrogen. The mixture was cooled to room temperature and concentrated in vacuo, and the residue was purified by silica gel chromatography (methanol/dichloromethane (v/v)=1/50) to give the title compound as a yellow solid (13.0 g, 63%).

MS (ES-API, neg. ion) m/z: 598.0 [M–2]$^-$.

Step 7) Synthesis of methyl 4-bromo-2-(trifluoromethyl)-1H-indole-6-carboxylate (2-Bromo-4-(methoxycarbonyl)-6(2,2,2-trifluoroacetamido)benzyl)triphenylphosphonium chloride (13.0 g, 20.4 mmol) and N,N-dimethylformamide (40 mL) were added to a 100 mL single-neck flask. The reaction mixture was stirred for 26 h at 140° C. The resulting mixture was cooled to room temperature and to the mixture was added saturated brine (60 mL). The mixture was extracted with ethyl acetate (60 mL×2). The combined organic phases were washed with saturated brine (60 mL), dried over anhydrous sodium sulfate, filtered, and concentrated in vacuo. The residue was purified by silica gel chromatography (ethyl acetate/petroleum ether (v/v)=1/10) to give the title compound as a pale yellow solid (2.5 g, 38%).

MS (ES-API, neg. ion) m/z: 319.1 [M–2]$^-$.

Step 8) Synthesis of 4-bromo-2-(trifluoromethyl)-1H-indole-6-carboxamide

Methyl 4-bromo-2-(trifluoromethyl)-1H-indole-6-carboxylate (2.7 g, 8.4 mmol) and ammonia (20 mL, 7 M in methanol) were added sequentially to a 100 mL sealed tube. The reaction mixture was stirred for 72 h at 130° C. The resulting mixture was cooled to room temperature and concentrated in vacuo to remove solvent. The residue was purified by silica gel chromatography (methanol/dichloromethane (v/v)=1/50) to give the title compound as a yellow solid (1.5 g, 58%).

MS (ES-API, pos. ion) m/z: 308.0 [M+2]$^+$.

Step 9) Synthesis of 4-bromo-2-(trifluoromethyl)-1H-indole-6-carbonitrile

4-Bromo-2-(trifluoromethyl)-1H-indole-6-carboxamide (1.5 g, 4.9 mmol) and toluene (25 mL) were added to a 100 mL single neck flask, then phosphorus oxychloride (2.3 mL, 24.5 mmol) was added dropwise, and the reaction mixture was stirred for 12 h at 120° C. The resulting mixture was cooled to room temperature and concentrated in vacuo to remove solvent. To the residue was added saturated brine (80 mL) and ethyl acetate (100 mL), and the resulting mixture was partitioned. The organic phase was washed with saturated brine (60 mL×2), dried over anhydrous sodium sulfate, filtered, and concentrated in vacuo, the residue was purified by silica gel chromatography (ethyl acetate/petroleum ether (v/v)=1/20) to give the title compound as a yellow solid (0.78 g, 55%).

MS (ES-API, neg. ion) m/z: 286.0 [M–2]$^-$.

Step 10) Synthesis of 4-bromo-1-methyl-2-(trifluoromethyl)-1H-indole-6-carbonitrile 4-Bromo-2-(trifluoromethyl)-1H-indole-6-carbonitrile (0.50 g, 1.73 mmol) and N,N-dimethylformamide (10 mL) were added to a 50 mL two-neck flask, then sodium hydride (0.50 g, 1.95 mmol, 60%) was added. The mixture was stirred for 0.5 h at 0° C., and then iodomethane (0.20 mL, 3.2 mmol) was added dropwise. The reaction mixture was stirred for 12 h at rt and concentrated in vacuo to remove solvent. To the residue was added saturated brine (80 mL) and ethyl acetate (80 mL), and the resulting mixture was partitioned. The organic phase was washed with saturated brine (40 mL×2), dried over anhydrous sodium sulfate, filtered, and concentrated in vacuo, the residue was purified by silica gel chromatography (ethyl acetate/petroleum ether (v/v)=1/10) to give the title compound as a yellow solid (0.36 g, 69%).

MS (ES-API, pos. ion) m/z: 304.0 [M+2]$^+$.

Step 11) Synthesis of methyl 4-(6-cyano-1-methyl-2-(trifluoromethyl)-1H-indol-4-yl)-2-hydroxybenzoate 4-Bromo-1-methyl-2-(trifluoromethyl)-1H-indole-6-carbonitrile (0.36 g, 1.19 mmol), methyl 2-hydroxy-4-(4,4,5, 5-tetramethyl-1,3,2-dioxaborolan-2-yl) benzoate (0.30 g, 1.08 mmol), 1,1'-bis(diphenylphosphino)ferrocene-palladium(II)dichloride dichloromethane complex (48 mg, 0.059 mmol) and N,N-dimethylformamide (8 mL) were added gradually to a 50 mL two-neck flask. A solution of potassium carbonate (1.1 mL, 2 M) in water was added under nitrogen, then the reaction mixture was stirred for 0.5 h at 90° C. The resulting mixture was cooled to room temperature, diluted with saturated brine (80 mL). The mixture was extracted with ethyl acetate (40 mL×2). The combined organic phases were washed with saturated brine (60 mL), dried over anhydrous sodium sulfate, filtered, and concentrated in vacuo. The residue was purified by silica gel chromatography (ethyl acetate/petroleum ether (v/v)=1/15) to give the title compound as a pale yellow solid (70 mg, 17%).

MS (ES-API, pos. ion) m/z: 375.2 [M+1]$^+$.

Step 12) Synthesis of 4-(6-cyano-1-methyl-2-(trifluoromethyl)-1H-indol-4-yl)-2-hydroxybenzoic Acid Methyl 4-(6-cyano-1-methyl-2-(trifluoromethyl)-1H-indol-4-yl)-2-hydroxybenzoate (70 mg, 0.19 mmol), methanol (6 mL), tetrahydrofuran (6 mL) and water (6 mL) were gradually added to a 100 mL single neck flask, then sodium hydroxide (75 mg, 1.88 mmol) was added. The reaction mixture was stirred for 12 h at rt. The mixture was concentrated in vacuo to remove solvent. To the residue was added water (60 mL). The resulting mixture was washed with ether (50 mL), and the aqueous phase was acidified to pH 1 with 2 N dilute hydrochloric acid and extracted with ethyl acetate (40 mL×2). The combined organic phases were washed with saturated brine (40 mL×2), dried over anhydrous sodium sulfate, filtered, and concentrated in vacuo. The residue was purified by silica gel chromatography (methanol/dichloromethane (v/v)=1/20) to give the title compound as a pale yellow solid (45 mg, 67%).

MS (ES-API, pos. ion) m/z: 361.2 [M+1]$^+$;
HPLC: purity=98%; and
$^1$H NMR (400 MHz, DMSO-d$_6$) δ: 8.41 (s, 1H), 7.93 (s, 1H), 7.65 (s, 1H), 7.23-7.19 (m, 3H), 3.98 (s, 3H).

Example 7: 4-(5-cyano-1H-indol-7-yl)-2-hydroxybenzoic Acid

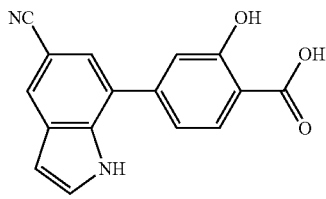 [SMILES: N#Cc1cc(-c2ccc(C(=O)O)c(O)c2)c2[nH]ccc2c1]

Step 1) Synthesis of 7-bromo-1H-indole-5-carboxylic Acid

3-Bromo-4-nitrobenzoic acid (0.30 g, 1.2 mmol) and anhydrous tetrahydrofuran (10 mL) were added to a 100 mL two-neck flask, then vinylmagnesium bromide (4.3 mL, 4.3 mmol, 1 mol/L in tetrahydrofuran) was added dropwise at −75° C. under nitrogen. The reaction mixture was stirred for 2 h at −75° C. To the resulting mixture was added saturated ammonium chloride (60 mL) and ethyl acetate (80 mL), and the mixture was partitioned. The organic phase was washed with saturated brine (40 mL×2), dried over anhydrous sodium sulfate, filtered, and concentrated in vacuo, then the residue was purified by silica gel chromatography (methanol/dichloromethane (v/v)=1/50) to give the title compound as a pale yellow solid (0.12 g, 41%).

MS (ES-API, pos. ion) m/z: 241.0 [M+2]$^+$.

Step 2) Synthesis of 7-bromo-1H-indole-5-carboxamide

7-Bromo-1H-indole-5-carboxylic acid (0.50 g, 2.1 mmol), ammonium chloride (0.22 g, 4.1 mmol) and anhydrous N,N-dimethylformamide (12 mL) were gradually added to a 50 mL two-neck flask, then 2-(7-aza-1H-benzotriazole-1-yl)-1,1,3,3-tetramethyluronium hexafluorophosphate (0.95 g, 2.5 mmol) and N,N-diisopropylethylamine (1.0 mL, 6.1 mmol) were added at 0° C. The reaction mixture was stirred for 2 h at rt. To the resulting mixture was added saturated ammonium chloride (100 mL) and ethyl acetate (100 mL). The organic phase was washed with saturated brine (60 mL×2), dried over anhydrous sodium sulfate, filtered, and concentrated in vacuo, then the residue was purified by silica gel chromatography (methanol/dichloromethane (v/v)=1/50) to give the title compound as a white solid (0.42 g, 84%).

MS (ES-API, neg. ion) m/z: 236.0 [M−2]$^-$.

Step 3) Synthesis of 7-bromo-1H-indole-5-carbonitrile

7-Bromo-1H-indole-5-carboxamide (0.91 g, 3.8 mmol) and toluene (20 mL) were added to a 100 mL single neck flask, and phosphorus oxychloride (2.4 mL, 26 mmol) was added dropwise, then the reaction mixture was stirred for 12 h at 120° C. The resulting mixture was cooled to room temperature and concentrated in vacuo to remove solvent. To the residue was added saturated brine (80 mL) and ethyl acetate (100 mL), and the resulting mixture was partitioned. The organic phase was washed with saturated brine (60 mL×2), dried over anhydrous sodium sulfate, filtered, and concentrated in vacuo, then the residue was purified by silica gel chromatography (ethyl acetate/petroleum ether (v/v)=1/5) to give the title compound as a white solid, 0.49 g, 58%).

MS (ES-API, neg. ion) m/z: 218.0 [M−1]$^-$.

Step 4) Synthesis of tert-butyl 7-bromo-5-cyano-1H-indole-1-carboxylate

7-Bromo-1H-indole-5-carbonitrile (0.49 g, 2.2 mmol), di-tert-butyl dicarbonate (0.59 mL, 2.6 mmol) and dichloromethane (20 mL) were added to a 100 mL single neck flask, then 4-dimethylaminopyridine (0.027 g, 0.22 mmol) was added. The reaction mixture was stirred for 3 h at rt. The resulting mixture was concentrated in vacuo to remove solvent, and the residue was purified by silica gel chromatography (ethyl acetate/petroleum ether (v/v)=1/50) to give the title compound as a white solid (0.67 g, 94%).

Step 5) Synthesis of tert-butyl 7-(4-tert-butoxycarbonyl)-3-hydroxyphenyl)-5-cyano-1H-indole-1-carboxylate tert-Butyl 7-bromo-5-cyano-1H-indole-1-carboxylate (0.67 g, 2.1 mmol), tert-butyl 2-hydroxy-4-(4,4,5,5-tetramethyl-1,3,2-dioxaborolan-2-yl) benzoate (0.53 g, 1.7 mmol), 1,1'-bis(diphenylphosphino)ferrocene-palladium(II)dichloride dichloromethane complex (140 mg, 0.19 mmol) and N,N-dimethylformamide (12 mL) were added gradually to a 50 mL two-neck flask. A solution of potassium carbonate (1.1 mL, 2 M) in water was added under nitrogen, then the reaction mixture was stirred for 0.5 h at 90° C. The resulting mixture was cooled to room temperature, diluted with saturated brine (80 mL). The mixture was extracted with ethyl acetate (40 mL×2). The combined organic phases were washed with saturated brine (60 mL), dried over anhydrous sodium sulfate, filtered, and concentrated in vacuo, then the residue was purified by silica gel chromatography (ethyl acetate/petroleum ether (v/v)=1/50) to give the title compound as a white solid (0.61 g, 85%).

MS (ES-API, neg. ion) m/z: 433.1 [M−1]$^-$.

Step 6) Synthesis of 4-(5-cyano-1H-indol-7-yl)-2-hydroxybenzoic Acid tert-Butyl 7-(4-tert-butoxycarbonyl)-3-hydroxyphenyl)-5-cyano-1H-indole-1-carboxylate (0.61 g, 1.4 mmol) and dichloromethane (12 mL) were added to a 100 mL single neck flask, then trifluoroacetic acid (5 mL) was added. The reaction mixture was stirred for 12 h at rt. The resulting mixture was concentrated in vacuo to remove solvent, and the residue was purified by silica gel chromatography (methanol/dichloromethane (v/v)=1/20) to give the title compound as a white solid (78 mg, 20%).

MS (ES-API, pos. ion) m/z: 279.1 [M+1]$^+$;

HPLC: purity=99%; and $^1$H NMR (400 MHz, DMSO) δ: 11.61 (s, 1H), 8.13 (s, 1H), 7.91 (d, J=7.8 Hz, 1H), 7.53 (s, 1H), 7.49 (s, 1H), 7.14-7.12 (m, 2H), 6.70 (s, 1H).

Example 8: 4-(5-cyano-2-(trifluoromethyl)-1H-indol-7-yl)-2-hydroxybenzoic Acid

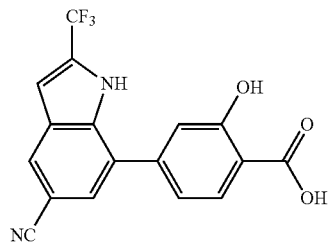 [SMILES: N#Cc1cc(-c2ccc(C(=O)O)c(O)c2)c2[nH]c(C(F)(F)F)cc2c1]

Step 1) Synthesis of N-(4-cyano-2-methylphenyl)-2,2,2-trifluoroacetamide

4-Amino-3-methylbenzonitrile (0.611 g, 4.62 mmol), triethylamine (1.28 mL, 9.21 mmol) and dichloromethane (20 mL) were added to a 100 mL two-neck flask, then trifluoroacetic anhydride (0.79 mL, 5.6 mmol) was added at 0° C. The reaction mixture was stirred for 1 h at rt. The resulting mixture was concentrated in vacuo to remove solvent. To the residue was added saturated brine (80 mL) and ethyl acetate (80 mL), and the mixture was partitioned. The organic phase was washed with saturated brine (40 mL×2), dried over anhydrous sodium sulfate, filtered, and concentrated in vacuo to give the title compound as a yellow solid (1.0 g, 95%).

MS (ES-API, pos. ion) m/z: 229.0 [M+1]$^+$.

Step 2) Synthesis of N-(2-(chloromethyl)-4-cyanophenyl)-2,2,2-trifluoroacetamide N-(4-cyano-2-methylphenyl)-2,2,2-trifluoroacetamide (1.0 g, 4.4 mmol), sulfuryl chloride (1.46 mL, 17.6 mmol), benzoyl peroxide (0.21 g, 0.88 mmol) and carbon tetrachloride (20 mL) were added to a 100 mL single neck flask. The reaction mixture was heated to 80° C. and stirred for 3 h under nitrogen. The resulting mixture was cooled to room temperature and concentrated in vacuo to remove solvent. To the residue was added saturated brine (80 mL) and ethyl acetate (80 mL), and the mixture was partitioned. The organic phase was washed with saturated brine (40 mL×2), dried over anhydrous sodium sulfate, filtered, and concentrated in vacuo to give the title compound as yellow oil (1.14 g, 99%).

MS (ES-API, pos. ion) m/z: 263.0 [M+1]$^+$.

Step 3) Synthesis of (5-cyano-2-(2,2,2-trifluoroacetamido)benzyl)triphenylphosphonium chloride N-(2-(chloromethyl)-4-cyanophenyl)-2,2,2-trifluoroacetamide (8.51 g, 32.4 mmol), triphenylphosphine (9.36 g, 35.7 mmol) and toluene (200 mL) were added to a 500 mL single neck flask. The reaction mixture was heated to 100° C. and stirred for 6 h under nitrogen. The resulting mixture was cooled to room temperature and concentrated in vacuo to remove the solvent, and the residue was purified by silica gel chromatography (methanol/dichloromethane (v/v)=1/50) to give the title compound as a yellow solid (7.99 g, 47%).

MS (ES-API, pos. ion) m/z: 525.1 [M+1]$^+$.

Step 4) Synthesis of (3-bromo-5-cyano-2-(2,2,2-trifluoroacetamido)benzyl) triphenylphosphonium bromide (5-Cyano-2-(2,2,2-trifluoro acetamido)benzyl)triphenylphosphonium chloride (1.00 g, 1.91 mmol), activated carbon (1.00 g) and N,N-dimethylformamide (20 mL) were added to a 100 mL single neck flask. The reaction mixture was stirred for 6 h at rt. The resulting mixture was filtered and the filter cake was washed with N,N-dimethylformamide (10 mL). To the combined filtrates was added N-bromosuccinimide (1.04 g, 5.73 mmol), and the reaction mixture was stirred 24 h at rt. Then to the mixture was added N-bromosuccinimide (1.04 g, 5.73 mmol), the reaction mixture was stirred for 36 h at rt. To the resulting mixture was added saturated aqueous sodium thiosulfate (80 mL) and ethyl acetate (80 mL), then the mixture was partitioned. The organic phase was washed with saturated brine (40 mL×2), dried over anhydrous sodium sulfate, filtered, and concentrated in vacuo, the residue was purified by silica gel chromatography (methanol/dichloromethane (v/v)=1/100) to give the title compound as a yellow solid (0.384 g, 31%).

MS (ES-API, pos. ion) m/z: 648.9 [M+3]$^+$.

Step 5) Synthesis of 7-bromo-2-(trifluoromethyl)-1H-indole-5-carbonitrile (3-Bromo-5-cyano-2-(2,2,2-trifluoro acetamido)benzyl) triphenylphosphonium bromide (1.3 g, 2.0 mmol) and N,N-dimethylformamide (20 mL) were added to a 100 mL single neck flask, and the reaction mixture was stirred for 3 h at 130° C. The resulting mixture was cooled to room temperature. To the resulting mixture was added saturated brine (100 mL). The mixture was extracted with ethyl acetate (60 mL×2). The combined organic phases were washed with saturated brine (60 mL), dried over anhydrous sodium sulfate, filtered, and concentrated in vacuo, and the residue was purified by silica gel chromatography (ethyl acetate/petroleum ether (v/v)=1/20) to give the title compound as a pale yellow solid (0.40 g, 70%).

$^1$H NMR (400 MHz, DMSO-d$_6$) δ (ppm): 13.15 (s, 1H), 8.32 (s, 1H), 8.01 (s, 1H), 7.33 (s, 1H).

Step 6) Synthesis of methyl 4-(5-cyano-2-(trifluoromethyl)-1H-indol-7-yl)-2-hydroxybenzoate 7-Bromo-2-(trifluoromethyl)-1H-indole-5-carbonitrile (340 mg, 1.19 mmol), methyl 2-hydroxy-4-(4,4,5,5-tetramethyl-1,3,2-dioxaborolan-2-yl) benzoate (300 mg, 1.08 mmol), 1,1'-bis(diphenylphosphino)ferrocene-palladium(II) dichloride dichloromethane complex (48 mg, 0.059 mmol) and N,N-dimethylformamide (8 mL) were added gradually to a 50 mL two-neck flask. A solution of potassium carbonate (1.1 mL, 2 M) in water was added under nitrogen, then the reaction mixture was stirred for 0.5 h at 90° C. The resulting mixture was cooled to room temperature. To the resulting mixture was added saturated brine (80 mL). The mixture was extracted with ethyl acetate (40 mL×2). The combined organic phases were washed with saturated brine (60 mL), dried over anhydrous sodium sulfate, filtered, and concentrated in vacuo, then the residue was purified by silica gel chromatography (ethyl acetate/petroleum ether (v/v)=1/15) to give the title compound as a pale yellow solid (240 mg, 57%).

MS (ES-API, pos. ion) m/z: 361.0 [M+1]$^+$.

Step 7) Synthesis of 4-(5-cyano-2-(trifluoromethyl)-1H-indol-7-yl)-2-hydroxybenzoic Acid Methyl 4-(5-cyano-2-(trifluoromethyl)-1H-indol-7-yl)-2-hydroxybenzoate (240 mg, 0.67 mmol), methanol (8 mL), tetrahydrofuran (8 mL) and water (8 mL) were gradually added to a 100 mL single neck flask, then sodium hydroxide (80 mg, 2.0 mmol) was added. The reaction mixture was stirred for 12 h at rt. The mixture was concentrated in vacuo to remove solvent. To the residue was added water (60 mL). The mixture was washed with ether (50 mL), and the aqueous phase was acidified to pH 1 with 2 N dilute hydrochloric acid and extracted with ethyl acetate (40 mL×2). The combined organic phases were washed with saturated brine (40 mL×2), dried over anhydrous sodium sulfate, filtered, and concentrated in vacuo. The residue was purified by silica gel chromatography (methanol/dichloromethane (v/v)=1/20) to give the title compound as a pale yellow solid (144 mg, 62%).

MS (ES-API, pos. ion) m/z: 347.0 [M+1]$^+$; and $^1$H NMR (400 MHz, DMSO-d$_6$) δ (ppm): 12.69 (s, 1H), 8.31 (s, 1H), 7.95 (d, J=7.9 Hz, 1H), 7.67 (s, 1H), 7.30 (s, 1H), 7.25-7.05 (m, 2H).

Example 9: 4-(5-cyano-1-methyl-2-(trifluoromethyl)-1H-indol-7-yl)-2-hydroxybenzoic Acid

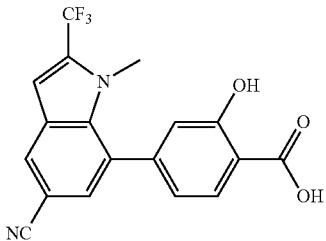 [SMILES: Cn1c(C(F)(F)F)cc2cc(C#N)cc(-c3ccc(C(=O)O)c(O)c3)c21]

Step 1) Synthesis of 7-bromo-1-methyl-2-(trifluoromethyl)-1H-indole-5-carbonitrile 7-Bromo-2-(trifluoromethyl)-1H-indole-5-carbonitrile (500 mg, 1.73 mmol) and N,N-dimethylformamide (10 mL) were added to a 50 mL two-neck flask, and 60% sodium hydride (500 mg, 1.95 mmol) was added. The mixture was stirred for 0.5 h at 0° C., iodomathane (0.20 mL, 3.2 mmol) was added dropwise. The reaction mixture was stirred for 12 h at rt. The resulting mixture was concentrated in vacuo to remove the solvent. To the residue was added saturated brine (80 mL) and ethyl acetate (80 mL), and the mixture was partitioned. The organic phase was washed with saturated brine (40 mL×2), dried over anhydrous sodium sulfate, filtered, and concentrated in vacuo, then the residue was purified by silica gel chromatography (ethyl acetate/petroleum ether (v/v)=1/50) to give the title compound as a yellow solid (500 mg, 96%).

MS (ES-API, pos. ion) m/z: 304.0 [M+2]$^+$.

Step 2) Synthesis of methyl 4-(5-cyano-1-methyl-2-(trifluoromethyl)-1H-indole-7-yl)-2-hydroxy-benzoate 7-Bromo-1-methyl-2-(trifluoromethyl)-1H-indole-5-carbonitrile (360 mg, 1.19 mmol), methyl 2-hydroxy-4-(4,4,5,5-tetramethyl-1,3,2-dioxaborolan-2-yl) benzoate (300 mg, 1.08 mmol), 1,1'-bis(diphenylphosphino)ferrocene-palladium(II)dichloride dichloromethane complex (48 mg, 0.059 mmol) and N,N-dimethylformamide (8 mL) were added gradually to a 50 mL two-neck flask. A solution of potassium carbonate (1.1 mL, 2 M) in water was added under nitrogen, then the reaction mixture was stirred for 0.5 h at 90° C. The resulting mixture was cooled to room temperature. To the resulting mixture was added saturated brine (80 mL). The mixture was extracted with ethyl acetate (40 mL×2). The combined organic phases were washed with saturated brine (60 mL), dried over anhydrous sodium sulfate, filtered, and concentrated in vacuo, then the residue was purified by silica gel chromatography (ethyl acetate/petroleum ether (v/v)=1/15) to give the title compound as a pale yellow solid (140 mg, 32%).

MS (ES-API, pos. ion) m/z: 375.1 [M+1]$^+$.

Step 3) Synthesis of 4-(5-cyano-1-methyl-2-(trifluoromethyl)-1H-indol-7-yl)-2-hydroxybenzoic Acid Methyl 4-(5-cyano-1-methyl-2-(trifluoromethyl)-1H-indole-7-yl)-2-hydroxybenzoate (140 mg, 0.37 mmol), methanol (8 mL), tetrahydrofuran (8 mL) and water (8 mL) were gradually added to a 100 mL single neck flask, then sodium hydroxide (45 mg, 1.12 mmol) was added. The reaction mixture was stirred for 12 h at rt. The mixture was concentrated in vacuo to remove solvent. To the residue was added water (60 mL). The mixture was washed with ether (50 mL), then the aqueous phase was acidified to pH 1 with 2 N dilute hydrochloric acid and extracted with ethyl acetate (40 mL×2). The combined organic phases were washed with saturated brine (40 mL×2), dried over anhydrous sodium sulfate, filtered, and concentrated in vacuo, then the residue was purified by silica gel chromatography (methanol/dichloromethane (v/v)=1/20) to give the title compound as a pale yellow solid (85 mg, 64%).

MS (ES-API, pos. ion) m/z: 361.0 [M+1]$^+$; and $^1$H NMR (400 MHz, DMSO-d6) δ (ppm): 8.34 (s, 1H), 7.89 (s, 1H), 7.51 (s, 1H), 7.40 (s, 1H), 7.12-7.05 (m, 2H), 3.40 (s, 3H).

Example 10: 4-(6-cyano-1-methyl-1H-indazol-4-yl)-2-hydroxybenzoic Acid

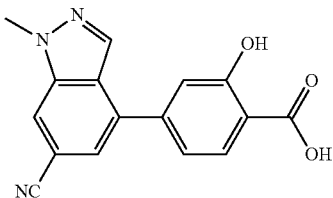 [SMILES: Cn1ncc2c(-c3ccc(C(=O)O)c(O)c3)cc(C#N)cc21]

Step 1) Synthesis of 3-bromo-4-methyl-5-nitrobenzoic Acid

4-Methyl-3-nitrobenzoic acid (5.43 g, 30 mmol) and concentrated sulfuric acid (45 mL, 98%) were added to a 250 mL two-neck flask, then 1,3-dibromo-5,5-dimethylhydantoin (4.29 g, 15 mmol) was added in portions. The reaction mixture was stirred for 16 h at rt. The resulting mixture was poured into ice-water (1000 mL). The mixture was extracted with ethyl acetate (150 mL×2). The combined organic phases were washed with saturated brine (100 mL), dried over anhydrous sodium sulfate, filtered, and concentrated in vacuo, then the residue was purified by silica gel chromatography (methanol/dichloromethane (v/v)=1/30) to give the title compound as a white solid (7.1 g, 91%).

MS (ES-API, pos. ion) m/z: 260.9 [M+2]$^+$.

Step 2) Synthesis of methyl 3-bromo-4-methyl-5-nitrobenzoate

3-Bromo-4-methyl-5-nitrobenzoic acid (7.10 g, 27.3 mmol) and methanol (100 mL) were added to a 250 mL single-neck flask, then dichloro sulfoxide (2.96 mL, 41.0 mmol) was added dropwise at 0° C. The reaction mixture was stirred for 12 h at 90° C. The resulting mixture was concentrated in vacuo to remove the solvent. To the residue was added saturated sodium bicarbonate (200 mL) and the mixture was extracted with ethyl acetate (100 mL×2). The combined organic phases were washed with saturated brine (100 mL), dried over anhydrous sodium sulfate, filtered, and concentrated in vacuo, then the residue was purified by silica gel chromatography (ethyl acetate/petroleum ether (v/v)=1/30) to give the title compound as a pale yellow solid (6.36 g, 85%).

Step 3) Synthesis of methyl 3-amino-5-bromo-4-methylbenzoate

Methyl 3-bromo-4-methyl-5-nitrobenzoate (8.50 g, 31.0 mmol), acetic acid (20 mL) and tetrahydrofuran (170 mL) were added to a 500 mL single-neck flask, then the iron (8.68 g, 155 mmol) was added in portions. The reaction mixture was stirred for 12 h at 75° C. The resulting mixture was cooled to room temperature, filtered to remove the insoluble solid, and the filtrate was concentrated in vacuo. To the residue was added water (500 mL). The mixture was extracted with ethyl acetate (100 mL×2). The combined organic phases were washed with saturated brine (100 mL), dried over anhydrous sodium sulfate, filtered, and concentrated in vacuo. The residue was purified by silica gel chromatography (ethyl acetate/petroleum ether (v/v)=1/10) to give the title compound as a pale yellow solid (5.52 g, 73%).

MS (ES-API, pos. ion) m/z: 244.9 [M+2]$^+$.

Step 4) Synthesis of methyl 4-bromo-1H-indazole-6-carboxylate

3-Amino-5-bromo-4-methylbenzoate (6.20 g, 25.4 mmol) and acetic acid (110 mL) were added to a 250 mL single-neck flask, and a solution of sodium nitrite (1.90 g, 27.5 mmol) in water (11 mL) was added dropwise. The reaction mixture was stirred for 24 h at rt. The resulting mixture was concentrated in vacuo to remove the solvent. To the residue was added saturated sodium bicarbonate (500 mL). The resulting mixture was extracted with ethyl acetate (100 mL×2). The combined organic phases were washed with saturated brine (100 mL), dried over anhydrous sodium sulfate, filtered, and concentrated in vacuo, the residue was purified by silica gel chromatography (ethyl acetate/petroleum ether (v/v)=1/6) to give the title compound as an orange solid (4.08 g, 63%).

MS (ES-API, pos. ion) m/z: 255.9 [M+2]$^+$.

Step 5) Synthesis of methyl 4-bromo-1-methyl-1H-indazole-6-carboxylate

Methyl 4-bromo-1H-indazole-6-carboxylate (1.53 g, 6.0 mmol), cesium carbonate (3.95 g, 12.1 mmol) and N,N-dimethylformamide (20 mL) were added to a 100 mL two-neck flask, and iodomethane (1.1 g, 7.7 mmol) was added. The reaction mixture was stirred for 24 h at rt. The resulting mixture was filtered to remove the insoluble solid. To the filtrate was added saturated ammonium chloride (150 mL). The mixture was extracted with ethyl acetate (80 mL×2). The combined organic phases were washed with saturated brine (100 mL), dried over anhydrous sodium sulfate, filtered, and concentrated in vacuo. The residue was purified by silica gel chromatography (ethyl acetate/petroleum ether (v/v)=1/15) to give the title compound as a pale yellow solid (1.1 g, 68%).

$^1$H NMR (400 MHz, CDCl$_3$) δ (ppm): 8.10 (s, 1H), 8.02 (s, 1H), 7.95 (d, J=0.7 Hz, 1H), 4.13 (s, 3H), 3.97 (s, 3H).

Step 6) Synthesis of 4-bromo-1-methyl-1H-indazole-6-carboxamide

Methyl 4-bromo-1-methyl-1H-indazole-6-carboxylate (1.0 g, 3.7 mmol) and ammonia (20 mL, 7 M in methanol) were added to a 50 mL sealed tube. The mixture was reacted for 24 h at 110° C. The resulting mixture was cooled to room temperature and concentrated in vacuo, then the residue was purified by silica gel chromatography (methanol/dichloromethane (v/v)=1/50) to give the title compound as a white solid (500 mg, 53%).

MS (ES-API, pos. ion) m/z: 254.9 [M+2]⁺.

Step 7) Synthesis of
4-bromo-1-methyl-1H-indazole-6-carbonitrile

4-Bromo-1-methyl-1H-indazole-6-carboxamide (500 mg, 1.97 mmol) and toluene (20 mL) were added to a 100 mL single-neck flask, then phosphorus oxychloride (3.0 g, 19.7 mmol) was added dropwise. The reaction mixture was stirred for 12 h at 120° C. The resulting mixture was cooled to room temperature. To the resulting mixture was added saturated brine (80 mL), and the mixture was partitioned. The aqueous phase was extracted with ethyl acetate (40 mL×2). The combined organic phases were washed with saturated brine (60 mL), dried over anhydrous sodium sulfate, filtered, and concentrated in vacuo. The residue was purified by silica gel chromatography (ethyl acetate/petroleum ether (v/v)=1/5) to give the title compound as a white solid (440 mg, 95%).

MS (ES-API, pos. ion) m/z: 236.9 [M+2]⁺.

Step 8) Synthesis of tert-butyl 4-(6-cyano-1-methyl-1H-indazol-4-yl)-2-hydroxybenzoate 4-Bromo-1-methyl-1H-indazole-6-carbonitrile (340 mg, 1.44 mmol), tert-butyl 2-hydroxy-4-(4,4,5,5-tetramethyl-1,3,2-dioxaborolan-2-yl) benzoate (420 mg, 1.31 mmol), 1,1'-bis(diphenylphosphino)ferrocene-palladium(II)dichloride dichloromethane complex (53 mg, 0.065 mmol) and N,N-dimethylformamide (8 mL) were added gradually to a 50 mL two-neck flask. A solution of potassium carbonate (1.3 mL, 2 M) in water was added under nitrogen, then the reaction mixture was stirred for 0.5 h at 90° C. The resulting mixture was cooled to room temperature. To the resulting mixture was added saturated brine (80 mL). The mixture was extracted with ethyl acetate (40 mL×2). The combined organic phase was washed with saturated brine (60 mL), dried over anhydrous sodium sulfate, filtered, and concentrated in vacuo. The residue was purified by silica gel chromatography (dichloromethane/petroleum ether (v/v)=2/1) to give the title compound as a white solid (394 mg, 86%).

MS (ES-API, pos. ion) m/z: 350.1 [M+1]⁺.

Step 9) Synthesis of 4-(6-cyano-1-methyl-1H-indazol-4-yl)-2-hydroxybenzoic Acid tert-Butyl 4-(6-cyano-1-methyl-1H-indazol-4-yl)-2-hydroxybenzoate (394 mg, 1.13 mmol) and dichloromethane (15 mL) were gradually added to a 100 mL single neck flask, then trifluoroacetate (2 mL) was added. The reaction mixture was stirred for 12 h at rt. The mixture was concentrated in vacuo to remove solvent. The residue was purified by silica gel chromatography (methanol/dichloromethane (v/v)=1/10) to give the title compound as a white solid (222 mg, 67%).

MS (ES-API, pos. ion) m/z: 294.1 [M+1]⁺; and

¹H NMR (400 MHz, DMSO-d₆) δ (ppm): 8.39 (s, 1H), 8.27 (s, 1H), 7.88 (d, J=8.5 Hz, 1H), 7.58 (s, 1H), 7.11 (d, J=7.1 Hz, 2H), 4.16 (s, 3H).

Example 11: 4-(6-cyano-2,3-dihydro-1H-inden-4-yl)-2-hydroxybenzoic Acid

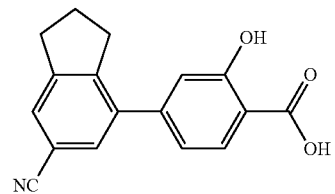 [SMILES: N#Cc1cc2c(c(-c3ccc(C(=O)O)c(O)c3)c1)CCC2]

Step 1) Synthesis of 1-(7-bromo-2,3-dihydro-1H-inden-5-yl)ethanone 1-(2,3-Dihydro-1H-inden-5-yl)ethanone (4.90 g, 30.6 mmol) and dichloromethane (100 mL) were added to a 250 mL single neck flask, and aluminum trichloride (10.2 g, 76.5 mmol) was added in portions at 0° C. The mixture was stirred for 0.2 h at rt under nitrogen. Then bromine (2.35 mL, 45.9 mmol) was added dropwise, and the mixture was reacted for 2 h at rt. The resulting mixture was poured into ice-water (500 mL) slowly. The aqueous phase was extracted with ethyl acetate (100 mL×2). The combined organic phases were washed with saturated brine (100 mL), dried over anhydrous sodium sulfate, filtered, and concentrated in vacuo. The residue was purified by silica gel chromatography (ethyl acetate/petroleum ether (v/v)=1/200) to give the title compound as yellow liquid (2.56 g, 35%).

MS (ES-API, pos. ion) m/z: 240.0 [M+2]⁺.

Step 2) Synthesis of 7-bromo-2,3-dihydro-1H-indene-5-carboxylic Acid 1-(7-Bromo-2,3-dihydro-1H-inden-5-yl)ethanone (2.53 g, 10.6 mmol), 10% aqueous sodium hydroxide (25.4 mL), 10% aqueous sodium hypochlorite (63.5 mL) were added to a 250 mL single neck flask. The reaction mixture was reacted for 27 h at 50° C. The resulting mixture was cooled to room temperature. To the resulting mixture was added saturated aqueous sodium thiosulfate (50 mL), and the mixture was extracted with ethyl acetate (100 mL×2). The combined organic phase was washed with saturated brine (100 mL), dried over anhydrous sodium sulfate, filtered, and concentrated in vacuo. The residue was purified by silica gel chromatography (methanol/dichloromethane (v/v)=1/50) to give the title compound as a yellow solid (1.71 g, 67%).

MS (ES-API, neg. ion) m/z: 237.9 [M–2]⁻.

Step 3) Synthesis of 7-bromo-2,3-dihydro-1H-indene-5-carbonyl Chloride

7-Bromo-2,3-dihydro-1H-indene-5-carboxylic acid (1.70 g, 7.05 mmol) and thionyl chloride (20 mL) were added to a 100 mL single neck flask. The reaction mixture was reacted for 12 h at 90° C. The resulting mixture was concentrated in vacuo to remove thionyl chloride to give the title compound as a yellow solid (1.83 g, 100%).

Step 4) Synthesis of 7-bromo-2,3-dihydro-1H-indene-5-carboxamide

A solution of 7-bromo-2,3-dihydro-1H-indene-5-carbonyl chloride (1.83 g, 7.05 mmol) in dichloromethane (20 mL) was added dropwise to ammonium hydroxide (20 mL, 28%) in a 100 mL single neck flask. The reaction mixture was stirred for 2 h at rt. To the mixture was added water (100 mL). The resulting mixture was extracted with ethyl acetate (80 mL×2). The combined organic phases were washed with saturated brine (100 mL), dried over anhydrous sodium sulfate, filtered, and concentrated in vacuo. The residue was purified by silica gel chromatography (ethyl acetate/dichloromethane (v/v)=1/30) to give the title compound as a pale yellow solid (0.85 g, 50%).

MS (ES-API, pos. ion) m/z: 241.0 [M+2]$^+$.

Step 5) Synthesis of 7-bromo-2,3-dihydro-1H-indene-5-carbonitrile

7-Bromo-2,3-dihydro-1H-indene-5-carboxamide (0.850 g, 3.54 mmol) and toluene (20 mL) were added to a 50 mL single neck flask, then phosphorus oxychloride (2.71, 17.7 mmol) was added. The reaction mixture was warmed to 120° C. and stirred for 12 h. The resulting mixture was cooled to room temperature. To the resulting mixture was added saturated brine (80 mL), and the mixture was partitioned. The aqueous phase was extracted with ethyl acetate (40 mL×2). The combined organic phases were washed with saturated brine (60 mL), dried over anhydrous sodium sulfate, filtered, and concentrated in vacuo. The residue was purified by silica gel chromatography (ethyl acetate/petroleum ether (v/v)=1/40) to give the title compound as a yellow solid (566 mg, 72%).

MS (ES-API, pos. ion) m/z: 222.9 [M+2]$^+$.

Step 6) Synthesis of methyl 4-(6-cyano-2,3-dihydro-1H-inden-4-yl)-2-hydroxybenzoate 7-Bromo-2,3-dihydro-1H-indene-5-carbonitrile (320 mg, 1.44 mmol), methyl 2-hydroxy-4-(4,4,5,5-tetramethyl-1,3,2-dioxaborolan-2-yl) benzoate (360 mg, 1.31 mmol), 1,1'-bis(diphenylphosphino)ferrocene-palladium(II)dichloride dichloromethane complex (53 mg, 0.065 mmol) and N,N-dimethylformamide (8 mL) were added gradually to a 50 mL two-neck flask. A solution of potassium carbonate (1.3 mL, 2 M) in water was added under nitrogen, then the reaction mixture was stirred for 0.5 h at 90° C. The resulting mixture was cooled to room temperature. To the resulting mixture was added saturated brine (80 mL). The mixture was extracted with ethyl acetate (40 mL×2). The combined organic phase was washed with saturated brine (60 mL), dried over anhydrous sodium sulfate, filtered, and concentrated in vacuo, then the residue was purified by silica gel chromatography (ethyl acetate/petroleum ether (v/v)=1/20) to give the title compound as a pale yellow solid (238 mg, 62%).

MS (ES-API, pos. ion) m/z: 294.1 [M+1]$^+$.

Step 7) Synthesis of 4-(6-cyano-2,3-dihydro-1H-inden-4-yl)-2-hydroxybenzoic Acid Methyl 4-(6-cyano-2,3-dihydro-1H-inden-4-yl)-2-hydroxybenzoate (238 mg, 0.81 mmol), methanol (8 mL), tetrahydrofuran (8 mL) and water (8 mL) were gradually added to a 100 mL single neck flask, then sodium hydroxide (162 mg, 4.05 mmol) was added. The reaction mixture was stirred for 12 h at rt. The mixture was concentrated in vacuo to remove solvent. To the residue was added water (60 mL). The mixture was washed with ether (50 mL), and the aqueous phase was acidified to pH 1 with 2 N dilute hydrochloric acid and extracted with ethyl acetate (40 mL×2). The combined organic phases were washed with saturated brine (40 mL×2), dried over anhydrous sodium sulfate, filtered, and concentrated in vacuo. The residue was purified by silica gel chromatography (methanol/dichloromethane (v/v)=1/20) to give the title compound as a white solid (195 mg, 86%).

MS (ES-API, pos. ion) m/z: 280.1 [M+1]$^+$; and
$^1$H NMR (400 MHz, DMSO-d6) δ (ppm): 7.84 (s, 1H), 7.68-7.63 (m, 2H), 7.02 (s, 2H), 2.95 (s, 4H), 2.00 (s, 2H).

Example 12: 4-(5-cyano-2-(trifluoromethyl)benzo[b]thiophen-7-yl)-2-hydroxybenzoic Acid

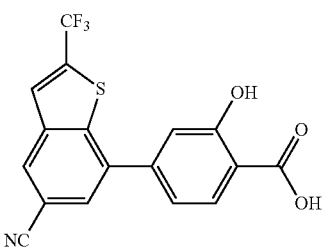 [SMILES: N#Cc1cc(-c2ccc(C(=O)O)c(O)c2)c2sc(C(F)(F)F)cc2c1]

Step 1) Synthesis of 2-bromo-3-methoxy-5-methylbenzaldehyde

N,N,N'-trimethylethylenediamine (3.80 g, 37.2 mmol) and tetrahydrofuran (10 mL) were added to a 250 mL two-neck flask, and n-butyllithium (16 mL, 38.4 mmol, 2.4 M in THF) was added dropwise at −65° C. The mixture was stirred for 0.5 h at −65° C. A solution of 3-methoxy-5-methylbenzaldehyde (5.33 g, 35.3 mmol) in tetrahydrofuran (35 mL) was added dropwise. The reaction mixture was stirred for 0.8 h at −65° C. Then n-butyllithium (16 mL, 38.4 mmol, 2.4 M in THF) was added dropwise. The mixture was stirred for 14 h at −20° C. Then 1,2-dibromo-1,1,2,2-tetrafluoroethane ethane (41.3 g, 159 mmol) was added dropwise, and the mixture was stirred for 1.5 h at rt. The resulting mixture was poured into ice-water (300 mL) slowly. The mixture was acidified to pH 1-2 with dilute hydrochloric acid and extracted with ethyl acetate (100 mL×2). The combined organic phases were washed with saturated brine (100 mL), dried over anhydrous sodium sulfate, filtered, and concentrated in vacuo. The residue was purified by silica gel chromatography (ethyl acetate/petroleum ether (v/v)=1/50) to give the title compound as a pale yellow solid (6.39 g, 79%).

$^1$H NMR (400 MHz, CDCl$_3$) δ (ppm): 10.39 (s, 1H), 7.33 (s, 1H), 6.94 (s, 1H), 3.93 (s, 3H), 2.37 (s, 3H).

Step 2) Synthesis of 1-(2-bromo-3-methoxy-5-methylphenyl)-2,2-dichloro-3,3,3-trifluoropropan-1-ol 2-Bromo-3-methoxy-5-methylbenzaldehyde (5.91 g, 25.8 mmol), 1,1,1-trichloro-2,2,2-trifluoroethane (9.71 g, 51.8 mmol) and dimethyl sulfoxide (30 mL) were added to a 100 mL two-neck flask, and anhydrous stannous chloride (7.80 g, 41.1 mmol) was added in portions. The reaction mixture was stirred for 4 h at rt. The resulting mixture was quenched with saturated aqueous ammonium chloride (200 mL). The aqueous phase was extracted with ethyl acetate (100 mL×2). The combined organic phases were washed with saturated brine (100 mL), dried over anhydrous sodium sulfate, filtered, and concentrated in vacuo. The residue was purified by silica gel chromatography (methanol/dichloromethane (v/v)=1/10) to give the title compound as pale yellow oil (4.93 g, 50%).

$^1$H NMR (400 MHz, CDCl$_3$) δ (ppm): 7.28 (s, 1H), 6.78 (s, 1H), 6.06 (d, J=6.0 Hz, 1H), 3.90 (s, 3H), 2.39 (s, 3H); and $^1$H NMR (376 MHz, CDCl$_3$) δ (ppm): −75.35 (s, 3F).

Step 3) Synthesis of 1-(2-bromo-3-methoxy-5-methylphenyl)-2,2-dichloro-3,3,3-trifluoropropyl methanesulfonate 1-(2-Bromo-3-methoxy-5-methylphenyl)-2,2-dichloro-3,3,3-trifluoropropan-1-ol (6.11 g, 16 mmol), triethylamine (3.24 g, 32 mmol) and dichloromethane (50 mL) were added to a 250 mL two-neck flask, then methanesulfonyl chloride (2.75 g, 24 mmol) was added dropwise at 0° C. The reaction mixture was stirred for 12 h at rt. To the resulting mixture was added saturated brine (200 mL), and the mixture was partitioned. The aqueous phase was extracted with ethyl acetate (100 mL×2). The combined organic phase was washed with saturated brine (100 mL), dried over anhydrous sodium sulfate, filtered, and concentrated in vacuo, the residue was purified by silica gel chromatography (methanol/dichloromethane (v/v)=1/20) to give the title compound as a white solid (6.18 g, 84%).

$^1$H NMR (400 MHz, CDCl$_3$) δ (ppm): 7.32 (s, 1H), 6.83 (s, 1H), 6.81 (s, 1H), 3.91 (s, 3H), 2.81 (s, 3H), 2.41 (s, 3H); and $^{19}$F NMR (376 MHz, CDCl$_3$) δ (ppm): −75.41 (s, 3F).

Step 4) Synthesis of (Z)-2-bromo-1-(2-chloro-3,3,3-trifluoroprop-1-en-1-yl)-3-methoxy-5-methylbenzene 1-(2-Bromo-3-methoxy-5-methylphenyl)-2,2-dichloro-3,3,3-trifluoropropylmethanesulfonate (4.78 g, 10.4 mmol) and N,N-dimethylformamide (25 mL) were added to a 100 mL single-neck flask, zinc (0.820 g, 12.5 mmol) was added in portions under nitrogen while controlling the reaction temperature should not exceed 50° C. The mixture was stirred for 0.5 h at rt, then warmed to 50° C. and stirred for 0.5 h. The resulting mixture was cooled to room temperature. To the mixture was added to saturated aqueous ammonium chloride (200 mL). The aqueous phase was extracted with ethyl acetate (100 mL×2). The combined organic phase was washed with saturated brine (100 mL), dried over anhydrous sodium sulfate, filtered, and concentrated in vacuo, the residue was purified by silica gel chromatography (ethyl acetate/petroleum ether (v/v)=1/50) to give the title compound as a pale yellow solid, 3.22 g, 94%).

$^1$H NMR (400 MHz, CDCl$_3$) δ (ppm): 7.50 (s, 1H), 7.13 (s, 1H), 6.75 (s, 1H), 3.91 (s, 3H), 2.37 (s, 3H); and $^{19}$F NMR (376 MHz, CDCl$_3$) δ (ppm): −68.96.

Step 5) Synthesis of 7-methoxy-5-methyl-2-(trifluoromethyl)benzo[b]thiophene (Z)-2-bromo-1-(2-chloro-3,3,3-trifluoroprop-1-en-1-yl)-3-methoxy-5-methylbenzene (4.09 g, 12.4 mmol), sodium sulfide nonahydrate (5.98 g, 24.9 mmol), copper iodide (236 mg, 1.24 mmol) and N,N-dimethylformamide (20 mL) were added gradually to a 100 mL single-neck flask. The mixture was stirred for 24 h at 80° C. The resulting mixture was cooled to room temperature. To the mixture was added to saturated brine (200 mL). The resulting mixture was extracted with ethyl acetate (100 mL×2). The combined organic phases were washed with saturated brine (100 mL), dried over anhydrous sodium sulfate, filtered, and concentrated in vacuo. The residue was purified by silica gel chromatography (ethyl acetate/petroleum ether (v/v)=1/100) to give the title compound as a white solid (2.14 g, 70%).

$^1$H NMR (400 MHz, CDCl$_3$) δ (ppm): 7.58 (d, J=0.9 Hz, 1H), 7.26 (s, 1H), 6.70 (s, 1H), 3.99 (s, 3H), 2.48 (s, 3H); and $^{19}$F NMR (376 MHz, CDCl$_3$) δ (ppm): −56.32 (s, 3F).

Step 6) Synthesis of 7-methoxy-2-(trifluoromethyl)benzo[b]thiophene-5-carbonitrile 7-Methoxy-5-methyl-2-(trifluoromethyl)benzo[b]thiophene (1.01 g, 4.1 mmol), tert-butyl nitrite (1.26 g, 12.2 mmol), N-hydroxyphthalimide (0.669 g, 4.1 mmol), palladium acetate (0.045 g, 0.20 mmol) and acetonitrile (20 mL) were added gradually to a 25 mL microwave tube under nitrogen. The reaction mixture was stirred for 48 h at 80° C. The resulting mixture was cooled to room temperature and concentrated in vacuo. The residue was purified by silica gel chromatography (dichloromethane/petroleum ether (v/v)=1/4) to give the title compound as a white solid (610 mg, 58%).

$^1$H NMR (400 MHz, CDCl$_3$) δ (ppm): 7.81 (s, 1H), 7.72 (d, J=0.8 Hz, 1H), 7.02 (s, 1H), 4.05 (s, 3H); and $^{19}$F NMR (376 MHz, CDCl$_3$) δ (ppm): −56.67 (s, 3F).

Step 7) Synthesis of 7-hydroxy-2-(trifluoromethyl)benzo[b]thiophene-carbonitrile 7-Methoxy-2-(trifluoromethyl)benzo[b]thiophene-5-carbonitrile (2.57 g, 10 mmol) and dichloromethane (20 mL) were added to a 100 mL single-neck flask, boron tribromide (7.5 g, 30 mmol) was added dropwise at −70° C. The reaction mixture was stirred for 24 h at rt. To the mixture was added ice-water (200 mL), and the mixture was partitioned. The aqueous phase was extracted with ethyl acetate (100 mL×2). The combined organic phases were washed with saturated brine (100 mL), dried over anhydrous sodium sulfate, filtered, and concentrated in vacuo. The residue was purified by silica gel chromatography (ethyl acetate/petroleum ether (v/v)=1/15) to give the title compound as a pale yellow solid (0.827 g, 34%).

MS (ES-API, neg. ion) m/z: 242.0 [M−1]$^-$.

Step 8) Synthesis of 5-cyano-2-(trifluoromethyl)benzo[b]thiophene-7-yl trifluoromethanesulfonate 7-Hydroxy-2-(trifluoromethyl)benzo[b]thiophene-carbonitrile (1.0 g, 4.1 mmol), pyridine (0.97 g, 12.3 mmol) and dichloromethane (80 mL) were added to a 250 mL single-neck flask, and trifluoromethanesulfonic anhydride (1.35 g, 4.8 mmol) was added dropwise at 0° C. The reaction mixture was stirred for 1 h at rt. The resulting mixture was concentrated in vacuo. The residue was purified by silica gel chromatography (dichloromethane/petroleum ether (v/v)=1/3) to give the title compound as a white solid (1.31 g, 85%).

$^1$H NMR (400 MHz, CDCl$_3$) δ (ppm): 8.24 (s, 1H), 7.87 (s, 1H), 7.70 (d, J=0.7 Hz, 1H); and $^{19}$F NMR (376 MHz, CDCl$_3$) δ (ppm): −56.84 (s, 3F), −72.67 (s, 3F).

Step 9) Synthesis of methyl 4-(5-cyano-2-(trifluoromethyl)benzo[b]thiophene-7-yl)-2-hydroxy benzoate 5-Cyano-2-(trifluoromethyl)benzo[b]thiophene-7-yltrifluoromethanesulfonate (540 mg, 1.44 mmol), methyl 2-hydroxy-4-(4,4,5,5-tetramethyl-1,3,2-dioxaborolan-2-yl) benzoate (360 mg, 1.31 mmol), 1,1'-bis(diphenylphosphino)ferrocene-palladium(II)dichloride dichloromethane complex (53 mg, 0.065 mmol), potassium carbonate (362 mg, 2.62 mmol) and anhydrous 1,4-dioxane (15 mL) were added gradually to a 50 mL two-neck flask. The reaction mixture was stirred for 5 h at 90° C. under nitrogen. The resulting mixture was cooled to room temperature. To the resulting mixture was added saturated brine (80 mL). The mixture was extracted with ethyl acetate (40 mL×2). The combined organic phases were washed with saturated brine (60 mL), dried over anhydrous sodium sulfate, filtered, and concentrated in vacuo, the residue was purified by silica gel chromatography (dichloromethane/petroleum ether (v/v)=1/4) to give the title compound as a white solid (0.336 g, 68%).

MS (ES-API, pos. ion) m/z: 378.0 [M+1]$^+$.

Step 10) Synthesis of 4-(5-cyano-2-(trifluoromethyl)benzo[b]thiophen-7-yl)-2-hydroxybenzoic Acid Methyl 4-(5-cyano-2-(trifluoromethyl)benzo[b]thiophene-7-yl)-2-hydroxybenzoate (0.306 g, 0.81 mmol), methanol (8 mL), tetrahydrofuran (8 mL) and water (8 mL) were gradually added to a 100 mL single neck flask, then sodium hydroxide (0.162 g, 4.05 mmol) was added. The reaction mixture was stirred for 12 h at rt. The mixture was concentrated in vacuo to remove solvent. To the residue was added water (60 mL). The mixture was washed with ether (50 mL), and the aqueous phase was acidified to pH 1 with 2 N dilute hydrochloric acid and extracted with ethyl acetate (40 mL×2). The combined organic phases were washed with saturated brine (40 mL×2), dried over anhydrous sodium sulfate, filtered, and concentrated in vacuo. The residue was purified by silica gel chromatography (methanol/dichloromethane (v/v)=1/30) to give the title compound as a white solid (0.118 g, 40%).

MS (ES-API, pos. ion) m/z: 364.0 [M+1];
$^1$H NMR (400 MHz, DMSO-d6) δ (ppm): 8.61 (s, 1H), 8.35 (s, 1H), 8.07 (s, 1H), 7.97 (d, J=7.9 Hz, 1H), 7.32 (d, J=9.1 Hz, 2H); and
$^{19}$F NMR (376 MHz, CDCl$_3$) δ (ppm): −55.49 (s, 3F).

Example 13: 4-(5-cyano-benzo[b]thiophen-7-yl)-2-hydroxybenzoic Acid

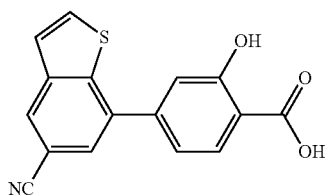 [SMILES: N#Cc1cc(-c2ccc(C(=O)O)c(O)c2)c2sccc2c1]

Step 1) Synthesis of methyl 7-bromo-5-methylbenzo[b]thiophene-2-carboxylate

3-Bromo-2-fluoro-5-methylbenzaldehyde (4.34 g, 20 mmol), potassium carbonate (5.53 g, 40 mmol), ethyl thioglycolate (2.88 g, 24 mmol) and N,N-dimethylformamide (40 mL) were added gradually to a 100 mL single-neck flask. The reaction mixture was stirred for 12 h at 80° C. under nitrogen. The resulting mixture was cooled to room temperature and quenched with saturated aqueous ammonium chloride (150 mL). The mixture was extracted with ethyl acetate (100 mL×2). The combined organic phases were washed with saturated brine (100 mL), dried over anhydrous sodium sulfate, filtered, and concentrated in vacuo. The residue was purified by silica gel chromatography (ethyl acetate/petroleum ether (v/v)=1/100) to give the title compound as a pale yellow solid (5.3 g, 93%).

$^1$H NMR (400 MHz, CDCl$_3$) δ (ppm): 8.04 (s, 1H), 7.60 (s, 1H), 7.45 (s, 1H), 4.41 (q, J=7.1 Hz, 2H), 2.46 (s, 3H), 1.42 (t, J=7.1 Hz, 3H).

Step 2) Synthesis of 7-bromo-5-methylbenzo[b]thiophene-2-carboxylic Acid

Methyl 7-bromo-5-methylbenzo[b]thiophene-2-carboxylate (2.0 g, 7.0 mmol), methanol (25 mL), tetrahydrofuran (25 mL) and water (25 mL) were gradually added to a 250 mL single neck flask, then sodium hydroxide (0.84 g, 21 mmol) was added. The reaction mixture was stirred for 12 h at rt. The mixture was concentrated in vacuo to remove solvent. To the residue was added water (120 mL). The mixture was washed with ether (80 mL), and the aqueous phase was acidified to pH 1 with 2 N dilute hydrochloric acid and extracted with ethyl acetate (80 mL×2). The combined organic phases were washed with saturated brine (80 mL×2), dried over anhydrous sodium sulfate, filtered, and concentrated in vacuo to give the title compound as a white solid (1.8 g, 95%).

MS (ES-API, neg. ion) m/z: 271.9 [M+2]$^+$.

Step 3) Synthesis of 7-bromo-5-methylbenzo[b]thiophene

7-Bromo-5-methylbenzo[b]thiophene-2-carboxylic acid (1.79 g, 6.6 mmol), copper (0.83 g, 13.1 mmol) and quinoline (15 mL) were added to a 25 mL microwave tube, and the mixture was heated to 200° C. and stirred for 0.5 h. The resulting mixture was cooled to room temperature. To the mixture was added to concentrated hydrochloric acid (100 mL, 12 M). The mixture was extracted with ethyl acetate (80 mL×2). The combined organic phases were washed with saturated brine (80 mL), dried over anhydrous sodium sulfate, filtered, and concentrated in vacuo. The residue was purified by silica gel chromatography (100% petroleum ether) to give the title compound as colorless liquid (1.41 g, 94%).

$^1$H NMR (400 MHz, CDCl$_3$) δ (ppm): 7.56 (s, 1H), 7.47 (d, J=5.4 Hz, 1H), 7.35 (d, J=5.4 Hz, 2H), 2.46 (s, 3H).

Step 4) Synthesis of 7-bromobenzo[b]thiophene-5-carbonitrile

7-Bromo-5-methylbenzo[b]thiophene (930 mg, 4.1 mmol), tert-butyl nitrite (1.26 g, 12.2 mmol), N-hydroxyphthalimide (669 mg, 4.1 mmol), palladium acetate (45 mg, 0.20 mmol) and acetonitrile (20 mL) were added gradually to a 25 mL microwave tube. The reaction mixture was heated to 80° C. and stirred for 48 h under nitrogen. The resulting mixture was cooled to room temperature and concentrated in vacuo, the residue was purified by silica gel chromatography (dichloromethane/petroleum ether (v/v)=1/4) to give the title compound as a white solid (185 mg, 19%).

$^1$H NMR (400 MHz, CDCl$_3$) δ (ppm): 8.10 (d, J=1.1 Hz, 1H), 7.7-7.67 (m, 3.2 Hz, 2H), 7.52 (d, J=5.5 Hz, 1H).

Step 5) Synthesis of methyl 4-(5-cyanobenzo[b]thiophen-7-yl)-2-hydroxybenzoate 7-Bromobenzo[b]thiophene-5-carbonitrile (340 mg, 1.44 mmol), methyl 2-hydroxy-4-(4,4,5,5-tetramethyl-1,3,2-dioxaborolan-2-yl) benzoate (360 mg, 1.31 mmol), 1,1'-bis(diphenylphosphino)ferrocene-palladium(II)dichloride dichloromethane complex (53 mg, 0.065 mmol) and N,N-dimethylformamide (8 mL) were added gradually to a 50 mL two-neck flask. A solution of potassium carbonate (1.3 mL, 2 M) in water was added under nitrogen, then the reaction mixture was stirred for 0.5 h at 90° C. The resulting mixture was cooled to room temperature. To the resulting mixture was added saturated brine (80 mL). The aqueous phase was extracted with ethyl acetate (40 mL×2). The combined organic phase was washed with saturated brine (60 mL), dried over anhydrous sodium sulfate, filtered, and concentrated in vacuo. The residue was purified by silica gel chromatography (dichloromethane/petroleum ether (v/v)=1/2) to give the title compound as a pale yellow solid (134 mg, 33%).

MS (ES-API, pos. ion) m/z: 310.0 [M+1]$^+$.

Step 6) Synthesis of 4-(5-cyanobenzo[b]thiophen-7-yl)-2-hydroxybenzoic Acid

Methyl 4-(5-cyanobenzo[b]thiophen-7-yl)-2-hydroxybenzoate (134 mg, 0.433 mmol), methanol (8 mL), tetrahydrofuran (8 mL) and water (8 mL) were gradually added to a 100 mL of single neck flask, then sodium hydroxide (87 mg, 2.16 mmol) was added. The reaction mixture was stirred for 12 h at rt. The mixture was concentrated in vacuo to remove solvent. To the residue was added water (60 mL). The mixture was washed with ether (50 mL), and the aqueous phase was acidified to pH 1 with 2 N dilute hydrochloric acid and extracted with ethyl acetate (40 mL×2). The combined organic phases were washed with saturated brine (40 mL×2), dried over anhydrous sodium sulfate, filtered, and concentrated in vacuo. The residue was purified by silica gel chromatography (methanol/dichloromethane (v/v)=1/40) to give the title compound as a white solid (93 mg, 73%).

MS (ES-API, pos. ion) m/z: 296.0 [M+1]$^+$; and
$^1$H NMR (400 MHz, DMSO-d$_6$) δ (ppm): 8.48 (s, 1H), 8.04 (d, J=5.3 Hz, 1H), 7.95 (d, J=7.9 Hz, 1H), 7.84 (s, 1H), 7.68 (d, J=5.4 Hz, 1H), 7.29-7.26 (m, 2H).

Example 14: 4-(6-cyano-1-isopropyl-1H-indol-4-yl)-2-hydroxybenzoic Acid

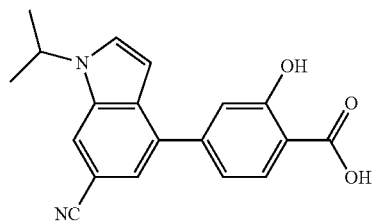 [SMILES: CC(C)n1ccc2c(-c3ccc(C(=O)O)c(O)c3)cc(C#N)cc21]

Step 1) Synthesis of 2-(2,6-dibromo-4-methylphenyl)acetaldehyde 2,6-Dibromo-4-methylaniline (21.2 g, 80.0 mmol), dilute hydrochloric acid (100 mL, 2 M) and acetone (150 mL) were added to a 500 mL single neck flask, a solution of sodium nitrite (6.07 g, 88 mmol) in water (30 mL) was added dropwise at 0° C. The mixture was stirred for 1 h at 0° C. Then a solution of ethyl vinyl ether (57.6, 800 mmol) and ferrocene (2.98 g, 16 mmol) in acetone (30 mL) was added. After it was stirred for 1 h at 0° C., the mixture was stirred for 12 h at rt. The resulting mixture was concentrated in vacuo to remove acetone. To the residue was added saturated aqueous ammonium chloride (300 mL). The aqueous phase was extracted with ethyl acetate (100 mL×2). The combined organic phases were washed with saturated brine (80 mL×2), dried over anhydrous sodium sulfate, filtered, and concentrated in vacuo, the residue was purified by silica gel chromatography (dichloromethane/petroleum ether (v/v)=1/10) to give the title compound as a pale yellow solid (10 g, 43%).

$^1$H NMR (400 MHz, CDCl$_3$) δ (ppm): 9.72 (s, 1H), 7.40 (s, 2H), 4.16 (s, 2H), 2.31 (s, 3H).

Step 2) Synthesis of 4-bromo-6-methyl-1H-indole 2-(2,6-Dibromo-4-methylphenyl)acetaldehyde (10.0 g, 34 mmol), ammonium hydroxide (40 mL, 28%), cuprous oxide (0.49 g, 3.4 mmol) and 1-methyl-2-pyrrolidinone (60 mL) were added gradually to a 100 mL two-neck flask. The reaction mixture was stirred for 3 h at 60° C. under nitrogen. The resulting mixture was cooled to room temperature. To the mixture was added saturated brine (150 mL). The mixture was extracted with ethyl acetate (100 mL×2). The combined organic phases were washed with saturated brine (100 mL), dried over anhydrous sodium sulfate, filtered, and concentrated in vacuo. The residue was purified by silica gel chromatography (dichloromethane/petroleum ether (v/v)=1/8) to give the title compound as a pale yellow solid (5.57 g, 78%).

MS (ESI, pos. ion) m/z: 210.9 [M+2]$^+$.

Step 3) Synthesis of 1-(4-bromo-6-methyl-1H-indol-1-yl)ethanone

4-Bromo-6-methyl-1H-indole (3.6 g, 17.2 mmol), pyridine (8.16, 103 mmol), 4-dimethylaminopyridine (0.40 g, 3.3 mmol) and anhydrous dichloromethane (80 mL) were added gradually to a 250 mL two-neck flask, then acetic oxide (7.09 g, 68.8 mmol) was added at 0° C. under nitrogen. The reaction mixture was stirred for 12 h at rt. The resulting mixture was concentrated in vacuo, and the residue was purified by silica gel chromatography (ethyl acetate/petroleum ether (v/v)=1/40) to give the title compound as light yellow oil (3.9 g, 90%).

MS (ESI, pos. ion) m/z: 252.9 [M+2]$^+$.

Step 4) Synthesis of 1-acetyl-4-bromo-1H-indole-6-carbonitrile 1-(4-Bromo-6-methyl-1H-indol-1-yl) ethanone (1.03 g, 4.1 mmol), tert-butyl nitrite (1.26 g, 12.2 mmol), N-hydroxyphthalimide (669 mg, 4.1 mmol), palladium diacetate (45 mg, 0.20 mmol) and acetonitrile (20 mL) were added gradually to a 250 mL microwave tube. The reaction mixture was stirred for 48 h at 80° C. under nitrogen. The resulting mixture was cooled to room temperature and concentrated in vacuo. The residue was purified by silica gel chromatography (dichloromethane/petroleum ether (v/v)=1/30) to give the title compound as a pale yellow solid (378 mg, 35%).

MS (ESI, pos. ion) m/z: 263.9 [M+2]$^+$.

Step 5) Synthesis of 4-bromo-1H-indole-6-carbonitrile

1-Acetyl-4-bromo-1H-indole-6-carbonitrile (526 mg, 2.0 mmol), 1,8-diazabicyclo[5.4.0]undec-7-ene (1.22 g, 8.0 mmol) and acetonitrile (20 mL) were gradually added to a 100 mL single neck flask. The reaction mixture was stirred for 24 h at 90° C. under nitrogen. The resulting mixture was cooled to room temperature and concentrated in vacuo to remove solvent, then the residue was purified by silica gel chromatography (ethyl acetate/petroleum ether (v/v)=1/4) to give the title compound as a pale yellow solid (186 mg, 42%).

MS (ESI, pos. ion) m/z: 221.9 [M+2]$^+$.

Step 6) Synthesis of 4-bromo-1-isopropyl-1H-indole-6-carbonitrile

4-Bromo-1H-indole-6-carbonitrile (180 mg, 0.81 mmol) and anhydrous N,N-dimethylformamide (10 mL) were added to a 100 mL single neck flask, then sodium hydride (65 mg, 1.62 mmol, 60%) was added at 0° C. The mixture was stirred for 0.5 h at 0° C., then isopropyl bromide (200 mg, 1.62 mmol) was added. The mixture was stirred for 12 h at rt. To the mixture were added saturated ammonium chloride (80 mL) and ethyl acetate (80 mL), and the resulting mixture was partitioned. The organic phase was washed with saturated brine (40 mL×2), dried over anhydrous sodium sulfate, filtered, and concentrated in vacuo. The residue was purified by silica gel chromatography (ethyl acetate/petroleum ether (v/v)=1/10) to give the title compound as a white solid (81 mg, 38%).

MS (ES-API, pos. ion) m/z: 264.0 [M+2]$^+$.

Step 7) Synthesis of tert-butyl 4-(6-cyano-1-isopropyl-1H-indol-4-yl)-2-hydroxybenzoate 4-bromo-1-isopropyl-1H-indole-6-carbonitrile (380 mg, 1.44 mmol), tert-butyl 2-hydroxy-4-(4,4,5,5-tetramethyl-1,3,2-dioxaborolan-2-yl) benzoate (420 mg, 1.31 mmol), 1,1'-bis(diphenylphosphino)ferrocene-palladium(II)dichloride dichloromethane complex (53 mg, 0.065 mmol) and N,N-dimethylformamide (8 mL) were added gradually to a 50 mL of two-neck flask. A solution of potassium carbonate (1.3 mL, 2 M) in water was added under nitrogen, then the reaction mixture was stirred for 0.5 h at 90° C. The resulting mixture was cooled to room temperature. To the resulting mixture was added saturated brine (80 mL). The mixture was extracted with ethyl acetate (40 mL×2). The combined organic phases were washed with saturated brine (60 mL), dried over anhydrous sodium sulfate, filtered, and concentrated in vacuo, the residue was purified by silica gel chromatography (dichloromethane/petroleum ether (v/v)=1/2) to give the title compound as a white solid (300 mg, 62%).

MS (ES-API, pos. ion) m/z: 377.1 [M+1]$^+$.

Step 8) Synthesis of 4-(6-cyano-1-isopropyl-1H-indol-4-yl)-2-hydroxybenzoic Acid tert-Butyl 4-(6-cyano-1-isopropyl-1H-indol-4-yl)-2-hydroxybenzoate (230 mg, 0.62 mmol) and dichloromethane (15 mL) were added to a 100 mL single neck flask, then trifluoroacetate (2 mL). The reaction mixture was stirred for 12 h at rt. The mixture was concentrated in vacuo to remove solvent, and the residue was purified by silica gel chromatography (methanol/dichloromethane (v/v)=1/10) to give the title compound as a white solid (85 mg, 43%).

MS (ES-API, neg. ion) m/z: 319.1 [M−1]$^-$; and $^1$H NMR (600 MHz, DMSO-d6) δ (ppm): 8.18 (s, 1H), 7.89 (d, J=3.1 Hz, 1H), 7.85 (d, J=7.7 Hz, 1H), 7.40 (s, 1H), 7.0-6.99 (m, 2H), 6.70 (d, J=3.0 Hz, 1H), 4.96-4.91 (m, 1H), 1.50 (d, J=6.6 Hz, 6H).

Example 15: 4-(6-cyano-1H-indol-4-yl)-2-hydroxybenzoic Acid

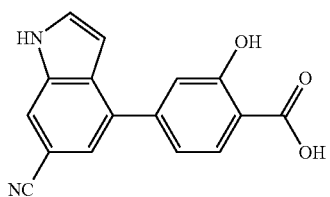 [SMILES: N#Cc1cc(-c2ccc(C(=O)O)c(O)c2)c2cc[nH]c2c1]

Step 1) Synthesis of tert-butyl 4-(6-cyano-1H-indol-4-yl)-2-hydroxybenzoate

4-Bromo-1H-indole-6-carbonitrile (318 mg, 1.44 mmol), tert-butyl 2-hydroxy-4-(4,4,5,5-tetramethyl-1,3,2-dioxaborolan-2-yl) benzoate (420 mg, 1.31 mmol), 1,1'-bis(diphenylphosphino)ferrocene-palladium(II)dichloride dichloromethane complex (53 mg, 0.065 mmol) and N,N-dimethylformamide (8 mL) were added gradually to a 50 mL two-neck flask. A solution of potassium carbonate (1.3 mL, 2 M) in water was added under nitrogen, then the reaction mixture was stirred for 0.5 h at 90° C. The resulting mixture was cooled to room temperature. To the resulting mixture was added saturated brine (80 mL). The mixture was extracted with ethyl acetate (40 mL×2). The combined organic phases were washed with saturated brine (60 mL), dried over anhydrous sodium sulfate, filtered, and concentrated in vacuo, the residue was purified by silica gel chromatography (ethyl acetate/petroleum ether (v/v)=1/6) to give the title compound as a white solid (145 mg, 33%).

MS (ES-API, pos. ion) m/z: 335.1 [M+1]$^+$.

Step 2) Synthesis of 4-(6-cyano-1H-indol-4-yl)-2-hydroxybenzoic Acid tert-Butyl 4-(6-cyano-1H-indol-4-yl)-2-hydroxybenzoate (207 mg, 0.62 mmol) and dichloromethane (15 mL) were added to a 100 mL single neck flask, then trifluoroacetate (2 mL). The reaction mixture was stirred for 12 h at rt. The mixture was concentrated in vacuo to remove the solvent, and the residue was purified by silica gel chromatography (methanol/dichloromethane (v/v)=1/20) to give the title compound as a white solid (135 mg, 78%).

MS (ES-API, neg. ion) m/z: 277.1 [M−1]$^-$; and $^1$H NMR (600 MHz, DMSO-d6) δ (ppm): 11.91 (s, 1H), 7.94 (s, 1H), 7.90 (d, J=7.9 Hz, 1H), 7.74-7.71 (m, 1H), 7.42 (s, 1H), 7.14-7.03 (m, 2H), 6.68 (s, 1H).

Example 16: 4-(6-cyano-1H-benzo[d]imidazol-4-yl)-2-hydroxybenzoic Acid

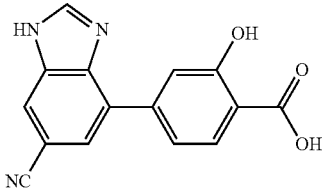 [SMILES: N#Cc1cc(-c2ccc(C(=O)O)c(O)c2)c2nc[nH]c2c1]

Step 1) Synthesis of tert-butyl 2'-amino-5'-cyano-3-hydroxy-3'-nitro-[1,1'-biphenyl]-4-carboxylate 4-Amino-3-bromo-5-nitrobenzonitrile (0.317 g, 1.31 mmol), tert-butyl 2-hydroxy-4-(4,4,5,5-tetramethyl-1,3,2-dioxaborolan-2-yl) benzoate (420 mg, 1.31 mmol), 1,1'-bis(diphenylphosphino)ferrocene-palladium(II)dichloride dichloromethane complex (53 mg, 0.065 mmol) and N,N-dimethylformamide (8 mL) were added gradually to a 50 mL two-neck flask. A solution of potassium carbonate (1.3 mL, 2 M) in water was added under nitrogen, then the reaction mixture was stirred for 0.5 h at 90° C. The resulting mixture was cooled to room temperature. To the resulting mixture was added saturated brine (80 mL). The aqueous phase was extracted with ethyl acetate (40 mL×2). The combined organic phase was washed with saturated brine (60 mL), dried over anhydrous sodium sulfate, filtered, and concentrated in vacuo. The residue was purified by silica gel chromatography (ethyl acetate/petroleum ether (v/v)=1/8) to give the title compound as a yellow solid (93 mg, 20%).

MS (ES-API, pos. ion) m/z: 356.1 [M+1]$^+$.

Step 2) Synthesis of tert-butyl 2',3'-diamino-5'-cyano-3-hydroxy-[1,1'-biphenyl]-4-carboxylate tert-Butyl 2'-amino-5'-cyano-3-hydroxy-3'-nitro-[1,1'-biphenyl]-4-carboxylate (0.782 g, 2.20 mmol), stannous chloride dihydrate (1.60 g, 7.10 mmol) and ethanol (80 mL) were added to a 250 mL single neck flask. The reaction mixture was heated to 90° C. and stirred for 12 h. The resulting mixture was cooled to room temperature. To the resulting mixture was added water (120 mL). The mixture was extracted with ethyl acetate (100 mL×2). The combined organic phases were washed with saturated brine (100 mL), dried over anhydrous sodium sulfate, filtered, and concentrated in vacuo to give the title compound as a yellow solid (0.680 g, 95%).

MS (ES-API, pos. ion) m/z: 326.1 [M+1]$^+$.

Step 3) Synthesis of tert-butyl 4-(6-cyano-1H-benzo[d]imidazol-4-yl)-2-hydroxybenzoate tert-Butyl 2',3'-diamino-5'-cyano-3-hydroxy-[1,1'-biphenyl]-4-carboxylate (0.740 g, 2.27 mmol) and triethyl orthoformate (20 mL) were added to a 100 mL single neck flask. The mixture was heated to 160° C. and stirred for 3 h. The mixture was cooled to room temperature and concentrated in vacuo, and the residue was purified by silica gel chromatography (ethyl acetate/petroleum ether (v/v)=1/1) to give the title compound as a white solid (0.412 g, 54%).

MS (ES-API, pos. ion) m/z: 336.1 [M+1]$^+$.

Step 4) Synthesis of 4-(6-cyano-1H-benzo[d]imidazol-4-yl)-2-hydroxybenzoic Acid tert-Butyl 4-(6-cyano-1H-benzo[d]imidazol-4-yl)-2-hydroxybenzoate (0.369 g, 1.10 mmol) and dichloromethane (15 mL) were added to a 100 mL single neck flask, then trifluoroacetate (2 mL) was added. The reaction mixture was stirred for 12 h at rt. The mixture was concentrated in vacuo to remove solvent, and the residue was purified by silica gel chromatography (methanol/dichloromethane (v/v)=1/10) to give the title compound as a white solid (261 mg, 85%).

MS (ES-API, neg. ion) m/z: 278.1 [M−1]$^-$; and $^1$H NMR (400 MHz, DMSO-d$_6$) δ (ppm): 13.18 (s, 1H), 8.56 (s, 1H), 8.16 (s, 1H), 7.89-7.83 (m, 3H), 7.64 (s, 1H).

Example 17: 4-(6-cyano-benzo[d]oxazol-4-yl)-2-hydroxybenzoic Acid

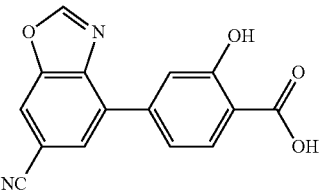 [SMILES: N#Cc1cc(-c2ccc(C(=O)O)c(O)c2)c2ncoc2c1]

Step 1) Synthesis of 4-amino-3-bromo-5-methoxybenzonitrile

4-Amino-3-methoxybenzonitrile (5.93 g, 40 mmol), acetic acid (40 mL) and methanol (100 mL) were added to a 250 mL single neck flask, then bromine (7.03 g, 44 mmol) was added dropwise at 0° C. The reaction mixture was stirred for 2 h at rt. To the mixture was added saturated aqueous sodium carbonate (200 mL). The mixture was extracted with ethyl acetate (100 mL×2). The combined organic phases were washed with saturated brine (100 mL), dried over anhydrous sodium sulfate, filtered, and concentrated in vacuo. The residue was purified by silica gel chromatography (ethyl acetate/petroleum ether (v/v)=1/10) to give the title compound as a pale yellow solid (7.63 g, 84%).

MS (ES-API, pos. ion) m/z: 227.9 [M+2]$^+$.

Step 2) Synthesis of 4-amino-3-bromo-5-hydroxybenzonitrile

4-Amino-3-bromo-5-methoxybenzonitrile (2.27 g, 10 mmol) and dichloromethane (20 mL) were added to a 100 mL single neck flask, then boron tribromide (7.5 g, 30 mmol) was added dropwise at −25° C. The reaction mixture was stirred for 12 h at rt. To the mixture was added saturated aqueous sodium bicarbonate (200 mL) and the resulting mixture was partitioned. The aqueous phase was extracted with ethyl acetate (100 mL×2). The combined organic phases were washed with saturated brine (100 mL), dried over anhydrous sodium sulfate, filtered, and concentrated in vacuo, then the residue was purified by silica gel chromatography (ethyl acetate/petroleum ether (v/v)=1/1) to give the title compound as a pale yellow solid (2.02 g, 95%).

MS (ES-API, pos. ion) m/z: 213.9 [M+2]$^+$.

Step 3) Synthesis of tert-butyl 2'-amino-5'-cyano-3,3'-dihydroxy-[1,1'-biphenyl]-4-carboxylate 4-Amino-3-bromo-5-hydroxybenzonitrile (0.279 g, 1.31 mmol), tert-butyl 2-hydroxy-4-(4,4,5,5-tetramethyl-1,3,2- dioxaborolan-2-yl) benzoate (420 mg, 1.31 mmol), 1,1'-bis(diphenylphosphino)ferrocene-palladium(II)dichloride dichloromethane complex (53 mg, 0.065 mmol) and N,N-dimethylformamide (8 mL) were added gradually to a 50 mL two-neck flask. A solution of potassium carbonate (1.3 mL, 2 M) in water was added under nitrogen, then the reaction mixture was stirred for 0.5 h at 90° C. The resulting mixture was cooled to room temperature. To the resulting mixture was added saturated brine (80 mL). The aqueous phase was extracted with ethyl acetate (40 mL×2). The combined organic phase was washed with saturated brine (60 mL), dried over anhydrous sodium sulfate, filtered, and concentrated in vacuo. The residue was purified by silica gel chromatography (ethyl acetate/petroleum ether (v/v)=1/4) to give the title compound as a yellow solid (0.205 g, 48%).

MS (ES-API, pos. ion) m/z: 327.1 [M+1]$^+$.

Step 4) Synthesis of tert-butyl 4-(6-cyanobenzo[d]oxazol-4-yl)-2-hydroxybenzoate tert-Butyl 2'-amino-5'-cyano-3,3'-dihydroxy-[1,1'-biphenyl]-4-carboxylate (0.741 g, 2.27 mmol) and triethyl orthoformate (20 mL) were added to a 100 mL single neck flask. The mixture was heated to 130° C. and stirred for 3 h. The mixture was cooled to room temperature and concentrated in vacuo, and the residue was purified by silica gel chromatography (ethyl acetate/petroleum ether (v/v)=1/8) to give the title compound as a white solid (92 mg, 12%).

MS (ES-API, pos. ion) m/z: 337.1 [M+1]$^+$.

Step 5) Synthesis of 4-(6-cyanobenzo[d]oxazol-4-yl)-2-hydroxybenzoic Acid tert-Butyl 4-(6-cyanobenzo[d]oxazol-4-yl)-2-hydroxybenzoate (0.370 g, 1.10 mmol) and dichloromethane (15 mL) were added to a 100 mL single neck flask, then trifluoroacetate (2 mL) was added. The reaction mixture was stirred for 12 h at rt. The mixture was concentrated in vacuo to remove the solvent, and the residue was purified by silica gel chromatography (methanol/dichloromethane (v/v)=1/10) to give the title compound as a white solid (0.185 g, 60%).

MS (ES-API, neg. ion) m/z: 279.1 [M−1]$^−$; and $^1$H NMR (400 MHz, DMSO-d$_6$) δ (ppm): 9.10 (s, 1H), 8.50 (s, 1H), 8.22 (s, 1H), 7.93 (d, J=8.5 Hz, 1H), 7.72 (s, 1H), 7.63 (d, J=8.2 Hz, 1H).

Example 18: 4-(6-cyano-2-methylbenzofuran-4-yl)-2-hydroxybenzoic Acid

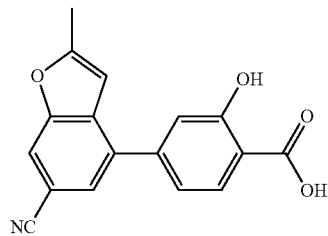 [SMILES: Cc1cc2c(-c3ccc(C(=O)O)c(O)c3)cc(C#N)cc2o1]

Step 1) Synthesis of methyl 4-hydroxy-2-methylbenzofuran-6-carboxylate

Methyl 3,5-dihydroxy-4-iodobenzoate (4.12 g, 14 mmol), cuprous iodide (130 mg, 0.68 mmol), bis(triphenylphosphine)palladium(II)chloride (477 mg, 0.68 mmol), piperidine (3.58 g, 42 mmol), 3% propyne (2.2 g, 55 mmol) in heptane (100 mL), N,N-dimethylacetamide (60 mL) and tetrahydrofuran (50 mL) were added gradually to a 500 mL two-neck flask. The reaction mixture was stirred for 24 h at 38° C. The mixture was concentrated in vacuo to remove solvent. To the residue was added saturated aqueous ammonium chloride (300 mL). The mixture was extracted with ethyl acetate (100 mL×2). The combined organic phases were washed with saturated brine (80 mL×2), dried over anhydrous sodium sulfate, filtered, and concentrated in vacuo. The residue was purified by silica gel chromatography (ethyl acetate/petroleum ether (v/v)=1/3) to give the title compound as a brown solid (2.22 g, 77%).

$^1$H NMR (400 MHz, CDCl$_3$) δ (ppm): 7.72 (s, 1H), 7.39 (s, 1H), 6.51 (s, 1H), 3.93 (s, 3H), 2.48 (s, 3H).

Step 2) Synthesis of 4-hydroxy-2-methylbenzofuran-6-carboxylic Acid

Methyl 4-hydroxy-2-methylbenzofuran-6-carboxylate (2.06 g, 10 mmol), methanol (20 mL), tetrahydrofuran (20 mL) and water (20 mL) were gradually added to a 250 mL single neck flask, then sodium hydroxide (2.0 g, 50 mmol) was added. The reaction mixture was stirred for 12 h at rt. The mixture was concentrated in vacuo to remove solvent. To the residue was added water (120 mL). The mixture was washed with ether (80 mL), and the aqueous phase was acidified to pH 1 with 2 N dilute hydrochloric acid and extracted with ethyl acetate (80 mL×2). The combined organic phases were washed with saturated brine (80 mL×2), dried over anhydrous sodium sulfate, filtered, and concentrated in vacuo to give the title compound as a white solid (1.84 g, 96%).

MS (ES-API, neg. ion) m/z: 191.0 [M−1]$^−$.

Step 3) Synthesis of 4-hydroxy-2-methylbenzofuran-6-carbonyl chloride

4-Hydroxy-2-methylbenzofuran-6-carboxylic acid (1.35 g, 7.05 mmol) and thionyl chloride (20 mL) were added to a 100 mL single neck flask. The reaction mixture was stirred for 12 h at 90° C. The mixture was concentrated in vacuo to remove thionyl chloride and give the title compound as brown viscous liquid (1.48 g, 100%).

Step 4) Synthesis of 4-hydroxy-2-methylbenzofuran-6-carboxamide

A solution of 4-hydroxy-2-methylbenzofuran-6-carbonyl chloride (1.48 g, 7.05 mmol) in dichloromethane (20 mL) was added dropwise to ammonium hydroxide (20 mL, 28%) in a 100 mL single neck flask. The reaction mixture was stirred for 2 h at rt. To the mixture was added water (100 mL), and the resulting mixture was partitioned. The aqueous phase was extracted with ethyl acetate (80 mL×2). The combined organic phase was washed with saturated brine (100 mL), dried over anhydrous sodium sulfate, filtered, and concentrated in vacuo. The residue was purified by silica gel chromatography (ethyl acetate/dichloromethane (v/v)=1/30) to give the title compound as a pale yellow solid (1.31 g, 97%).

MS (ES-API, pos. ion) m/z: 192.0 [M+1]$^+$.

Step 5) Synthesis of 4-hydroxy-2-methylbenzofuran-6-carbonitrile

4-Hydroxy-2-methylbenzofuran-6-carboxamide (0.677 g, 3.54 mmol) and toluene (20 mL) were added to a 50 mL single neck flask, then phosphorus oxychloride (2.71, 17.7 mmol) was added dropwise. The mixture was stirred for 12 h at 120° C. The resulting mixture was cooled to room temperature. To the resulting mixture was added saturated brine (80 mL), and the mixture was partitioned. The aqueous phase was extracted with ethyl acetate (40 mL×2). The combined organic phases were washed with saturated brine (60 mL), dried over anhydrous sodium sulfate, filtered, and concentrated in vacuo. The residue was purified by silica gel chromatography (ethyl acetate/petroleum ether (v/v)=1/3) to give the title compound as a pale yellow solid (0.490 g, 80%).

MS (ES-API, pos. ion) m/z: 174.0 [M+1]⁺.

Step 6) Synthesis of 6-cyano-2-methylbenzofuran-4-yl trifluoromethanesulfonate

4-Hydroxy-2-methylbenzofuran-6-carbonitrile (0.710 g, 4.1 mmol), pyridine (0.970 g, 12.3 mmol) and dichloromethane (80 mL) were added to a 250 mL single neck flask, and trifluoromethanesulfonic anhydride (1.35 g, 4.8 mmol) was added dropwise at 0° C. The mixture was stirred for 1 h at rt. The mixture was concentrated in vacuo, and the residue was purified by silica gel chromatography (ethyl acetate/petroleum ether (v/v)=1/10) to give the title compound as a white solid, 0.726 g, 58%).

MS (ES-API, pos. ion) m/z: 306.0 [M+1]⁺.

Step 7) Synthesis of tert-butyl 4-(6-cyano-2-methyl-benzofuran-4-yl)-2-hydroxybenzoate 6-Cyano-2-methylbenzofuran-4-yl trifluoromethanesulfonate (0.440 g, 1.44 mmol), tert-butyl 2-hydroxy-4-(4,4,5,5-tetramethyl-1,3,2-dioxaborolan-2-yl) benzoate (420 mg, 1.31 mmol), 1,1'-bis(diphenylphosphino)ferrocene-palladium(II)dichloride dichloromethane complex (53 mg, 0.065 mmol), potassium carbonate (0.362 g, 2.62 mmol) and anhydrous 1,4-dioxane (15 mL) were added gradually to a 50 mL two-neck flask. The reaction mixture was stirred for 5 h at 90° C. under nitrogen. The resulting mixture was cooled to room temperature. To the resulting mixture was added saturated brine (80 mL). The mixture was extracted with ethyl acetate (40 mL×2). The combined organic phases were washed with saturated brine (60 mL), dried over anhydrous sodium sulfate, filtered, and concentrated in vacuo. The residue was purified by silica gel chromatography (ethyl acetate/petroleum ether (v/v)=1/10) to give the title compound as a white solid, 0.307 g, 67%).

MS (ES-API, pos. ion) m/z: 350.1 [M+1]⁺.

Step 8) Synthesis of 4-(6-cyano-2-methylbenzofuran-4-yl)-2-hydroxybenzoic Acid tert-Butyl 4-(6-cyano-2-methylbenzofuran-4-yl)-2-hydroxybenzoate (0.217 g, 0.62 mmol) and dichloromethane (15 mL) were added to a 100 mL single-neck flask, then trifluoroacetate (2 mL) was added. The reaction mixture was stirred for 12 h at rt. The resulting mixture was concentrated in vacuo to remove solvent, and the residue was purified by silica gel chromatography (methanol/dichloromethane (v/v)=1/20) to give the title compound as a white solid (0.167 g, 92%).

MS (ES-API, neg. ion) m/z: 292.0 [M−1]⁻; and

¹H NMR (400 MHz, DMSO-d₆) δ (ppm): 11.60 (s, 1H), 8.21 (s, 1H), 8.01-7.92 (m, 1H), 7.83 (s, 1H), 7.27 (d, J=5.1 Hz, 2H), 6.93 (s, 1H), 2.57 (s, 3H).

Example 19: 4-(5-cyano-2-methylbenzofuran-7-yl)-2-hydroxybenzoic Acid

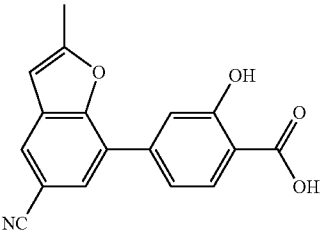 [SMILES: Cc1cc2cc(C#N)cc(-c3ccc(C(=O)O)c(O)c3)c2o1]

Step 1) Synthesis of 4-(allyloxy)-3-bromobenzonitrile

3-Bromo-4-hydroxybenzonitrile (1.98 g, 10 mmol), allyl bromide (2.78 g, 23 mmol), potassium carbonate (4.15 g, 30 mmol) and acetone (100 mL) were added gradually to a 250 mL two-neck flask. The reaction mixture was stirred for 24 h at rt. The mixture was filtered and the filter cake was washed with acetone (50 mL). The combined filtrates were concentrated in vacuo, and the residue was purified by silica gel chromatography (ethyl acetate/petroleum ether (v/v)=1/40) to give the title compound as colorless oil (2.29 g, 96%).

MS (ES-API, pos. ion) m/z: 238.9 [M+2]⁺.

Step 2) Synthesis of 3-allyl-5-bromo-4-hydroxybenzonitrile 4-(Allyloxy)-3-bromobenzonitrile (1.50 g, 6.3 mmol) and 1-methyl-2-pyrrolidinone (15 mL) were added to a 50 mL single neck flask. The reaction mixture was stirred for 18 h at 190° C. The resulting mixture was cooled to room temperature. To the resulting mixture was added saturated brine (80 mL). The mixture was extracted with ethyl acetate (40 mL×2). The combined organic phase was washed with saturated brine (60 mL), dried over anhydrous sodium sulfate, filtered, and concentrated in vacuo. The residue was purified by silica gel chromatography (ethyl acetate/petroleum ether (v/v)=1/40) to give the title compound as colorless liquid (1.30 g, 87%).

MS (ES-API, pos. ion) m/z: 238.9 [M+2]⁺.

Step 3) Synthesis of 7-bromo-2-(bromomethyl)-2,3-dihydrobenzofuran-5-carbonitrile 3-Allyl-5-bromo-4-hydroxybenzonitrile (0.476 g, 2.0 mmol) and anhydrous tetrahydrofuran (10 mL) were added to a 50 mL single neck flask, and N-bromosuccinimide (0.399 g, 2.24 mmol) was added at 0° C. The reaction mixture was stirred for 18 h at rt. To the mixture was added saturated brine (80 mL). The mixture was extracted with ethyl acetate (40 mL×2). The combined organic phases were washed with saturated brine (60 mL), dried over anhydrous sodium sulfate, filtered, and concentrated in vacuo to give the title compound as a white solid (0.609 g, 96%).

MS (ES-API, pos. ion) m/z: 317.9 [M+3]⁺.

Step 4) Synthesis of 7-bromo-2-methylbenzofuran-5-carbonitrile

7-Bromo-2-(bromomethyl)-2,3-dihydrobenzofuran-5-carbonitrile (0.600 g, 1.89 mmol), 1,8-diazabicyclo[5.4.0]

undec-7-ene (0.320 g, 2.10 mmol) and anhydrous N,N-dimethylformamide (10 mL) were added to a 50 mL single neck flask. The reaction mixture was stirred for 8 h at 55° C. under nitrogen. The resulting mixture was cooled to room temperature. To the resulting mixture was added saturated brine (80 mL). The mixture was extracted with ethyl acetate (40 mL×2). The combined organic phases were washed with saturated brine (60 mL), dried over anhydrous sodium sulfate, filtered, and concentrated in vacuo. The residue was purified by silica gel chromatography (ethyl acetate/petroleum ether (v/v)=1/40) to give the title compound as a white solid (0.299 g, 67%).

$^1$H NMR (600 MHz, CDCl$_3$) δ (ppm): 7.77 (d, J=1.2 Hz, 1H), 7.67 (d, J=1.2 Hz, 1H), 6.55 (d, J=1.0 Hz, 1H), 2.57 (s, 3H).

Step 5) Synthesis of tert-butyl 4-(5-cyano-2-methylbenzofuran-7-yl)-2-hydroxybenzoate 7-Bromo-2-methylbenzofuran-5-carbonitrile (0.309 g, 1.31 mmol), tert-butyl 2-hydroxy-4-(4,4,5,5-tetramethyl-1,3,2-dioxaborolan-2-yl) benzoate (420 mg, 1.31 mmol), 1,1'-bis(diphenylphosphino)ferrocene-palladium(II)dichloride dichloromethane complex (53 mg, 0.065 mmol) and N,N-dimethylformamide (8 mL) were added gradually to a 50 mL of two-neck flask. A solution of potassium carbonate (1.3 mL, 2 M) in water was added under nitrogen, then the reaction mixture was stirred for 0.5 h at 90° C. The resulting mixture was cooled to room temperature. To the resulting mixture was added saturated brine (80 mL). The mixture was extracted with ethyl acetate (40 mL×2). The combined organic phases were washed with saturated brine (60 mL), dried over anhydrous sodium sulfate, filtered, and concentrated in vacuo. The residue was purified by silica gel chromatography (ethyl acetate/petroleum ether (v/v)=1/8) to give the title compound as a pale yellow solid (0.416 g, 91%).

MS (ES-API, pos. ion) m/z: 350.1 [M+1]$^+$.

Step 6) Synthesis of 4-(5-cyano-2-methylbenzofuran-7-yl)-2-hydroxybenzoic Acid tert-Butyl 4-(5-cyano-2-methylbenzofuran-7-yl)-2-hydroxybenzoate (0.416 g, 1.19 mmol) and dichloromethane (15 mL) were added to a 100 mL of single-neck flask, and trifluoroacetate (2 mL) was added. The reaction mixture was stirred for 12 h at rt. The resulting mixture was concentrated in vacuo to remove the solvent, and the residue was purified by silica gel chromatography (methanol/dichloromethane (v/v)=1/20) to give the title compound as a white solid (0.286 g, 82%).

MS (ES-API, neg. ion) m/z: 292.0 [M−1]$^-$; and
$^1$H NMR (400 MHz, DMSO-d$_6$) δ (ppm): 11.40 (s, 1H), 8.12 (s, 1H), 7.95 (s, 1H), 7.93 (d, J=8.3 Hz, 1H), 7.50 (s, 1H), 7.46 (d, J=8.3 Hz, 1H), 6.80 (s, 1H), 2.53 (s, 3H).

Example 20: 4-(5-cyano-3-(trifluoromethyl)benzofuran-7-yl)-2-hydroxybenzoic Acid

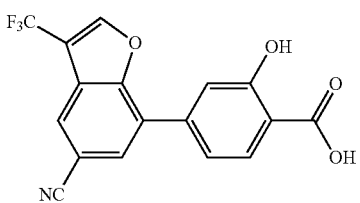 [SMILES: N#Cc1cc(-c2ccc(C(=O)O)c(O)c2)c2occ(C(F)(F)F)c2c1]

Step 1) Synthesis of 7-bromo-5-methyl-3-(trifluoromethyl)-2,3-dihydrobenzofuran-2-ol 2,2,2-Trifluoroethyl amine hydrochloride (8.13 g, 60 mmol) and dichloromethane (90 mL) were added to a 250 mL two-neck flask, and a solution of sodium nitrite (4.97 g, 72 mmol) in water (3 mL) was added dropwise at 0° C. The mixture was stirred for 1 h at 0° C. Then 3-bromo-5-methyl-2-hydroxybenzaldehyde (2.15 g, 10.0 mmol) and boron trifluoride etherate (5.68 g, 40 mmol) were added gradually at −78° C. The reaction mixture was stirred for 12 h at −78° C., and then stirred for 12 h at rt. To the resulting mixture was added methanol (40 mL), saturated sodium bicarbonate (200 mL) and ethyl acetate (200 mL), and the mixture was partitioned. The organic phase was washed with saturated brine (100 mL), dried over anhydrous sodium sulfate, filtered, and concentrated in vacuo. The residue was purified by silica gel chromatography (ethyl acetate/petroleum ether (v/v)=1/10) to give the title compound as a yellow solid (1.93 g, 65%).

$^1$H NMR (400 MHz, CDCl$_3$) δ (ppm): 7.28 (s, 1H), 7.09 (s, 1H), 6.16-6.14 (m, 1H), 4.04-4.02 (m, 1H), 2.31 (s, 3H); and
$^{19}$F NMR (376 MHz, CDCl$_3$) δ (ppm): −70.45 (s, 3F).

Step 2) Synthesis of 7-bromo-5-methyl-3-(trifluoromethyl)benzofuran

7-Bromo-5-methyl-3-(trifluoromethyl)-2,3-dihydrobenzofuran-2-ol (2.97 g, 10.0 mmol) and concentrated sulfuric acid (20 mL, 98%) were added to a 250 mL single-neck flask. The mixture was stirred for 0.5 h at rt. The resulting mixture was poured into ice-water (200 mL) slowly. The mixture was extracted with ethyl acetate (80 mL×2). The combined organic phases were washed with saturated brine (80 mL×2), dried over anhydrous sodium sulfate, filtered, and concentrated in vacuo. The residue was purified by silica gel chromatography (ethyl acetate/petroleum ether (v/v)=1/100) to give the title compound as a white solid (2.48 g, 89%).

$^1$H NMR (400 MHz, CDCl$_3$) δ (ppm): 7.98 (d, J=1.3 Hz, 1H), 7.41 (s, 2H), 2.46 (s, 3H); and
$^{19}$F NMR (376 MHz, CDCl$_3$) δ (ppm): −59.68 (s, 3F).

Step 3) Synthesis of 7-bromo-3-(trifluoromethyl)benzofuran-5-carbonitrile

7-Bromo-5-methyl-3-(trifluoromethyl)benzofuran (1.14 g, 4.1 mmol), tert-butyl nitrite (1.26 g, 12.2 mmol), N-hydroxyphthalimide (669 mg, 4.1 mmol), palladium diacetate (45 mg, 0.20 mmol) and acetonitrile (20 mL) were added gradually to a 25 mL microwave tube. The reaction mixture was stirred for 48 h at 80° C. under nitrogen. The resulting mixture was cooled to room temperature and concentrated in vacuo, and the residue was purified by silica gel chromatography (dichloromethane/petroleum ether (v/v)=1/30) to give the title compound as a white solid (0.309 g, 26%).

$^1$H NMR (400 MHz, CDCl$_3$) δ (ppm) 8.18 (d, J=1.3 Hz, 1H), 8.00 (s, 1H), 7.88 (d, J=1.2 Hz, 1H).

Step 4) Synthesis of tert-butyl 4-(5-cyano-3-((trifluoromethyl)benzofuran-7-yl)-2-hydrobenzoate 7-Bromo-3-(trifluoromethyl)benzofuran-5-carbonitrile (0.380 g, 1.31 mmol), tert-butyl 2-hydroxy-4-(4,4,5,5-tetramethyl-1,3,2-dioxaborolan-2-yl) benzoate (420 mg, 1.31 mmol), 1,1'-bis(diphenylphosphino)ferrocene-palladium(II)

dichloride dichloromethane complex (53 mg, 0.065 mmol) and N,N-dimethylformamide (8 mL) were added gradually to a 50 mL two-neck flask. A solution of potassium carbonate (1.3 mL, 2 M) in water was added under nitrogen, then the reaction mixture was stirred for 0.5 h at 90° C. The resulting mixture was cooled to room temperature. To the resulting mixture was added saturated brine (80 mL). The mixture was extracted with ethyl acetate (40 mL×2). The combined organic phases were washed with saturated brine (60 mL), dried over anhydrous sodium sulfate, filtered, and concentrated in vacuo. The residue was purified by silica gel chromatography (dichloromethane/petroleum ether (v/v)=1/4) to give the title compound as a white solid (0.328 g, 62%).

MS (ES-API, pos. ion) m/z: 404.1 [M+1]$^+$.

Step 5) Synthesis of 4-(5-cyano-3-(trifluoromethyl)benzofuran-7-yl)-2-hydroxybenzoic Acid tert-Butyl 4-(5-cyano-3-((trifluoromethyl)benzofuran-7-yl)-2-hydroxybenzoate (0.480 g, 1.19 mmol) and dichloromethane (15 mL) were added to a 100 mL single-neck flask, and trifluoroacetate (2 mL) was added. The reaction mixture was stirred for 12 h at rt. The resulting mixture was concentrated in vacuo to remove the solvent, and the residue was purified by silica gel chromatography (methanol/dichloromethane (v/v)=1/20) to give the title compound as a white solid (0.347 g, 84%).

MS (ES-API, neg. ion) m/z: 346.0 [M−1]$^-$;

$^1$H NMR (400 MHz, DMSO-d$_6$) δ (ppm): 9.09 (d, J=1.4 Hz, 1H), 8.36 (s, 1H), 8.25 (d, J=1.3 Hz, 1H), 7.95 (d, J=8.2 Hz, 1H), 7.52 (d, J=1.5 Hz, 1H), 7.48-7.45 (m, 1H); and $^{19}$F NMR (376 MHz, DMSO-d$_6$) δ (ppm): −58.00 (s, 3F).

Example 21:
4-(6-cyanobenzofuran-4-yl)-2-hydroxybenzoic Acid

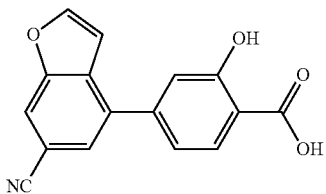

Step 1) Synthesis of 3-(ethoxycarbonyl)-4-(furan-2-yl)-3-butenoic Acid

Potassium t-butoxide (126.0 g, 1123 mmol) and t-butanol (350 mL) were added to a 1000 mL two-neck flask, then a mixture of diethyl succinate (294 g, 1688 mmol) and furan-2-carbaldehyde (36.0 g, 375 mmol) was added dropwise. The reaction mixture was stirred for 3 h at 110° C. under nitrogen. The resulting mixture was cooled to room temperature and concentrated in vacuo to remove t-butanol. To the residue was added diluted hydrochloric acid (1000 mL, 6 M). The mixture was extracted with diethyl ether (40 mL×2). The combined organic phases were washed with saturated brine (100 mL), dried over anhydrous sodium sulfate, filtered, and concentrated in vacuo. The residue was purified by silica gel chromatography (ethyl acetate/petroleum ether (v/v)=1/1) to give the title compound as a pale yellow solid (83.2 g, 99%).

MS (ES-API, neg. ion) m/z: 223.1 [M−1]$^-$.

Step 2) Synthesis of ethyl 4-acetoxybenzofuran-6-carboxylate 3-(Ethoxycarbonyl)-4-(furan-2-yl)-3-butenoic acid (84.1 g, 375 mmol), sodium acetate (123 g, 1499 mmol) and acetic anhydride (350 mL) were added to a 1000 mL single neck flask. The reaction mixture was stirred for 5 h at 180° C. The resulting mixture was cooled to room temperature and concentrated in vacuo to remove acetic anhydride. To the residue was added 15% aqueous sodium carbonate to adjust pH to weakly alkaline. The aqueous phase was extracted with ethyl acetate (100 mL×2). The combined organic phases were washed with saturated brine (100 mL), dried over anhydrous sodium sulfate, filtered, and concentrated in vacuo. The residue was purified by silica gel chromatography (ethyl acetate/petroleum ether (v/v)=1/6) to give the title compound as light yellow oil (55.6 g, 60%).

MS (ES-API, pos. ion) m/z: 249.1 [M+1]$^+$.

Step 3) Synthesis of 4-hydroxybenzofuran-6-carboxylic Acid

Ethyl 4-acetoxybenzofuran-6-carboxylate (24.8 g, 100 mmol), methanol (100 mL), tetrahydrofuran (100 mL) and water (100 mL) were added a 1000 mL single neck flask, and sodium hydroxide (12 g, 300 mmol) was added. The reaction mixture was stirred for 12 h at rt. The resulting mixture was concentrated in vacuo to remove solvent. To the residue was added water (600 mL). The mixture was washed with diethyl ether (200 mL), and the aqueous phase was acidified to pH 1 with 2 N dilute hydrochloric acid and filtered. The filter cake was washed with water (300 mL×2), dried to give the title compound as a white solid (16.9 g, 95%).

MS (ES-API, neg. ion) m/z: 177.0 [M−1]$^-$.

Step 4) Synthesis of methyl 4-methoxybenzofuran-6-carboxylate

4-Hydroxybenzofuran-6-carboxylic acid (1.78 g, 10 mmol), cesium carbonate (8.15 g, 25 mmol) and N,N-dimethylformamide (20 mL) were added to a 100 mL single neck flask, and iodomethane (3.12 g, 22 mmol) was added dropwise. The reaction mixture was stirred for 24 h at rt The mixture was quenched with saturated ammonium chloride (200 mL). The aqueous phase was extracted with ethyl acetate (100 mL×2). The combined organic phases were washed with saturated brine (100 mL), dried over anhydrous sodium sulfate, filtered, and concentrated in vacuo. The residue was purified by silica gel chromatography (ethyl acetate/petroleum ether (v/v)=1/10) to give the title compound as a white solid (1.92 g, 93%).

MS (ES-API, pos. ion) m/z: 207.1 [M+1]$^+$.

Step 5) Synthesis of 4-methoxybenzofuran-6-carboxylic Acid

Methyl 4-methoxybenzofuran-6-carboxylate (2.06 g, 10 mmol), methanol (10 mL), tetrahydrofuran (10 mL) and water (10 mL) were gradually added to a 100 mL single neck flask, then sodium hydroxide (1.2 g, 30 mmol) was added. The reaction mixture was stirred for 12 h at rt. The mixture was concentrated in vacuo to remove solvent. To the residue was added water (80 mL). The mixture was washed with ether (80 mL), and the aqueous phase was acidified to pH 1 with 2 N dilute hydrochloric acid, filtered. The filter cake was washed with water (60 mL×2), dried to give the title compound as a white solid (1.75 g, 91%).

MS (ES-API, neg. ion) m/z: 191.0 [M−1]⁻.

Step 6) Synthesis of 4-methoxybenzofuran-6-carbonyl chloride

4-Methoxybenzofuran-6-carboxylic acid (1.35 g, 7.05 mmol), thionyl chloride (20 mL) were added to a 100 mL single neck flask. The reaction mixture was stirred for 12 h at 90° C. The mixture was concentrated in vacuo to remove thionyl chloride to give the title compound as brown viscous liquid (1.48 g, 100%).

Step 7) Synthesis of 4-methoxybenzofuran-6-carboxamide

A solution of 4-methoxybenzofuran-6-carbonyl chloride (1.48 g, 7.05 mmol) in dichloromethane (20 mL) was added dropwise to ammonium hydroxide (20 mL, 28%) in a 100 mL single neck flask. The reaction mixture was stirred for 2 h at rt. To the mixture was added water (100 mL). The aqueous phase was extracted with ethyl acetate (80 mL×2). The combined organic phase was washed with saturated brine (100 mL), dried over anhydrous sodium sulfate, filtered, and concentrated in vacuo. The residue was purified by silica gel chromatography (ethyl acetate/dichloromethane (v/v)=1/30) to give the title compound as a pale yellow solid (1.31 g, 97%).

MS (ES-API, pos. ion) m/z: 192.0 [M+1]⁺.

Step 8) Synthesis of 4-methoxybenzofuran-6-carbonitrile

4-Methoxybenzofuran-6-carboxamide (0.677 g, 3.54 mmol) and toluene (20 mL) were added to a 50 mL single neck flask, then phosphorus oxychloride (2.71, 17.7 mmol) was added dropwise. The mixture was stirred for 12 h at 120° C. The resulting mixture was cooled to room temperature. To the resulting mixture was added saturated brine (80 mL), and the mixture was partitioned. The aqueous phase was extracted with ethyl acetate (40 mL×2). The combined organic phases were washed with saturated brine (60 mL), dried over anhydrous sodium sulfate, filtered, and concentrated in vacuo. The residue was purified by silica gel chromatography (ethyl acetate/petroleum ether (v/v)=1/3) to give the title compound as a pale yellow solid (0.490 g, 80%).

MS (ES-API, pos. ion) m/z: 174.0 [M+1]⁺.

Step 9) Synthesis of 4-hydroxybenzofuran-6-carbonitrile

4-Methoxybenzofuran-6-carbonitrile (1.73 g, 10 mmol) and dichloromethane (20 mL) were added to a 100 mL single neck flask, then boron tribromide (7.5 g, 30 mmol) was added dropwise at −70° C. The reaction mixture was stirred for 24 h at rt. To the mixture was added ice-water (200 mL). The mixture was extracted with ethyl acetate (100 mL×2). The combined organic phases were washed with saturated brine (100 mL), dried over anhydrous sodium sulfate, filtered, and concentrated in vacuo. The residue was purified by silica gel chromatography (ethyl acetate/petroleum ether (v/v)=1/6) to give the title compound as a pale yellow solid (1.42 g, 89%).

MS (ES-API, neg. ion) m/z: 158.0 [M−1]⁻.

Step 10) Synthesis of 6-cyanobenzofuran-4-yl trifluoromethanesulfonate

4-Hydroxybenzofuran-6-carbonitrile (0.652 g, 4.1 mmol), pyridine (0.970 g, 12.3 mmol) and dichloromethane (80 mL) were added to a 250 mL single neck flask, then trifluoromethanesulfonic anhydride (1.35 g, 4.8 mmol) was added dropwise at 0° C. The mixture was stirred for 1 h at rt. The mixture was concentrated in vacuo, and the residue was purified by silica gel chromatography (dichloromethane/petroleum ether (v/v)=1/5) to give the title compound as a white solid (0.991 g, 83%).

MS (ES-API, pos. ion) m/z: 291.9 [M+1]⁺.

Step 11) Synthesis of tert-butyl 4-(6-cyanobenzafuran-4-yl)-2-hydroxybenzoate 6-cyanobenzofuran-4-yl trifluoromethanesulfonate (0.419 g, 1.44 mmol), tert-butyl 2-hydroxy-4-(4,4,5,5-tetramethyl-1,3,2-dioxaborolan-2-yl) benzoate (420 mg, 1.31 mmol), 1,1'-bis(diphenylphosphino)ferrocene-palladium(II)dichloride dichloromethane complex (53 mg, 0.065 mmol), potassium carbonate (0.362 g, 2.62 mmol) and anhydrous 1,4-dioxane (15 mL) were added gradually to a 50 mL two-neck flask. The reaction mixture was stirred for 7 h at 90° C. under nitrogen. The resulting mixture was cooled to room temperature. To the resulting mixture was added saturated brine (80 mL). The mixture was extracted with ethyl acetate (40 mL×2). The combined organic phases were washed with saturated brine (60 mL), dried over anhydrous sodium sulfate, filtered, and concentrated in vacuo. The residue was purified by silica gel chromatography (dichloromethane/petroleum ether (v/v)=1/4) to give the title compound as a white solid, 0.185 g, 42%).

MS (ES-API, pos. ion) m/z: 336.1 [M+1]⁺.

Step 12) Synthesis of 4-(6-cyanobenzofuran-4-yl)-2-hydroxybenzoic Acid tert-Butyl 4-(6-cyanobenzafuran-4-yl)-2-hydroxybenzoate (0.185 g, 0.552 mmol) and dichloromethane (15 mL) were added to a 100 mL single-neck flask, then trifluoroacetate (2 mL) was added. The reaction mixture was stirred for 12 h at rt. The resulting mixture was concentrated in vacuo to remove solvent, and the residue was purified by silica gel chromatography (methanol/dichloromethane (v/v)=1/20) to give the title compound as a white solid (0.128 g, 83%).

MS (ES-API, neg. ion) m/z: 278.0 [M−1]⁻; and

¹H NMR (600 MHz, DMSO-d₆) δ (ppm): 11.44 (s, 1H), 8.39 (d, J=2.2 Hz, 1H), 8.33 (s, 1H), 7.95 (d, J=8.5 Hz, 1H), 7.88 (d, J=1.0 Hz, 1H), 7.27-7.26 (m, 2H), 7.22 (d, J=1.3 Hz, 1H). Example 22: 4-(5-cyanobenzofuran-7-yl)-2-(trifluoromethyl)benzoic Acid

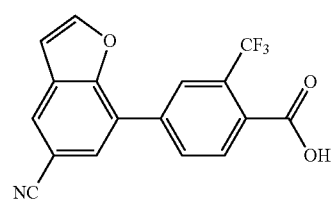 [SMILES: N#Cc1cc(-c2ccc(C(=O)O)c(C(F)(F)F)c2)c2occc2c1]

Step 1) Synthesis of 7-(4,4,5,5-tetramethyl-1,3,2-dioxaborolan-2-yl)benzofuran-5-carbonitrile 7-Bromo-5-carbonitrile (2.2 g, 10 mmol), bis(pinacolato)diboron (3.30 g, 13 mmol), 1,1'-bis(diphenylphosphino)ferrocene-palladium(II)dichloride dichloromethane complex (816 mg, 1.0 mmol), anhydrous potassium acetate (3.43 g, 35 mmol) and N,N-dimethylformamide (15 mL) were added gradually to a 50 mL two-neck flask. The reaction mixture was stirred for 6 h at 90° C. under nitrogen. The resulting mixture was cooled to room temperature. To the resulting mixture was added saturated brine (100 mL). The mixture was extracted with ethyl acetate (80 mL×2). The combined organic phases were washed with saturated brine (80 mL), dried over anhydrous sodium sulfate, filtered, and concentrated in vacuo. The residue was purified by silica gel chromatography (ethyl acetate/petroleum ether (v/v)=1/2) to give the title compound as a white solid (2.29 g, 85%).

MS (ES-API, pos. ion) m/z: 270.1 [M+1]$^+$.

Step 2) Synthesis of methyl 4-(5-cyanobenzofuran-7-yl)-2-(trifluoromethyl)benzoate Methyl 4-bromo-2-(trifluoromethyl)benzoate (0.408 g, 1.44 mmol), 7-(4,4,5,5-tetramethyl-1,3,2-dioxaborolan-2-yl)benzofuran-5-carbonitrile (0.353 g, 1.31 mmol), 1,1'-bis(diphenylphosphino)ferrocene-palladium(II)dichloride dichloromethane complex (53 mg, 0.065 mmol) and N,N-dimethylformamide (8 mL) were added gradually to a 50 mL two-neck flask. A solution of potassium carbonate (1.3 mL, 2 M) in water was added under nitrogen, then the reaction mixture was stirred for 0.5 h at 90° C. The resulting mixture was cooled to room temperature. To the resulting mixture was added saturated brine (80 mL). The mixture was extracted with ethyl acetate (40 mL×2). The combined organic phase was washed with saturated brine (60 mL), dried over anhydrous sodium sulfate, filtered, and concentrated in vacuo. The residue was purified by silica gel chromatography (dichloromethane/petroleum ether (v/v)=1/15) to give the title compound as a white solid (0.348 g, 77%).

MS (ES-API, pos. ion) m/z: 346.1 [M+1]$^+$.

Step 3) Synthesis of 4-(5-cyanobenzofuran-7-yl)-2-(trifluoromethyl)benzoic Acid Methyl 4-(5-cyanobenzofuran-7-yl)-2-(trifluoromethyl)benzoate (0.345 g, 0.99 mmol), methanol (8 mL), tetrahydrofuran (8 mL) and water (8 mL) were added into a 100 mL single neck flask, then sodium hydroxide (0.4 g, 9.9 mmol) was added. The reaction mixture was stirred for 12 h at rt. The resulting mixture was concentrated in vacuo to remove solvent. To the residue was added water (60 mL). The mixture was washed with diethyl ether (50 mL), and the aqueous phase was acidified to pH 1 with 2 N dilute hydrochloric acid. The resulting mixture was extracted with ethyl acetate (40 mL×2). The combined organic phases were washed with saturated brine (40 mL×2), dried over anhydrous sodium sulfate, filtered, and concentrated in vacuo. The residue was purified by silica gel chromatography (methanol/dichloromethane (v/v)=1/50) to give the title compound as a white solid (0.243 g, 74%).

MS (ES-API, pos. ion) m/z: 332.0 [M+1]$^+$;

$^1$H NMR (400 MHz, DMSO-d$_6$) δ (ppm): 8.34-8.30 (m, 4H), 8.18 (s, 1H), 7.99 (d, J=7.1 Hz, 1H), 7.20 (s, 1H); and $^{19}$F NMR (376 MHz, DMSO-d$_6$) δ (ppm): −58.05.

Example 23: 4-(5-cyanobenzofuran-7-yl)benzoic Acid

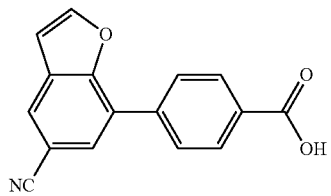 [SMILES: N#Cc1cc(-c2ccc(C(=O)O)cc2)c2occc2c1]

Step 1) Synthesis of methyl 4-(5-cyanobenzofuran-7-yl)benzoate

Methyl 4-bromobenzoate (0.310 g, 1.44 mmol), 7-(4,4,5,5-tetramethyl-1,3,2-dioxaborolan-2-yl)benzofuran-5-carbonitrile (0.353 g, 1.31 mmol), 1,1'-bis(diphenylphosphino)ferrocene-palladium(II)dichloride dichloromethane complex (53 mg, 0.065 mmol) and N,N-dimethylformamide (8 mL) were added gradually to a 50 mL two-neck flask. A solution of potassium carbonate (1.3 mL, 2 M) in water was added under nitrogen, then the reaction mixture was stirred for 0.5 h at 90° C. The resulting mixture was cooled to room temperature. To the resulting mixture was added saturated brine (80 mL). The mixture was extracted with ethyl acetate (40 mL×2). The combined organic phases were washed with saturated brine (60 mL), dried over anhydrous sodium sulfate, filtered, and concentrated in vacuo. The residue was purified by silica gel chromatography (ethyl acetate/petroleum ether (v/v)=1/10) to give the title compound as a white solid (0.272 g, 75%).

MS (ES-API, pos. ion) m/z: 278.1 [M+1]$^+$.

Step 2) Synthesis of 4-(5-cyanobenzofuran-7-yl)benzoic Acid

Methyl 4-(5-cyanobenzofuran-7-yl)benzoate (0.274 g, 0.99 mmol), methanol (8 mL), tetrahydrofuran (8 mL) and water (8 mL) were added to a 100 mL single neck flask, then sodium hydroxide (0.4 g, 9.9 mmol) was added. The reaction mixture was stirred for 12 h at rt. The resulting mixture was concentrated in vacuo to remove solvent. To the residue was added water (60 mL). The mixture was washed with diethyl ether (50 mL), and the aqueous phase was acidified to pH 1 with 2 N dilute hydrochloric acid. The resulting mixture was extracted with ethyl acetate (40 mL×2). The combined organic phases were washed with saturated brine (40 mL×2), dried over anhydrous sodium sulfate, filtered, and concentrated in vacuo. The residue was purified by silica gel chromatography (methanol/dichloromethane (v/v)=1/50) to give the title compound as a white solid (0.227 g, 87%).

MS (ES-API, pos. ion) m/z: 264.1 [M+1]$^-$; and $^1$H NMR (400 MHz, DMSO-d6) δ (ppm): 13.13 (s, 1H), 8.31-8.29 (m, 2H), 8.12-8.10 (m, 2H), 8.07-8.05 (m, 3H), 7.21 (d, J=2.0, 1H).

Example 24: 2-hydroxy-4-(5-(trifluoromethyl)benzofuran-7-yl)benzoic Acid

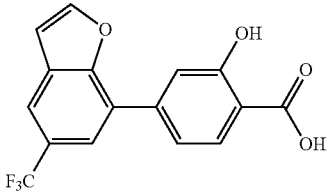 [SMILES: O=C(O)c1ccc(-c2cc(C(F)(F)F)cc3ccoc23)cc1O]

Step 1) Synthesis of 2-bromo-1-(2,2-diethoxyethoxy)-4-(trifluoromethyl)benzene 2-Bromo-4-(trifluoromethyl)phenol (10.4 g, 43.3 mmol), 2-bromo-1,1-diethoxyethane (8.06 mL, 52.0 mmol), cesium carbonate (28.2 g, 86.6 mmol) and anhydrous N,N-dimethylformamide (60 mL) were added gradually to a 100 mL single neck flask. The reaction was stirred for 18 h at 150° C. under nitrogen. The resulting mixture was cooled to room temperature. To the resulting mixture was added saturated aqueous ammonium chloride (200 mL). The mixture was extracted with ethyl acetate (100 mL×2). The combined organic phases were washed with saturated brine (100 mL), dried over anhydrous sodium sulfate, filtered, and concentrated in vacuo. The residue was purified by silica gel chromatography (ethyl acetate/petroleum ether (v/v)=1/30) to give the title compound as pale yellow liquid (10.4 g, 67%).

Step 2) Synthesis of 7-bromo-5-(trifluoromethyl)benzofuran

Polyphosphoric acid (5.00 g) and chlorobenzene (40 mL) were added to a 250 mL single neck flask, and the mixture was heated to reflux under nitrogen. Then a solution of 2-bromo-1-(2,2-diethoxyethoxy)-4-(trifluoromethyl)benzene (3.79 g, 10.6 mmol) in chlorobenzene (30 mL) was added dropwise. The reaction was stirred for 2 h at 145° C. The resulting mixture was cooled to room temperature. The upper organic layer was poured out and concentrated in vacuo, and the residue was purified by silica gel chromatography (ethyl acetate/petroleum ether (v/v)=1/30) to give the title compound as colorless liquid (0.478 g, 17%).

$^1$H NMR (400 MHz, CDCl$_3$) δ (ppm): 7.87 (s, 1H), 7.81 (s, 1H), 7.76 (s, 1H), 6.95 (d, J=2.0 Hz, 1H).

Step 3) Synthesis of tert-butyl 2-hydroxy-4-(5-(trifluoromethyl)benzofuran-7-yl)benzoate 7-Bromo-5-(trifluoromethyl)benzofuran (0.347 g, 1.31 mmol), tert-butyl 2-hydroxy-4-(4,4,5,5-tetramethyl-1,3,2-dioxaborolan-2-yl) benzoate (420 mg, 1.31 mmol), 1,1'-bis(diphenylphosphino)ferrocene-palladium(II)dichloride dichloromethane complex (53 mg, 0.065 mmol) and N,N-dimethylformamide (8 mL) were added gradually to a 50 mL two-neck flask. A solution of potassium carbonate (1.3 mL, 2 M) in water was added under nitrogen, then the reaction mixture was stirred for 0.5 h at 90° C. The resulting mixture was cooled to room temperature. To the resulting mixture was added saturated brine (80 mL). The mixture was extracted with ethyl acetate (40 mL×2). The combined organic phases were washed with saturated brine (60 mL), dried over anhydrous sodium sulfate, filtered, and concentrated in vacuo. The residue was purified by silica gel chromatography (dichloromethane/petroleum ether (v/v)=1/4) to give the title compound as a white solid (0.287 g, 58%).

MS (ES-API, pos. ion) m/z: 379.1 [M+1]$^+$.

Step 4) Synthesis of 2-hydroxy-4-(5-(trifluoromethyl)benzofuran-7-yl)benzoic Acid tert-Butyl 2-hydroxy-4-(5-(trifluoromethyl)benzofuran-7-yl)benzoate (0.287 g, 0.76 mmol) and dichloromethane (15 mL) were added to a 100 mL single-neck flask, then trifluoroacetate (2 mL) was added. The reaction mixture was stirred for 12 h at rt. The resulting mixture was concentrated in vacuo to remove solvent, and the residue was purified by silica gel chromatography (methanol/dichloromethane (v/v)=1/20) to give the title compound as a white solid (0.171 g, 70%).

MS (ES-API, neg. ion) m/z: 321.0 [M−1]$^-$;
$^1$H NMR (400 MHz, DMSO-d6) δ (ppm): 8.27 (s, 1H), 8.15 (s, 1H), 7.94 (s, 1H), 7.85 (s, 1H), 7.51-7.47 (m, 2H), 7.19 (s, 1H); and
$^{19}$F NMR (376 MHz, DMSO-d$_6$) δ (ppm): −59.32 (s, 3F).

Example 25: 4-(6-cyano-2-(trifluoromethyl)benzofuran-4-yl)-2-hydroxybenzoic Acid

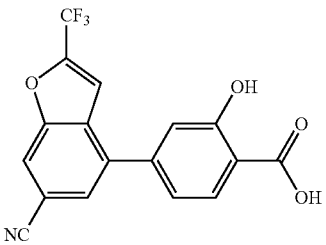 [SMILES: N#Cc1cc(-c2ccc(C(=O)O)c(O)c2)c2cc(C(F)(F)F)oc2c1]

Step 1) Synthesis of ethyl (Z)-3-bromo-2-(2-chloro-3,3,3-trifluoro-1-propen-1-yl)-5-methyl phenylacetate 2-Bromo-6-hydroxy-4-methylbenzaldehyde (5.60 g, 26 mmol), zinc (8.50 g, 130 mmol), acetic anhydride (7.96 g, 78 mmol) and N,N-dimethylformamide (30 mL) were added gradually to a 100 mL single-neck flask, then 1,1,1-trichlorotrifluoroethane (7.80 g, 41.1 mmol) was added dropwise under nitrogen while maintaining the reaction temperature not exceeding 50° C. The reaction mixture was stirred for 4 h at rt. To the resulting mixture was added saturated aqueous ammonium chloride (200 mL). The mixture was extracted with ethyl acetate (100 mL×2). The combined organic phases were washed with saturated brine (100 mL), dried over anhydrous sodium sulfate, filtered, and concentrated in vacuo. The residue was purified by silica gel chromatography (ethyl acetate/petroleum ether (v/v)=1/50) to give the title compound as pale yellow liquid (1.49 g, 16%).

$^1$H NMR (400 MHz, CDCl$_3$) δ (ppm): 7.36 (s, 1H), 7.13 (s, 1H), 6.98 (s, 1H), 2.37 (s, 3H), 2.23 (s, 3H); and
$^{19}$F NMR (376 MHz, CDCl$_3$) δ (ppm): −69.00 (s, 3F).

Step 2) Synthesis of 4-bromo-6-methyl-2-(trifluoromethyl)benzofuran (Z)-3-Bromo-2-(2-chloro-3,3,3-trifluoro-1-propen-1-yl)-5-methylphenylacetate (4.00 g, 11.2 mmol) and N,N-dimethylformamide (25 mL) were added to a 100 mL single-neck flask, then potassium tert-butoxide (3.77 g, 33.6 mmol) was added in portions at 0° C. The reaction mixture was stirred for 6 h at rt. To the resulting mixture was added saturated ammonium chloride (200 mL). The mixture was extracted with ethyl acetate (100 mL×2). The combined organic phases were washed with saturated brine (100 mL), dried over anhydrous sodium sulfate, filtered, and concentrated in vacuo. The residue was purified by silica gel chromatography (ethyl acetate/petroleum ether (v/v)=1/100) to give the title compound as a white solid (1.66 g, 53%).

$^1$H NMR (400 MHz, CDCl$_3$) δ (ppm): 7.34 (s, 1H), 7.31 (s, 1H), 7.16 (s, 1H), 2.48 (s, 3H); and $^{19}$F NMR (376 MHz, CDCl$_3$) δ (ppm): −64.90 (s, 3F).

Step 3) Synthesis of 4-bromo-2-(trifluoromethyl) benzofuran-6-carbonitrile

4-Bromo-6-methyl-2-(trifluoromethyl)benzofuran (1.14 g, 4.1 mmol), tert-butyl nitrite (1.26 g, 12.2 mmol), N-hydroxyphthalimide (669 mg, 4.1 mmol), palladium diacetate (45 mg, 0.20 mmol) and acetonitrile (20 mL) were added gradually to a 25 mL microwave tube. The reaction mixture was stirred for 48 h at 80° C. under nitrogen. The resulting mixture was cooled to room temperature and concentrated in vacuo. The residue was purified by silica gel chromatography (dichloromethane/petroleum ether (v/v)=1/8) to give the title compound as a white solid (0.333 g, 28%).

$^1$H NMR (400 MHz, CDCl$_3$) δ (ppm): 7.88 (s, 1H), 7.78 (s, 1H), 7.31 (s, 1H); and $^{19}$F NMR (376 MHz, CDCl$_3$) δ (ppm): −65.20 (s, 3F).

Step 4) Synthesis of tert-butyl 4-(6-cyano-2-(trifluoromethyl)benzofuran-4-yl)-2-hydroxybenzoate 4-Bromo-2-(trifluoromethyl)benzofuran-6-carbonitrile (0.380 g, 1.31 mmol), tert-butyl 2-hydroxy-4-(4,4,5,5-tetramethyl-1,3,2-dioxaborolan-2-yl) benzoate (420 mg, 1.31 mmol), 1,1'-bis(diphenylphosphino)ferrocene-palladium(II) dichloride dichloromethane complex (53 mg, 0.065 mmol) and N,N-dimethylformamide (8 mL) were added gradually to a 50 mL two-neck flask. A solution of potassium carbonate (1.3 mL, 2 M) in water was added under nitrogen, then the reaction mixture was stirred for 0.5 h at 90° C. The resulting mixture was cooled to room temperature. To the resulting mixture was added saturated brine (80 mL). The mixture was extracted with ethyl acetate (40 mL×2). The combined organic phases were washed with saturated brine (80 mL), dried over anhydrous sodium sulfate, filtered, and concentrated in vacuo. The residue was purified by silica gel chromatography (ethyl acetate/petroleum ether (v/v)=1/40) to give the title compound as a white solid (0.380 g, 72%).

MS (ES-API, pos. ion) m/z: 404.1 [M+1]$^+$.

Step 5) Synthesis of 4-(6-cyano-2-(trifluoromethyl) benzofuran-4-yl)-2-hydroxybenzoic Acid tert-Butyl 4-(6-cyano-2-(trifluoromethyl)benzofuran-4-yl)-2-hydroxybenzoate (0.307 g, 0.76 mmol) and dichloromethane (15 mL) were added to a 100 mL single-neck flask, then trifluoroacetate (2 mL) was added. The reaction mixture was stirred for 12 h at rt. The resulting mixture was concentrated in vacuo to remove the solvent, and the residue was purified by silica gel chromatography (methanol/dichloromethane (v/v)=1/20) to give the title compound as a white solid, 0.185 g, 70%).

MS (ES-API, neg. ion) m/z: 346.0 [M−1]$^−$;

$^1$H NMR (400 MHz, DMSO-d$_6$) δ (ppm): 8.54 (s, 1H), 7.98 (m 8.03-7.94, 3H), 7.28 (m, 7.30-7.27, 2H); and $^{19}$F NMR (376 MHz, DMSO-d$_6$) δ (ppm): −63.70 (s, 3F).

Example 26:
2-hydroxy-4-(5-nitrobenzofuran7-yl)benzoic Acid

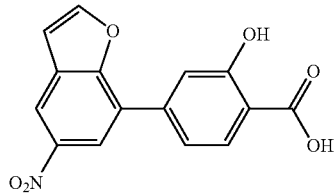 [SMILES: O=C(O)c1ccc(-c2cc([N+](=O)[O-])cc3ccoc23)cc1O]

Step 1) Synthesis of
3-bromo-2-hydroxy-5-nitrobenzaldehyde

2-Hydroxy-5-nitro-benzaldehyde (2.0 g, 12 mmol) and dichloromethane (30 mL) were added to a 100 mL two-neck flask, then bromine (2.24 g, 14 mmol) was added dropwise. The mixture was stirred for 1 h at rt. The mixture was quenched with saturated aqueous sodium thiosulfate (100 mL), and the resulting mixture was partitioned. The aqueous phase was extracted with ethyl acetate (100 mL×2). The combined organic phases were washed with saturated brine (80 mL×2), dried over anhydrous sodium sulfate, filtered, and concentrated in vacuo, the residue was purified by silica gel chromatography (ethyl acetate/petroleum ether (v/v)=1/20) to give the title compound as a yellow solid (2.89 g, 98%).

MS (ES-API, pos. ion) m/z: 246.9 [M+2]$^+$.

Step 2) Synthesis of ethyl
7-bromo-5-nitrobenzofuran-2-carboxylate

3-Bromo-2-hydroxy-5-nitrobenzaldehyde (4.92 g, 20 mmol), potassium carbonate (5.53 g, 40 mmol), diethyl bromomalonate (5.74 g, 24 mmol) and butanone (40 mL) were added gradually to a 250 mL single-neck flask. The reaction mixture was stirred for 2 h at 85° C. under nitrogen. The resulting mixture was cooled to room temperature. To the resulting mixture was added saturated ammonium chloride (150 mL). The mixture was extracted with ethyl acetate (100 mL×2). The combined organic phases were washed with saturated brine (100 mL), dried over anhydrous sodium sulfate, filtered, and concentrated in vacuo. The residue was purified by silica gel chromatography (ethyl acetate/petroleum ether (v/v)=1/6) to give the title compound as a pale yellow solid (3.77 g, 60%).

MS (ES-API, pos. ion) m/z: 314.9 [M+2]$^+$.

Step 3) Synthesis of
7-bromo-5-nitrobenzofuran-2-carboxylic Acid

Ethyl 7-bromo-5-nitrobenzofuran-2-carboxylate (2.20 g, 7.0 mmol), methanol (25 mL), tetrahydrofuran (25 mL) and water (25 mL) were added into a 250 mL single neck flask, then sodium hydroxide (0.840 g, 21 mmol) was added. The reaction mixture was stirred for 12 h at rt. The resulting mixture was concentrated in vacuo to remove the solvent. To the residue was added water (120 mL). The mixture was washed with diethyl ether (80 mL), and the aqueous phase was acidified to pH 1 with 2 N dilute hydrochloric acid. The resulting mixture was extracted with ethyl acetate (80 mL×2). The combined organic phases were washed with saturated brine (80 mL×2), dried over anhydrous sodium sulfate, filtered, and concentrated in vacuo to give the title compound as a yellow solid (1.90 g, 95%).

MS (ES-API, neg. ion) m/z: 282.9 [M−1]⁻.

Step 4) Synthesis of 7-bromo-5-nitrobenzofuran

7-Bromo-5-nitrobenzofuran-2-carboxylic acid (1.89 g, 6.6 mmol), copper (0.83 g, 13.1 mmol) and quinoline (15 mL) were added to a 25 mL microwave tube, the mixture was heated to 200° C. and stirred for 0.5 h. The resulting mixture was cooled to room temperature. To the mixture was added concentrated hydrochloric acid (100 mL, 12 M). The mixture was extracted with ethyl acetate (80 mL×2). The combined organic phases were washed with saturated brine (80 mL), dried over anhydrous sodium sulfate, filtered, and concentrated in vacuo. The residue was purified by silica gel chromatography (ethyl acetate/petroleum ether (v/v)=1/10) to give the title compound as a orange solid (0.671 g, 42%).

¹H NMR (400 MHz, CDCl₃) δ (ppm): 8.50 (d, J=2.0 Hz, 1H), 8.43 (d, J=2.0 Hz, 1H), 7.86 (d, J=2.1 Hz, 1H), 7.02 (d, J=2.2 Hz, 1H).

Step 5) Synthesis of tert-butyl 2-hydroxy-4-(5-nitrobenzofuran-7-yl)benzoate

7-Bromo-5-nitrobenzofuran (0.317 g, 1.31 mmol), tert-butyl 2-hydroxy-4-(4,4,5,5-tetramethyl-1,3,2-dioxaborolan-2-yl) benzoate (420 mg, 1.31 mmol), 1,1'-bis(diphenylphosphino)ferrocene-palladium(II)dichloride dichloromethane complex (53 mg, 0.065 mmol) and N,N-dimethylformamide (8 mL) were added gradually to a 50 mL two-neck flask. A solution of potassium carbonate (1.3 mL, 2 M) in water was added under nitrogen, then the reaction mixture was stirred for 0.5 h at 90° C. The resulting mixture was cooled to room temperature. To the resulting mixture was added saturated brine (80 mL). The mixture was extracted with ethyl acetate (40 mL×2). The combined organic phase was washed with saturated brine (60 mL), dried over anhydrous sodium sulfate, filtered, and concentrated in vacuo. The residue was purified by silica gel chromatography (dichloromethane/petroleum ether (v/v)=1/1) to give the title compound as a white solid (0.275 g, 59%).

MS (ES-API, pos. ion) m/z: 356.1 [M+1]⁺.

Step 6) Synthesis of 2-hydroxy-4-(5-nitrobenzofuran-7-yl)benzoic Acid tert-Butyl 2-hydroxy-4-(5-nitrobenzofuran-7-yl)benzoate (0.275 g, 0.77 mmol) and dichloromethane (15 mL) were added to a 100 mL single-neck flask, then trifluoroacetate (2 mL) was added. The reaction mixture was stirred for 12 h at rt. The resulting mixture was concentrated in vacuo to remove the solvent, and the residue was purified by silica gel chromatography (methanol/dichloromethane (v/v)=1/20) to give the title compound as a white solid (0.177 g, 77%).

MS (ES-API, neg. ion) m/z: 298.0 [M−1]⁻; and

¹H NMR (400 MHz, DMSO-d₆) δ (ppm): 8.69 (d, J=2.1 Hz, 1H), 8.38 (d, J=2.1 Hz, 1H), 8.33 (d, J=1.9 Hz, 1H), 7.97 (d, J=8.2 Hz, 1H), 7.53 (d, J=1.1 Hz, 1H), 7.49 (d, J=8.3 Hz, 1H), 7.30 (d, J=2.0 Hz, 1H).

Example 27: 4-(2-chloro-6-cyanobenzofuran-4-yl)-2-hydroxybenzoic Acid

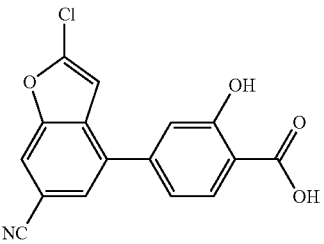 [SMILES: N#Cc1cc(-c2ccc(C(=O)O)c(O)c2)c2cc(Cl)oc2c1]

Step 1) Synthesis of 2-chloro-4-methoxybenzofuran-6-carbonitrile

4-Methoxybenzofuran-6-carbonitrile (1.73 g, 10 mmol) and tetrahydrofuran (30 mL) were added to a 100 mL two-neck flask, then N-butyllithium (5.0 mL, 12 mmol, 2.4 M in THF) was added dropwise at −70° C. The mixture was stirred for 1.5 h at −70° C. under nitrogen. A solution of hexachloroethane (4.73 g, 20 mmol) in tetrahydrofuran (30 mL) was added dropwise. The mixture was stirred for 12 h at rt. To the mixture was added saturated aqueous ammonium chloride (800 mL). The aqueous phase was extracted with ethyl acetate (100 mL×2). The combined organic phase was washed with saturated brine (100 mL), dried over anhydrous sodium sulfate, filtered, and concentrated in vacuo. The residue was purified by silica gel chromatography (dichloromethane/petroleum ether (v/v)=1/4) to give the title compound as a white solid (1.35 g, 65%).

MS (ES-API, pos. ion) m/z: 208.0 [M+1]⁺.

Step 2) Synthesis of 2-chloro-4-hydroxybenzofuran-6-carbonitrile

2-Chloro-4-methoxybenzofuran-6-carbonitrile (2.08 g, 10 mmol) and dichloromethane (20 mL) were added to a 100 mL single neck flask, and boron tribromide (7.5 g, 30 mmol) was added dropwise at −70° C. The reaction mixture was stirred for 24 h at rt. To the mixture was added ice-water (200 mL), and the resulting mixture was partitioned. The aqueous phase was extracted with ethyl acetate (100 mL×2). The combined organic phases were washed with saturated brine (100 mL), dried over anhydrous sodium sulfate, filtered, and concentrated in vacuo. The residue was purified by silica gel chromatography (ethyl acetate/petroleum ether (v/v)=1/6) to give the title compound as a pale yellow solid (1.78 g, 92%).

MS (ES-API, neg. ion) m/z: 191.9 [M−1]⁻.

Step 3) Synthesis of 2-chloro-6-cyanobenzofuran-4-yl trifluoromethanesulfonate

2-Chloro-4-hydroxybenzofuran-6-carbonitrile (0.794 g, 4.1 mmol), pyridine (0.970 g, 12.3 mmol) and dichloromethane (80 mL) were added to a 250 mL single neck flask, then trifluoromethanesulfonic anhydride (1.35 g, 4.8 mmol) was added dropwise at 0° C. The mixture was stirred for 1 h at rt. The mixture was concentrated in vacuo, and the residue was purified by silica gel chromatography (dichloromethane/petroleum ether (v/v)=1/5) to give the title compound as a white solid (1.13 g, 85%).

MS (ES-API, pos. ion) m/z: 325.9 [M+1]+.

Step 4) Synthesis of tert-butyl 4-(2-chloro-6-cyanobenzafuran-4-yl)-2-hydroxybenzoate 2-Chloro-6-cyanobenzofuran-4-yl-trifluoromethanesulfonate (0.469 g, 1.44 mmol), tert-butyl 2-hydroxy-4-(4,4,5,5-tetramethyl-1,3,2-dioxaborolan-2-yl) benzoate (420 mg, 1.31 mmol), 1,1'-bis(diphenylphosphino)ferrocene-palladium(II)dichloride dichloromethane complex (53 mg, 0.065 mmol), potassium carbonate (0.362 g, 2.62 mmol) and anhydrous 1,4-dioxane (15 mL) were added gradually to a 50 mL two-neck flask. The reaction mixture was stirred for 7 h at 90° C. under nitrogen. The resulting mixture was cooled to room temperature. To the resulting mixture was added saturated brine (80 mL). The mixture was extracted with ethyl acetate (40 mL×2). The combined organic phases were washed with saturated brine (60 mL), dried over anhydrous sodium sulfate, filtered, and concentrated in vacuo. The residue was purified by silica gel chromatography (dichloromethane/petroleum ether (v/v)=1/4) to give the title compound as a white solid (0.194 g, 40%).

MS (ES-API, pos. ion) m/z: 370.1 [M+1]+.

Step 5) Synthesis of 4-(2-chloro-6-cyanobenzofuran-4-yl)-2-hydroxybenzoic Acid tert-Butyl 4-(2-chloro-6-cyanobenzafuran-4-yl)-2-hydroxybenzoate (0.194 g, 0.524 mmol) and dichloromethane (15 mL) were added to a 100 mL single-neck flask, trifluoroacetate (2 mL) was added. The reaction mixture was stirred for 12 h at rt. The resulting mixture was concentrated in vacuo to remove solvent, and the residue was purified by silica gel chromatography (methanol/dichloromethane (v/v)=1/20) to give the title compound as a white solid (0.141 g, 86%).

MS (ES-API, neg. ion) m/z: 312.0 [M−1]−; and
1H NMR (400 MHz, DMSO-d6) δ (ppm): 8.31 (s, 1H), 7.91 (s, 2H), 7.32 (s, 1H), 7.24 (s, 2H).

Example 28: 4-(6-cyano-2-fluorobenzofuran-4-yl)-2-hydroxybenzoic Acid

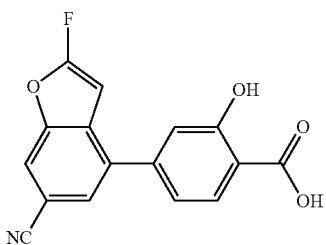 [SMILES: N#Cc1cc(-c2ccc(C(=O)O)c(O)c2)c2cc(F)oc2c1]

Step 1) Synthesis of 2-fluoro-4-methoxybenzofuran-6-carbonitrile

4-Methoxybenzofuran-6-carbonitrile (17.3 g, 100 mmol) and tetrahydrofuran (300 mL) were added to a 1000 mL two-neck flask, then N-butyllithium (50 mL, 120 mmol, 2.4 M in THF) was added dropwise at −70° C. The mixture was stirred for 1.5 h at −70° C. under nitrogen. A solution of N-fluorobenzenesulfonimide (63.1 g, 200 mmol) in tetrahydrofuran (200 mL) was added dropwise. The mixture was stirred for 12 h at rt. To the mixture was added saturated aqueous ammonium chloride (800 mL). The mixture was extracted with ethyl acetate (300 mL×2). The combined organic phases were washed with saturated brine (300 mL), dried over anhydrous sodium sulfate, filtered, and concentrated in vacuo. The residue was purified by silica gel chromatography (dichloromethane/petroleum ether (v/v)=1/4) to give the crude product. The crude product was further purified by reversed phase preparative column (H2O/CH3CN, 0.1% TFA) to give the title compound as a white solid (0.956 g, 5%).

MS (ES-API, pos. ion) m/z: 192.0 [M+1]+.

Step 2) Synthesis of 2-fluoro-4-hydroxybenzofuran-6-carbonitrile

2-Fluoro-4-methoxybenzofuran-6-carbonitrile (0.208 g, 1.0 mmol) and dichloromethane (10 mL) were added to a 100 mL single neck flask, then boron tribromide (0.75 g, 3.0 mmol) was added dropwise at −70° C. The reaction mixture was stirred for 24 h at rt. To the mixture was added ice-water (80 mL), and the resulting mixture was partitioned. The aqueous phase was extracted with ethyl acetate (60 mL×2). The combined organic phases were washed with saturated brine (80 mL), dried over anhydrous sodium sulfate, filtered, and concentrated in vacuo, the residue was purified by silica gel chromatography (ethyl acetate/petroleum ether (v/v)=1/6) to give the title compound as a white solid (62 mg, 35%).

MS (ES-API, neg. ion) m/z: 176.0 [M−1]−.

Step 3) Synthesis of 6-cyano-2-fluorobenzofuran-4-yl trifluoromethanesulfonate

2-Fluoro-4-hydroxybenzofuran-6-carbonitrile (0.726 g, 4.1 mmol), pyridine (0.970 g, 12.3 mmol) and dichloromethane (80 mL) were added to a 250 mL single neck flask, then trifluoromethanesulfonic anhydride (1.35 g, 4.8 mmol) was added dropwise at 0° C. The mixture was stirred for 1 h at rt. The mixture was concentrated in vacuo, and the residue was purified by silica gel chromatography (dichloromethane/petroleum ether (v/v)=1/5) to give the title compound as a white solid (1.09 g, 86%).

MS (ES-API, pos. ion) m/z: 309.9 [M+1]+.

Step 4) Synthesis of tert-butyl 4-(6-cyano-2-fluorobenzafuran-4-yl)-2-hydroxybenzoate 6-Cyano-2-fluorobenzofuran-4-yltrifluoromethanesulfonate (0.405 g, 1.31 mmol), tert-butyl 2-hydroxy-4-(4,4,5,5-tetramethyl-1,3,2-dioxaborolan-2-yl) benzoate (420 mg, 1.31 mmol), 1,1'-bis(diphenylphosphino)ferrocene-palladium(II)dichloride dichloromethane complex (53 mg, 0.065 mmol), potassium carbonate (0.362 g, 2.62 mmol) and anhydrous 1,4-dioxane (15 mL) were added gradually to a 50 mL two-neck flask. The reaction mixture was stirred for 7 h at 90° C. under nitrogen. The resulting mixture was cooled to room temperature. To the resulting mixture was added saturated brine (80 mL). The mixture was extracted with ethyl acetate (40 mL×2). The combined organic phases were washed with saturated brine (60 mL), dried over anhydrous sodium sulfate, filtered, and concentrated in vacuo. The residue was purified by silica gel chromatography (dichloromethane/petroleum ether (v/v)=1/4) to give the title compound as a white solid (0.222 g, 48%).

MS (ES-API, pos. ion) m/z: 354.1 [M+1]$^+$.

Step 5) Synthesis of 4-(6-cyano-2-fluorobenzofuran-4-yl)-2-hydroxybenzoic Acid tert-Butyl 4-(6-cyano-2-fluorobenzafuran-4-yl)-2-hydroxybenzoate (0.222 g, 0.629 mmol) and dichloromethane (15 mL) were added to a 100 mL single-neck flask, then trifluoroacetate (2 mL) was added. The reaction mixture was stirred for 12 h at rt. The resulting mixture was concentrated in vacuo to remove solvent, and the residue was purified by silica gel chromatography (methanol/dichloromethane (v/v)=1/20) to give the title compound as a white solid (0.141 g, 86%).

MS (ES-API, neg. ion) m/z: 296.0 [M−1]$^-$;

$^1$H NMR (400 MHz, DMSO-d$_6$) δ (ppm): 8.31 (s, 1H), 7.93 (s, 2H), 7.23-7.21 (m, 2H), 6.70 (d, J=5.9 Hz, 1H); and $^{19}$F NMR (376 MHz, DMSO-d$_6$) δ (ppm): −106.40 (s, 1F).

Example 29: 4-(5-cyano-2-fluorobenzofuran-7-yl)-2-hydroxybenzoic Acid

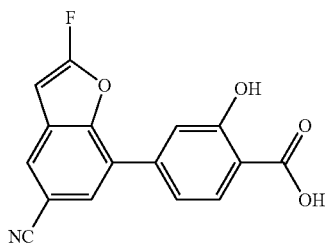 [SMILES: N#Cc1cc(-c2ccc(C(=O)O)c(O)c2)c2oc(F)cc2c1]

Step 1) Synthesis of 7-bromo-2-fluorobenzofuran-5-carbonitrile

7-Bromobenzofuran-5-carbonitrile (22.2 g, 100 mmol) and tetrahydrofuran (300 mL) were added to a 1000 mL two-neck flask, then lithium diisopropylamide (60 mL, 120 mmol, 2.0 M in THF) was added dropwise at −70° C. The mixture was stirred for 1.5 h at −70° C. under nitrogen. Then a solution of N-fluorobenzenesulfonimide (63.1 g, 200 mmol) in tetrahydrofuran (200 mL) was added dropwise. The mixture was stirred for 12 h at rt. To the mixture was added saturated ammonium chloride (800 mL). The mixture was extracted with ethyl acetate (300 mL×2). The combined organic phases were washed with saturated brine (300 mL), dried over anhydrous sodium sulfate, filtered, and concentrated in vacuo. The residue was purified by silica gel chromatography (dichloromethane/petroleum ether (v/v)=1/4) to give the crude product. The crude product was further purified by reversed phase preparative column (H$_2$O/CH$_3$CN, 0.1% TFA) to give the title compound as a white solid (1.44 g, 6%).

$^1$H NMR (400 MHz, CDCl$_3$) δ (ppm): 7.77 (s, 1H), 7.71 (s, 1H), 6.07 (d, J=6.6 Hz, 1H); and $^{19}$F NMR (376 MHz, CDCl$_3$) δ (ppm): −106.46 (s, 1F).

Step 2) Synthesis of tert-butyl 4-(5-cyano-2-fluorobenzofuran-7-yl)-2-hydroxybenzoate 7-Bromo-2-fluorobenzofuran-5-carbonitrile (0.338 g, 1.41 mmol), tert-butyl 2-hydroxy-4-(4,4,5,5-tetramethyl-1,3,2-dioxaborolan-2-yl) benzoate (420 mg, 1.31 mmol), 1,1'-bis(diphenylphosphino)ferrocene-palladium(II)dichloride dichloromethane complex (53 mg, 0.065 mmol) and N,N-dimethylformamide (8 mL) were added gradually to a 50 mL two-neck flask. A solution of potassium carbonate (1.3 mL, 2 M) in water was added under nitrogen, then the reaction mixture was stirred for 0.5 h at 90° C. The resulting mixture was cooled to room temperature. To the resulting mixture was added saturated brine (80 mL). The mixture was extracted with ethyl acetate (40 mL×2). The combined organic phases were washed with saturated brine (60 mL), dried over anhydrous sodium sulfate, filtered, and concentrated in vacuo.

The residue was purified by silica gel chromatography (dichloromethane/petroleum ether (v/v)=1/1) to give the title compound as a white solid (0.245 g, 53%).

MS (ES-API, pos. ion) m/z: 354.1 [M+1]$^+$.

Step 3) Synthesis of 4-(5-cyano-2-fluorobenzofuran-7-yl)-2-hydroxybenzoic Acid tert-Butyl 4-(5-cyano-2-fluorobenzofuran-7-yl)-2-hydroxybenzoate (0.245 g, 0.69 mmol) and dichloromethane (15 mL) were added to a 100 mL single-neck flask, then trifluoroacetic acid (2 mL) was added. The reaction mixture was stirred for 12 h at rt. The resulting mixture was concentrated in vacuo to remove solvent, and the residue was purified by silica gel chromatography (methanol/dichloromethane (v/v)=1/20) to give the title compound as a white solid (0.177 g, 77%).

MS (ES-API, neg. ion) m/z: 296.0 [M−1]$^-$;

$^1$H NMR (400 MHz, DMSO-d$_6$) δ (ppm): 8.18 (s, 1H), 8.04 (s, 1H), 7.93 (d, J=8.2 Hz, 1H), 7.44 (s, 1H), 7.41 (d, J=8.2 Hz, 1H), 6.58 (d, J=6.2 Hz, 1H); and $^{19}$F NMR (376 MHz, DMSO-d$_6$) δ (ppm): −109.18 (s, 1F).

Example 30: 4-(6-cyano-2-fluorobenzo[b]thiophen-4-yl)-2-hydroxybenzoic Acid

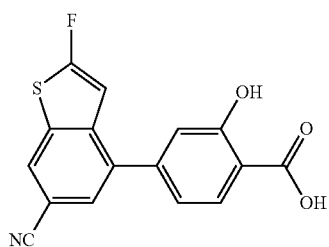 [SMILES: N#Cc1cc(-c2ccc(C(=O)O)c(O)c2)c2cc(F)sc2c1]

Step 1) Synthesis of 4-bromo-2-fluorobenzo[b]thiophene-6-carbonitrile

4-Bromobenzo[b]thiophene-6-carbonitrile (23.8 g, 100 mmol) and tetrahydrofuran (300 mL) were added to a 1000 mL two-neck flask, then lithium diisopropylamide (60 mL, 120 mmol, 2.0 M in THF) was added dropwise at −70° C.

The mixture was stirred for 1.5 h at −70° C. under nitrogen. Then a solution of N-fluorobenzenesulfonimide (63.1 g, 200 mmol) in tetrahydrofuran (200 mL) was added dropwise. The mixture was stirred for 12 h at rt. To the mixture was added saturated aqueous ammonium chloride (800 mL). The aqueous phase was extracted with ethyl acetate (300 mL×2). The combined organic phases were washed with saturated brine (300 mL), dried over anhydrous sodium sulfate, filtered, and concentrated in vacuo. The residue was purified by silica gel chromatography (dichloromethane/petroleum ether (v/v)=1/4) to give the crude product. The crude product was further purified by reversed phase preparative column (H₂O/CH₃CN, 0.1% TFA) to give the title compound as a white solid (2.05 g, 8%).

¹H NMR (400 MHz, CDCl₃) δ (ppm): 7.95 (s, 1H), 7.78 (s, 1H), 6.99 (d, J=2.2 Hz, 1H); and ¹H NMR (376 MHz, CDCl₃) δ (ppm): −114.38 (s, 1F).

Step 2) Synthesis of tert-butyl 4-(6-cyano-2-fluorobenzo[b]thiophene-4-yl)-2-hydroxybenzoate 4-Bromo-2-fluorobenzo[b]thiophene-6-carbonitrile (0.361 g, 1.41 mmol), tert-butyl 2-hydroxy-4-(4,4,5,5-tetramethyl-1,3,2-dioxaborolan-2-yl) benzoate (420 mg, 1.31 mmol), 1,1'-bis(diphenylphosphino)ferrocene-palladium(II) dichloride dichloromethane complex (53 mg, 0.065 mmol) and N,N-dimethylformamide (8 mL) were added gradually to a 50 mL two-neck flask. A solution of potassium carbonate (1.3 mL, 2 M) in water was added under nitrogen, then the reaction mixture was stirred for 0.5 h at 90° C. The resulting mixture was cooled to room temperature. To the resulting mixture was added saturated brine (80 mL). The mixture was extracted with ethyl acetate (40 mL×2). The combined organic phase was washed with saturated brine (60 mL), dried over anhydrous sodium sulfate, filtered, and concentrated in vacuo. The residue was purified by silica gel chromatography (dichloromethane/petroleum ether (v/v)=1/1) to give the title compound as a white solid (0.290 g, 60%).

MS (ES-API, pos. ion) m/z: 354.1 [M+1]⁺.

Step 3) Synthesis of 4-(6-cyano-2-fluorobenzo[b]thiophen-4-yl)-2-hydroxybenzoic Acid tert-Butyl 4-(6-cyano-2-fluorobenzo[b]thiophen-4-yl)-2-hydroxybenzoate (0.290 g, 0.786 mmol) and dichloromethane (15 mL) were added to a 100 mL single-neck flask, trifluoroacetic acid (2 mL) was added. The reaction mixture was stirred for 12 h at rt. The resulting mixture was concentrated in vacuo to remove solvent, and the residue was purified by silica gel chromatography (methanol/dichloromethane (v/v)=1/20) to give the title compound as a white solid (0.177 g, 77%).

MS (ES-API, neg. ion) m/z: 312.0 [M−1]⁻;

¹H NMR (400 MHz, DMSO-d₆) δ (ppm) 8.60 (s, 1H), 7.92 (d, J=8.0 Hz, 1H), 7.83 (s, 1H), 7.15 (m, 7.17-7.12, 3H); and ¹⁹F NMR (376 MHz, DMSO-d₆) δ (ppm): −117.54 (s, 1F).

Example 31: 4-(6-cyanobenzo[b]thiophen-4-yl)-2-hydroxybenzoic Acid

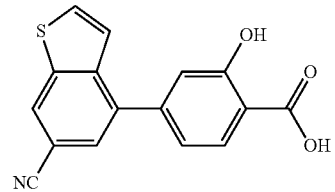 [SMILES: N#Cc1cc(-c2ccc(C(=O)O)c(O)c2)c2ccsc2c1]

Step 1) Synthesis of 2-bromo-6-fluoro-4-methylaniline

2-Fluoro-4-methylaniline (12.5 g, 100 mmol), glacial acetic acid (80 mL) and methanol (80 mL) were added to a 250 mL single-neck flask, then to the mixture in flask was added dropwise slowly bromine (17.6 g, 110 mmol) at 0° C. After the addition, the reaction mixture was stirred at 0° C. for 0.5 h, then stirred for 4 h at rt. To the reaction mixture was added saturated aqueous sodium sulfite (300 mL), and the resulting mixture was concentrated in vacuo to remove organic solvent. The residue was extracted with ethyl acetate (100 mL×2), and the organic layers were combined. The combined organic layers were washed with saturated brine (100 mL), dried over anhydrous sodium sulfate, and filtered. The filtrate was concentrated in vacuo. The residue was purified by silica-gel column chromatography (ethyl acetate/petroleum ether (v/v)=1/100) to give the title compound as an orange solid (17.5 g, 86%).

MS (ES-API, pos. ion) m/z: 204.9 [M+2]k.

Step 2) Synthesis of 1-bromo-3-fluoro-5-methylbenzene

2-Bromo-6-fluoro-4-methylaniline (11.2 g, 55 mmol), diluted hydrochloric acid (28.5 mL, 6 M) and acetonitrile (300 mL) were added to a 500 mL single-neck flask, then to the mixture in flask was added dropwise slowly a solution of sodium nitrite (5.69 g, 82.4 mmol) in water (40 mL) at 0° C. After the addition, the reaction mixture was stirred at 0° C. for 1 h, then to the flask was added a solution of potassium iodide (18.3 g, 110 mmol) in water (30 mL). After the addition, the mixture was stirred at 0° C. for 0.5 h, then stirred at rt overnight. To the reaction mixture was added saturated aqueous sodium sulfite (300 mL), and the resulting mixture was concentrated in vacuo to remove acetonitrile. The residue was extracted with ethyl acetate (100 mL×2), and the organic layers were combined. The combined organic layers were washed with saturated brine (100 mL), dried over anhydrous sodium sulfate, and filtered. The filtrate was concentrated in vacuo. The residue was purified by silica-gel column chromatography (ethyl acetate/petroleum ether (v/v)=1/100) to give the title compound as a white solid (13.2 g, 76%).

¹H NMR (400 MHz, CDCl₃) δ (ppm): 7.29 (s, 1H), 6.81 (d, J=8.4 Hz, 1H), 2.31 (s, 3H).

Step 3) Synthesis of 2-bromo-6-fluoro-4-methylbenzaldehyde

1-Bromo-3-fluoro-5-methylbenzene (18.5 g, 58.7 mmol) and anhydrous tetrahydrofuran (250 mL) were added to a 500 mL single-neck flask, then to the mixture in flask was added dropwise slowly isopropylmagnesium chloride solution (35.2 mL, 2 M in THF) at −45° C. After the addition, the reaction mixture was stirred at −45° C. for 1.0 h, then to the flask was added anhydrous N,N-dimethylformamide (17.2 g, 235 mmol). After the addition, the reaction mixture was warmed slowly to rt and stirred overnight. To the reaction mixture was added diluted hydrochloric acid (200 mL, 4 M), and the resulting mixture was stirred at rt for 2 h. The mixture was concentrated in vacuo to remove tetrahydrofuran. The residue was extracted with ethyl acetate (100 mL×2), and the organic layers were combined. The combined organic layers were washed with saturated brine (100 mL), dried over anhydrous sodium sulfate, and filtered. The filtrate was concentrated in vacuo. The residue was purified by silica-gel column chromatography (ethyl acetate/petroleum ether (v/v)=1/200) to give the title compound as a light yellow solid (12.3 g, 96%).

$^1$H NMR (400 MHz, CDCl$_3$) δ (ppm): 10.31 (s, 1H), 7.31 (s, 1H), 6.95 (d, J=11.2 Hz, 1H), 2.39 (s, 3H).

Step 4) Synthesis of ethyl 4-bromo-6-methylbenzo[b]thiophene-2-carboxylate

2-Bromo-6-fluoro-4-methylbenzaldehyde (4.34 g, 20 mmol), potassium carbonate (5.53 g, 40 mmol), ethyl 2-mercaptoacetate (2.88 g, 24 mmol) and N,N-dimethylformamide (40 mL) were added to a 100 mL single-neck flask. The resulting mixture was stirred at 80° C. for 12 h under nitrogen. The reaction mixture was cooled to room temperature and to the mixture was added saturated aqueous ammonium chloride (150 mL). The resulting mixture was extracted with ethyl acetate (100 mL×2), and the organic layers were combined. The combined organic layers were washed with saturated brine (100 mL), dried over anhydrous sodium sulfate, and filtered. The filtrate was concentrated in vacuo. The residue was purified by silica-gel column chromatography (ethyl acetate/petroleum ether (v/v)=1/100) to give the title compound as a white solid (5.09 g, 85%).

$^1$H NMR (400 MHz, CDCl$_3$) δ (ppm): 8.10 (s, 1H), 7.57 (s, 1H), 7.42 (s, 1H), 4.41 (q, J=7.1 Hz, 2H), 2.46 (s, 3H), 1.42 (t, J=7.1 Hz, 3H).

Step 5) Synthesis of 4-bromo-6-methylbenzo[b]thiophene-2-carboxylic Acid

Ethyl 4-bromo-6-methylbenzo[b]thiophene-2-carboxylate (2.0 g, 7.0 mmol), methanol (25 mL), tetrahydrofuran (25 mL) and water (25 mL) were added to a 250 mL single-neck flask, then to the mixture in flask was added sodium hydroxide (0.840 g, 21 mmol). After the addition, the reaction mixture was stirred at rt for 12 h. The reaction mixture was concentrated in vacuo to remove solvent, and to the residue was added water (120 mL). The resulting mixture was washed with ethyl ether (80 mL). Then the aqueous layer was acidified with diluted hydrochloric acid (2 N) to pH 1, and the resulting mixture was extracted with ethyl acetate (80 mL×2). The combined organic layers were washed with saturated brine (80 mL×2), dried over anhydrous sodium sulfate, and filtered. The filtrate was concentrated in vacuo to give the title compound as a white solid (1.80 g, 95%).

MS (ES-API, neg. ion) m/z: 271.9 [M+2]$^+$.

Step 6) Synthesis of 4-bromo-6-methylbenzo[b]thiophene

4-Bromo-6-methylbenzo[b]thiophene-2-carboxylic acid (1.79 g, 6.6 mmol), copper powder (0.83 g, 13.1 mmol) and quinoline (15 mL) were added to a 25 mL microwave tube, and the resulting mixture was stirred at 200° C. for 0.5 h. The reaction mixture was cooled to room temperature and to the mixture was added concentrated hydrochloric acid (100 mL, 12 M). The resulting mixture was extracted with ethyl acetate (80 mL×2), and the organic layers were combined. The combined organic layers were washed with saturated brine (80 mL), dried over anhydrous sodium sulfate, and filtered. The filtrate was concentrated in vacuo. The residue was purified by silica-gel column chromatography (100% petroleum ether) to give the title compound as colorless liquid (1.33 g, 89%).

$^1$H NMR (400 MHz, CDCl$_3$) δ (ppm): 7.60 (s, 1H), 7.41 (s, 2H), 7.39 (s, 1H), 2.45 (s, 3H).

Step 7) Synthesis of 4-bromobenzo[b]thiophene-6-carbonitrile

4-Bromo-6-methylbenzo[b]thiophene (0.931 g, 4.1 mmol), tert-butyl nitrite (1.26 g, 12.2 mmol), N-hydroxyphthalimide (0.669 g, 4.1 mmol), palladium acetate (0.045 g, 0.20 mmol) and acetonitrile (20 mL) were added to a 25 mL microwave tube, and the resulting mixture was stirred at 80° C. for 48 h. The reaction mixture was cooled to room temperature and concentrated in vacuo. The residue was purified by silica-gel column chromatography (dichloromethane/petroleum ether (v/v)=1/4) to give the title compound as a white solid (0.420 g, 43%).

$^1$H NMR (400 MHz, CDCl$_3$) δ (ppm): 8.15 (s, 1H), 7.82-7.75 (m, 2H), 7.57 (d, J=5.5 Hz, 1H).

Step 8) Synthesis of tert-butyl 4-(6-cyanobenzo[b]thiophen-4-yl)-2-hydroxybenzoate 4-Bromobenzo[b]thiophene-6-carbonitrile (0.340 g, 1.44 mmol), tert-butyl 2-hydroxy-4-(4,4,5,5-tetramethyl-1,3,2-dioxaborolan-2-yl) benzoate (0.420 g, 1.31 mmol), 1,1′-bis(diphenylphosphino)ferrocene-palladium(II)dichloride dichloromethane complex (53 mg, 0.065 mmol) and N,N-dimethylformamide (8 mL) were added to a 50 mL two-neck flask. To the reaction mixture was added aqueous potassium carbonate (1.3 mL, 2 M) under nitrogen, and the resulting mixture was stirred at 90° C. for 0.5 h. The reaction mixture was cooled to room temperature and to the mixture was added saturated brine (80 mL). The resulting mixture was extracted with ethyl acetate (40 mL×2), and the organic layers were combined. The combined organic layers were washed with saturated brine (60 mL), dried over anhydrous sodium sulfate, and filtered. The filtrate was concentrated in vacuo. The residue was purified by silica-gel column chromatography (dichloromethane/petroleum ether (v/v)=1/4) to give the title compound as a white solid (0.313 g, 68%).

MS (ES-API, pos. ion) m/z: 352.1 [M+1]$^+$.

Step 9) Synthesis of 4-(6-cyanobenzo[b]thiophen-4-yl)-2-hydroxybenzoic Acid tert-Butyl 4-(6-cyanobenzo[b]thiophen-4-yl)-2-hydroxybenzoate (0.313 g, 0.891 mmol) and dichloromethane (15 mL) were added to a 100 mL single-neck flask, then to the mixture in flask was added trifluoroacetic acid (2 mL). After the addition, the reaction mixture was stirred at rt for 12 h, and concentrated to remove solvent. The residue was purified by silica-gel column chromatography (dichloromethane/petroleum ether (v/v)=1/20) to give the title compound as a white solid (0.145 g, 55%).

MS (ES-API, neg. ion) m/z: 294.0 [M−1]$^-$; and

¹H NMR (400 MHz, DMSO-d₆) δ (ppm): 8.72 (s, 1H), 8.19 (d, J=5.5 Hz, 1H), 7.94 (d, J=7.9 Hz, 1H), 7.81 (s, 1H), 7.54 (d, J=5.5 Hz, 1H), 7.19-7.7 (m, 2H).

Example 32: 4-(6-cyano-1-methyl-1H-indol-4-yl)-2-hydroxybenzoic Acid

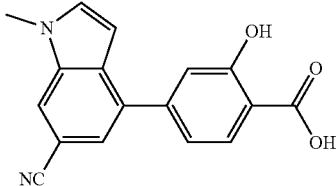 [SMILES: Cn1ccc2c(-c3ccc(C(=O)O)c(O)c3)cc(C#N)cc21]

Step 1) Synthesis of tert-butyl 4-(6-cyano-1-methyl-1H-indol-4-yl)-2-methoxybenzoate tert-Butyl 4-(6-cyano-1H-indol-4-yl)-2-hydroxybenzoate (0.578 g, 1.73 mmol) and anhydrous tetrahydrofuran (10 mL) were added to a 50 mL two-neck flask, then to the mixture in flask was added dropwise slowly sodium hydride (0.500 g, 1.95 mmol, 60%) at 0° C. After the addition, the reaction mixture was stirred at 0° C. for 0.5 h, then to the flask was added potassium iodide (18.3 g, 110 mmol). After the addition, the mixture was stirred at rt for 12 h. To the reaction mixture was added saturated aqueous ammonium chloride (80 mL). The resulting mixture was extracted with ethyl acetate (40 mL×2), and the organic layers were combined. The combined organic layers were washed with saturated brine (60 mL), dried over anhydrous sodium sulfate, and filtered. The filtrate was concentrated in vacuo. The residue was purified by silica-gel column chromatography (dichloromethane/petroleum ether (v/v)=1/1) to give the title compound as a white solid (0.464 g, 74%).

MS (ES-API, pos. ion) m/z: 363.1 [M+1]⁺.

Step 2) Synthesis of 4-(6-cyano-1-methyl-1H-indol-4-yl)-2-hydroxybenzoic Acid tert-Butyl 4-(6-cyano-1-methyl-1H-indol-4-yl)-2-methoxybenzoate (0.362 g, 1.0 mmol) and dichloromethane (10 mL) were added to a 100 mL single-neck flask, then to the mixture in flask was added dropwise boron tribromide (0.750 g, 3.0 mmol) at −20° C. After the addition, the reaction mixture was stirred at rt for 12 h. To the reaction mixture was added ice-water (80 mL) and the resulting mixture was extracted with ethyl acetate (60 mL×2). The combined organic layers were washed with saturated brine (80 mL), dried over anhydrous sodium sulfate, and filtered. The filtrate was concentrated in vacuo concentrated to remove solvent. The residue was purified by silica-gel column chromatography (methanol/dichloromethane (v/v)=1/20) to give the title compound as a white solid (0.091 g, 31%).

MS (ES-API, neg. ion) m/z: 291.1 [M−1]⁻; and

¹H NMR (400 MHz, DMSO-d₆) δ (ppm): 11.43 (s, 1H), 8.20 (s, 1H), 7.96 (d, J=8.1 Hz, 1H), 7.79 (d, J=3.1 Hz, 1H), 7.55 (s, 1H), 7.35-7.23 (m, 2H), 6.71 (d, J=3.0 Hz, 1H), 3.96 (s, 3H).

Example 33: 4-(2-chloro-6-cyanobenzo[b]thiophen-4-yl)-2-hydroxybenzoic Acid

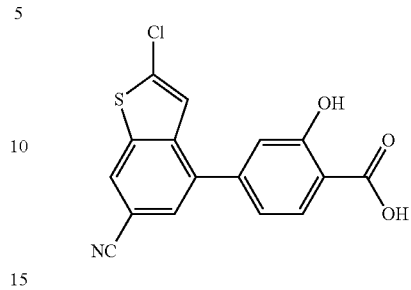

Step 1) Synthesis of 4-bromo-2-chlorobenzo[b]thiophene-6-carbonitrile

4-Bromobenzo[b]thiophene-6-carbonitrile (2.38 g, 10 mmol) and anhydrous tetrahydrofuran (30 mL) were added to a 100 mL two-neck flask, then to the mixture in flask was added dropwise slowly lithium diisopropylamide solution (6.0 mL, 12 mmol, 2.0 M in THF) at −70° C. After the addition, the reaction mixture was stirred at −70° C. for 1.5 h, then to the flask was added a solution of hexachloroethane (4.73 g, 20 mmol) in tetrahydrofuran (20 mL). After the addition, the reaction mixture was warmed slowly to room temperature and stirred for overnight. To the reaction mixture was added saturated aqueous ammonium chloride (100 mL). The resulting mixture was extracted with ethyl acetate (80 mL×2), and the organic layers were combined. The combined organic layers were washed with saturated brine (100 mL), dried over anhydrous sodium sulfate, and filtered. The filtrate was concentrated in vacuo. The residue was purified by silica-gel column chromatography (dichloromethane/petroleum ether (v/v)=1/4) to give the title compound as a white solid (2.34 g, 86%).

¹H NMR (400 MHz, CDCl₃) δ (ppm) 7.97 (s, 1H), 7.76 (s, 1H), 7.42 (s, 1H).

Step 2) Synthesis of tert-butyl 4-(2-chloro-6-cyanobenzo[b]thiophen-4-yl)-2-hydroxybenzoate 4-Bromo-2-chlorobenzo[b]thiophene-6-carbonitrile (0.384 g, 1.41 mmol), tert-butyl 2-hydroxy-4-(4,4,5,5-tetramethyl-1,3,2-dioxaborolan-2-yl) benzoate (0.420 g, 1.31 mmol), 1,1'-bis(diphenylphosphino)ferrocene-palladium(II) dichloride dichloromethane complex (53 mg, 0.065 mmol) and N,N-dimethylformamide (8 mL) were added to a 50 mL two-neck flask. To the reaction mixture was added aqueous potassium carbonate (1.3 mL, 2 M) under nitrogen, and the resulting mixture was stirred at 90° C. for 0.5 h. The reaction mixture was cooled to room temperature and to the resulting mixture was added saturated brine (80 mL). The resulting mixture was extracted with ethyl acetate (40 mL×2), and the organic layers were combined. The combined organic layers were washed with saturated brine (60 mL), dried over anhydrous sodium sulfate, and filtered. The filtrate was concentrated in vacuo. The residue was purified by silica-gel column chromatography (dichloromethane/petroleum ether (v/v)=1/1) to give the title compound as a white solid (0.212 g, 42%).

MS (ES-API, pos. ion) m/z: 386.0 [M+1]⁺.

Step 3) Synthesis of 4-(2-chloro-6-cyanobenzo[b]thiophen-4-yl)-2-hydroxybenzoic Acid tert-Butyl 4-(2-chloro-6-cyanobenzo[b]thiophen-4-yl)-2-hydroxybenzoate (0.212 g, 0.55 mmol) and dichloromethane (15 mL) were added to a 100 mL single-neck flask, then to the mixture in flask was added trifluoroacetic acid (2 mL). After the addition, the reaction mixture was stirred at rt for 12 h, and concentrated in vacuo to remove organic solvent. The residue was purified by silica-gel column chromatography (dichloromethane/petroleum ether (v/v)=1/20) to give the title compound as a white solid (0.177 g, 77%).

MS (ES-API, neg. ion) m/z: 327.9 [M−1]⁻; and
¹H NMR (400 MHz, DMSO-d6) δ (ppm): 8.62 (s, 1H), 7.93 (d, J=8.0 Hz, 1H), 7.84 (d, J=1.2 Hz, 1H), 7.53 (s, 1H), 7.21-7.07 (m, 2H).

Example 34:
4-(2-cyanoquinolin-4-yl)-2-hydroxybenzoic Acid

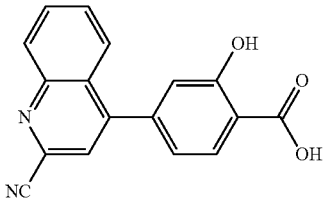 [SMILES: N#Cc1cc(-c2ccc(C(=O)O)c(O)c2)c2ccccc2n1]

Step 1) Synthesis of 2-methylquinolin-4-ol

Aniline (3.73 g, 40.0 mmol) and polyphosphoric acid (50 mL) were added to a 250 mL single-neck flask, then to the mixture in flask was added dropwise ethyl acetoacetate (6.25 g, 48 mmol) at 80° C. After the addition, the reaction mixture was stirred at 120° C. for 16 h. The reaction mixture was cooled to room temperature and to the mixture was added ice-water (300 mL) and ammonium hydroxide (100 mL). The resulting mixture was extracted with ethyl acetate (100 mL×2), and the organic layers were combined. The combined organic layers were washed with saturated brine (100 mL), dried over anhydrous sodium sulfate, and filtered. The filtrate was concentrated in vacuo and concentrated to remove organic solvent, then the residue was purified by silica-gel column chromatography (methanol/dichloromethane (v/v)=1/10) to give the title compound as a white solid (4.46 g, 70%).

MS (ES-API, pos. ion) m/z: 160.1 [M+1]⁺.

Step 2) Synthesis of 4-bromo-2-methylquinoline

2-Methylquinolin-4-ol (4.46 g, 28.0 mmol) and N,N-dimethylformamide (80 mL) were added to a 250 mL single-neck flask, then to the mixture in flask was added dropwise phosphorus tribromide (11.37 g, 42 mmol) at 0° C. After the addition, the reaction mixture was stirred at rt for 3 h. To the reaction mixture was added ice-water (100 mL) and ammonium hydroxide (100 mL, 25%), then the resulting mixture was extracted with ethyl acetate (100 mL×2). The combined organic layers were washed with saturated brine (100 mL), dried over anhydrous sodium sulfate, and filtered. The filtrate was concentrated in vacuo. The residue was purified by silica-gel column chromatography (ethyl acetate/petroleum ether (v/v)=1/10) to give the title compound as light yellow liquid (0.995 g, 16%).

MS (ES-API, pos. ion) m/z: 222.9 [M+2]⁺.

Step 3) Synthesis of 4-bromoquinoline-2-carbaldehyde

4-Bromo-2-methylquinoline (0.995 g, 4.48 mmol), selenium dioxide (0.99 g, 8.9 mmol) and 1,4-dioxane (25 mL) were added to a 100 mL single-neck flask. After the addition, the reaction mixture was stirred at 80° C. for 2 h. The reaction mixture was cooled to room temperature and filtered to remove the insoluble substance, then the filtrate was concentrated in vacuo. The residue was purified by silica-gel column chromatography (ethyl acetate/petroleum ether (v/v)=1/10) to give the title compound as a pale yellow solid (0.825 g, 78%).

MS (ES-API, pos. ion) m/z: 236.9 [M+2]⁺.

Step 4) Synthesis of 4-bromoquinoline-2-carbonitrile

4-Bromoquinoline-2-carbaldehyde (1.89 g, 8.0 mmol), ammonium hydroxide (20 mL, 28%) and tetrahydrofuran (20 mL) were added to a 100 mL single-neck flask, then to the mixture in flask was added in portions iodine (2.23 g, 8.8 mmol). After the addition, the reaction mixture was stirred at rt for 4 h. To the reaction mixture was added saturated aqueous sodium thiosulfate (80 mL), and the resulting mixture was extracted with ethyl acetate (60 mL×2). The combined organic layers were washed with saturated brine (60 mL×2), dried over anhydrous sodium sulfate and filtered. The residue was purified by silica-gel column chromatography (ethyl acetate/petroleum ether (v/v)=1/10) to give the title compound as a white solid (1.51 g, 81%).

MS (ES-API, pos. ion) m/z: 233.9 [M+2]⁺.

Step 5) Synthesis of tert-butyl 4-(2-cyanoquinolin-4-yl)-2-hydroxybenzoate 4-bromoquinoline-2-carbonitrile (0.305 g, 1.31 mmol), tert-butyl 2-hydroxy-4-(4,4,5,5-tetramethyl-1,3,2-dioxaborolan-2-yl) benzoate (0.42 g, 1.31 mmol), 1,1'-bis(diphenylphosphino)ferrocene-palladium(II)dichloride dichloromethane complex (53 mg, 0.065 mmol) and N,N-dimethylformamide (8 mL) were added to a 50 mL two-neck flask. To the reaction mixture was added aqueous potassium carbonate (1.3 mL, 2 M) under nitrogen, and the resulting mixture was stirred at 90° C. for 0.5 h. The reaction mixture was cooled to room temperature and to the mixture was added saturated brine (80 mL). The resulting mixture was extracted with ethyl acetate (40 mL×2), and the organic layers were combined. The combined organic layers were washed with saturated brine (60 mL), dried over anhydrous sodium sulfate, and filtered. The filtrate was concentrated in vacuo. The residue was purified by silica-gel column chromatography (dichloromethane/petroleum ether (v/v)=1/2) to give the title compound as a white solid (0.263 g, 58%).

MS (ES-API, pos. ion) m/z: 347.1 [M+1]⁺.

Step 6) Synthesis of 4-(2-cyanoquinolin-4-yl)-2-hydroxybenzoic Acid tert-Butyl 4-(2-cyanoquinolin-4-yl)-2-hydroxybenzoate (0.263 g, 0.760 mmol) and dichloromethane (15 mL) were added to a 100 mL single-neck flask, then to the mixture in flask was added trifluoroacetic acid (2 mL). After the addition, the reaction mixture was stirred at rt for 12 h, and concentrated in vacuo to remove organic solvent. The residue was purified by silica-gel column chromatography (methanol/dichloromethane (v/v)=1/10) to give the title compound as a white solid (0.174 g, 79%).

MS (ES-API, neg. ion) m/z: 289.0 [M−1]⁻; and
¹H NMR (400 MHz, DMSO-d₆) δ (ppm): 8.20 (d, J=8.4 Hz, 1H), 8.00-7.93 (m, 4H), 7.79 (t, J=7.6 Hz, 1H), 7.05-6.87 (m, 2H).

Example 35: 4-(5-cyano-3-(trifluoromethyl)benzo[d]isoxazol-7-yl)-2-hydroxybenzoic Acid

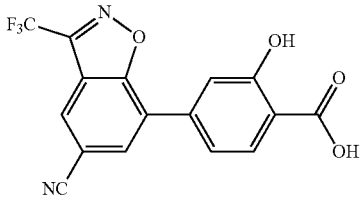 [SMILES: N#Cc1cc(-c2ccc(C(=O)O)c(O)c2)c2onc(C(F)(F)F)c2c1]

Step 1) Synthesis of 3-bromo-2-fluoro-5-methylbenzaldehyde

2-Bromo-1-fluoro-4-methylbenzene (18.9 g, 100 mmol) and anhydrous tetrahydrofuran (150 mL) were added to a 500 mL single-neck flask, then to the mixture in flask was added dropwise slowly lithium diisopropylamide solution (60 mL, 2 M in THF) at −70° C. After the addition, the reaction mixture was stirred at −70° C. for 3 h, then to the flask was added anhydrous N,N-dimethylformamide (17.2 g, 235 mmol). After the addition, the reaction mixture was warmed slowly to rt and stirred for overnight. To the reaction mixture was added diluted hydrochloric acid (200 mL, 4 M), and the resulting mixture was stirred at rt for 2 h. The mixture was concentrated in vacuo to remove tetrahydrofuran. The residue was extracted with ethyl acetate (100 mL×2), and the organic layers were combined. The combined organic layers were washed with saturated brine (100 mL), dried over anhydrous sodium sulfate, and filtered. The filtrate was concentrated in vacuo. The residue was purified by silica-gel column chromatography (ethyl acetate/petroleum ether (v/v)=1/100) to give the title compound as an orange solid (10.9 g, 50%).

MS (ES-API, pos. ion) m/z: 217.9 [M+2]+.

Step 2) Synthesis of 1-(3-bromo-2-fluoro-5-methylphenyl)-2,2,2-trifluoroethanol 3-Bromo-2-fluoro-5-methylbenzaldehyde (13.0 g, 59.9 mmol), (trifluoromethyl)trimethylsilane (10.2 g, 71.7 mmol) and tetrahydrofuran (150 mL) were added to a 500 mL single-neck flask, then to the mixture in flask was added dropwise tetrabutylammonium fluoride solution (1.2 mL, 1.0 M in THF) at 0° C. After the addition, the reaction mixture was stirred at rt for 2 h, then to the flask was added dropwise tetrabutylammonium fluoride solution (1.2 mL, 1.0 M in THF). After the addition, the reaction mixture was stirred at rt for 3 h. To the reaction mixture was added diluted hydrochloric acid (300 mL) and the resulting mixture was extracted with ethyl acetate (100 mL×2). The combined organic layers were washed with saturated brine (100 mL), dried over anhydrous sodium sulfate, and filtered. The filtrate was concentrated in vacuo. The residue was purified by silica-gel column chromatography (ethyl acetate/petroleum ether (v/v)=1/50) to give the title compound as light yellow liquid (13.4 g, 78%).

MS (ES-API, pos. ion) m/z: 287.9 [M+2]+.

Step 3) Synthesis of 1-(3-bromo-2-fluoro-5-methylphenyl)-2,2,2-trifluoroethanone 1-(3-Bromo-2-fluoro-5-methylphenyl)-2,2,2-trifluoroethanol (9.85 g, 34.3 mmol), 2-iodoxybenzoicacid (30.3 g, 103 mmol) and ethyl acetate (120 mL) were added to a 250 mL single-neck flask. The resulting mixture was stirred at 90° C. for 24 h. The reaction mixture was cooled to room temperature and filtered, then the filtrate was concentrated in vacuo. The residue was purified by silica-gel column chromatography (ethyl acetate/petroleum ether (v/v)=1/50) to give the title compound as light yellow oil (7.53 g, 77%).

$^1$H NMR (400 MHz, CDCl$_3$) δ (ppm): 7.72 (dd, J=6.0, 1.7 Hz, 1H), 7.60 (d, J=5.7 Hz, 1H), 2.42 (s, 3H).

Step 4) Synthesis of 1-(3-bromo-2-fluoro-5-methylphenyl)-2,2,2-trifluoroethanone oxime 1-(3-Bromo-2-fluoro-5-methylphenyl)-2,2,2-trifluoroethanone (2.50 g, 8.77 mmol), sodium acetate (10.2 g, 106 mmol), hydroxylamine hydrochloride (6.35 g, 87.7 mmol) and methanol (30 mL) were added to a 100 mL single-neck flask. The resulting mixture was stirred at 80° C. for 30 h under nitrogen protection. The reaction mixture was cooled to room temperature and to the mixture was added saturated aqueous ammonium chloride (150 mL). The resulting mixture was extracted with ethyl acetate (100 mL×2), and the organic layers were combined. The combined organic layers were washed with saturated brine (100 mL), dried over anhydrous sodium sulfate, and filtered. The filtrate was concentrated in vacuo to give the title compound as light yellow oil (2.60 g, 99%).

Step 5) Synthesis of 7-bromo-5-methyl-3-(trifluoromethyl)benzo[d]isoxazole 1-(3-Bromo-2-fluoro-5-methylphenyl)-2,2,2-trifluoroethanone oxime (2.60 g, 8.7 mmol), 1,8-diazabicyclo[5.4.0]undec-7-ene (1.55 mL, 10.4 mmol) and tetrahydrofuran (15 mL) were added to a 20 mL microwave tube. The resulting mixture was stirred at 150° C. for 0.5 h under microwave condition. The reaction mixture was cooled to room temperature, then to the mixture was added with diluted hydrochloric acid (80 mL, 1 M). The resulting mixture was extracted with ethyl acetate (60 mL×2). The combined organic layers were washed with saturated brine (60 mL×2), dried over anhydrous sodium sulfate, and filtered. The filtrate was concentrated in vacuo to give the title compound as a white solid (2.10 g, 87%).

$^1$H NMR (400 MHz, CDCl$_3$) δ (ppm) 7.68 (s, 1H), 7.53 (s, 1H), 2.53 (s, 3H).

Step 6) Synthesis of 7-bromo-3-(trifluoromethyl)benzo[d]isoxazole-5-carbonitrile 7-Bromo-5-methyl-3-(trifluoromethyl)benzo[d]isoxazole (1.15 g, 4.1 mmol), tert-butyl nitrite (1.26 g, 12.2 mmol), N-hydroxyphthalimide (0.669 g, 4.1 mmol), palladium acetate (0.045 g, 0.20 mmol) and acetonitrile (20 mL) were added to 25 mL microwave tube, and the resulting mixture was stirred at 80° C. for 48 h. The reaction mixture was cooled to room temperature and concentrated in vacuo. The residue was purified by silica-gel column chromatography (dichloromethane/petroleum ether (v/v)=1/4) to give the title compound as a white solid (0.538 g, 42%).

MS (ES-API, pos. ion) m/z: 291.9 [M+2]+.

Step 7) Synthesis of tert-butyl 4-(5-cyano-3-(trifluoromethyl)benzo[d]isoxazol-7-yl)-2-hydroxybenzoate 7-Bromo-3-(trifluoromethyl)benzo[d]isoxazole-5-carbonitrile (0.419 g, 1.44 mmol), tert-butyl 2-hydroxy-4-(4,4,5, 5-tetramethyl-1,3,2-dioxaborolan-2-yl) benzoate (0.420 g, 1.31 mmol), 1,1'-bis(diphenylphosphino)ferrocene-palladium(II)dichloride dichloromethane complex (53 mg, 0.065 mmol) and N,N-dimethylformamide (8 mL) were added to a 50 mL two-neck flask. To the reaction mixture was added aqueous potassium carbonate (1.3 mL, 2 M) under nitrogen, and the resulting mixture was stirred at 90° C. for 0.5 h. The reaction mixture was cooled to room temperature and to the mixture was added saturated brine (80 mL). The resulting mixture was extracted with ethyl acetate (40 mL×2), and the organic layers were combined. The combined organic layers were washed with saturated brine (60 mL), dried over anhydrous sodium sulfate, and filtered. The filtrate was concentrated in vacuo. The residue was purified by silica-gel column chromatography (dichloromethane/petroleum ether (v/v)=1/4) to give the title compound as a white solid (0.212 g, 40%).

MS (ES-API, pos. ion) m/z: 405.1 [M+1]$^+$.

Step 8) Synthesis of 4-(5-cyano-3-(trifluoromethyl)benzo[d]isoxazole-7-yl)-2-hydroxybenzoic Acid tert-Butyl 4-(5-cyano-3-(trifluoromethyl)benzo[d]isoxazol-7-yl)-2-hydroxybenzoate (0.212 g, 0.524 mmol) and dichloromethane (15 mL) were added to a 100 mL single-neck flask, then to the mixture in flask was added trifluoroacetic acid (2 mL). After the addition, the reaction mixture was stirred at rt for 12 h, and concentrated in vacuo to remove organic solvent. The residue was purified by silica-gel column chromatography (methanol/dichloromethane (v/v)=1/20) to give the title compound as a white solid (0.119 g, 65%).

MS (ES-API, neg. ion) m/z: 347.0 [M−1]$^-$; and
$^1$H NMR (400 MHz, DMSO-d6) δ (ppm): 8.66 (s, 1H), 8.48 (s, 1H), 7.90 (s, 1H), 7.30-7.26 (m, 2H).

Example 36: 4-(6-cyano-2-methyl-2H-indazol-4-yl)-2-hydroxybenzoic Acid

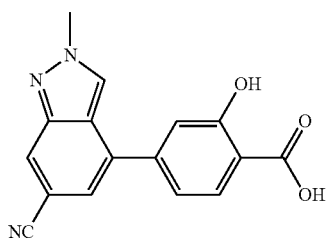 [SMILES: Cn1cc2c(-c3ccc(C(=O)O)c(O)c3)cc(C#N)cc2n1]

Step 1) Synthesis of methyl 4-bromo-2-methyl-2H-indazole-6-carboxylate

Methyl 4-bromo-1H-indazole-6-carboxylate (1.53 g, 6.0 mmol), cesium carbonate (3.95 g, 12.1 mmol) and N,N-dimethylformamide (20 mL) were added to a 100 mL two-neck flask, then to the mixture in flask was added iodomethane (1.1 g, 7.7 mmol). After the addition, the reaction mixture was stirred at rt for 24 h. The reaction mixture was filtered to remove the insoluble substance and to the filtrate was added saturated aqueous ammonium chloride (150 mL). The resulting mixture was extracted with ethyl acetate (80 mL×2), and the organic layers were combined. The combined organic layers were washed with saturated brine (100 mL), dried over anhydrous sodium sulfate, and filtered. The filtrate was concentrated in vacuo. The residue was purified by silica-gel column chromatography (ethyl acetate/petroleum ether (v/v)=1/15) to give the title compound as a light yellow solid (0.517 g, 32%).

$^1$H NMR (400 MHz, CDCl$_3$) δ (ppm): 8.42 (s, 1H), 7.96 (s, 1H), 7.88 (s, 1H), 4.26 (s, 3H), 3.95 (s, 3H).

Step 2) Synthesis of 4-bromo-2-methyl-2H-indazole-6-carboxamide

Methyl 4-bromo-2-methyl-2H-indazole-6-carboxylate (1.0 g, 3.7 mmol) and a solution of ammonia in methanol (20 mL, 7 M) were added to a 50 mL sealed tube. The tube was sealed and the reaction mixture in sealed tub was stirred at 110° C. for 24 h. The reaction mixture was cooled to rt and concentrated in vacuo to remove solvent. The residue was purified by silica-gel column chromatography (methanol/dichloromethane (v/v)=1/50) to give the title compound as a white solid (0.50 g, 53%).

MS (ES-API, pos. ion) m/z: 254.9 [M+2]$^+$.

Step 3) Synthesis of 4-bromo-2-methyl-2H-indazole-6-carbonitrile

4-Bromo-2-methyl-2H-indazole-6-carboxamide (0.50 g, 1.97 mmol) and toluene (20 mL) were added to a 100 mL single-neck flask, then to the mixture in flask was added phosphorus oxychloride (3.0 g, 19.7 mmol). After the addition, the reaction mixture was stirred at 120° C. for 12 h. The reaction mixture was cooled to rt and to the mixture was added saturated brine (80 mL). The resulting mixture was extracted with ethyl acetate (40 mL×2), and the organic layers were combined. The combined organic layers were washed with saturated brine (60 mL), dried over anhydrous sodium sulfate, and filtered. The filtrate was concentrated in vacuo. The residue was purified by silica-gel column chromatography (ethyl acetate/petroleum ether (v/v)=1/5) to give the title compound as a white solid (0.44 g, 95%).

MS (ES-API, pos. ion) m/z: 236.9 [M+2]$^+$.

Step 4) Synthesis of tert-butyl 4-(6-cyano-2-methyl-2H-indazol-4-yl)-2-hydroxybenzoate 4-Bromo-2-methyl-2H-indazole-6-carbonitrile (0.340 g, 1.44 mmol), tert-butyl 2-hydroxy-4-(4,4,5,5-tetramethyl-1,3,2-dioxaborolan-2-yl) benzoate (0.420 g, 1.31 mmol), 1,1'-bis(diphenylphosphino)ferrocene-palladium(II)dichloride dichloromethane complex (53 mg, 0.065 mmol) and N,N-dimethylformamide (8 mL) were added to a 50 mL two-neck flask. To the reaction mixture was added aqueous potassium carbonate (1.3 mL, 2 M) under nitrogen protection, and the resulting mixture was stirred at 90° C. for 0.5 h. The reaction mixture was cooled to rt and to the mixture was added saturated brine (80 mL). The resulting mixture was extracted with ethyl acetate (40 mL×2), and the organic layers were combined. The combined organic layers were washed with saturated brine (60 mL), dried over anhydrous sodium sulfate, and filtered. The filtrate was concentrated in vacuo. The residue was purified by silica-gel column chromatography (dichloromethane/petroleum ether (v/v)=2/1) to give the title compound as a white solid (0.384 g, 84%).

MS (ES-API, pos. ion) m/z: 350.1 [M+1]$^+$.

Step 5) Synthesis of 4-(6-cyano-2-methyl-2H-indazol-4-yl)-2-hydroxybenzoic Acid tert-Butyl 4-(6-cyano-2-methyl-2H-indazol-4-yl)-2-hydroxybenzoate (0.384 g, 1.10 mmol) and dichloromethane (15 mL) were added to a 100 mL single-neck flask, then to the mixture was added trifluoroacetic acid (2 mL). After the addition, the reaction mixture was stirred at rt for 12 h, and concentrated in vacuo to remove solvent, The residue was purified by silica-gel column chromatography (methanol/dichloromethane (v/v)=1/10) to give the title compound as a white solid (0.210 g, 65%).

MS (ES-API, pos. ion) m/z: 294.1 [M+1]$^+$; and $^1$H NMR (400 MHz, DMSO-d$_6$) δ (ppm): 8.74 (s, 1H), 8.35 (s, 1H), 8.03-7.85 (m, 1H), 7.50 (s, 1H), 7.31 (d, J=4.4 Hz, 2H), 4.27 (s, 3H).

Example 37: 4-(6-cyano-2-(trifluoromethyl)-1H-indol-4-yl)-2-hydroxybenzoic Acid

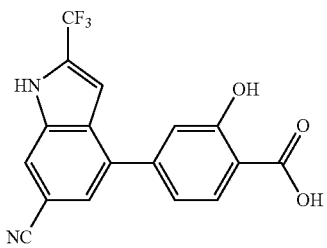 [SMILES: N#Cc1cc(-c2ccc(C(=O)O)c(O)c2)c2cc(C(F)(F)F)[nH]c2c1]

Step 1) Synthesis of methyl 4-(6-cyano-2-(trifluoromethyl)-1H-indol-4-yl)-2-hydroxybenzoate 4-Bromo-2-(trifluoromethyl)-1H-indole-6-carbonitrile (0.344 g, 1.19 mmol), methyl 2-hydroxy-4-(4,4,5,5-tetramethyl-1,3,2-dioxaborolan-2-yl) benzoate (0.300 g, 1.08 mmol), 1,1'-bis(diphenylphosphino)ferrocene-palladium(II) dichloride dichloromethane complex (48 mg, 0.059 mmol) and N,N-dimethylformamide (8 mL) were added to a 50 mL two-neck flask. To the reaction mixture was added aqueous potassium carbonate (1.1 mL, 2 M) under nitrogen, and the resulting mixture was stirred at 90° C. for 0.5 h. The reaction mixture was cooled to room temperature and to the mixture was added saturated brine (80 mL). The resulting mixture was extracted with ethyl acetate (40 mL×2), and the organic layers were combined. The combined organic layers were washed with saturated brine (60 mL), dried over anhydrous sodium sulfate, and filtered. The filtrate was concentrated in vacuo. The residue was purified by silica-gel column chromatography (ethyl acetate/petroleum ether (v/v)=1/10) to give the title compound as a white solid (0.17 g, 39%).

MS (ES-API, pos. ion) m/z: 361.0 [M+1]$^+$.

Step 2) Synthesis of 4-(6-cyano-2-(trifluoromethyl)-1H-indol-4-yl)-2-hydroxybenzoic Acid Methyl 4-(6-cyano-2-(trifluoromethyl)-1H-indol-4-yl)-2-hydroxybenzoate (0.133 g, 0.37 mmol), methanol (8 mL), tetrahydrofuran (8 mL) and water (8 mL) were added to a 100 mL single-neck flask, then to the mixture was added sodium hydroxide (45 mg, 1.12 mmol). After the addition, the reaction mixture was stirred at rt for 12 h. The reaction mixture was concentrated in vacuo to remove the organic solvent, and to the residue was added water (60 mL). The resulting mixture was washed with ethyl ether (50 mL). Then the aqueous layer was acidified with diluted hydrochloric acid (2 N) to pH 1, and the resulting mixture was extracted with ethyl acetate (40 mL×2). The combined organic layers were washed with saturated brine (40 mL×2), dried over anhydrous sodium sulfate, and filtered. The filtrate was concentrated in vacuo, and the residue was purified by silica-gel column chromatography (methanol/dichloromethane (v/v)=1/20) to give the title compound as a pale yellow solid (89 mg, 67%).

MS (ES-API, neg. ion) m/z: 345.1 [M−1]$^-$; and $^1$H NMR (400 MHz, DMSO-d$_6$) δ (ppm): 13.21 (s, 1H), 8.06 (s, 1H), 7.93 (d, J=7.4 Hz, 1H), 7.61 (s, 1H), 7.25-7.16 (m, 3H).

Example 38: 4-(5-cyano-2-(trifluoromethyl)benzofuran-7-yl)-2-hydroxybenzoic Acid

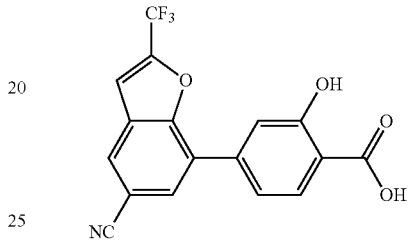

Step 1) Synthesis of (Z)-2-bromo-4-(2-chloro-3,3,3-trifluoroprop-1-en-1-yl)-6-methylphenyl acetate 3-Bromo-2-hydroxy-5-methylbenzaldehyde (5.60 g, 26 mmol), zinc powder (8.50 g, 130 mmol), acetic anhydride (7.96 g, 78 mmol) and N,N-dimethylformamide (30 mL) were added to a 100 mL single-neck flask, then to the mixture was added dropwise slowly 1,1,1-trichlorotrifluoroethane (7.80 g, 41.1 mmol) under nitrogen while maintaining the mixture temperature not exceeding 50° C. After the addition, the reaction mixture was stirred at rt for 4 h. To the reaction mixture was added saturated aqueous ammonium chloride (200 mL). The resulting mixture was extracted with ethyl acetate (100 mL×2), and the organic layers were combined. The combined organic layers were washed with saturated brine (100 mL), dried over anhydrous sodium sulfate, and filtered. The filtrate was concentrated in vacuo. The residue was purified by silica-gel column chromatography (ethyl acetate/petroleum ether (v/v)=1/50) to give the title compound as light yellow liquid (4.83 g, 52%).

$^1$H NMR (400 MHz, CDCl$_3$) δ (ppm): 7.56 (s, 1H), 7.49 (s, 1H), 7.20 (s, 1H), 2.38 (s, 3H), 2.35 (s, 3H); and $^{19}$F NMR (376 MHz, CDCl$_3$) δ (ppm): −69.06 (s, 3F).

Step 2) Synthesis of 7-bromo-5-methyl-2-(trifluoromethyl)benzofuran (Z)-2-Bromo-4-(2-chloro-3,3,3-trifluoroprop-1-en-1-yl)-6-methylphenyl acetate (4.00 g, 11.2 mmol) and N,N-dimethylformamide (25 mL) were added to a 100 mL single-neck flask, then to the mixture in flask was added in portions potassium tert-butoxide (3.77 g, 33.6 mmol) at 0° C. After the addition, the reaction mixture was stirred at rt for 6 h. To the reaction mixture was added saturated aqueous ammonium chloride (200 mL). The resulting mixture was extracted with ethyl acetate (100 mL×2), and the organic layers were combined. The combined organic layers were washed with saturated brine (100 mL), dried over anhydrous sodium sulfate, and filtered. The filtrate was concentrated in vacuo. The residue was purified by silica-gel column chromatography (ethyl acetate/petroleum ether (v/v)=1/100) to give the title compound as colorless liquid (1.78 g, 57%).

¹H NMR (400 MHz, CDCl₃) δ (ppm): 7.43 (s, 1H), 7.37 (s, 1H), 7.14 (s, 1H), 2.44 (s, 3H); and ¹H NMR (376 MHz, CDCl₃) δ (ppm): −64.77 (s, 3F).

Step 3) Synthesis of 7-bromo-2-(trifluoromethyl) benzofuran-5-carbonitrile

7-Bromo-5-methyl-2-(trifluoromethyl)benzofuran (1.14 g, 4.1 mmol), tert-butyl nitrite (1.26 g, 12.2 mmol), N-hydroxyphthalimide (0.669 g, 4.1 mmol), palladium acetate (0.045 g, 0.20 mmol) and acetonitrile (20 mL) were added to a 25 mL microwave tube, and the resulting mixture was stirred at 80° C. for 48 h. The reaction mixture was cooled to room temperature and concentrated in vacuo. The residue was purified by silica-gel column chromatography (dichloromethane/petroleum ether (v/v)=1/8) to give the title compound as a white solid (0.166 g, 14%).

¹H NMR (400 MHz, CDCl₃) δ (ppm): 8.00 (d, J=1.1 Hz, 1H), 7.90 (d, J=1.1 Hz, 1H), 7.33 (s, 1H); and ¹⁹F NMR (376 MHz, CDCl₃) δ (ppm): −65.01 (s, 3F).

Step 4) Synthesis of tert-butyl 4-(5-cyano-2-(trifluoromethyl)benzofuran-7-yl)-2-hydroxybenzoate 7-Bromo-2-(trifluoromethyl)benzofuran-5-carbonitrile (0.380 g, 1.31 mmol), tert-butyl 2-hydroxy-4-(4,4,5,5-tetramethyl-1,3,2-dioxaborolan-2-yl) benzoate (0.42 g, 1.31 mmol), 1,1'-bis(diphenylphosphino)ferrocene-palladium(II) dichloride dichloromethane complex (53 mg, 0.065 mmol) and N,N-dimethylformamide (8 mL) were added to a 50 mL two-neck flask. To the reaction mixture was added aqueous potassium carbonate (1.3 mL, 2 M) under nitrogen protection, and the resulting mixture was stirred at 90° C. for 0.5 h. The reaction mixture was cooled to room temperature and to the mixture was added saturated brine (80 mL). The resulting mixture was extracted with ethyl acetate (40 mL×2), and the organic layers were combined. The combined organic layers were washed with saturated brine (60 mL), dried over anhydrous sodium sulfate, and filtered. The filtrate was concentrated in vacuo. The residue was purified by silica-gel column chromatography (ethyl acetate/petroleum ether (v/v)=1/40) to give the title compound as a white solid (0.391 g, 74%).

MS (ES-API, pos. ion) m/z: 404.1 [M+1]⁺.

Step 5) Synthesis of 4-(5-cyano-2-(trifluoromethyl) benzofuran-7-yl)-2-hydroxybenzoic Acid tert-Butyl 4-(5-cyano-2-(trifluoromethyl)benzofuran-7-yl)-2-hydroxybenzoate (0.391 g, 0.97 mmol) and dichloromethane (15 mL) were added to a 100 mL single-neck flask, then to the mixture was added trifluoroacetic acid (2 mL). After the addition, the reaction mixture was stirred at rt for 12 h, and concentrated in vacuo to remove organic solvent. The residue was purified by silica-gel column chromatography (methanol/dichloromethane (v/v)=1/20) to give the title compound as a white solid (0.257 g, 74%).

MS (ES-API, neg. ion) m/z: 346.0 [M−1]⁻;

¹H NMR (400 MHz, DMSO-d₆) δ (ppm): 8.44 (d, J=1.1 Hz, 1H), 8.27 (d, J=1.1 Hz, 1H), 8.06 7.89 (m, 2H), 7.56-7.37 (m, 2H); and ¹⁹F NMR (376 MHz, DMSO-d₆) δ (ppm): −63.66 (s, 3F).

Example 39: 4-(6-cyano-1-cyclopropyl-2-(trifluoromethyl)-1H-indol-4-yl)-2-hydroxybenzoic Acid

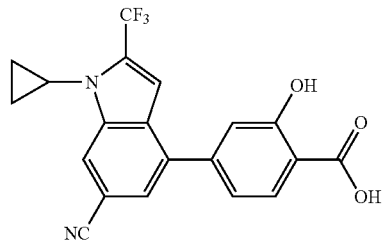 [SMILES: N#Cc1cc(-c2ccc(C(=O)O)c(O)c2)c2cc(C(F)(F)F)n(C3CC3)c2c1]

Step 1) Synthesis of 4-bromo-1-cyclopropyl-2-(trifluoromethyl)-1H-indole-6-carbonitrile 4-Bromo-2-(trifluoromethyl)-1H-indole-6-carbonitrile (0.500 g, 1.73 mmol), 2,2'-dipyridyl (0.270 g, 1.7 mmol), cyclopropyl boronic acid (0.300 g, 3.5 mmol), cupric acetate (0.310 g, 1.7 mmol), potassium carbonate (0.480 g, 3.5 mmol) and 1,2-dichloromethane (12 mL) were added to a 50 mL two-neck flask. After the addition, the reaction mixture was stirred at 70° C. for 16 h in an oxygen atmosphere. The reaction mixture was cooled to room temperature, then to the mixture were added saturated brine (80 mL) and ethyl acetate (80 mL). The resulting mixture was partitioned, and the organic layer was washed with saturated brine (40 mL×2), dried over anhydrous sodium sulfate, and filtered. The filtrate was concentrated in vacuo. The residue was purified by silica-gel column chromatography (ethyl acetate/ petroleum ether (v/v)=1/20) to give the title compound as a white solid (0.400 g, 70%).

MS (ES-API, pos. ion) m/z: 329.9 [M+2]⁺.

Step 2) Synthesis of methyl 4-(6-cyano-1-cyclopropyl-2-(trifluoromethyl)-1H-indol-4-yl)-2-hydroxybenzoate 4-Bromo-1-cyclopropyl-2-(trifluoromethyl)-1H-indole-6-carbonitrile (0.392 g, 1.19 mmol), methyl 2-hydroxy-4-(4,4,5,5-tetramethyl-1,3,2-dioxaborolan-2-yl) benzoate (0.300 g, 1.08 mmol), 1,1'-bis(diphenylphosphino)ferrocene-palladium(II)dichloride dichloromethane complex (48 mg, 0.059 mmol) and N,N-dimethylformamide (8 mL) were added to a 50 mL two-neck flask. To the reaction mixture was added aqueous potassium carbonate (1.1 mL, 2 M) under nitrogen protection, and the resulting mixture was stirred at 90° C. for 0.5 h. The reaction mixture was cooled to rt and to the mixture was added saturated brine (80 mL). The resulting mixture was extracted with ethyl acetate (40 mL×2), and the organic layers were combined. The combined organic layers were washed with saturated brine (60 mL), dried over anhydrous sodium sulfate, and filtered. The filtrate was concentrated in vacuo. The residue was purified by silica-gel column chromatography (ethyl acetate/petroleum ether (v/v)=1/15) to give the title compound as a yellow solid (0.337 g, 78%).

MS (ES-API, pos. ion) m/z: 401.1 [M+1]⁺.

Step 3) Synthesis of 4-(6-cyano-1-cyclopropyl-2-(trifluoromethyl)-1H-indol-4-yl)-2-hydroxybenzoic Acid Methyl 4-(6-cyano-1-cyclopropyl-2-(trifluoromethyl)-1H-indol-4-yl)-2-hydroxybenzoate (0.148 g, 0.37 mmol), methanol (8 mL), tetrahydrofuran (8 mL) and water (8 mL) were added to a 100 mL single-neck flask, then to the mixture in flask was added sodium hydroxide (45 mg, 1.12 mmol). After the addition, the reaction mixture was stirred at rt for 12 h. The reaction mixture was concentrated in vacuo to remove solvent, and to the residue was added water (60 mL). The resulting mixture was washed with ethyl ether (50 mL). Then the aqueous layer was acidified with diluted hydrochloric acid (2 N) to pH 1, and the resulting mixture was extracted with ethyl acetate (40 mL×2). The combined organic layers were washed with saturated brine (40 mL×2), dried over anhydrous sodium sulfate, and filtered. The filtrate was concentrated in vacuo, and the residue was purified by silica-gel column chromatography (methanol/dichloromethane (v/v)=1/20) to give the title compound as a pale yellow solid (0.107 g, 75%).

MS (ES-API, pos. ion) m/z: 387.1 [M+1]$^+$;

$^1$H NMR (400 MHz, DMSO-d6) δ (ppm): 8.30 (s, 1H), 7.93 (d, J=8.3 Hz, 1H), 7.67 (s, 1H), 7.21-7.19 (m, 3H), 3.41-3.35 (m, 1H), 1.31-1.09 (m, 6H); and $^{19}$F NMR (376 MHz, DMSO-d$_6$) δ (ppm): −57.68 (s, 3F).

Example 40: 4-(2-chloro-5-cyanobenzofuran-7-yl)-2-hydroxybenzoic Acid

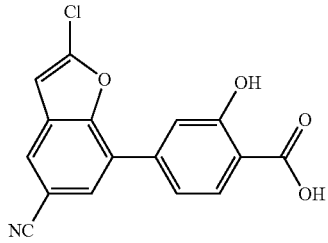

Step 1) Synthesis of 7-bromo-2-chlorobenzofuran-5-carbonitrile

7-Bromobenzofuran-5-carbonitrile (22.2 g, 100 mmol) and tetrahydrofuran (300 mL) were added to a 1000 mL two-neck flask, then to the mixture in flask was added dropwise slowly lithium diisopropylamide solution (60 mL, 120 mmol, 2.0 M in THF) at −70° C. After the addition, the reaction mixture was stirred at −70° C. for 1.5 h under nitrogen, then to the flask was added a solution of hexachloroethane (28.4 g, 120 mmol) in tetrahydrofuran (200 mL). After the addition, the reaction mixture was warmed slowly to room temperature and stirred for overnight. To the reaction mixture was added saturated aqueous ammonium chloride (800 mL) and the resulting mixture was extracted with ethyl acetate (300 mL×2). The combined organic layers were washed with saturated brine (300 mL), dried over anhydrous sodium sulfate, and filtered. The filtrate was concentrated in vacuo. The residue was purified by silica-gel column chromatography (dichloromethane/petroleum ether (v/v)=1/4) to give a crude product, which was further purified by reversed phase column (H$_2$O/CH$_3$CN, 0.1% TFA) to give the title compound as a white solid (16.7 g, 65%).

$^1$H NMR (400 MHz, CDCl$_3$) δ (ppm): 7.79 (d, J=1.0 Hz, 1H), 7.73 (d, J=1.0 Hz, 1H), 6.75 (s, 1H).

Step 2) Synthesis of tert-butyl 4-(2-chloro-5-cyanobenzofuran-7-yl)-2-hydroxybenzoate 7-Bromo-2-chlorobenzofuran-5-carbonitrile (0.362 g, 1.41 mmol), tert-butyl 2-hydroxy-4-(4,4,5,5-tetramethyl-1,3,2-dioxaborolan-2-yl) benzoate (0.420 g, 1.31 mmol), 1,1'-bis(diphenylphosphino)ferrocene-palladium(II)dichloride dichloromethane complex (53 mg, 0.065 mmol) and N,N-dimethylformamide (8 mL) were added to a 50 mL two-neck flask. To the reaction mixture was added aqueous potassium carbonate (1.3 mL, 2 M) under nitrogen, and the resulting mixture was stirred at 90° C. for 0.5 h. The reaction mixture was cooled to room temperature and to the mixture was added saturated brine (80 mL). The resulting mixture was extracted with ethyl acetate (40 mL×2), and the organic layers were combined. The combined organic layers were washed with saturated brine (60 mL), dried over anhydrous sodium sulfate, and filtered. The filtrate was concentrated in vacuo. The residue was purified by silica-gel column chromatography (dichloromethane/petroleum ether (v/v)=1/2) to give the title compound as a white solid (0.271 g, 56%).

MS (ES-API, pos. ion) m/z: 370.1 [M+1]$^+$.

Step 3) Synthesis of 4-(2-chloro-5-cyanobenzofuran-7-yl)-2-hydroxybenzoic Acid tert-Butyl 4-(2-chloro-5-cyanobenzofuran-7-yl)-2-hydroxybenzoate (0.271 g, 0.734 mmol) and dichloromethane (15 mL) were added to a 100 mL single-neck flask, then to the mixture was added trifluoroacetic acid (2 mL). After the addition, the reaction mixture was stirred at rt for 12 h, and concentrated in vacuo to remove solvent. The residue was purified by silica-gel column chromatography (methanol/dichloromethane (v/v)=1/20) to give the title compound as a white solid (0.182 g, 79%).

MS (ES-API, neg. ion) m/z: 312.1 [M−1]$^-$; and $^1$H NMR (400 MHz, DMSO-d$_6$) δ (ppm): 8.21 (s, 1H), 8.07 (s, 1H), 7.95 (d, J=8.2 Hz, 1H), 7.46 (s, 1H), 7.42 (d, J=8.2 Hz, 1H), 7.26 (s, 1H).

Biological Assay

Example 1 XO (Xanthine Oxidase) Inhibition Activity Assay

1) Test Method

The compound was diluted 2.5 fold with a buffer of 50 mM KH$_2$PO$_4$ to give a series of concentrations from 2000 nM to 0.524 nM. Then the diluted solution was added to a 384 well plate at 30 μL/well, and then to each well was added 30 μL of 21 mU/mL xanthine oxidase. The resulting solution was centrifuged at 3000 rpm for 1 min, shook and incubated at room temperature for 10 min, then to each well was added 30 μL of 600 μM substrate (xanthine); at the same time, the well was treated with the buffer (no compound, added the same concentration of enzyme and substrate) and a negative control well (no compound and enzyme, added the same concentration of substrate) were set up. After being incubated at room temperature for 5 min, absorbance at 290 nm was read by using PHERAstar FS microplate reader. The inhibition rate of the compound against xanthine oxidase (XO) was calculated by the following formula, and IC$_{50}$ values were calculated by using GraphPad Prism 5. The results were shown in Table 1:

Inhibition rate(%)=[1−(OD$_{drug\text{-}treated\ well}$−OD$_{negative\ control\ well}$)/(OD$_{buffer\text{-}treated\ well}$−OD$_{negative\ control\ well}$)]×100

2) Test Results

TABLE 1

| The test results of XO inhibition activity | |
|---|---|
| Example Number | IC$_{50}$ (nM) |
| Example 1 | 19.56 |
| Example 2 | 667 |

TABLE 1-continued

The test results of XO inhibition activity

| Example Number | IC$_{50}$ (nM) |
|---|---|
| Example 3 | 101.2 |
| Example 4 | 60.42 |
| Example 5 | 94.79 |
| Example 6 | 66.23 |
| Example 7 | 10.87 |
| Example 17 | 90.22 |
| Example 18 | 63.28 |
| Example 21 | 39.48 |
| Example 25 | 164.0 |
| Example 27 | 88.79 |
| Example 28 | 146.0 |
| Example 29 | 34.64 |
| Example 30 | 179.0 |
| Example 31 | 57.76 |
| Example 33 | 102.0 |
| Example 40 | 53.64 |

Conclusion: The test results indicate that the compounds of the invention exhibited good inhibitory activity against XO.

Example 2 URAT1 (Urate Anion Transporter) Inhibition Activity Assay

1) Test Method
a. Construction of a Cell Line Stably Expressing hURAT1
hURAT1 plasmid was transfected into HEK293T cell, and a cell line stably expressing hURAT1 was obtained by using G418 (Geneticin) for screening.
b. Uric Acid Absorption Inhibition
The cell line stably expressing hURAT1 obtained through the above steps was seeded into a 96 well plate. After being incubated for at least 12 h, the medium was removed, and then cells were washed with (Cl$^-$)-free HBSS buffer. The compound was diluted 4-fold with a buffer to give a series of concentrations of compound solutions from 200 μM to 0.8 nM. 5 μL of resulting compound solution and 45 μL of butter containing [8-$^{14}$C] uric acid were mixed uniformly, and then the resulting mixed solution was added to the 96 well plate containing the cell line stably expressing hURAT1 (i.e. the final concentration of compound is range from 20 μM to 0.08 nM). At the same time, a buffer well (the cell line stably expressing hURAT1, without drug) and a negative well (HEK293T cell, without drug) were set up. After incubated at 37° C. for 5 min, the buffer was removed, and the cells were washed with buffer. 50 μL of lysis buffer (100 mM NaOH) was added to each well to lyse cells, and the well was shook at 600 rpm for 10 min, centrifuged at 1000 rpm for 5 min, and then 45 μL of supernatant was pipetted to an Isoplate-96 microplate. To each well was added 150 μL of Ultima Gold™ XR, and the microplate was shook at 600 rpm for 10 min. MicroBeta Trilux scintillation/luminescent counter (PerkinElmer) was used to count, remaining amount of [8-$^{14}$C] uric acid was read. Absorption inhibition ratio of the compound against [8-$^{14}$C] uric acid was calculated by the following formula, and IC$_{50}$ values were then calculated by software XLfit, and IC$_{50}$ values were shown in Table 2.

Inhibition ratio (%)=[1−($^{14}$C uptaken by drug well−$^{14}$C uptaken by negative well)/($^{14}$C uptaken by buffer well−$^{14}$C uptaken by negative well)]×100;

Wherein, the negative well was unvaccinated cell line stably expressing hURAT1.

2) Test Results

TABLE 2

The results of URAT1 inhibition activity assay

| Example Number | IC$_{50}$ (μM) |
|---|---|
| Example 1 | 0.140 |
| Example 2 | 0.019 |
| Example 3 | 0.804 |
| Example 4 | 0.499 |
| Example 5 | 0.179 |
| Example 6 | 0.234 |
| Example 7 | 2.875 |
| Example 17 | 0.271 |
| Example 18 | 0.070 |
| Example 21 | 0.172 |
| Example 25 | 0.068 |
| Example 27 | 0.014 |
| Example 28 | 0.034 |
| Example 29 | 0.038 |
| Example 30 | 0.015 |
| Example 31 | 0.045 |
| Example 33 | 0.091 |
| Example 40 | 0.030 |

Conclusion: The test results indicate that the compounds of the invention exhibited good inhibitory activity against URAT1.

Example 3 Pharmacokinetic Evaluation

1) Test Method
SD rats were fasted for 15 h overnight and grouped randomly according to body weight. The test compound was dissolved in a solution of 5% DMSO+5% Solutol+90% Saline. For intravenous administration of the test group, the animals were administered with a dose of 1 mg/kg; for oral administration of the test group, the animals were administered with a dose of 5 mg/kg. Then venous blood (approximately 0.2 mL) was collected at the time point of 0, 0.083 (only intravenous injection group), 0.25, 0.5, 1.0, 2.0, 5.0, 7.0 and 24 h after drug administration. The venous blood was placed in EDTAK2 anticoagulant tube and centrifuged at 11000 rpm for 2 min. Plasma was collected and stored at −20° C. or at −70° C. until LC/MS/MS analysis. The drug concentration in plasma was measured at each time point, and pharmacokinetic parameters were calculated according to the curve of drug concentration-time.

Pharmacokinetic properties of the compounds of the present invention were calculated by the test above, and pharmacokinetic parameters were shown in Table 3.

2) Test Results

TABLE 3

Pharmacokinetic activity of the compound of the invention

| Example Number | Administration route | Dose (mg/kg) | F (%) | AUC$_{INF}$ (h*ng/ml) | AUC$_{last}$ (h*ng/ml) | Cl (ml/min/kg) | C$_{max}$ (ng/ml) | MRT$_{INF}$ (h) | T$_{1/2}$ (h) | T$_{max}$ (h) | V$_{ss}$ (l/kg) |
|---|---|---|---|---|---|---|---|---|---|---|---|
| Example 1 | iv | 1 | 131 | 7000 | 6860 | 2.4 | 6030 | 2.84 | 1.53 | 0.083 | 0.399 |
| | po | 5 | | 45800 | 44400 | / | 6830 | 5.98 | 3.45 | 0.417 | / |

TABLE 3-continued

Pharmacokinetic activity of the compound of the invention

| Example Number | Administration route | Dose (mg/kg) | F (%) | $AUC_{INF}$ (h*ng/ml) | $AUC_{last}$ (h*ng/ml) | Cl (ml/min/kg) | $C_{max}$ (ng/ml) | $MRT_{INF}$ (h) | $T_{1/2}$ (h) | $T_{max}$ (h) | $V_{ss}$ (l/kg) |
|---|---|---|---|---|---|---|---|---|---|---|---|
| Example 2 | iv | 1 | 74.9 | 2210 | 2170 | 7.59 | 4380 | 1.86 | 3.1 | 0.083 | 0.828 |
|  | po | 5 |  | 8140 | 8130 | / | 6290 | 1.5 | 3.86 | 0.417 | / |
| Example 29 | iv | 1 | 145 | 11300 | 10900 | 1.51 | 4540 | 3.49 | 2.76 | 0.083 | 0.311 |
|  | po | 5 |  | 82100 | 81700 | / | 17200 | 3.8 | 2.84 | 1.33 | / |
| Example 40 | iv | 1 | 94 | 6020 | 5480 | 2.77 | 4090 | 2.42 | 2.33 | 0.083 | 0.401 |
|  | po | 5 |  | 28200 | 28100 | / | 3700 | 4.95 | 3.05 | 0.5 | / |

"/" refers to not tested.

Conclusions: The test results shown in table 3 indicate that the compounds of the present invention had high plasma concentrations and exposure levels in rats after oral administration, and had low clearance rates and long half-lives. So the compounds of the present invention had good pharmacokinetic characteristics.

Finally, it should be noted that there are other ways to practice the invention. Accordingly, although explanatory embodiments have been shown and described, it would be appreciated by those skilled in the art that the above embodiments can not be construed to limit the present disclosure, and changes, equivalent alternatives, and modifications can be made without departing from the scope of the present disclosure. All publications or patents are incorporated herein by reference.

What is claimed is:

1. A compound of Formula (I) or a stereoisomer, a geometric isomer, a tautomer, an N-oxide, a metabolite, an ester, or a pharmaceutically acceptable salt thereof

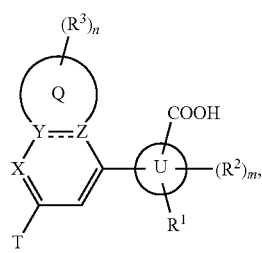

(I)

wherein:
U is phenyl or 5- to 6-membered heteroaryl;
each $R^1$ and $R^2$ is independently H, D, halogen, OH, $NH_2$, $NO_2$, CN, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylamino, $C_{1-6}$ haloalkylamino, 3- to 8-membered cycloalkyl or 3- to 8-membered heterocyclyl, wherein each of the $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylamino, $C_{1-6}$ haloalkylamino, 3- to 8-membered cycloalkyl or 3- to 8-membered heterocyclyl is independently and optionally substituted with 1, 2, 3, 4 or 5 substituents selected from OH, oxo (=O), $NH_2$, $NO_2$ or CN;
T is H, D, F, Cl, Br, $NO_2$, CN or $CF_3$;
X is $CR^4$ or N;
$R^4$ is H, D, halogen, $C_{1-6}$ alkyl, $C_{1-6}$ haloalkyl, $C_{1-6}$ alkoxy, $C_{1-6}$ alkylamino or $C_{1-6}$ haloalkoxy;
each of Y and Z is independently C, CH or N;
"=====" refers to a single bond or a double bond;

Q is phene, $C_{4-7}$ carbocycle, 4- to 7-membered heterocycle or 5- to 6-membered heteroaromatic ring;
each $R^3$ is independently H, D, halogen, oxo (=O), OH, $NH_2$, $NO_2$, CN, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylamino, $C_{1-6}$ haloalkylamino, 3- to 8-membered cycloalkyl, 3- to 8-membered heterocyclyl, 5- to 10-membered heteroaryl, phenyl, naphthyl or G, wherein each of the $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylamino, $C_{1-6}$ haloalkylamino, 3- to 8-membered cycloalkyl, 3- to 8-membered heterocyclyl, or 5- to 10-membered heteroaryl is independently and optionally substituted with 1, 2, 3, 4 or 5 substituents selected from OH, oxo (=O), $NH_2$, $NO_2$, CN or G;
G is substituted $C_{1-6}$ aliphatic hydrocarbon, wherein each of the methylene groups of the $C_{1-6}$ aliphatic hydrocarbon is optionally and independently substituted with J;
J is —NH—, —S—, —O—, —C(=O)—, —C(=O)NH—, —SO—, —SO$_2$—, —NHC(=O)—, —C(=O)O—, —SO$_2$NH— or —NHC(=O)NH—;
m is 0, 1, 2 or 3; and
n is 0, 1, 2, 3 or 4;
with the proviso that:
(1) when T is F, Cl, Br or $CF_3$, $R^1$ is OH;
(2) when T is H,

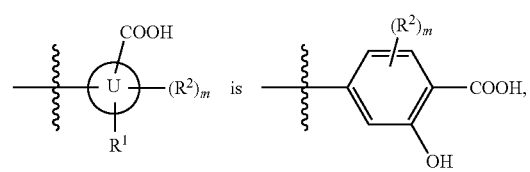

and Q is not phene;
(3) when T is $NO_2$, $R^1$ is not H.

2. The compound of claim 1 having Formula (II) or a stereoisomer, a geometric isomer, a tautomer, an N-oxide, a metabolite, an ester, or a pharmaceutically acceptable salt thereof,

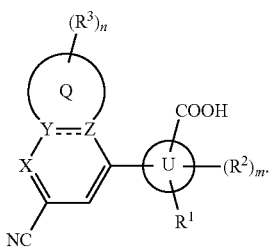

(II)

3. The compound of claim 1, wherein U is phenyl, pyridyl, pyrimidinyl, pyrazinyl, pyridazinyl, 1,3,5-triazinyl, pyrrolyl, furanyl, thiazolyl, thienyl, oxazolyl or isoxazolyl.

4. The compound of claim 1, wherein U is phenyl,

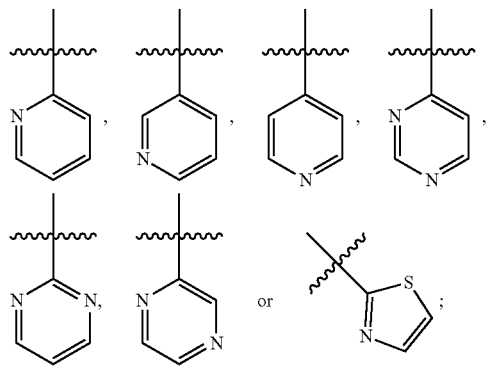

wherein * refers to the position of the U ring attached to

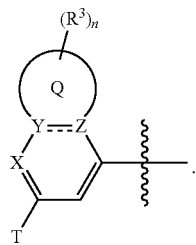

5. The compound of claim 1 having Formula (III) or a stereoisomer, a geometric isomer, a tautomer, an N-oxide, a metabolite, an ester, or a pharmaceutically acceptable salt thereof,

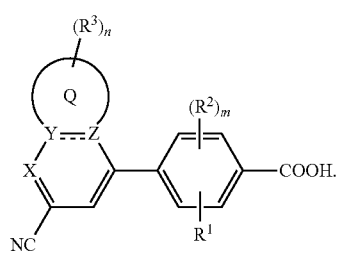

(III)

6. The compound of claim 1, wherein each $R^1$ and $R^2$ is independently H, D, halogen, OH, $NH_2$, $NO_2$, CN, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ haloalkoxy, $C_{1-4}$ alkylamino, $C_{1-4}$ haloalkylamino, 3- to 6-membered cycloalkyl or 3- to 6-membered heterocyclyl, wherein each of the $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ haloalkoxy, $C_{1-4}$ alkylamino, $C_{1-4}$ haloalkylamino, 3- to 6-membered cycloalkyl or 3- to 6-membered heterocyclyl is independently and optionally substituted with 1, 2 or 3 substituents selected from OH, oxo (=O), $NH_2$, $NO_2$ or CN.

7. The compound of claim 1, wherein each $R^1$ and $R^2$ is independently H, D, halogen, OH, $NH_2$, $NO_2$, CN, methyl, ethyl, i-propyl, butyl, hydroxymethyl, hydroxyethyl, aminomethyl, difluoromethyl, trifluoromethyl, methoxy, ethoxy, i-propoxy, t-butoxy, n-butoxy, methylamino, ethylamino, difluoromethoxy, trifluoromethoxy, acetyl, acetoxy, acetylamino, cyclopropyl, cyclobutyl, cyclopentyl, cyclohexyl, oxiranyl, pyrrolidinyl or tetrahydrofuranyl.

8. The compound of claim 1, wherein each $R^3$ is independently H, D, halogen, oxo (=O), OH, $NH_2$, $NO_2$, CN, methyl, ethyl, i-propyl, difluoromethyl, trifluoromethyl, methoxy, ethoxy, i-propoxy, difluoromethoxy, trifluoromethoxy, formyl, carboxy, formamido, acetyl, carbamoyl, propylsulfonamido, cyclopropyl, cyclobutyl, imidazolyl, pyrazolyl, thiazolyl, oxazolyl, pyridyl, pyrimidinyl, quinolyl, indolyl, phenyl or naphthyl.

9. The compound of claim 1, wherein $R^4$ is H, D, halogen, methyl, ethyl, i-propyl, t-butyl, n-butyl, difluoromethyl, trifluoromethyl, methoxy, ethoxy, t-butoxy, methylamino, difluoromethoxy or trifluoromethoxy; and

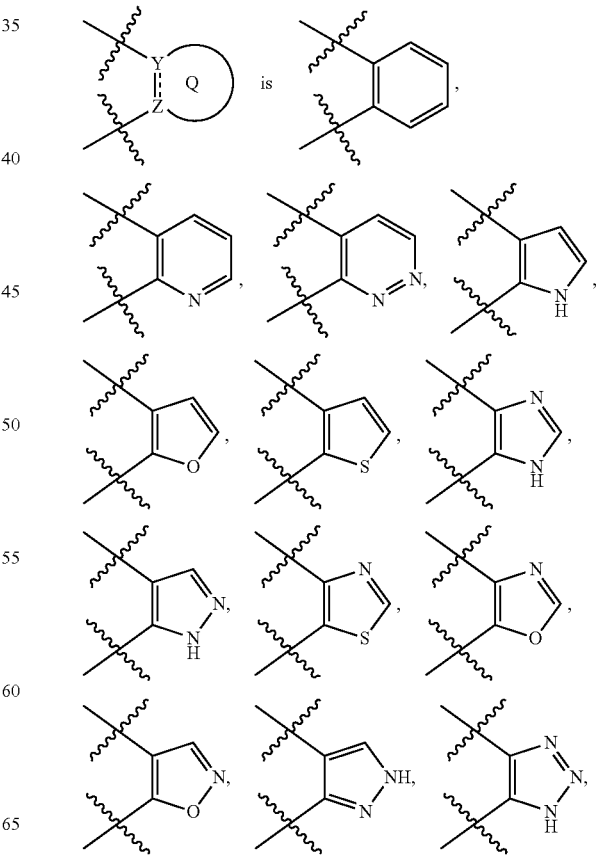

-continued
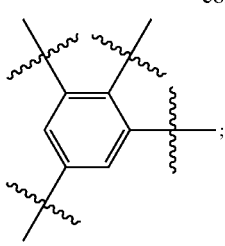
wherein *1 refers to the position attached to the U ring.
11. The compound of claim 1 having one of the following formulas:
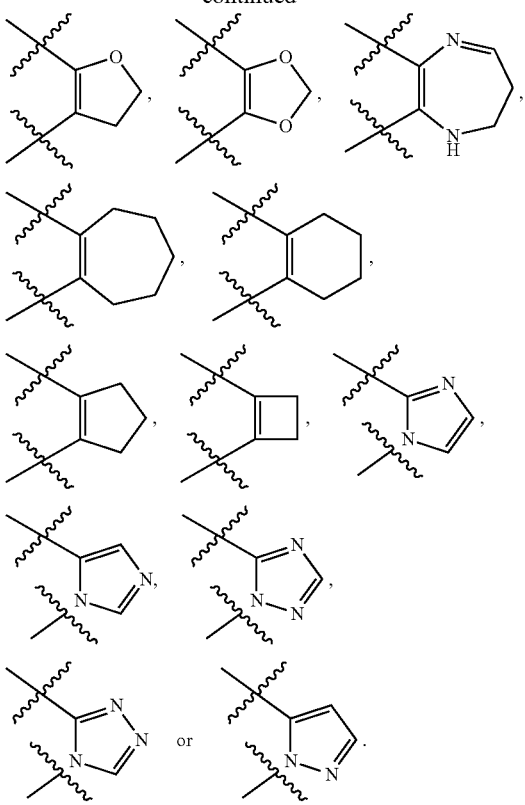
10. The compound of claim 1, wherein
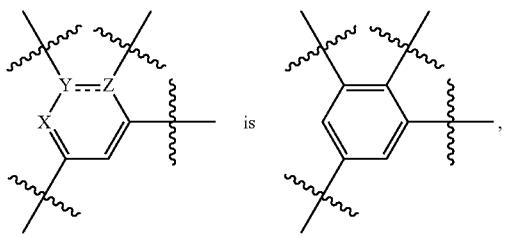 is 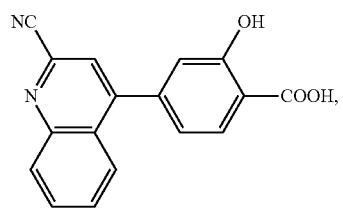,
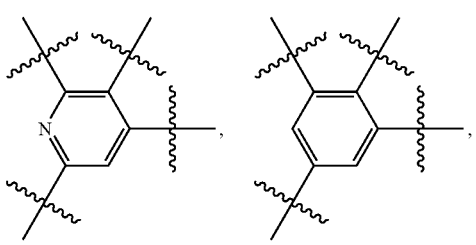
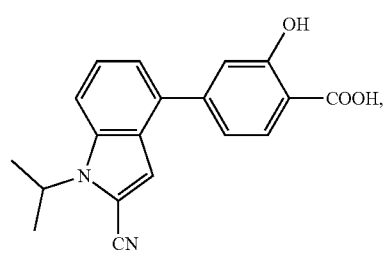
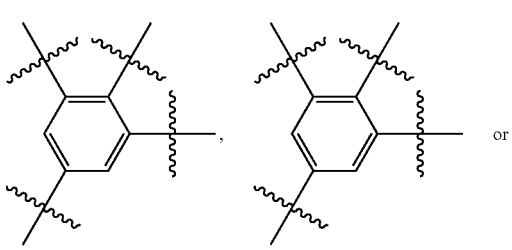 or
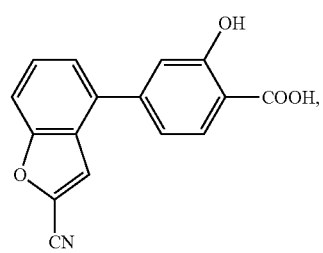
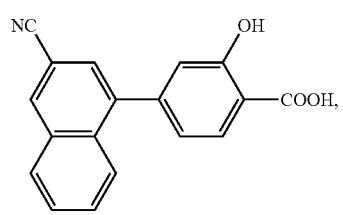
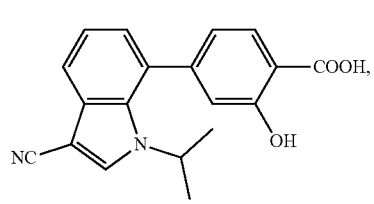

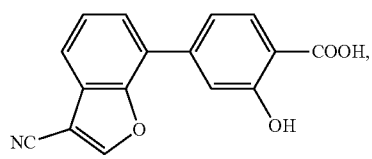
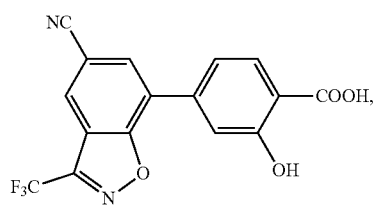
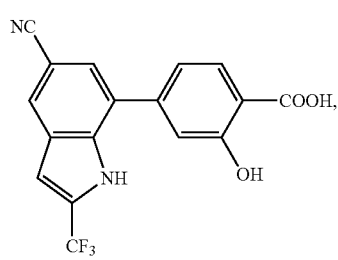
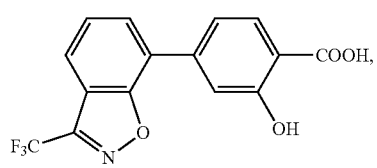
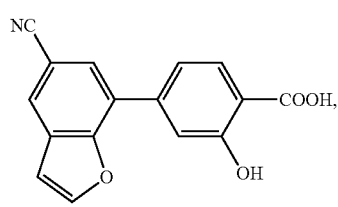
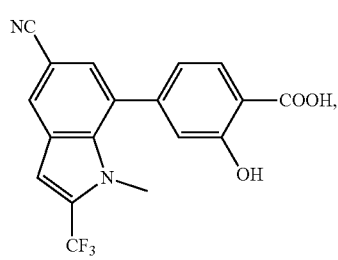
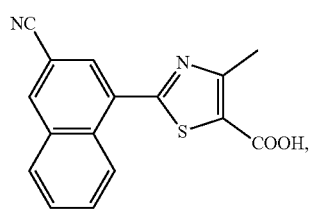
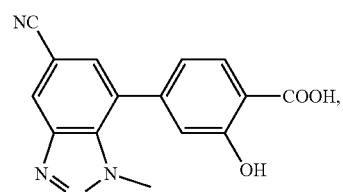
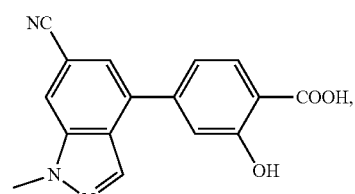
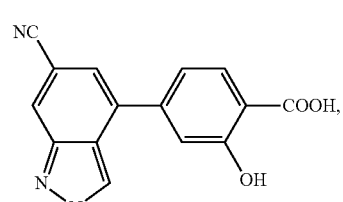
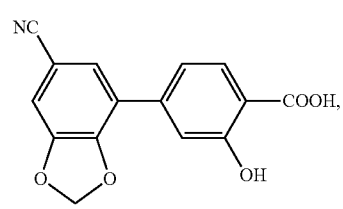
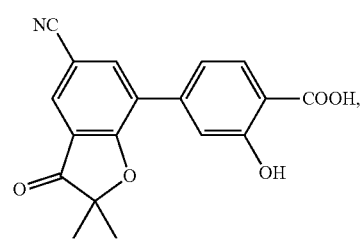
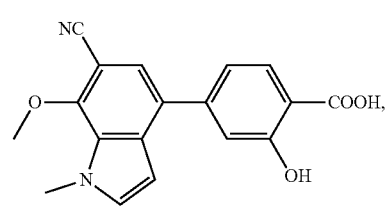
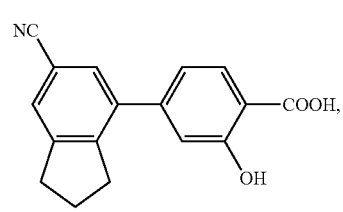

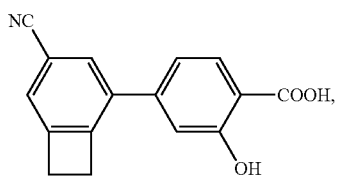
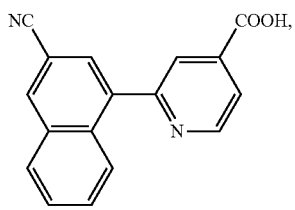
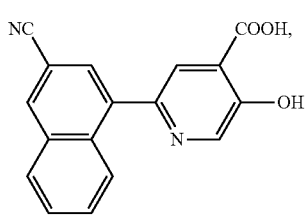
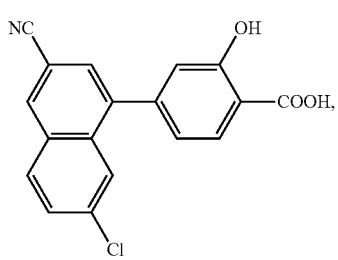
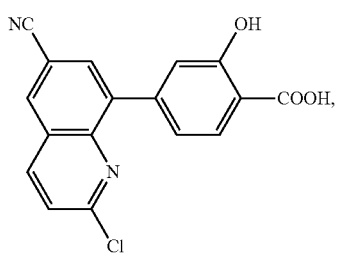
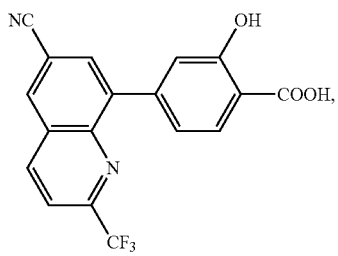
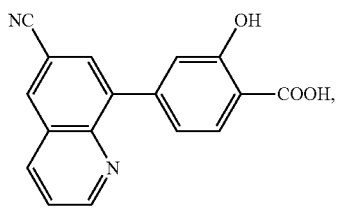
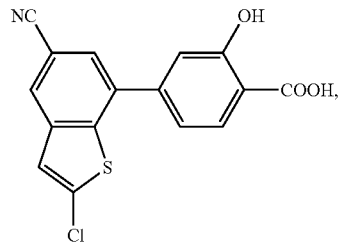
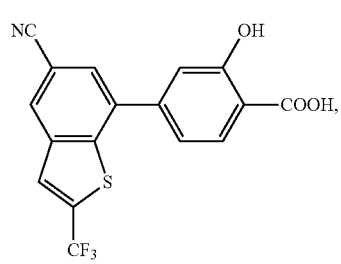
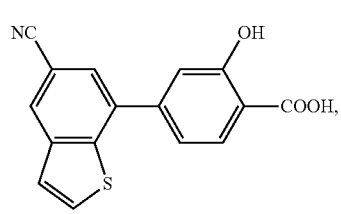
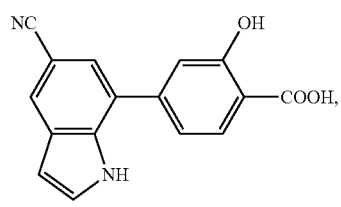
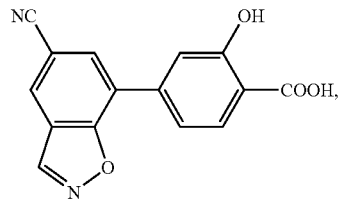
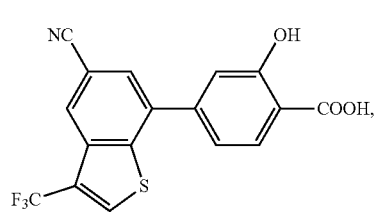
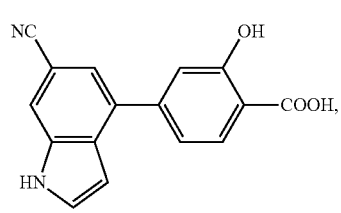

34
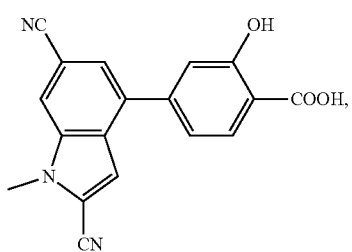
35
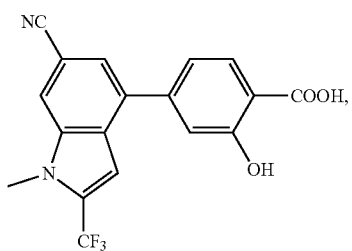
36
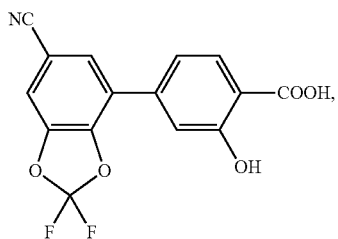
37
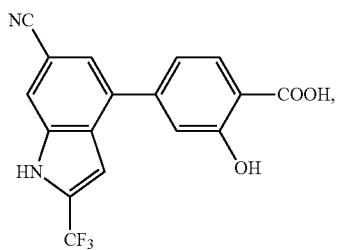
38
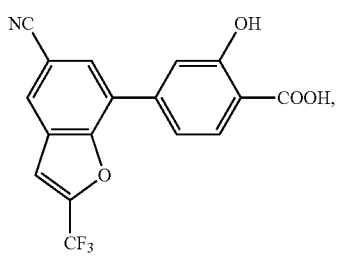
39
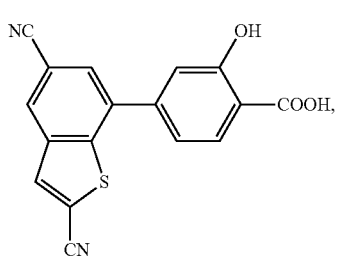
40
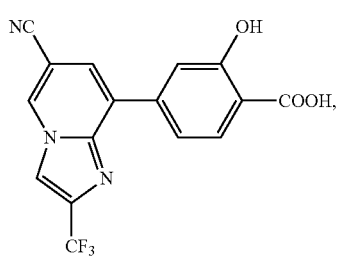
41
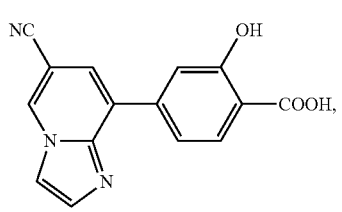
42
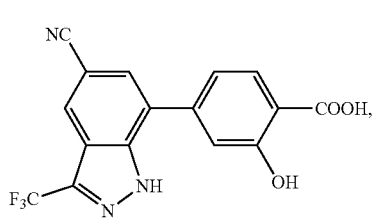
43
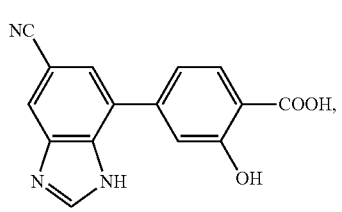
44
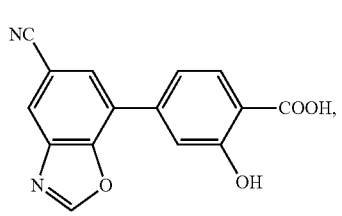
45
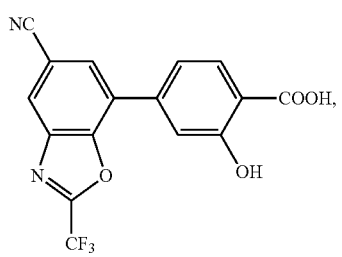
46
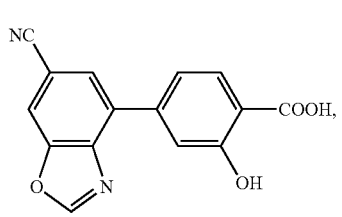

47
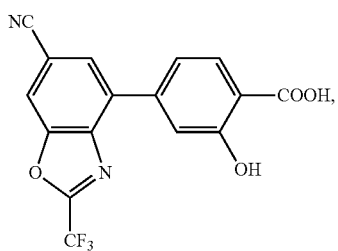
48
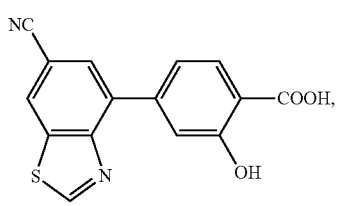
49
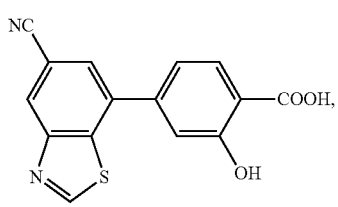
50
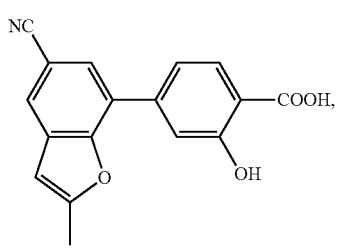
51
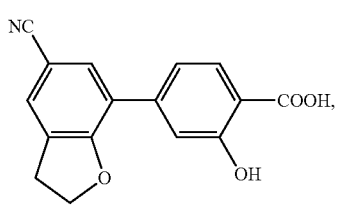
52
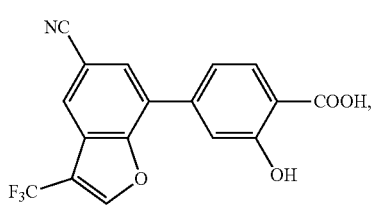
53
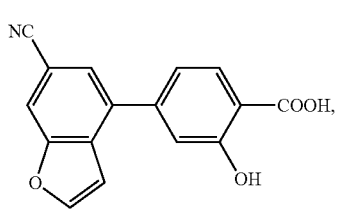
54
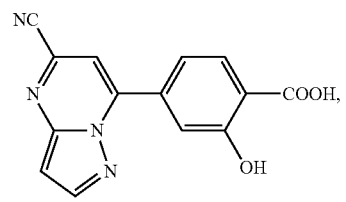
55
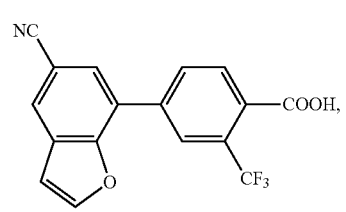
56
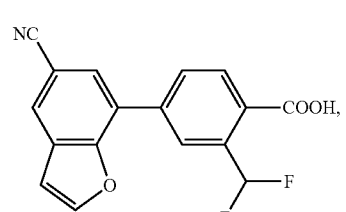
57
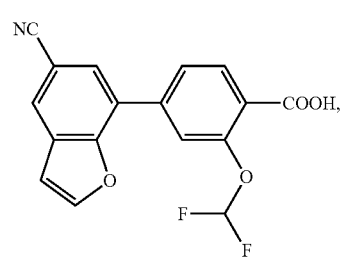
58
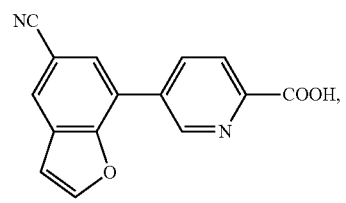
59
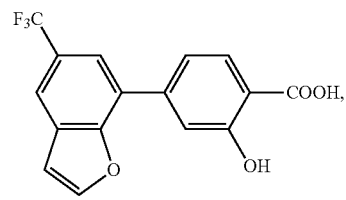
60
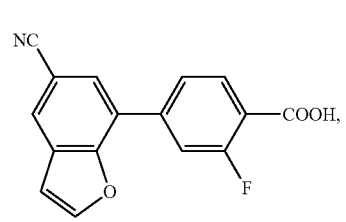

-continued
| | |
|---|---|
| 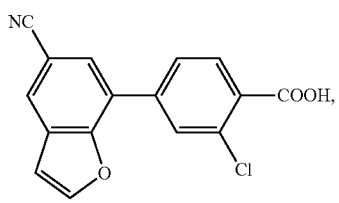 61 | 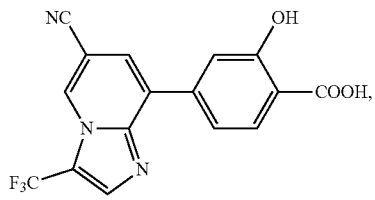 68 |
| 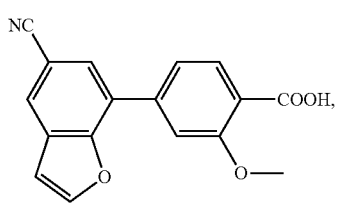 62 | 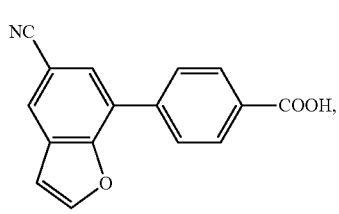 69 |
| 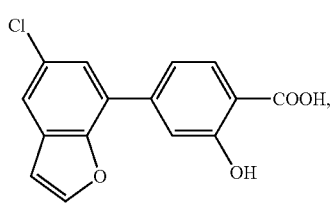 63 | 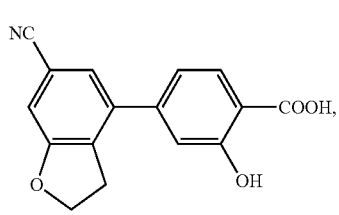 70 |
| 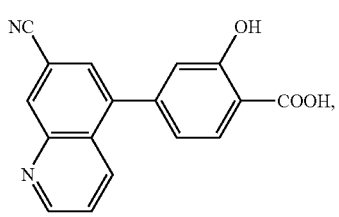 64 | 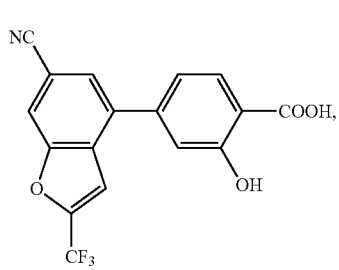 71 |
| 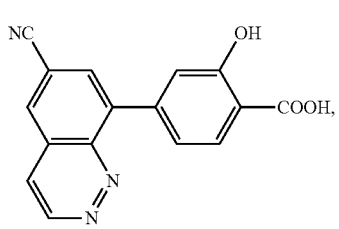 65 | 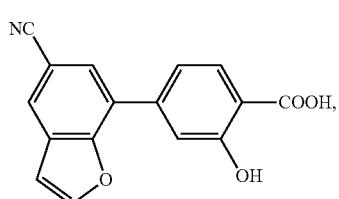 72 |
| 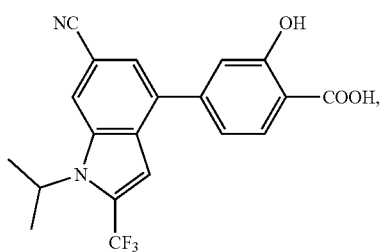 66 | 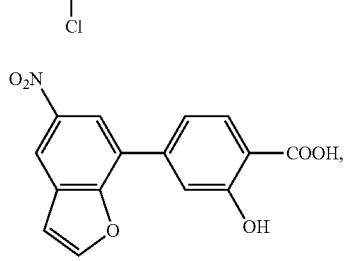 73 |
| 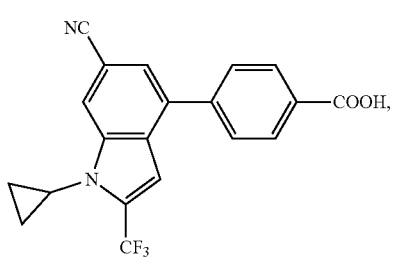 67 | 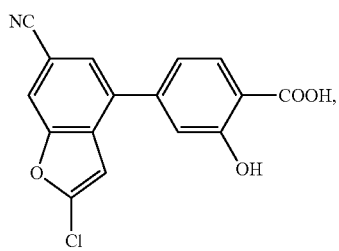 74 |

75
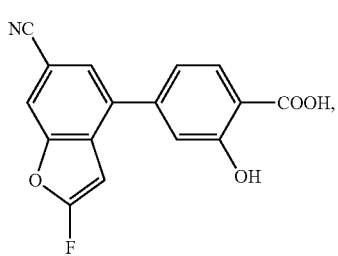
76
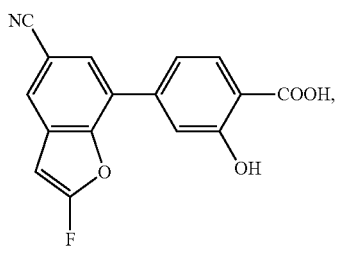
77
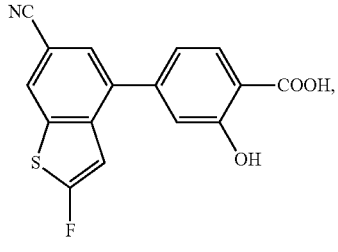
78
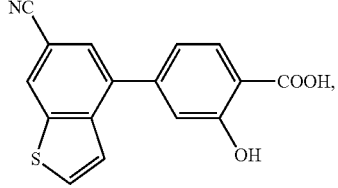
79
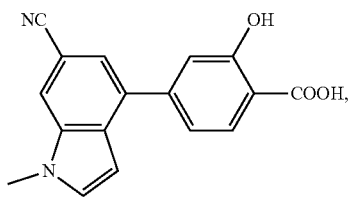
80
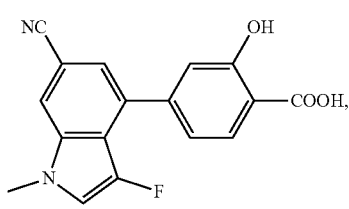
81
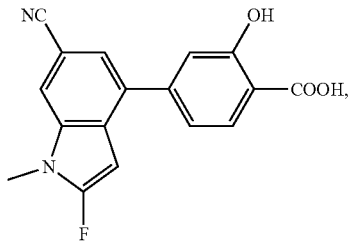
82
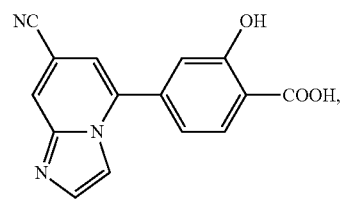
83
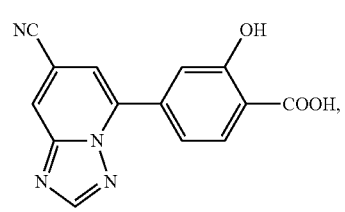
84
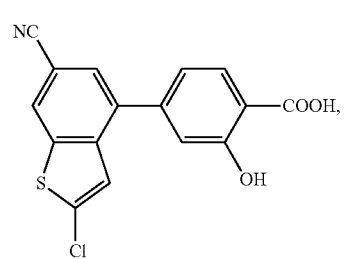
85
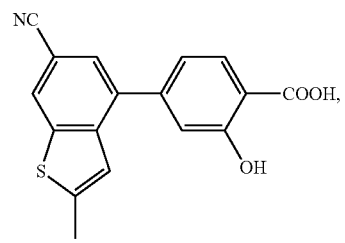
86
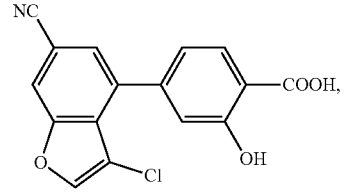
87
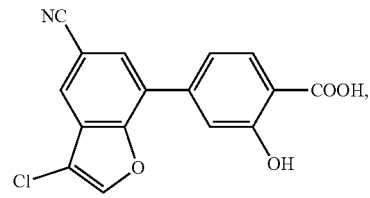
88
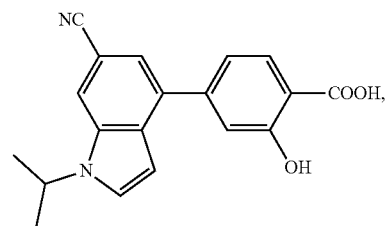

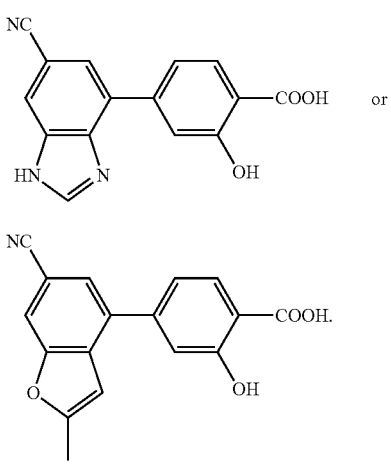

12. A pharmaceutical composition comprising the compound of claim 1.

13. The pharmaceutical composition of claim 12 further comprising a pharmaceutically acceptable excipient, carrier, adjuvant, solvent or a combination thereof.

14. The pharmaceutical composition of claim 13 further comprising a drug for preventing or treating hyperuricemia, tophi, gouty arthritis, kidney disorders associated with hyperuricemia or urolithiasis, wherein the drug comprises colchicine, a nonsteroidal anti-inflammatory drug, a glucocorticoid, an anti-uric acid drug, a uricosuric drug, a urinary alkalizing agent or a combination thereof.

15. A method for treating hyperuricemia, tophi, gouty arthritis, kidney disorders associated with hyperuricemia or urolithiasis in a subject, comprising administering to the subject a therapeutically effective amount of the compound according to claim 1.

16. A method for lowering the level of uric acid in blood of a subject comprising administering to the subject a therapeutically effective amount of the compound according to claim 1.

17. A method for inhibiting xanthine oxidase and urate anion transporter 1 in a subject comprising administering to the subject a therapeutically effective amount of the compound according to claim 1.

18. A method for treating hyperuricemia, tophi, gouty arthritis, kidney disorders associated with hyperuricemia or urolithiasis in a subject, comprising administering to the subject a therapeutically effective amount of the pharmaceutical composition according claim 12.

19. A method for lowering the level of uric acid in blood of a subject comprising administering to the subject a therapeutically effective amount of the pharmaceutical composition according to claim 12.

20. A method for inhibiting xanthine oxidase and urate anion transporter 1 in a subject comprising administering to the subject a therapeutically effective amount of the pharmaceutical composition according to claim 12.

* * * * *